US008304434B2

(12) United States Patent
Chakravarty et al.

(10) Patent No.: US 8,304,434 B2
(45) Date of Patent: Nov. 6, 2012

(54) SUBSTITUTED ARYL SULFONE DERIVATIVES AS CALCIUM CHANNEL BLOCKERS

(75) Inventors: Prasun K. Chakravarty, Edison, NJ (US); Yanbing Ding, Richmond (CA); Joseph L. Duffy, Cranford, NJ (US); Hassan Pajouhesh, West Vancouver (CA); Pengcheng Patrick Shao, Fanwood, NJ (US); Sriram Tyagarajan, Edison, NJ (US); Feng Ye, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 242 days.

(21) Appl. No.: 12/678,454

(22) PCT Filed: Sep. 30, 2008

(86) PCT No.: PCT/US2008/011286
§ 371 (c)(1),
(2), (4) Date: Mar. 16, 2010

(87) PCT Pub. No.: WO2009/045382
PCT Pub. Date: Apr. 9, 2009

(65) Prior Publication Data
US 2010/0210620 A1 Aug. 19, 2010

Related U.S. Application Data

(60) Provisional application No. 60/997,615, filed on Oct. 4, 2007.

(51) Int. Cl.
*A61K 31/445* (2006.01)
*C07D 401/12* (2006.01)

(52) U.S. Cl. ........ 514/318; 514/252; 514/255; 514/256; 514/303; 514/321; 514/323; 514/326; 514/330; 544/238; 544/300; 544/353; 544/405; 546/121; 546/139; 546/156; 546/194; 546/202; 546/208; 546/210; 546/226

(58) Field of Classification Search .................. 514/252, 514/255, 256, 259, 303, 301, 308, 321, 323, 514/326, 330, 315, 317, 318; 544/238, 300, 544/353, 405; 546/121, 139, 156, 194, 202, 546/208, 210, 226
See application file for complete search history.

(56) References Cited

U.S. PATENT DOCUMENTS

| 5,618,720 A | 4/1997 | Ellis et al. |
|---|---|---|
| 5,686,241 A | 11/1997 | Ellis et al. |
| 5,710,250 A | 1/1998 | Ellis et al. |
| 5,726,035 A | 3/1998 | Jay et al. |
| 5,792,846 A | 8/1998 | Harpold et al. |
| 5,846,757 A | 12/1998 | Harpold et al. |
| 5,851,824 A | 12/1998 | Harpold et al. |
| 5,874,236 A | 2/1999 | Harpold et al. |
| 5,876,958 A | 3/1999 | Harpold et al. |
| 6,011,035 A | 1/2000 | Snutch et al. |
| 6,013,474 A | 1/2000 | Ellis et al. |
| 6,057,114 A | 5/2000 | Akong et al. |
| 6,096,514 A | 8/2000 | Harpold et al. |
| 6,294,533 B1 | 9/2001 | Snutch et al. |
| 6,617,322 B2 | 9/2003 | Snutch |
| 2004/0044004 A1 | 3/2004 | Snutch et al. |
| 2005/0277665 A1 | 12/2005 | Fan et al. |
| 2006/0183783 A1 | 8/2006 | Polisetti et al. |
| 2011/0172236 A1* | 7/2011 | Chakravarty et al. ......... 514/249 |

FOREIGN PATENT DOCUMENTS

| JP | 2002088073 | 3/2002 |
|---|---|---|
| WO | 9422835 | 10/1994 |
| WO | 9928342 | 6/1999 |
| WO | 0125200 | 4/2001 |
| WO | 02055516 | 7/2002 |
| WO | 03075853 | 9/2003 |
| WO | 03084948 | 10/2003 |
| WO | 2004031138 | 4/2004 |
| WO | 2004096217 | 11/2004 |
| WO | 2005000798 | 1/2005 |
| WO | 2007028638 | 3/2007 |
| WO | 2007056075 | 5/2007 |
| WO | 2007075524 | 7/2007 |
| WO | 2007075525 | 7/2007 |
| WO | 2007085357 | 8/2007 |

OTHER PUBLICATIONS

Catterall "structure and regulation . . . " Ann. Rev. Cell Dev. Biol. v. 16, p. 521-55 (2000).*
Pexton"Targeting voltage . . . " Expert. opin. onvestig. drugs 20(9) 1277-1284 (2011).*
Triggle "Drug targets in the . . . " Assay and Drug dev. tech. 1(5) 719-733 (2003).*
Xue et al. "Preparation of . . . " CA137:93692 (2002).*
W. A. Catterall et al., "Structure and Regulation of Voltage-Gated Ca2+ Channels", vol. 16, pp. 521-555, 2000, Annu. Rev. Cell Dev. Biol.
G. H. Hockerman et al., "Construction of a Hig-Affinity Receptor Site for Dihydropyridine Agonists and Antagonists by Single Amino Acid Substitutions in a Non-L-Type CA2+ Channel" vol. 94, pp. 14906-14911, 1997, Proc. Natl. Acad. Sci.
P. S. Staats et al., "Intrathecal Ziconotide in the Treatment of Refractory Pain in Patients with Cancer or AIDS", vol. 291, pp. 63-70, 2004, JAMA.
F. Colburne et al, "Continuing Postischemic Neuronal Death in CA1, Influence of Ischemia Duration and Cytoprotective Doses of NBQX ad SNX-111 in Rats", 199, vol. 30, pp. 662-668, Stroke.

(Continued)

Primary Examiner — Celia Chang
(74) Attorney, Agent, or Firm — Sylvia A. Ayler; Gerard M. Devlin

(57) ABSTRACT

A series of substituted aryl sulfone derivatives represented by Formula I, or pharmaceutically acceptable salts thereof. Pharmaceutical compositions comprise an effective amount of the instant compounds, either alone, or in combination with one or more other therapeutically active compounds, and a pharmaceutically acceptable carrier. Methods of treating conditions associated with, or caused by, calcium channel activity, including, for example, acute pain, chronic pain, visceral pain, inflammatory pain, neuropathic pain, urinary incontinence, itchiness, allergic dermatitis, epilepsy, diabetic neuropathy, irritable bowel syndrome, depression, anxiety, multiple sclerosis, sleep disorder, bipolar disorder and stroke, comprise administering an effective amount of the present compounds, either alone, or in combination with one or more other therapeutically active compounds.

9 Claims, No Drawings

OTHER PUBLICATIONS

J. E. McRory et al., "Molecular and Functional Characterization of a Family of Rat Brain T-Type Calcium Channels", vol. 276, pp. 3999-4011, 2001, J. of Biological Chemistry.

U. Klockner et al., "Comparison of the CA2+ Currents Induced by Expression of Three Cloned Alpha1 Subunits, Alpha1G, Alpha1H and Alpha11, of Low-Voltage-Activated T-Type Ca2+ Channels", vol. 11, pp. 4171-4178, 1999, E. J. of Neurosciences.

E. Perez-Reyes et al., "Three for T: Molecular Analysis of the Low Voltage-Activated Calcium Channel Family", vol. 56, pp. 660-669, 1999, CMLS.

S. J. L. Flatters et al., "T-Type Calcium Channels: A potential Target for the Treatment of Chronic Pain", vol. 30, pp. 573-580, 2005, Drugs of the Future.

J. G. McGivern et al., "Targeting N-type and T-type Calcium Channels for the Treatment of Pain", 2006, vol. 11, pp. 245-253, Drug Discovery Today.

M. Xia et al., "Generation and Characterization of a Cell Line with Inducible Expression of Cav3.2 (T-Type) Channels", vol. 1, pp. 637-645, 2003, Assay and Drug Development Technologies.

J. Lee et al., "Cloning and Expression of Novel Member of the Low Voltage-Activated T-Type Calcium Channel Family", 1999, vol. 19, pp. 1912-1921, J. of Neuroscience.

O.P. Hamill et al., "Improved Patch-Clamp Techniques for High-Resolution Current Recording from Cells and Cell-Free Membrane Patches",1981, vol. 391, pp. 85-100, Pflugers Archiv E. J. of Physiology.

L. Kiss et al., "High Throughput Ion-Channel Pharmacology: Planar-Array-Based Voltage Clamp", 2003, Vol. , pp. 127-136, Assay and Drug Development Technologies.

C. S. Li et al., "An Efficient Copper-Catalyzed Coupling Reaction of Pyrididn-2-Ones with Aryl and Heterocyclic Halidies Based on Buchwalds' Protocol", 2004, vol. 45, p. 4527-4260, Tetrahedron Letters.

K. R. Campos et al., "Asymmetric Synthesis of a Prostaglandin D2 Receptor Antagonist", 2005, vol. 70, pp. 268-274, J. Org. Chem.

A. I. Meyers et al., "The Synthetic Utility of Oxazolines in Aromatic Substitution", 1985, vol. 41, pp. 837-860, Tetrahedron.

P. D. O'Shea et al., "Practical Asymmetric Synthesis of a Potent PDE4 Inhibitor via Steroselective Enolate alkylation of a Chiral Aryl-Heteroaryl Secondary Tosylate", 2005, vol. 70, pp. 3021-3030, J. Org. Chem.

Y. Ishii et al., "Development of Highly Efficient Catalytic Method for Synthesis of Vinyl Ethers", 2002, vol. 124, pp. 1590-1591, J. Am. Chem. Soc.

P. Vesdo et al., "Synthesis of Ortho Substituted Arylboronic Esters by in Situ Trapping of Unstable Lithio Intermediates", 2001, vol. 3, pp. 1435-1437, Organic Letters.

J. H. Hwu et al., "Ceric Ammonium nitrate in the Deprotection of tert-Butoxycarbonyl Group", 1996, vol. 37, pp. 2035-2038, Tetrahedron Letters.

S. L. Buckwald et al, "A General and Efficient Method for the Palladium-Catalyzed Cross-Coupling of Thiols and Secondary Phosphines".

Y. Bessard et al, "Synthetic Process Development and Scale UP of Palladium-Catalyzed Alkoycarbonylation of Chloropyridines", 2001, vol. 5, pp. 572-574, Organic Process Research & Development.

C. Beaulieu et al., "A Mild and Efficient new Synthesis of Aryl Sulfones from Boronic Acids and Sulfinic Acid Salts", 2004, vol. 45, pp. 3233-3236, Tetrahedron Letters.

M. Schlosser et al., "Logistic Flexibility in the Preparation of Isomeric Halopyridinecarboxylic Acids", 2004, vol. 60, pp. 11869-11874, Tetrahedron.

J. R. Huguenard et al., "Intrathalamic Rhythmicity Studied in Vitro: Nominal T-Current Modulation Causes Robust Antioscillartory Effects", 1994, vol. 14, pp. 5485-5502, J. of Neuroscience.

* cited by examiner

US 8,304,434 B2

SUBSTITUTED ARYL SULFONE DERIVATIVES AS CALCIUM CHANNEL BLOCKERS

CROSS REFERENCE TO RELATED APPLICATIONS

This application is the National Stage of International Application No. PCT/US2008/011286 filed on Sep. 30, 2008, which claims the benefit under 35 U.S.C. 119(e) of U.S. Provisional Applications No. 60/997,615, filed Oct. 4, 2007.

FIELD OF THE INVENTION

This invention relates to a series of substituted aryl sulfone derivatives. In particular, this invention relates to substituted aryl sulfone derivatives that are N-type voltage-gated calcium channel blockers useful for the treatment of a variety of pain conditions including chronic and neuropathic pain. The compounds of the present invention also display activity in connection with blockage of T-type voltage-gated calcium channels. The compounds described in this invention are useful for the treatment of chronic and acute pain, including neuropathic, inflammatory, and visceral pain. The compounds described in this invention are also useful for the treatment of conditions including disorders of bladder function, pruritis, itchiness, allergic dermatitis and disorders of the central nervous system (CNS) such as stroke, epilepsy, essential tremor, schizophrenia, Parkinson's disease, manic depression, bipolar disorder, depression, anxiety, sleep disorder, diabetic neuropathy, hypertension, cancer, diabetes, infertility and sexual dysfunction.

BACKGROUND TO THE INVENTION

Ion channels control a wide range of cellular activities in both excitable and non-excitable cells (Hille, Bertil—"Ion Channels of Excitable Membranes", 3rd Edition, (2001), 814 pp; Sinauer Associates, Sunderlan, Mass., USA). Ion channels are attractive therapeutic targets due to their involvement in many physiological processes. In excitable cells, the coordinated function of the resident set of ion channels controls the electrical behavior of the cell. Plasma membrane calcium channels are members of a diverse superfamily of voltage gated channel proteins. Calcium channels are membrane-spanning, multi-subunit proteins that allow controlled entry of Ca2+ ions into cells from the extracellular fluid. Excitable cells throughout the animal kingdom, and at least some bacterial, fungal and plant cells, possess one or more types of calcium channel. Nearly all "excitable" cells in animals, such as neurons of the central nervous system (CNS), peripheral nerve cells and muscle cells, including those of skeletal muscles, cardiac muscles, and venous and arterial smooth muscles, have voltage-gated calcium channels. Voltage-gated calcium channels provide an important link between electrical activity at the plasma membrane and cell activities that are dependent on intracellular calcium, including muscle contraction, neurotransmitter release, hormone secretion and gene expression. Voltage-gated calcium channels serve to integrate and transduce plasma membrane electrical activity into changes in intracellular calcium concentration, and can do this on a rapid time scale.

Multiple types of calcium channels have been identified in mammalian cells from various tissues, including skeletal muscle, cardiac muscle, lung, smooth muscle and brain. A major family of this type is the L-type calcium channels, which include $Ca_v1.1$, $Ca_v1.2$, $Ca_v1.3$, and $Ca_v1.4$, whose function is inhibited by the familiar classes of calcium channel blockers (dihydropyridines such as nifedipine, phenylalkylamines such as verapamil, and benzothiazepines such as diltiazem). Additional classes of plasma membrane calcium channels are referred to as T ($Ca_v3.1$, $Ca_v3.2$, and Cav3.3), N ($Ca_v2.2$), P/Q ($Ca_v2.1$) and R ($Ca_v2.3$). The "T-type" (or "low voltage-activated") calcium channels are so named because they open for a shorter duration (T=transient) than the longer (L=long-lasting) openings of the L-type calcium channels. The L, N, P and Q-type channels activate at more positive potentials (high voltage activated) and display diverse kinetics and voltage-dependent properties.

Because of the crucial role in cell physiology, modulation of calcium channel activity can have profound effects. Mutations in calcium channel subunits have been implicated in a number of genetic diseases including familial hemiplegic migraine, spinocerebellar ataxia, Timothy Syndrome, incomplete congenital stationary night blindness and familial hypokalemic periodic paralysis. Modulation of voltage-gated calcium channels by signaling pathways, including c-AMP-dependent protein kinases and G proteins is an important component of signaling by hormones and neurotransmitters (Catteall, W. A., *Ann. Rev. Cell and Dev. Biol.* 16, 521-555 (2000)). Pharmacological modulation of calcium channels can have significant therapeutic effects, including the use of L-type calcium channel ($Ca_v1.2$) blockers in the treatment of hypertension (Hockerman, G. H et. al, *Proc. Natl Acad Sci.* (USA) 94, 14906-1491 (1997)) and more recently, use of Ziconitide, a peptide blocker of N-type calcium channels ($Ca_v2.2$), for the treatment of intractable pain (Staals, P. S. et. al, *Journal of the American Medical Association* 291, 63-70 (2004)). Zicontide is derived from Conotoxin, a peptide toxin isolated from cone snail venom, must be applied by intrathecal injection to allow its access to a site of action in the spinal cord and to minimize exposure to channels in the autonomic nervous system that are involved in regulating cardiovascular function. Ziconotide has also been shown to highly effective as a neuroprotective agent in rat models of global and focal ischemia (Colburne et. Al., *Stroke* 30, 662-668 (1999)) suggesting that modulation of N-type calcium channels ($Ca_v2.2$) has implication in the treatment of stroke.

Clinical and preclinical experiments with ziconitide and related peptides confirm a key role of N-type calcium channels in transmitting nociceptive signals into the spinal cord. Identification of N-type calcium channel blockers that can be administered systemically, and effectively block N-type calcium channels in the nociceptive signaling pathway, while sparing N-type calcium channel function in the periphery would provide important new tools for treating some forms of pain. The present invention describes blockers of N-type calcium channels ($Ca_v2.2$) that display functional selectivity by blocking N-type calcium channel activity needed to maintain pathological nociceptive signaling, while exhibiting a lesser potency at blocking N-type calcium channels involved in maintaining normal cardiovascular function.

There are three subtypes of T-type calcium channels that have been identified from various warm blooded animals including rat [*J Biol. Chem.* 276(6) 3999-4011 (2001); *Eur J Neurosci* 11(12):4171-8(1999); reviewed in *Cell Mol Life Sci* 56(7-8):660-9 (1999)]. These subtypes are termed α1G, α1H, and α1I, and the molecular properties of these channels demonstrate 60-70% homology in the amino acid sequences. The electrophysiological characterization of these individual subtypes has revealed differences in their voltage-dependent activation, inactivation, deactivation and steady-state inactivation levels and their selectivity to various ions such as barium (*J Biol. Chem.* 276(6) 3999-4011 (2001)). Pharmacologically, these subtypes have shown differing sensitivities to blockade by ionic nickel. These channel subtypes are also expressed in various forms due to their ability to undergo various splicing events during their assembly (*J Biol. Chem.* 276 (6) 3999-4011 (2001)).

U.S. Pat. Nos. 6,011,035; 6,294,533; and 6,617,322; and publication numbers WO2007/075525, US2004/044004, JP2002/088073, WO2007085357, W2007028638, WO94/22835, US20030408, and WO2004/096217, describe calcium channel blockers in the treatment of pain. See also WO2004/031138, WO2003084948, WO2003/075853, WO2001/025200, WO2007056075, WO2005000798 and WO2002/055516.

T-type calcium channels have been implicated in pathologies related to various diseases and disorders, including epilepsy, essential tremor, pain, neuropathic pain, schizophrenia, Parkinson's disease, depression, anxiety, sleep disorders, sleep disturbances, psychosis, schizophrenia, cardiac arrhythmia, hypertension, pain, cancer, diabetes, infertility and sexual dysfunction (*J Neuroscience,* 14, 5485 (1994); *Drugs Future* 30(6), 573-580 (2005); *EMBO J,* 24, 315-324 (2005); *Drug Discovery Today,* 11, 5/6, 245-253 (2006)).

SUMMARY OF THE INVENTION

The present invention is directed to a series of substituted aryl sulfone derivatives that are N-type calcium channel (Cav2.2) blockers useful for the treatment of acute pain, chronic pain, cancer pain, visceral pain, inflammatory pain, neuropathic pain, post-herpetic neuralgia, diabatic neuropathy, trigeminal neuralgia, migrane, fibromyalgia and stroke. The compounds of the present invention also display activities on T-type voltage-activated calcium channels (Cav 3.1 and Cav 3.2). The compounds described in this invention are also useful for the treatment of other conditions, including disorders of bladder function, pruritis, itchiness, allergic dermatitis and disorders of the central nervous system (CNS) such as stroke, epilepsy, essential tremor, schizophrenia, Parkinson's disease, manic depression, bipolar disorder, depression, anxiety, sleep disorder, hypertension, cancer, diabetes, infertility and sexual dysfunction. This invention also provides pharmaceutical compositions comprising a compound of the present invention, either alone, or in combination with one or more therapeutically active compounds, and a pharmaceutically acceptable carrier. The compounds of the present invention provide greater stability and maintain Cav2.2 potency and efficacy than prior known sulfonamides.

This invention further comprises methods for the treatment of acute pain, chronic pain, visceral pain, inflammatory pain, neuropathic pain and disorders of the CNS including, but not limited to, epilepsy, manic depression, depression, anxiety and bipolar disorder comprising administering the compounds and pharmaceutical compositions of the present invention.

DETAILED DESCRIPTION OF THE INVENTION

The compounds of this invention are represented by Formula I:

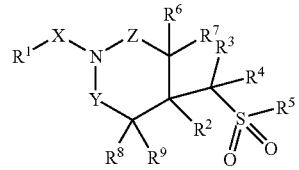

and pharmaceutically acceptable salts thereof and individual enantiomers and diastereomers thereof:

X is a bond, $CR^{10}R^{11}$, C=O, C=$ONR^{10}$, $CO_2$, $SO_2$, $C_{6-10}$ aryl, or $C_{5-10}$ heteroaryl;

Y is $CR^{10}R^{11}$, C=O or absent;

Z is $CR^{10}R^{11}$, C=O or absent;

$R^1$ is H, $C_{1-6}$-alkyl, $C_{3-7}$-cycloalkyl, $OR^{10}$, $C(O)R^{10}$, $(CH_2)_n$ $C_{5-10}$ heterocycle, $(CH_2)_n C_{6-10}$ aryl, $(CH_2)_n C_{5-10}$ heteroaryl, fused aryl or fused heteroaryl, wherein said alkyl, cycloalkyl, heterocycle, aryl and heteroaryl is optionally substituted with one to three groups of $R^a$;

$R^2$ is H, $C_{1-4}$ alkyl and $C_{1-4}$-perfluoroalkyl, $C_{3-5}$-cycloalkyl, $C_{6-10}$ aryl, $C_{5-10}$ heteroaryl, F, Cl, CN, $NR^{10}R^{11}$, wherein said alkyl, cycloalkyl, aryl and heteroaryl is optionally substituted with one to three groups of $R^a$;

$R^3$ and $R^4$ are each and independently selected from H, or $C_{1-6}$ alkyl, $C_{1-4}$-perfluoroalkyl, $C_{3-7}$-cycloalkyl, $C_{6-10}$ aryl, $C_{5-10}$ heteroaryl, F, Cl, CN, $OR^{10}$, $NR^{10}R^{11}$, $SO_2R^{10}$, $SO_2NR^{10}R^{11}$, $CO_2R^{10}$, $CONHR^{10}$, $CONR^{10}R^{11}$, or $R^3$ and $R^4$ join to form a 3-7 member carbocyclic or heterocyclic ring, wherein said alkyl, cycloalkyl, heterocycle, aryl and heteroaryl is optionally substituted with one to three groups of $R^a$;

$R^5$ is $C_{6-10}$ aryl, $C_{5-10}$ heteroaryl, $C_{3-7}$ cycloalkyl, $C_{5-10}$ heterocycle, wherein said cycloalkyl, heterocycle, aryl and heteroaryl is optionally substituted with one to three groups of $R^a$;

$R^6$, $R^7$, $R^8$, and $R^9$ independently represent H, $C_{1-4}$alkyl and $C_{1-4}$perfluoroalkyl, $C_{3-6}$-cycloalkyl, $C_{6-10}$ aryl, $C_{5-10}$ heteroaryl, F, Cl, CN, $OR^{10}$, $NR^{10}R^{11}$, or $R^8$ and $R^9$ combined with the carbon atom they are attached to can form C(O);

$R^{10}$ and $R^{11}$ are each and independently selected from H, or $C_{1-6}$alkyl, $(CH_2)_n C_{1-4}$-fluoroalkyl, $C_{3-7}$cycloalkyl, $C_{6-10}$ aryl, $C_{5-10}$ heteroaryl, or $R^{10}$ and $R^{11}$ join to form a 3-7 member carbocyclic or heterocyclic ring with the atom to which they are attached; said alkyl, aryl, or heteroaryl optionally substituted with 1 to 3 groups of $R^a$, n represents 0 to 6, and $R^a$ represents $C_{1-6}$ alkyl, $C_{3-7}$ cycloalkyl, $C_{1-4}$-fluoroalkyl, $C_{6-10}$ aryl, $C_{5-10}$ heteroaryl, halogen, CN, —$OCF_3$, —$OCHF_2$, —$C(O)CF_3$, —$C(OR^{10})(CF_3)_2$, $SR^{10}$, —$OR^{10}$, $NR^{10}R^{11}$, $SOR^{10}$, $SO_2R^{10}$, $NR^{10}COR^{11}$, $NR^{10}COOR^{11}$, $NR^{10}CONR^{10}R^{11}$, $NR^{10}SO_2NR^{10}R^{11}$, $SO_2NR^{10}R^{11}$, $NR^{10}SO_2R^{11}$, $CO_2R^{10}$, $CONR^{10}R^{11}$, said aryl and heteroaryl optionally substituted with 1 to 3 groups of $C_{1-6}$ alkyl, $C_{3-7}$ cycloalkyl, halogen, $CF_3$, CN or $OR^{10}$; with the proviso that when X=$SO_2$, the compound of formula I cannot be 4-[(4-Chlorobenzenesulfonyl)(2,5-difluorophenyl)methyl]-1-(trifluoromethanesulfonyl)piperidine; or 4-[(4-Chlorobenzenesulfonyl)(2,5-difluorophenyl)methyl]-1-(methanesulfonyl)piperidine; or when X=C=O, the compound of formula I cannot be 4-[[[4-[[5-[2-(2-Aminobenzothiazol-6-yl)vinyl]pyrimidin-2-yl]amino] phenyl]sulfonyl]-methyl]piperidine-1-carboxylic acid tert-butyl ester; 4-[[[4-[(5-Vinylpyrimidin-2-yl)amino] phenyl]sulfonyl]methyl]piperidine-1-carboxylic acid tert-butyl ester; Piperidinecarboxylic acid, 4-[[[4-[[5-[(1E)-2-

(3-methoxyphenyl)ethenyl]-2-pyrimidinyl]amino]
phenyl]sulfonyl]methyl]-, 1,1-dimethylethyl ester; 4-[[(4-Bromophenyl)sulfonyl]methyl]piperidine-1-carboxylic acid tert-butyl ester; Piperidinecarboxylic acid, 4-[[(4-fluorophenyl)sulfonyl]methyl]; Piperidinecarboxylic acid, 4-[[(2-fluorophenyl)sulfonyl]methyl]-, 1,1-dimethylethyl ester; Piperidinecarboxylic acid, 3-hydroxy-4-[[[4-(methylthio)phenyl]sulfonyl]methyl]-, 1,1-dimethylethyl ester, (3R,4S); tert-Butyl 4-[(4-chlorobenzenesulfonyl)(2,5-difluorophenyl)methyl]piperidine-1-carboxylate; 4-[[(4-Fluorophenyl)sulfonyl]methyl]-1-piperidinecarboxylate hydrochloride; tert-Butyl 4-[[(4-fluorophenyl)sulfonyl]methyl]-1-piperidinecarboxylate; or Piperidine, 1-(bromoacetyl)-4-[[(4-methylphenyl)sulfonyl]methyl]; or when Y and Z are $CH_2$, X is not $CR^{10}R^{11}$; or the compound of formula I is not piperidinyl-1-(bromoacetyl-4-[[4-methylphenyl)sulfonyl]methyl], or benzonitrilyl-4-[4-[[(4-fluorophenyl)sulfonyl]methyl]-4-hydroxy-1-piperidinyl]-2-(trifluoromethyl).

One embodiment of the present invention is realized when X is C=O and $R^1$ is $(CH_2)_nC_{5-10}$ heterocycle, $(CH_2)_nC_{6-10}$ aryl, $(CH_2)_nC_{5-10}$ heteroaryl, fused aryl or fused heteroaryl, wherein said heterocycle, aryl and heteroaryl is optionally substituted with one to three groups of $R^a$ and all other variables are as described herein. A sub-embodiment of this invention is realized when $R^1$ is phenyl, or pyridyl optionally substituted with 1 to 3 groups of $R^a$, and all other variables are as described herein. Still another sub-embodiment of this invention is realized when $R^a$ is $C_{1-6}$ alkyl, $C_{3-7}$ cycloalkyl, $C_{1-4}$-fluoroalkyl halogen, CN, —$OCF_3$, —$OCHF_2$, $OR^{10}$, or $SO_2R^{10}$.

Another embodiment of the present invention is realized when X is C=O and $R^1$ is $C_{1-6}$ alkyl, wherein said alkyl is optionally substituted with one to three groups of $R^a$ and all other variables are as described herein.

Another embodiment of the present invention is realized when X is C=O and $R^5$ is $C_{6-10}$ aryl, $C_{5-10}$ heteroaryl, or $C_{5-10}$ heterocycle, wherein said heterocycle, aryl and heteroaryl is optionally substituted with one to three groups of $R^a$ and all other variables are as described herein. A sub-embodiment of this invention is realized when $R^5$ is phenyl, or pyridyl, optionally substituted with 1 to 3 groups of $R^a$, and all other variables are as described herein. Still another sub-embodiment of this invention is realized when $R^a$ is $C_{1-6}$ alkyl, $C_{3-7}$ cycloalkyl, $C_{1-4}$-fluoroalkyl halogen, CN, —$OCF_3$, —$OCHF_2$, $OR^{10}$, or $SO_2R^{10}$.

In another embodiment of the present invention X is $C_{6-10}$aryl, or $C_{5-10}$ heteroaryl and all other variables are as described herein.

In another embodiment of the present invention X is C=O and all other variables are as described herein.

In another embodiment of the present invention Y is absent and all other variables are as described herein.

In another embodiment of the present invention Y is $CR^{10}R^{11}$, and all other variables are as described herein.

In another embodiment of the present invention Y is C=O and all other variables are as described herein.

In another embodiment of the present invention Z is C=O and all other variables are as described herein.

In still another embodiment of the present invention Z is absent and all other variables are as described herein.

In another embodiment of the present invention Z is $CR^{10}R^{11}$ and all other variables are as described herein.

In another embodiment of the present invention $R^1$ is phenyl optionally substituted with 1 to 3 groups of $R^a$ and all other variables are as described herein.

In another embodiment of the present invention $R^1$ is pyridyl optionally substituted with 1 to 3 groups of $R^a$ and all other variables are as described herein.

In another embodiment of the present invention R5 is phenyl optionally substituted with 1 to 3 groups of $R^a$ and all other variables are as described herein.

In another embodiment of the present invention $R^5$ is pyridyl optionally substituted with 1 to 3 groups of $R^a$ and all other variables are as described herein.

In yet another embodiment of the present invention, both Y and Z are $CH_2$, and $R^6$, $R^7$, $R^8$, and $R^9$ are each H and all other variables are as described herein, as depicted in formula Ia:

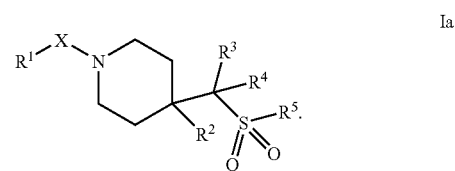

Ia

A sub-embodiment of structural formula Ia is realized when X is C=O and $R^2$ is H. A further sub-embodiment is realized when both $R^3$ and $R^4$ are H or $CH_3$, or one of $R^3$ and $R^4$ is H and the other is $CH_3$, with the resulting stereocenter having either the R or S stereochemical configuration. Still another sub-embodiment of this invention is realized when $R^1$ is $C_{1-6}$ alkyl, phenyl, or pyridyl all optionally substituted with 1 to 3 groups of $R^a$. Yet another sub-embodiment of this invention is realized when $R^5$ is phenyl or pyridyl optionally substituted with 1 to 3 groups of $R^a$. Another sub-embodiment of this invention is realized when both $R^1$ and $R^5$ are phenyl, optionally substituted with 1 to 3 groups of $R^a$. Another sub-embodiment of this invention is realized one of $R^1$ and $R^5$ is phenyl and the other is pyridyl, said phenyl and pyridyl optionally substituted with 1 to 3 groups of $R^a$.

In still another embodiment of the present invention, Y is $CH_2$, Z is absent, and $R^6$, $R^7$, $R^8$, and $R^9$ are each H and all other variables are as described herein, as depicted in formula Ib:

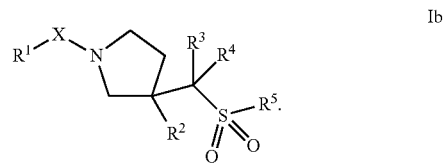

Ib

A sub-embodiment of structural Ib is realized when X is C=O and $R^2$ is H. A further sub-embodiment of this invention is realized when both $R^3$ and $R^4$ are $CH_3$. Still another sub-embodiment of this invention is realized when $R^1$ is $C_{1-6}$ alkyl, phenyl, or pyridyl all optionally substituted with 1 to 3 groups of $R^a$. Yet another sub-embodiment of this invention is realized when $R^5$ is phenyl or pyridyl optionally substituted with 1 to 3 groups of $R^a$. Another sub-embodiment of this invention is realized when both $R^1$ and $R^5$ are phenyl, optionally substituted with 1 to 3 groups of $R^a$. Another sub-embodiment of this invention is realized when one of $R^1$ and $R^5$ is phenyl and the other is pyridyl, said phenyl and pyridyl optionally substituted with 1 to 3 groups of $R^a$.

In still another embodiment of the present invention, both Y and Z are absent, and $R^6$, $R^7$, $R^8$, and $R^9$ are each H and all other variables are as described herein, as depicted in Ic:

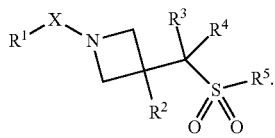

Ic

A sub-embodiment of structural Ic is realized when X is C=O and $R^2$ is H. A further sub-embodiment of this invention is realized when both $R^3$ and $R^4$ are H or $CH_3$. Still another sub-embodiment of this invention is realized when $R^1$ is $C_{1-6}$ alkyl, phenyl, or pyridyl all optionally substituted with 1 to 3 groups of $R^a$. Yet another sub-embodiment of this invention is realized when $R^5$ is phenyl or pyridyl optionally substituted with 1 to 3 groups of $R^a$. Another sub-embodiment of this invention is realized when both $R^1$ and $R^5$ are phenyl, optionally substituted with 1 to 3 groups of $R^a$. Another sub-embodiment of this invention is realized when one of $R^1$ and $R^5$ is phenyl and the other is pyridyl, said phenyl and pyridyl optionally substituted with 1 to 3 groups of $R^a$.

In another embodiment of the compounds of the present invention, Ar is aryl, both Y and Z are $CH_2$, $R^2$ is H, and both $R^3$ and $R^4$ are $CH_3$, and $R^6$, $R^7$, $R^8$, and $R^9$ are each H and all other variables are as described herein, as depicted in Id:

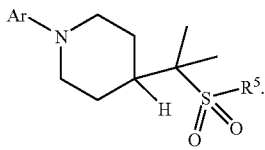

Id

A sub-embodiment of this invention is realized when Ar is phenyl optionally substituted with 1 to 3 groups of $R^a$. Yet another sub-embodiment of this invention is realized when $R^5$ is phenyl or pyridyl optionally substituted with 1 to 3 groups of $R^a$. Another sub-embodiment of this invention is realized when both Ar and $R^5$ are phenyl, optionally substituted with 1 to 3 groups of $R^a$. Another sub-embodiment of this invention is realized when Ar is phenyl and $R^5$ is pyridyl, said phenyl and pyridyl optionally substituted with 1 to 3 groups of $R^a$.

In another embodiment of the present invention, Het is heteroaryl, both Y and Z are $CH_2$, $R^2$ is H, both $R^3$ and $R^4$ are $CH_3$, and $R^6$, $R^7$, $R^8$, and $R^9$ are each H and all other variables are as described herein, as depicted in Ie:

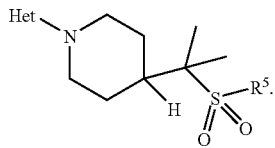

Ie

A sub-embodiment of formula Ie invention is realized when Het is pyridyl optionally substituted with 1 to 3 groups of $R^a$. Yet another sub-embodiment of this invention is realized when $R^5$ is phenyl or pyridyl optionally substituted with 1 to 3 groups of $R^a$. Another sub-embodiment of this invention is realized when $R^5$ is phenyl, optionally substituted with 1 to 3 groups of $R^a$.

When any variable (e.g. aryl, heterocycle, $R^1$, $R^5$ etc.) occurs more than one time in any constituent, its definition on each occurrence is independent at every other occurrence. Also, combinations of substituents/or variables are permissible only if such combinations result in stable compounds.

When $R^a$ is —O— and attached to a carbon it is referred to as a carbonyl group and when it is attached to a nitrogen (e.g., nitrogen atom on a pyridyl group) or sulfur atom it is referred to a N-oxide and sulfoxide group, respectively.

As used herein, "alkyl" encompasses groups having the prefix "alk" such as, for example, alkoxy, alkanoyl, alkenyl, and alkynyl and means carbon chains which may be linear or branched or combinations thereof. Examples of alkyl groups include methyl, ethyl, propyl, isopropyl, butyl, sec- and tert-butyl, pentyl, hexyl, and heptyl. "Alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl. Preferably, alkenyl is $C_2$-$C_6$ alkenyl. Preferred alkynyla are $C_2$-$C_6$ alkynyl. "Alkenyl," "alkynyl" and other like terms include carbon chains containing at least one unsaturated C—C bond.

As used herein, "fluoroalkyl" refers to an alkyl substituent as described herein containing at least one flurine substituent.

The term "cycloalkyl" refers to a saturated hydrocarbon containing one ring having a specified number of carbon atoms. Examples of cycloalkyl include cyclopropyl, cyclobutyl, cyclopentyl, and cyclohexyl.

The term "$C_{1-6}$" includes alkyls containing 6, 5, 4, 3, 2, or 1 carbon atoms The term "alkoxy" as used herein, alone or in combination, includes an alkyl group connected to the oxy connecting atom. The term "alkoxy" also includes alkyl ether groups, where the term 'alkyl' is defined above, and 'ether' means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as 'dimethyl ether'), and methoxyethane (also referred to as 'ethyl methyl ether').

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term heterocycle, heterocyclyl, or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocycle or heterocyclic includes heteroaryl and heterocycloalkyl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. An embodiment of the examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, 2-pyridinonyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl and triazolyl.

In certain embodiments, the heterocyclic group is a heteroaryl group. As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, between one and about three heteroatoms selected from the group consisting of N, O, and S. heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl.

In certain other embodiments, the heterocyclic group is fused to an aryl or heteroaryl group. Examples of such fused heterocycles include, without limitation, tetrahydroquinolinyl and dihydrobenzofuranyl.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

Examples of heterocycloalkyls include azetidinyl, pyrolidinyl, piperidinyl, piperazinyl, morpholinyl, tetrahydrofuranyl, imidazolinyl, pyrolidin-2-one, piperidin-2-one, and thiomorpholinyl.

The term "heteroatom" means O, S or N, selected on an independent basis.

A moiety that is substituted is one in which one or more hydrogens have been independently replaced with another chemical substituent. As a non-limiting example, substituted phenyls include 2-flurophenyl, 3,4-dichlorophenyl, 3-chloro-4-fluoro-phenyl, 2,4fluor-3-propylphenyl. As another non-limiting example, substituted n-octyls include 2,4 dimethyl-5-ethyl-octyl and 3-cyclopentyloctyl. Included within this definition are methylenes (—$CH_2$—) substituted with oxygen to form carbonyl (—CO—).

Unless otherwise stated, as employed herein, when a moiety (e.g., cycloalkyl, hydrocarbyl, aryl, alkyl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—), nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, and (b) $C_1$-$C_6$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $SO_2CF_3$, $CF_3$, $SO_2Me$, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$ alkylsulfinyl, arylalkylsulfnyl, arylsulfnyl, $C_1$-$C_8$ alkylsulfonyl, aralkylsulfonyl, arylsulfonyl, $C_0$-$C_6$ N-alkylcarbamoyl, $C_2$-$C_{15}$ N,N dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, or any of these rings fused or spiro-fused to a cycloalkyl, heterocyclyl, or aryl, wherein each of the foregoing is further optionally substituted with one more moieties listed in (a), above.

"Halogen" refers to fluorine, chlorine, bromine and iodine.

The term "mammal" "mammalian" or "mammals" includes humans, as well as animals, such as dogs, cats, horses, pigs and cattle.

Compounds described herein may contain one or more double bonds and may thus give rise to cis/trans isomers as well as other conformational isomers. The present invention includes all such possible isomers as well as mixtures of such isomers unless specifically stated otherwise.

The compounds of the present invention may contain one or more asymmetric centers and may thus occur as racemates, racemic mixtures, single enantiomers, diastereomeric mixtures, and individual diastereomers.

It will be understood that, as used herein, references to the compounds of structural formula I are meant to also include the pharmaceutically acceptable salts, and also salts that are not pharmaceutically acceptable when they are used as precursors to the free compounds or in other synthetic manipulations.

The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and tromethamine.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

The pharmaceutical compositions of the present invention comprise compounds of the invention (or pharmaceutically acceptable salts thereof) as an active ingredient, a pharmaceutically acceptable carrier, and optionally one or more additional therapeutic agents or adjuvants. Such additional therapeutic agents can include, for example, i) opiate agonists or antagonists, ii) calcium channel antagonists, iii) 5HT receptor agonists or antagonists, iv) sodium channel antagonists, v) NMDA receptor agonists or antagonists, vi) COX-2 selective inhibitors, vii) NK1 antagonists, viii) non-steroidal anti-inflammatory drugs ("NSAID"), ix) selective serotonin reuptake inhibitors ("SSRI") and/or selective serotonin and norepinephrine reuptake inhibitors ("SSNRI"), x) tricyclic antidepressant drugs, xi) norepinephrine modulators, xii) lithium, xiii) valproate, xiv) neurontin (gabapentin), xv) pregabalin, and xvi) sodium channel blockers. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The present compounds and compositions are useful for the treatment of chronic, visceral, inflammatory and neuropathic pain syndromes. They are useful for the treatment of pain resulting from traumatic nerve injury, nerve compression or entrapment, postherpetic neuralgia, trigeminal neuralgia, small fiber neuropathy, and diabetic neuropathy. The present compounds and compositions are also useful for the treatment of chronic lower back pain, phantom limb pain, chronic pelvic pain, neuroma pain, complex regional pain syndrome, chronic arthritic pain and related neuralgias, and pain associated with cancer, chemotherapy, HIV and HIV treatment-induced neuropathy. Compounds of this invention may also be utilized as local anesthetics. Compounds of this invention are useful for the treatment of irritable bowel syndrome and related disorders, as well as Crohn's disease.

The instant compounds have clinical uses for the treatment of epilepsy and partial and generalized tonic seizures. They are also useful for neuroprotection under ischaemic conditions caused by stroke or neural trauma and for treating multiple sclerosis. The present compounds are useful for the treatment of tachy-arrhythmias. Additionally, the instant compounds are useful for the treatment of neuropsychiatric disorders, including mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders.

In addition to primates, such as humans, a variety of other mammals can be treated according to the method of the present invention. For instance, mammals including, but not limited to, cows, sheep, goats, horses, dogs, cats guinea pigs, or other bovine, ovine, equine, canine, feline, rodent such as mouse, species can be treated. However, the method can also be practiced in other species, such as avian species (e.g., chickens).

It will be appreciated that for the treatment of depression or anxiety, a compound of the present invention may be used in conjunction with other anti-depressant or anti-anxiety agents, such as norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), α-adrenoreceptor antagonists, atypical anti-depressants, benzodiazepines, $5\text{-HT}_{1A}$ agonists or antagonists, especially $5\text{-HT}_{1A}$ partial agonists, neurokinin-1 receptor antagonists, corticotropin releasing factor (CRF) antagonists, and pharmaceutically acceptable salts thereof.

Further, it is understood that compounds of this invention can be administered at prophylactically effective dosage levels to prevent the above-recited conditions and disorders, as well as to prevent other conditions and disorders associated with calcium channel activity.

Creams, ointments, jellies, solutions, or suspensions containing the instant compounds can be employed for topical use. Mouth washes and gargles are included within the scope of topical use for the purposes of this invention.

Dosage levels from about 0.01 mg/kg to about 140 mg/kg of body weight per day are useful in the treatment of inflammatory and neuropathic pain, or alternatively about 0.5 mg to about 7 g per patient per day. For example, inflammatory pain may be effectively treated by the administration of from about 0.01 mg to about 75 mg of the compound per kilogram of body weight per day, or alternatively about 0.5 mg to about 3.5 g per patient per day. Neuropathic pain may be effectively treated by the administration of from about 0.01 mg to about 125 mg of the compound per kilogram of body weight per day, or alternatively about 0.5 mg to about 5.5 g per patient per day.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may ary from about 5 to about 95 percent of the total composition. Unit dosage forms will generally contain between from about 1 mg to about 1000 mg of the active ingredient, typically 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors. Such patient-related factors include the age, body weight, general health, sex, and diet of the patient. Other factors include the time and route of administration, rate of excretion, drug combination, and the severity of the particular disease undergoing therapy.

In practice, the compounds of the invention, or pharmaceutically acceptable salts thereof, can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt. The compounds of the invention, or pharmaceutically acceptable salts thereof, can also be included in pharmaceutical compositions in combination with one or more therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. As described previously, in preparing the compositions for oral dosage form, any of the usual pharmaceutical media can be employed. For example, in the case of oral liquid preparations such as suspensions, elixirs and solutions, water, glycols, oils, alcohols, flavoring agents, preservatives, coloring agents and the like may be used; or in the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which solid pharmaceutical carriers are employed. If desired, tablets may be coated by standard aqueous or nonaqueous techniques. In addition to the common dosage forms set out above, controlled release means and/or delivery devices may also be used in administering the instant compounds and compositions.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, and disintegrating agents can be used to form oral solid preparations such as powders, capsules and tablets. Because of their ease of administration, tablets and capsules are advantageous oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet advantageously contains from about 0.1 mg to about 500 mg of the active ingredient and each cachet or capsule advantageously containing from about 0.1 mg to about 500 mg of the active ingredient. Thus, a tablet, cachet, or capsule conveniently contains 0.1 mg, 1 mg, 5 mg, 25 mg, 50 mg, 100 mg, 200 mg, 300 mg, 400 mg, or 500 mg of the active ingredient taken one or two tablets, cachets, or capsules, once, twice, or three times daily.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage, and thus should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, and dusting powder. Further, the compositions can be in a form suitable for use in transdermal devices. These formulations may be prepared, utilizing a compound represented of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid, such as, for example, where the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, and preservatives (including anti-oxidants). Furthermore, other adjuvants can be included to render the formulation isotonic with the blood of the intended recipient. Compositions containing a compound of the invention, or pharmaceutically acceptable salts thereof, can also be prepared in powder or liquid concentrate form.

The compounds and pharmaceutical compositions of this invention have been found to block N-type, T-type, and L-type calcium channels. Accordingly, an aspect of the invention is the treatment and prevention in mammals of conditions that are amenable to amelioration through blockage of said calcium channels by administering an effective amount of a compound of this invention. Such conditions include, for example, acute pain, chronic pain, visceral pain, inflammatory pain and neuropathic pain. These conditions may also include epilepsy, essential tremor, schizophrenia, Parkinson's disease, depression, anxiety, sleep disorders, sleep disturbances, psychosis, infertility, and sexual dysfunction. These conditions may further include cardiac arrhythmia and hypertension. The instant compounds and compositions are useful for treating and preventing the above-recited conditions, in humans and non-human mammals such as dogs and cats. It is understood that the treatment of mammals other than humans refers to the treatment of clinical conditions in non-human mammals that correlate to the above-recited conditions.

Further, as described above, the instant compounds can be utilized in combination with one or more therapeutically active compounds. In particular, the inventive compounds can be advantageously used in combination with i) opiate agonists or antagonists, ii) other calcium channel antagonists, iii) 5HT receptor agonists or antagonists, including 5-$HT_{1A}$ agonists or antagonists, and 5-$HT_{1A}$ partial agonists, iv) sodium channel antagonists, v) N-methyl-D-aspartate (NMDA) receptor agonists or antagonists, vi) COX-2 selective inhibitors, vii) neurokinin receptor 1 (NK1) antagonists, viii) non-steroidal anti-inflammatory drugs (NSAID), ix) selective serotonin reuptake inhibitors (SSRI) and/or selective serotonin and norepinephrine reuptake inhibitors (SSNRI), x) tricyclic antidepressant drugs, xi) norepinephrine modulators, xii) lithium, xiii) valproate, xiv) norepinephrine reuptake inhibitors, xv) monoamine oxidase inhibitors (MAOIs), xvi) reversible inhibitors of monoamine oxidase (RIMAs), xvii) alpha-adrenoreceptor antagonists, xviii) atypical anti-depressants, xix) benzodiazepines, xx) corticotropin releasing factor (CRF) antagonists, xxi) neurontin (gabapentin) and xxii) pregabalin.

The abbreviations used herein have the following meanings (abbreviations not shown here have their meanings as commonly used unless specifically stated otherwise): Ac (acetyl), Bn (benzyl), Boc (tertiary-butoxy carbonyl), Bop reagent (benzotriazol-1-yloxy)tris(dimethylamino)phosonium hexafluorophosphate, CAMP (cyclic adenosine-3',5'-monophosphate), DAST ((diethylamino)sulfur trifluoride), DBU (1,8-diazabicyclo[5.4.0]undec-7-ene), DIBAL (di-isobutylaluminum hydride), DIEA (diisopropylethyl amine), DMAP (4-(dimethylamino)pyridine), DMF (N,N-dimethyl-formamide), DPPF (1,1'-bisdiphenylphosphinoferrocene), EDC (1-(3-dimethylaminopropyl)-3-ethylcarbodiimide hydrochloride), $Et_3N$ (triethylamine), GST (glutathione transferase), HOBt (1-hydroxybenzotriazole), LAH (lithium aluminum hydride), Ms (methanesulfonyl; mesyl; or $SO_2Me$), MsO (methanesulfonate or mesylate), MCPBA (meta-chloro perbenzoic acid), NaHMDS (sodium hexamethyldisilazane), NBS (N-bromosuccinimide), NCS (N-chlorosuccinimide), NSAID (non-steroidal anti-inflammatory drug), PDE (Phosphodiesterase), Ph (Phenyl), r.t. or RT (room temperature), Rac (Racemic), SAM (aminosulfonyl; sulfonamide or $SO_2NH_2$), SPA (scintillation proximity assay), Th (2- or 3-thienyl), TFA (trifluoroacetic acid), THF (Tetrahydrofuran), Thi (Thiophenediyl), TLC (thin layer chromatography), TMEDA (N,N,N',N'-tetramethylethylenediamine), TMSI (trimethylsilyl iodide), Tr or trityl (N-triphenylmethyl), $C_3H_5$ (Allyl), Me (methyl), Et (ethyl), n-Pr (normal propyl), i-Pr (isopropyl), n-Bu (normal butyl), i-Butyl (isobutyl), s-Bu (secondary butyl), t-Bu (tertiary butyl), c-Pr (cyclopropyl), c-Bu (cyclobutyl), c-Pen (cyclopentyl), c-Hex (cyclohexyl).

The present compounds can be prepared according to the general Schemes provided below as well as the procedures provided in the Examples. The following Schemes and Examples further describe, but do not limit, the scope of the invention.

Unless specifically stated otherwise, the experimental procedures were performed under the following conditions: All operations were carried out at room or ambient temperature; that is, at a temperature in the range of 18-25° C. Inert gas protection was used when reagents or intermediates were air and moisture sensitive. Evaporation of solvent was carried out using a rotary evaporator under reduced pressure (600-4000 pascals: 4.5-30 mm Hg) with a bath temperature of up to 60° C. The course of reactions was followed by thin layer chromatography (TLC) or by high-pressure liquid chromatography-mass spectrometry (HPLC-MS), and reaction times are given for illustration only. The structure and purity of all final products were assured by at least one of the following techniques: TLC, mass spectrometry, nuclear magnetic resonance (NMR) spectrometry or microanalytical data. When given, yields are for illustration only. When given, NMR data is in the form of delta ($\delta$) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. Broad; etc. In addition, "Ar" signifies an aromatic signal. Chemical symbols have their usual meanings; the following abbreviations are used: v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

Assay Example 1

Fluorescent Assay for Cav2.2 Channels Using Potassium Depolarization to Initiate Channel Opening Human Cav2.2 channels were stably expressed in HEK293 cells along with alpha2-delta and beta subunits of voltage-gated calcium channels. An inwardly rectifying potassium channel (Kir2.3) was also expressed in these cells to allow more precise control of the cell membrane potential by extracellular potassium concentration. At low bath potassium concentration, the membrane potential is relatively negative, and is depolarized as the bath potassium concentration is raised. In this way, the bath potassium concentration can be used to regulate the voltage-dependent conformations of the channels. Compounds are incubated with cells in the presence of low (4 mM) potassium or elevated (12, 25 or 30 mM) potassium to determine the affinity for compound block of resting (closed) channels at 4 mM potassium or affinity for block of open and inactivated channels at 12, 25 or 30 mM potassium. After the incubation period, Cav2.2 channel opening is triggered by addition of higher concentration of potassium (70 mM final concentration) to further depolarize the cell. The degree of state-dependent block can be estimated from the inhibitory potency of compounds after incubation in different potassium concentrations.

Calcium influx through Cav2.2 channels is determined using a calcium-sensitive fluorescent dye in combination with a fluorescent plate reader. Fluorescent changes were measured with either a VIPR (Aurora Instruments) or FLIPR (Molecular Devices) plate reader.

Protocol
1. Seed cells in Poly-D-Lysine Coated 96- or 384-well plate and keep in a 37° C.-10% $CO_2$ incubator overnight
2. Remove media[1], wash cells with 0.2 ml (96-well plate) or 0.05 ml (384-well plate) Dulbecco's Phosphate Buffered Saline (D-PBS) with calcium & magnesium (Invitrogen; 14040)
3. Add 0.1 ml (96-well plate) or 0.05 ml (384-well plate) of 4 μM fluo-4 (Molecular Probes; F-14202) and 0.02% Pluronic acid (Molecular Probes; P-3000) prepared in D-PBS with calcium & magnesium (Invitrogen; 14040) supplemented with 10 mM Glucose & 10 mM Hepes/NaOH; pH 7.4
4. Incubate in the dark at 25° C. for 60-70 min
5. Remove dye[2], wash cells with 0.1 ml (96-well plate) or 0.06 ml (384-well plate) of 4, 12, 25, or 30 mM Potassium Pre-polarization Buffer. (PPB)
6. Add 0.1 ml (96-well plate) or 0.03 ml (384-well plate) of 4, 12, 25, 30 mM PPB, with or without test compound
7. Incubate in the dark at 25° C. for 30 min
8. Read cell plate on VIPR instrument, Excitation=480 nm, Emission=535 nm
9. With VIPR continuously reading, add 0.1 ml (96-well plate) or 0.03 ml (384-well plate) of Depolarization Buffer, which is 2× the final assay concentration, to the cell plate.

Assay Reagents:

| 4 mM K Pre-Polarization Buffer | 12 mM K Pre-Polarization Buffer | 25 mM K Pre-Polarization Buffer | 30 mM K Pre-Polarization Buffer | 140 mM K Depolarization Buffer |
|---|---|---|---|---|
| 146 mM NaCl | 138 mM NaCl | 125 mM NaCl | 120 mM NaCl | 10 mM NaCl |
| 4 mM KCl | 12 mM KCl | 25 mM KCl | 30 mM KCl | 140 mM KCl |
| 0.8 mM $CaCl_2$ | 0.8 mM $CaCl_2$ | 0.8 mM $CaCl_2$ | 0.8 mM $CaCl_2$ | 0.8 mM $CaCl_2$ |
| 1.7 mM $MgCl_2$ | 1.7 mM $MgCl_2$ | 1.7 mM $MgCl_2$ | 1.7 mM $MgCl_2$ | 1.7 mM $MgCl_2$ |
| 10 mM HEPES | 10 mM HEPES | 10 mM HEPES | 10 mM HEPES | 10 mM HEPES |
| pH = 7.2 | pH = 7.2 | pH = 7.2 | pH = 7.2 | pH = 7.2 |

Assay Example 2

Electrophysiological Measurement of Block of Cav2.2 Channels Using Automated Electrophysiology Instruments Block of N-type calcium channels is evaluated utilizing the IonWorks HT 384 well automated patch clamp electrophysiology device. This instrument allows synchronous recording from 384 wells (48 at a time). A single whole cell recording is made in each well. Whole cell recording is established by perfusion of the internal compartment with amphotericin B.

The voltage protocol is designed to detect use-dependent block. A 2 Hz train of depolarizations (twenty 25 ms steps to +20 mV). The experimental sequence consists of a control train (pre-compound), incubation of cells with compound for 5 minutes, followed by a second train (post-compound). Use dependent block by compounds is estimated by comparing fractional block of the first pulse in the train to block of the 20th pulse.

Protocol

Parallel patch clamp electrophysiology is performed using IonWorks HT (Molecular Devices Corp.) essentially as described by Kiss and colleagues [Kiss et al. 2003; Assay and Drug Development Technologies, 1:127-135]. Briefly, a stable HEK 293 cell line (referred to as CBK) expressing the N-type calcium channel subunits (alpha$_{1B}$, alpha$_2$-delta, beta$_{3a}$) and an inwardly rectifying potassium channel ($K_{ir}$2.3) is used to record barium current through the N-type calcium channel. Cells are grown in T75 culture plates to 60-90% confluence before use. Cells are rinsed 3× with 10 ml PBS (Ca/Mg-free) followed by addition of 1.0 ml 1× trypsin to the flask. Cells are incubated at 37° C. until rounded and free from plate (usually 1-3 min). Cells are then transferred to a 15 ml conical tube with 13 ml of CBK media containing serum and antibiotics and spun at setting 2 on a table top centrifuge for 2 min. The supernatant is poured off and the pellet of cells is resuspended in external solution (in mM): 120 NaCl, 20 $BaCl_2$, 4.5 KCl, 0.5 $MgCl_2$, 10 HEPES, 10 Glucose, pH=7.4). The concentration of cells in suspension is adjusted to achieve 1000-3000 cells per well. Cells are used immediately once they have been resuspended. The internal solution is (in mM): 100 K-Gluconate, 40 KCl, 3.2 $MgCl_2$, 3 EGTA, 5 HEPES, pH 7.3 with KOH. Perforated patch whole cell recording is achieved by added the perforating agent amphotericin B to the internal solution. A 36 mg/ml stock of amphtericn B is made fresh in dimethyl sulfoxide for each run. 166 μl of this stock is added to 50 ml of internal solution yielding a final working solution of 120 ug/ml.

Voltage protocols and the recording of membrane currents are performed using the IonWorks HT software/hardware system. Currents are sampled at 1.25 kHz and leakage subtraction is performed using a 10 mV step from the holding potential and assuming a linear leak conductance. No correction for liquid junction potentials is employed. Cells are voltage clamped at −70 mV for 10 s followed by a 20 pulse train of 25 ms steps to +20 mV at 2 Hz. After a control train, the cells are incubated with compound for 5 minutes and a second train is applied. Use dependent block by compounds is estimated by comparing fractional block of the first pulse to block of the 20th pulse. Wells with seal resistances less than 70 MOhms or less than 0.1 nA of Ba current at the test potential (+20 mV) are excluded from analysis. Current amplitudes are calculated with the IonWorks software. Relative current, percent inhibition and IC50s are calculated with a custom Excel/Sigmaplot macro.

Compounds are added to cells with a fluidics head from a 96-well compound plate. To compensate for the dilution of compound during addition, the compound plate concentration is 3× higher than the final concentration on the patch plate.

Two types of experiments are generally performed: screens and titrations. In the screening mode, 10-20 compounds are evaluated at a single concentration (usually 3 uM). The percent inhibition is calculated from the ratio of the current amplitude in the presence and absence of compound, normalized to the ratio in vehicle control wells. For generation of IC50s, a 10-point titration is performed on 2-4 compounds per patch plate. The range of concentrations tested is generally 0.001 to 20 uM. IC50s are calculated from the fits of the Hill equation to the data. The form of the Hill equation used is: Relative Current=Max−Min)/(1+(conc/IC50)^slope))+Min. Vehicle controls (dimethyl sulfoxide) and 0.3 mM $CdCl_2$ (which inhibits the channel completely) are run on each plate for normalization purposes and to define the Max and Min.

Assay Example 3

Electrophysiological Measurement of Block of Cav2.2 Channels Using Whole Cell Voltage Clamp and Using PatchXpress Automated Electrophysiology Instrument Block of N-type calcium channels is evaluated utilizing manual and automated (PatchXpress) patch clamp electrophysiology. Voltage protocols are designed to detect state-dependent block. Pulses (50 ms) are applied at a slow frequency (0.067 Hz) from polarized (−90 mV) or depolarized (−40 mV) holding potentials. Compounds which preferentially block inactivated/open channels over resting channels will have higher potency at −40 mV compared to −90 mV. Protocol:

A stable HEK 293 cell line (referred to as CBK) expressing the N-type calcium channel subunits (alpha$_{1B}$, alpha$_2$-delta, beta$_{3a_1}$) and an inwardly rectifying potassium channel ($K_{ir}2.3$) is used to record barium current through the N-type calcium channel. Cells are grown either on poly-D-lysine coated coverglass (manual EP) or in T75 culture plates (PatchXpress). For the PatchXpress, cells are released from the flask using tryspin. In both cases, the external solution is (in mM): 120 NaCl, 20 $BaCl_2$, 4.5 KCl, 0.5 $MgCl_2$, 10 HEPES, 10 Glucose, pH 7.4 with NaOH. The internal solution is (in mM): 130 CsCl, 10 EGTA, 10 HEPES, 2 $MgCl_2$, 3 MgATP, pH 7.3 with CsOH.

Barium currents are measured by manual whole-cell patch clamp using standard techniques (Hamill et. al. Pfluegers Archiv 391:85-100 (1981)). Microelectrodes are fabricated from borosilicate glass and fire-polished. Electrode resistances are generally 2 to 4 MOhm when filled with the standard internal saline. The reference electrode is a silver-silver chloride pellet. Voltages are not corrected for the liquid junction potential between the internal and external solutions and leak is subtracted using the P/n procedure. Solutions are applied to cells by bath perfusion via gravity. The experimental chamber volume is ~0.2 ml and the perfusion rate is 0.5-2 ml/min. Flow of solution through the chamber is maintained at all times. Measurement of current amplitudes is performed with PULSEFIT software (HEKA Elektronik).

PatchXpress (Molecular Devices) is a 16-well whole-cell automated patch clamp device that operates asynchronously with fully integrated fluidics. High resistance (gigaohm) seals are achieved with 50-80% success. Capacitance and series resistance compensation is automated. No correction for liquid junction potentials is employed. Leak is subtracted using the P/n procedure. Compounds are added to cells with a pipettor from a 96-well compound plate. Voltage protocols and the recording of membrane currents are performed using the PatchXpress software/hardware system. Current amplitudes are calculated with DataXpress software.

In both manual and automated patch clamp, cells are voltage clamped at −40 mV or −90 mV and 50 ms pulses to +20 mV are applied every 15 sec (0.067 Hz). Compounds are added in escalating doses to measure % Inhibition. Percent inhibition is calculated from the ratio of the current amplitude in the presence and absence of compound. When multiple doses are achieved per cell, IC50s are calculated. The range of concentrations tested is generally 0.1 to 30 uM. IC50s are calculated from the fits of the Hill equation to the data. The form of the Hill equation used is: Relative Current=1/(1+(conc/IC50)^slope)).

The intrinsic N-type calcium channel antagonist activity of a compound which may be used in the present invention may be determined by these assays.

In particular, the compounds of the following examples had activity in antagonizing the N-type calcium channel in the aforementioned assays, generally with an $IC_{50}$ of less than about 10 uM. Preferred compounds within the present invention had activity in antagonizing the N-type calcium channel in the aforementioned assays with an $IC_{50}$ of less than about 1 uM. Such a result is indicative of the intrinsic activity of the compounds in use as antagonists of N-type calcium channel activity.

Assay Example 4

Assay for Cav3.1 and Cav3.2 Channels

The T-type calcium channel blocking activity of the compounds of this invention may be readily determined using the methodology well known in the art described by Xia, et al., Assay and Drug Development Tech., 1(5), 637-645 (2003).

In a typical experiment ion channel function from HEK 293 cells expressing the T-type channel alpha-1G, H, or I (CaV 3.1, 3.2, 3.3) is recorded to determine the activity of compounds in blocking the calcium current mediated by the T-type channel alpha-1G, H, or I (CaV 3.1, 3.2, 3.3). In this T-type calcium ($Ca^{2+}$) antagonist voltage-clamp assay calcium currents are elicited from the resting state of the human alpha-1G, H, or I (CaV 3.1, 3.2, 3.3) calcium channel as follows. Sequence information for T-type (Low-voltage activated) calcium channels are fully disclosed in e.g., U.S. Pat. No. 5,618,720, U.S. Pat. No. 5,686,241, U.S. Pat. No. 5,710,250, U.S. Pat. No. 5,726,035, U.S. Pat. No. 5,792,846, U.S. Pat. No. 5,846,757, U.S. Pat. No. 5,851,824, U.S. Pat. No. 5,874,236, U.S. Pat. No. 5,876,958, U.S. Pat. No. 6,013,474, U.S. Pat. No. 6,057,114, U.S. Pat. No. 6,096,514, WO 99/28342, and J. Neuroscience, 19(6):1912-1921 (1999). Cells expressing the t-type channels were grown in H3D5 growth media which is comprised DMEM, 6% bovine calf serum (HYCLONE), 30 micromolar Verapamil, 200 microgram/ml. Hygromycin B, 1× Penicillin/Streptomycin. Glass pipettes are pulled to a tip diameter of 1-2 micrometer on a pipette puller. The pipettes are filled with the intracellular solution and a chloridized silver wire is inserted along its length, which is then connected to the headstage of the voltage-clamp amplifier. Trypsinization buffer was 0.05% Trypsin, 0.53 mM EDTA. The extracellular recording solution consists of (mM): 130 mM NaCl, 4 mM KCl, 1 mM MgCl2, 2 mM CaCl2, 10 mM HEPES, 30 Glucose, pH 7.4. The internal solution consists of (mM): 135 mM CsMeSO4, 1 MgCl2, 10 CsCl, 5 EGTA, 10 HEPES, pH 7.4, or 135 mM CsCl, 2 MgCl2, 3 MgATP, 2 Na2ATP, 1 Na2GTP, 5 EGTA, 10 HEPES, pH 7.4. Upon insertion of the pipette tip into the bath, the series resistance is noted (acceptable range is between 1-4 megaohm). The junction potential between the pipette and bath solutions is zeroed on the amplifier. The cell is then patched, the patch broken, and, after compensation for series resistance (>=80%), the voltage protocol is applied while recording the whole cell Ca2+ current response. Voltage protocols: (1) −80 mV holding potential every 20 seconds pulse to −20 mV for 40 msec duration; the effectiveness of the drug in inhibiting the current mediated by the channel is measured directly from measuring the reduction in peak current amplitude initiated by the voltage shift from −80 mV to −20 mV; (2). −100 mV holding potential every 15 seconds pulse to −20 mV for 40 msec duration; the effectiveness of the drug in inhibiting the current mediated by the channel is measured directly from measuring the reduction in peak current amplitude initiated by the shift in potential from −100 mV to −30 mV. The difference in block at the two holding potentials was used to determine the effect of drug at differing levels of inactivation induced by the level of resting state potential of the cells. After obtaining control baseline calcium currents, extracellular solutions containing increasing concentrations of a test compound are washed on. Once steady state inhibition at a given compound concentration is reached, a higher concentration of compound is applied. % inhibition of the peak inward control Ca2+ current during the depolarizing step to −20 mV is plotted as a function of compound concentration.

The intrinsic T-type calcium channel antagonist activity of a compound which may be used in the present invention may be determined by these assays.

In particular, the compounds of the following examples had activity in antagonizing the T-type calcium channel in the aforementioned assays, generally with an $IC_{50}$ of less than about 10 uM. Preferred compounds within the present invention had activity in antagonizing the T-type calcium channel in the aforementioned assays with an $IC_{50}$ of less than about 1 uM. Such a result is indicative of the intrinsic activity of the compounds in use as antagonists of T-type calcium channel activity.

In Vivo Assay: (Rodent CFA Model):

Male Sprague Dawley rats (300-400 gm) were administered 200 microl CFA (Complete Freund's Adjuvant) three days prior to the study. CFA is mycobacterium tuberculosis suspended in saline (1:1; Sigma) to form an emulsion that contains 0.5 mg mycobacterium/ml. The CFA was injected into the plantar area of the left hind paw.

Rats are fasted the night before the study only for oral administration of compounds. On the morning of test day using a Ugo Basile apparatus, 2 baseline samples are taken 1 hour apart. The rat is wrapped in a towel. Its paw is placed over a ball bearing and under the pressure device. A foot pedal is depressed to apply constant linear pressure. Pressure is stopped when the rat withdraws its paw, vocalizes, or struggles. The right paw is then tested. Rats are then dosed with compound and tested at predetermined time points.

Compounds were prepared in dimethyl sulfoxide (15%)/PEG300 (60%)/Water (25%) and were dosed in a volume of 2 ml/kg.

Percent maximal possible effect (% MPE) was calculated as: (post-treatment−pre-treatment)/(pre-injury threshold−pre-treatment)×100. The % responder is the number of rats that have a MPE.30% at any time following compound administration. The effect of treatment was determined by one-way ANOVA Repeated Measures Friedman Test with a Dunn's post test.

Methods of Synthesis:

Compounds of the present invention can be prepared according to the Schemes provided below as well as the procedures provided in the Examples. The substituents are the same as in the above Formulas except where defined otherwise or otherwise apparent to the ordinary skilled artisan.

The novel compounds of the present invention can be readily synthesized using techniques known to those skilled in the art, such as those described, for example, in *Advanced Organic Chemistry*, March, 5$^{th}$ Ed., John Wiley and Sons, New York, N.Y., 2001; *Advanced Organic Chemistry*, Carey and Sundberg, Vol. A and B, 3$^{rd}$ Ed., Plenum Press, Inc., New York, N.Y., 1990; *Protective groups in Organic Synthesis*, Green and Wuts, 2$^{nd}$ Ed., John Wiley and Sons, New York, N.Y., 1991; *Comprehensive Organic Transformations*, Larock, VCH Publishers, Inc., New York, N.Y., 1988; *Handbook of Heterocyclic Chemistry*, Katritzky and Pozharskii, 2$^{nd}$ Ed., Pergamon, New York, N.Y., 2000 and references cited therein. Other references used for synthesizing novel compounds in the present invention include: Li, et al., *Tetrahedron Lett.*, 2004, 45, 4257-4260; O'Shea, et al., *J. Org. Chem.*, 2005, 70, 3021-3030; Ishii, et al., *J. Am. Chem. Soc.*, 2002, 124, 1590-1591; Vedso, et el., *Org. Lett.*, 2001, 3, 1435-1437; Hwu et el., *Tetrahedron Lett.*, 1996, 37, 2035-2038; Buckwald et el, *Tetrahedron*, 2004, 60, 7397-7403; Dessard et el., *Org. Proc. Res. Dev.*, 2001, 5, 572-574; Beaulieu et el, *Tetrahedron lett.*, 2004, 45, 3233-3236; Schlosser et el., *Tetrahedron*, 2004, 60, 11869-11874; Meyers et el, *Tetrahedron*, 1984, 41, 837-860; Campos et el., *J. Org. Chem.*, 2005, 70, 268-274. The starting materials for the present compounds may be prepared using standard synthetic transformations of chemical precursors that are readily available from commercial sources, including Aldrich Chemical Co. (Milwaukee, Wis.); Sigma Chemical Co. (St. Louis, Mo.); Lancaster Synthesis (Windham, N.H.); Ryan Scientific (Columbia, S.C.); Maybridge (Cornwall, UK); Matrix Scientific (Columbia, S.C.); Arcos, (Pittsburgh, Pa.) and Trans World Chemicals (Rockville, Md.).

The procedures described herein for synthesizing the compounds may include one or more steps of protecting group manipulations and of purification, such as, re-crystallization, distillation, column chromatography, flash chromatography, thin-layer chromatography (TLC), radial chromatography and high-pressure chromatography (HPLC). The products can be characterized using various techniques well known in the chemical arts, including proton and carbon-13 nuclear magnetic resonance ($^{1}H$ and $^{13}C$ NMR), infrared and ultraviolet spectroscopy (IR and UV), X-ray crystallography, elemental analysis and HPLC and mass spectrometry (HPLC-MS). Methods of protecting group manipulation, purification, structure identification and quantification are well known to one skilled in the art of chemical synthesis.

Appropriate solvents are those which will at least partially dissolve one or all of the reactants and will not adversely interact with either the reactants or the product. Suitable solvents are aromatic hydrocarbons (e.g, toluene, xylenes), halogenated solvents (e.g, methylene chloride, chloroform, carbontetrachloride, chlorobenzenes), ethers (e.g, diethyl ether, diisopropylether, tert-butyl methyl ether, diglyme, tetrahydrofuran, dioxane, anisole), nitriles (e.g, acetonitrile, propionitrile), ketones (e.g, 2-butanone, dithyl ketone, tert-butyl methyl ketone), alcohols (e.g, methanol, ethanol, n-propanol, iso-propanol, n-butanol, t-butanol), N,N-dimethyl formamide (DMF), dimethylsulfoxide (DMSO) and water. Mixtures of two or more solvents can also be used. Suitable bases are, generally, alkali metal hydroxides, alkaline earth metal hydroxides such as lithium hydroxide, sodium hydroxide, potassium hydroxide, barium hydroxide, and calcium hydroxide; alkali metal hydrides and alkaline earth metal hydrides such as lithium hydride, sodium hydride, potassium hydride and calcium hydride; alkali metal amides such as lithium amide, sodium amide and potassium amide; alkali metal carbonates and alkaline earth metal carbonates such as lithium carbonate, sodium carbonate, cesium carbonate, sodium hydrogen carbonate, and cesium hydrogen carbonate; alkali metal alkoxides and alkaline earth metal alkoxides such as sodium methoxide, sodium ethoxide, potassium tert-butoxide and magnesium ethoxide; alkali metal alkyls such as methyllithium, n-butyllithium, sec-butyllithium, t-bultyl-lithium, phenyllithium, alkyl magnaesium halides, organic bases such as trimethylamine, triethylamine, triisopropylamine, N,N-diisopropylethyl amine, piperidine, N-methyl piperidine, morpholine, N-methyl morpholine, pyridine, collidines, lutidines, and 4-dimethylaminopyridine; and bicyclic amines such as DBU and DABCO.

It is understood that the functional groups present in compounds described in the Schemes below can be further manipulated, when appropriate, using the standard functional group transformation techniques available to those skilled in the art, to provide desired compounds described in this invention.

It is also understood that compounds listed in the Schemes and Tables below that contain one or more stereocenters may be prepared as single enantiomers or diastereomers, or as mixtures containing two or more enantiomers or diastereomers in any proportion.

Other variations or modifications, which will be obvious to those skilled in the art, are within the scope and teachings of this invention. This invention is not to be limited except as set forth in the following claims.

Amine intermediates 5 were synthesized as shown in Scheme 1. Commercially available Boc protected amino alcohols 1 such as tert-butyl 3-(hydroxymethyl)azetidine-1-carboxylate (m, n=1), tert-butyl 3-(hydroxymethyl)pyrrolidine-1-carboxylate (m=1, n=2) and tert-butyl 4-(hydroxymethyl)piperidine-1-carboxylate (m, n=2) were converted to mesylates 2 by treatment of methanesulfonyl chloride or methanesulfonic anhydride and an appropriate base such as triethylamine. The resulted mesylates 2 can be displaced by selected thiols in present of a suitable base such as $K_2CO_3$ to give desired thioether products 3, which were oxidized with Oxone™ or meta chloroperbenzoic acid (MCPBA) to give sulfone products 4. Deprotection of the Boc group with trifluoroacetic acid gave desired aminesulfone products 5.

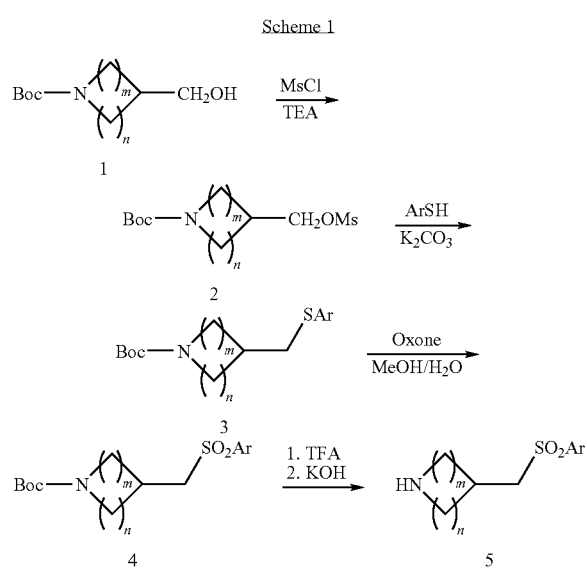

Scheme 1

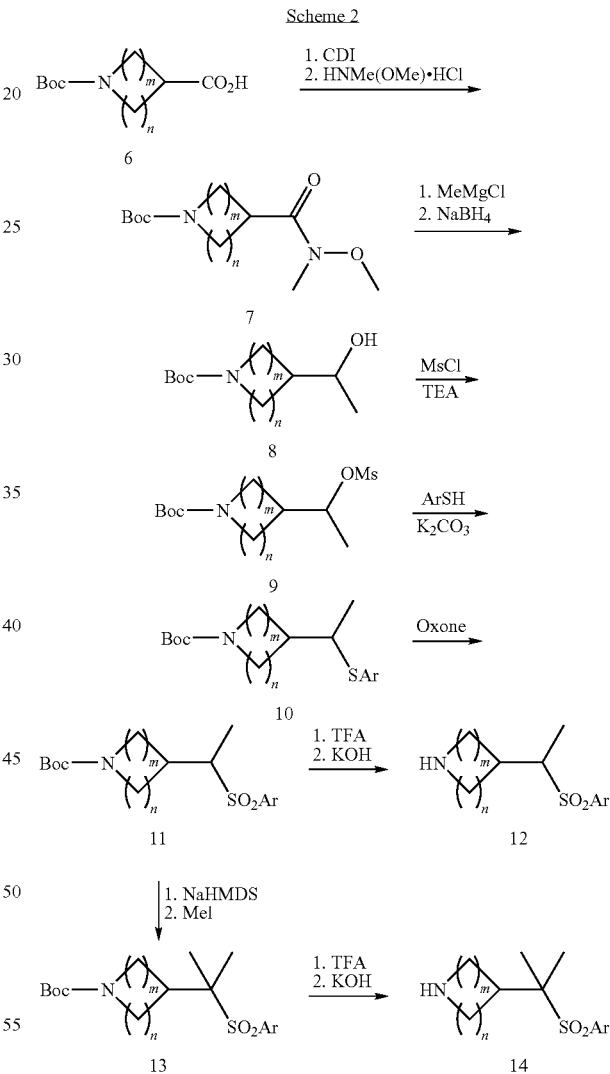

Scheme 2

To introduce substitutions such as methyl or gem dimethyl groups at α position to the sulfone group, Boc protected amino acids 6 such as 1-(tert-butoxycarbonyl)azetidine-3-carboxylic acid (m, n=1), 1-(tert-butoxycarbonyl)pyrrolidine-3-carboxylic acid (m=1, n=2) and 1-(tert-butoxycarbonyl)piperidine-4-carboxylic acid (m, n=2) were converted to their corresponding Weinreb amides 7 using procedures known to those of ordinary skill in the art. Weinreb amides 7 were then treated with methyl Grignard reagent to give methyl ketone intermediates which were sequentially reduced to alcohols 8 with NaBH$_4$. Alcohol compounds 8 were converted to mesylates 9 by treatment of methanesulfonyl chloride or methanesulfonic anhydride and an appropriate base such as triethylamine. The resulted mesylates 9 can be displaced by selected thiols in present of a suitable base such as K$_2$CO$_3$ to give desired thioether products 10, which were oxidized with Oxone™ or MCPBA to give sulfone products 11. Deprotection of the Boc group with trifluroacetic acid gave desired amine products 12. To synthesize gem dimethyl compounds 13, sulfone compounds 11 were treated with sodium bis(trimethylsilyl)amide (NaHMDS) to generate sulfone anions which were alkylated by addition of iodomethane (MeI). Boc protecting group was then removed by treating with trifluoroacetic acid to give desired aminesulfone compounds 14.

Scheme 3

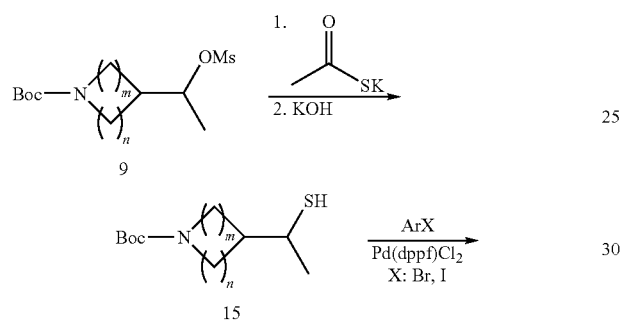

Alternatively, thioethers such compounds 10 can be synthesized following Scheme 3. Mesylates 9 were treated with potassium ethanethiolate to give thioesters which were hydrolyzed to give thio compounds 15. Palladium mediated coupling reaction between 15 and selected aryl halides gave desired thioethers 10. Thioethers 10 can be converted to amines 12 and 14 following the reactions outlined in Scheme 2.

Example 1

1-benzoyl-4-(1-methyl-1-{[3-(trifluoromethyl)phenyl]sulfonyl}ethyl)piperidine

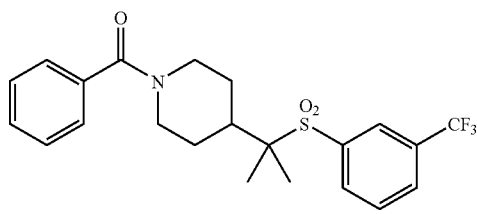

Step 1: tert-butyl-4-{[methoxy(methyl)amino]carbonyl}piperidine-1-carboxylate

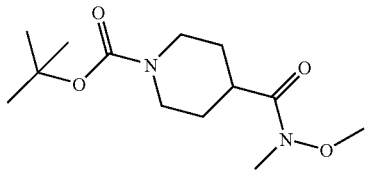

To a 500 ml round bottom flask was added 150 ml tetrahydrofuran and 24.8 g 1-(tert-butoxycarbonyl)piperidine-4-carboxylic acid (108 mmol). Carbonyldiimidazole (CDI) (18.4 g, 114 mmol) was added in portions. The reaction mixture was stirred at room temperature for 1 hour. Methylmehoxy amine hydrochloride salt (14.8 g, 151 mmol) was added followed by 22.6 ml triethylamine. The reaction mixture was heated at 55° C. for 1 hour. It was cooled with ice bath and diluted with 200 ml ether. The resulting mixture was washed sequentially twice with 150 ml of saturated ammonium chloride solution, 150 ml 5% KOH solution and 100 ml brine. The organic layers were dried over sodium sulfate, filtered and concentrated. The residue was dissolved in 50 ml toluene and then reconcentrated under vacuum to give 29 g colorless oil which was used for next step without further purification.

$^1$H-NMR (CDCl$_3$): δ 4.17 (b, 2H), 3.74 (s, 3H), 3.21 (s, 3H), 2.8 (b, 3H), 1.7 (b, 4H), 1.49 (s, 9H)

Mass Spectra (m/e): 273 (M+1).

Step 2: tert-butyl 4-acetylpiperidine-1-carboxylate

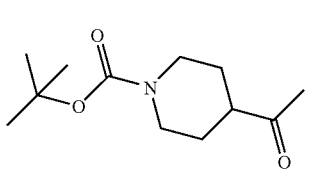

To a 500 ml round bottom flask was added tert-butyl-4-{[methoxy(methyl)amino]carbonyl}piperidine-1-carboxylate (29 g, 106 mmol) and 150 ml tetrahydrofuran. The resulting solution was cooled with ice bath and methylmagnesium chloride tetrahydrofuran solution (42.6 ml, 3M, 128 mmol) was added by a syringe. The mixture was stirred at 0° C. for 30 minutes. It was diluted with 200 ml of ether and the resulting mixture was washed twice with 150 ml saturated ammonium chloride solution. The organics were dried over sodium sulfate, filtered and concentrated. The crude product was used for next step without further purification.

$^1$H-NMR (CDCl$_3$): δ4.12 (b, 2H), 2.8 (b, 2H), 2.48 (m, 1H), 2.19 (s, 3H), 1.85 (b, 2H), 1.5 (m, 2H), 1.48 (s, 9H).

Step 3: tert-butyl 4-(1-hydroxyethyl)piperidine-1-carboxylate

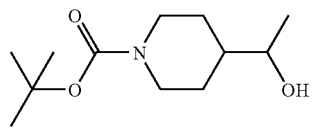

tert-Butyl 4-acetylpiperidine-1-carboxylate from the previous step was dissolved in 50 ml methanol. NaBH$_4$ (2.01 g, 53 mmol) was added in batches at 0° C. The resulting reaction mixture was stirred at 0° C. for 30 minutes. The volatiles were removed under vacuum. The residue was partitioned between 150 ml 10% KOH solution and 200 ml ether. The organic layers were washed with 100 ml brine, dried over sodium sulfate and concentrated to give 22.5 g colorless oil, which was azotropically dried by addition of 50 ml toluene and reconcentration under vacuum. This material was used for next step without further purification.

$^1$H-NMR (CDCl$_3$): δ4.17 (b, 2H), 3.62 (m, 1H), 2.69 (b, 2H), 1.85 (m, 1H), 1.6 (m, 1H), 1.48 (s, 9H), 1.46 (m, 1H), 1.24 (m, 11H), 1.22 (d, J=6.2 Hz, 3H).

Step 4: tert-butyl 4-{1-[(methylsulfonyl)oxy]ethyl}piperidine-1-carboxylate

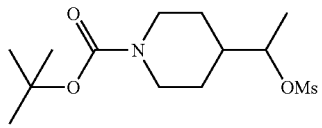

To a 250 ml round bottom flask was added tert-butyl 4-{1-[(methylsulfonyl)oxy]ethyl}piperidine-1-carboxylate from the previous step, triethylamine (27.4 ml, 196 mmol) and 100 ml methylene chloride. Methanesulfonyl chloride was added via a syringe at 0° C. The resulting reaction mixture was stirred at 0° C. for 30 minutes. It was diluted with 300 ml ether, washed sequentially with 150 ml 1N HCl, 100 ml saturated aqueous Na$_2$CO$_3$ and 100 ml brine. The organic layers were dried over sodium sulfate, filtered and concentrated to give 29 g light yellow sticky material.

Step 5: tert-butyl 4-(1-{[3-(trifluoromethyl)phenyl]thio}ethyl)piperidine-1-carboxylate

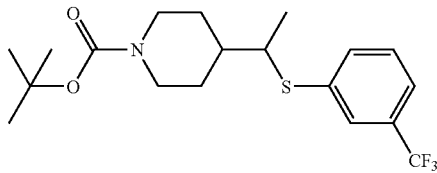

To a 250 ml round bottom flask was added tert-butyl 4-{1-[(methylsulfonyl)oxy]ethyl}piperidine-1-carboxylate (11 g, 35.8 mmol), 3-(trifluoromethyl)benzenethiol (7.6 g, 43 mmol), K$_2$CO$_3$ (9.9 g, 72 mmol) and 80 ml dimethylformamide. The reaction mixture was heated at 50° C. for 36 hr under N$_2$, then cooled down to room temperature, 150 ml ether was added. The resulting mixture was sequentially washed with 250 ml water, 100 ml 5% KOH solution and 75 ml brine. The organic layers were dried over sodium sulfate, filtered and concentrated to give 13.7 g crude product. It was used for next step without further purification.

$^1$H-NMR (CDCl$_3$): δ7.63 (s, 1H), 7.56 (d, J=7.8 Hz, 1H), 7.48 (d, J=8 Hz, 1H), 7.43 (t, J=7.8, 1H), 4.2 (b, 2H), 3.23 (m, 1H), 2.66 (b, 2H), 1.83 (m, 2H), 1.66 (m, 1H), 1.49 (s, 9H), 1.34 (m, 1H), 1.31 (d, J=6.9 Hz, 3H).

Step 6: tert-butyl 4-(1-{[3-(trifluoromethyl)phenyl]sulfonyl}ethyl)piperidine-1-carboxylate

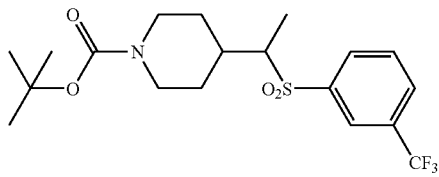

To a 500 ml round bottom flask was loaded with tert-butyl 4-(1-{[3-(trifluoromethyl)phenyl]thio}ethyl)piperidine-1-carboxylate (13.7 g, 35.2 mmol) from the previous step and 150 ml methanol. Oxone™ (43.2 g, 70.4 mmol) in 150 ml water (pH was adjusted to 3 with addition of potassium carbonate solution). The reaction mixture was stirred at room temperature for 30 minutes, followed by the addition of another 5 g of Oxone™ in 30 ml water. The reaction mixture was stirred at room temperature for an additional 20 minutes. The reaction mixture was diluted with 250 ml ether and 100 ml water and filtered. The organic layers were separated from the filtrate and washed with 150 ml brine, dried over sodium sulfate, filtered and concentrated. The residue was purified on silica gel column eluted with 1:4 to 1:2 ethylacetate/hexane to give 10.8 g colorless sticky material.

$^1$H-NMR (CDCl$_3$): δ8.18 (s, 1H), 8.12 (d, J=7.8 Hz, 1H), 7.96 (d, J=7.8 Hz, 1H), 7.77 (t, J=7.8, 1H), 4.2 (b, 2H), 3.0 (m, 1H), 2.75 (b, 2H), 2.45 (m, 1H), 1.95 (m, 1H), 1.48 (s, 9H), 1.4 (m, 2H), 1.23 (d, J=7.1 Hz, 3H).

Step 7: tert-butyl 4-(1-methyl-1-{[3-(trifluoromethyl)phenyl]sulfonyl}ethyl)piperidine-1-carboxylate

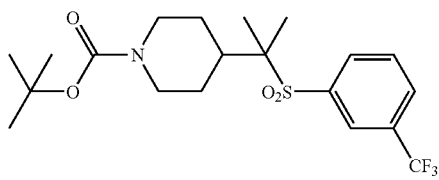

To a 100 ml round bottom flask was added tert-butyl 4-(1-{[3-(trifluoromethyl)phenyl]sulfonyl}ethyl)piperidine-1-carboxylate (5.4 g, 12.8 mmol) and 30 ml tetrahydrofuran. The resulting solution was cooled to −78° C. Sodium bis(trimethylsilyl)amide (NaHMDS) tetrahydrofuran solution (1M, 15.4 ml) was added via a syringe. The reaction mixture turned deep orange-red. It was stirred at −78 C for 5 minutes. MeI (0.96 ml, 15.4 mmol) was then added dropwise with a syringe until reaction mixture turned light yellow. More NaHMDS (1M, 3 ml tetrahydrofuran solution) was added. The reaction mixture was stirred at −78° C. for 5 more minutes and 0.3 ml MeI was added. NH$_4$Cl (60 ml) was added at −78° C. to quench the reaction. The resulting mixture was diluted with 120 ml ether and 60 ml water. The layers were separated, and the organics were dried over sodium sulfate, filtered and concentrated. The residue was purified on silica gel column eluted with 1:4 to 1:2 ethylacetate/hexane to give desired product which was used for the next directly.

¹H-NMR (CDCl₃): δ8.16 (s, 1H), 8.09 (d, J=8 Hz, 1H), 7.96 (d, J=7.6 Hz, 1H), 7.76 (t, J=7.8, 1H), 4.2 (b, 2H), 2.72 (b, 2H), 2.1 (m, 1H), 2.05 (m, 2H), 1.49 (s, 9H), 1.4 (m, 2H), 1.26 (s, 6H).

Step 8: 4-(1-methyl-1-{[3-(trifluoromethyl)phenyl]sulfonyl}ethyl)piperidine

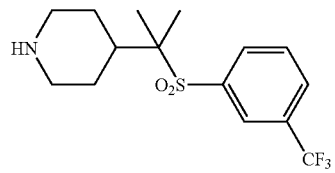

To a 250 ml round bottom flask was added tert-butyl 4-(1-methyl-1-{[3-(trifluoromethyl)phenyl]sulfonyl}ethyl)piperidine-1-carboxylate from the previous step, 60 ml ethyl acetate and 60 ml 3N HCl. The reaction mixture was heated at reflux for 3 hours. NMR showed complete conversion. The volatiles were removed and the residue was dissolved in 50 ml water, washed with 50 ml ether. The aqueous portion was basified with addition of KOH and extracted twice with 60 ml ethyl acetate. The extracts were dried over sodium sulfate, filtered and concentrated to give 3.5 g colorless solid.

¹H-NMR (CDCl₃) (HCl salt): δ8.15 (s, 1H), 8.09 (d, J=8 Hz, 1H), 7.98 (d, J=8 Hz, 1H), 7.78 (t, J=7.8, 1H), 3.6 (m, 2H), 2.95 (m, 2H), 2.4 (m, 1H), 2.3 (m, 2H), 2.0 (m, 2H), 1.49 (s, 9H), 1.28 (s, 6H).

Step 9: 1-benzoyl-4-(1-methyl-1-{[3-(trifluoromethyl)phenyl]sulfonyl}ethyl)piperidine

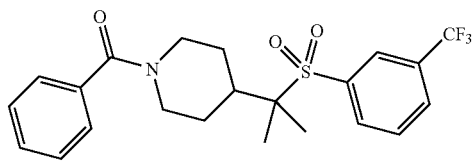

To a 10 ml vial was added 4-(1-methyl-1-{[3-(trifluoromethyl)phenyl]sulfonyl}ethyl)piperidine (33 mg, 0.098 mmol), benzoic acid (10 mg, 0.082 mmol), Bop reagent (43.5 mg, 0.098 mmol), diisopropylethyl amine (0.029 ml, 0.164 mmol) and 2 ml dimethylformamide. The resulting solution was stirred at room temperature for 10 minutes. LC-Mass showed clean desired product. The reaction mixture was diluted with 1 ml dimethyl sulfoxide, 1 ml water and 0.03 ml of trifluoroacetic acid. This mixture was loaded on a reverse phase column and purified on HPLC eluted with water/acetonitrile gradient solvent. Desired fraction was collected and lyophilized to give the title compound as a fluffy white solid.

¹H-NMR (CDCl₃): δ8.14 (s, 1H), 8.08 (d, J=7.6 Hz, 1H), 7.95 (d, J=7.5 Hz, 1H), 7.75 (t, J=7.8, 1H), 7.42 (m, 5H), 4.86 (b, 1H), 3.89 (b, 1H), 3.06 (b, 1H), 2.79 (b, 1H), 2.3 (m, 1H), 2.1 (b, 2H), 1.5 (b, 2H), 1.26 (s, 6H).

Mass Spectra (m/e): 440 (M+1).

Example 2

1-[2-(methylsulfonyl)-4-(trifluoromethoxy)benzoyl]-4-(1-methyl-1-{[3-(trifluoromethyl)phenyl]sulfonyl}ethyl)piperidine

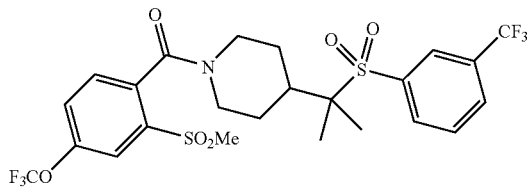

Step 1: N-(2-hydroxy-1,1-dimethylethyl)-4-(trifluoromethoxy)benzamide

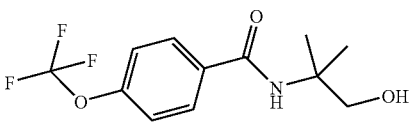

To a 100 ml round bottom flask was loaded 4-(trifluoromethoxy)benzoic acid (4.85 g, 23.5 mmol). Thionyl chloride (5.15 ml, 70.6 mmol) was added at 0° C. The reaction mixture was allowed to warm up to room temperature and then heated at 80° C. for 1 hour. After cooling down to room temperature, the volatiles were removed. The residue was diluted with 50 ml methylene chloride, and 2-amino-2-methylpropan-1-ol (7.34 g, 82 mmol) was added at 0° C. The reaction mixture was allowed to warm up to room temperature. It was diluted with 150 ml ether, washed sequentially with 100 ml 1N HCl, 100 ml 5% KOH and 50 ml brine. The organics were dried over sodium sulfate, filtered and concentrated to give 4.2 g desired product. It was used for the next step directly without further purification.

¹H-NMR (CDCl₃): δ7.8 (d, J=8.7 Hz, 2H), 7.29 (d, J=8.1 Hz, 2H), 3.72 (s, 2H), 1.44 (s, 6H).

Step 2: 4,4-dimethyl-2-[4-(trifluoromethoxy)phenyl]-4,5-dihydro-1,3-oxazole

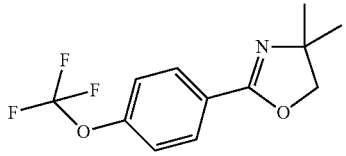

To a 25 ml round bottom flask was added N-(2-hydroxy-1,1-dimethylethyl)-4-(trifluoromethoxy)benzamide (4.2 g, 15.2 mmol). Thionyl chloride (3.32 ml, 45.5 mmol) was added. The resulting reaction mixture was stirred at room temperature for 1 hour. The reaction mixture was poured into 100 g crushed ice. Solid KOH was added until the mixture became strongly basic. The mixture was extracted twice with 50 ml ethyl acetate. The extracts were dried over sodium sulfate, filtered and concentrated. The crude product was purified on silica gel column eluted with 1:10 ethyl acetate/hexane to give 2.6 g colorless liquid.

¹H-NMR (CDCl₃): δ8.01 (d, J=9 Hz, 2H), 7.26 (d, J=8.3 Hz, 2H), 4.15 (s, 2H), 1.41 (s, 6H).

Mass Spectra (m/e): 260 (M+1).

Step 3: 2-[2-bromo-4-(trifluoromethoxy)phenyl]-4,4-dimethyl-4,5-dihydro-1,3-oxazole

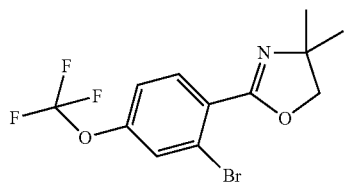

To a 50 ml round bottom flask was loaded 4,4-dimethyl-2-[4-(trifluoromethoxy)phenyl]-4,5-dihydro-1,3-oxazole (0.5 g, 1.93 mmol) and 7 ml tetrahydrofuran. The resulting solution was cooled with dry ice acetone bath, and nbutyllithium (nBuLi) (2.5 M hexane solution, 0.85 ml, 2.12 mmol) was added via a syringe. The resulting reaction mixture was allowed to warm up to −20° C. and stirred at this temperature for 30 minutes. The reaction mixture was cooled back to −78° C. It was quenched by addition of bromine (0.109 ml, 2.12 mmol), followed by 10 ml saturated sodium carbonate and 10 ml sodium thiosulfate solution. The resulting mixture was diluted with 30 ml ether. The layers were separated, and the organics were dried over sodium sulfate, filtered and concentrated to give 0.60 g light yellow liquid. It was used for the next step without further purification.

¹H-NMR (CDCl₃): δ7.78 (d, J=8.5 Hz, 1H), 7.54 (s, 1H), 7.24 (d, J=8.7 Hz, 1H), 4.20 (s, 2H), 1.46 (s, 6H).

Mass Spectra (m/e): 340 (M+1).

Step 4: 2-bromo-4-(trifluoromethoxy)benzoic acid

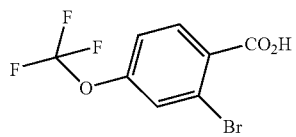

To a 50 ml round bottom flask fitted with a magnetic stirring bar and a reflux condensor was loaded 2-[2-bromo-4-(trifluoromethoxy)phenyl]-4,4-dimethyl-4,5-dihydro-1,3-oxazole (0.56 g, 1.66 mmol) and 10 ml 5N HCl. The reaction mixture was heated at 90° C. overnight. After cooling to room temperature, the reaction mixture was diluted with 20 ml water and extracted with 40 ml ethyl acetate. The extracts were dried over sodium sulfate, filtered and concentrated to give 0.42 g light brown solid.

¹H-NMR (CDCl₃): δ8.10 (d, J=8.6 Hz, 1H), 7.61 (s, 1H), 7.30 (d, 1H).

Step 5: 2-(methylsulfonyl)-4-(trifluoromethoxy)benzoic acid

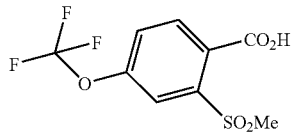

To a 16 ml vial was loaded 2-bromo-4-(trifluoromethoxy)benzoic acid (225 mg, 0.79 mmol), sodium methylsulfinate (161 mg, 1.58 mmol), CuI (301 mg, 1.58 mmol), KOH (44 mg, 0.79 mmol, in 0.1 ml water) and 4 ml dimethyl sulfoxide. The reaction mixture was flushed with nitrogen, sealed and heated at 120° C. for 5 hours. After cooling to room temperature, it was diluted with 40 ml ether/ethyl acetate (1:1), 30 ml brine and 10 ml 3N HCl. The mixture was filtered through a pad of celite. The layers were separated, and the organic portion was dried over sodium sulfate, filtered and concentrated. The residue was purified with HPLC on a reverse phase column eluted with water and acetonitrile gradient solvent to give desire product as white solid.

¹H-NMR (CDCl₃): δ8.07 (s, 1H), 8.01 (d, J=8.5 Hz, 1H), 7.59 (m, 1H), 3.47 (s, 3H).

Step 6: 1-[2-(methylsulfonyl)-4-(trifluoromethoxy)benzoyl]-4-(1-methyl-1-{[3-(trifluoromethyl)phenyl]sulfonyl}ethyl)piperidine

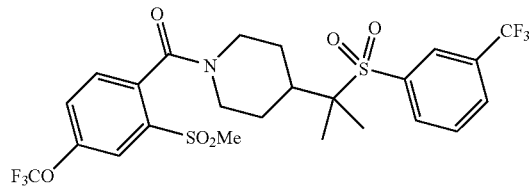

To a 10 ml vial was added 4-(1-methyl-1-{[3-(trifluoromethyl)phenyl]sulfonyl}ethyl)piperidine (70.8 mg, 0.211 mmol), 2-(methylsulfonyl)-4-(trifluoromethoxy)benzoic acid (50 mg, 0.176 mmol), Bop reagent (93 mg, 0.211 mmol), diisopropylethyl amine (0.062 ml, 0.352 mmol) and 2 ml dimethylformamide. The resulting solution was stirred at room temperature for 10 minutes. The reaction mixture was diluted with 1 ml dimethyl sulfoxide, 1 ml water and 0.03 ml of trifluoroacetic acid. This mixture was loaded on a reverse phase column and purified with HPLC eluted with water/acetonitrile gradient solvent. Desired fraction was collected and lyophilized to give to give title compound as fluffy white solid.

¹H-NMR (CDCl₃): δ8.15 (s, 1H), 8.1 (m, 1H), 7.95 (m, 2H), 7.75 (m, 1H), 7.4 (m, 1H), 4.8 (m, 1H), 3.5 (m, 1H), 3.34, 3.28 (s, 3H), 3.1 (m, 1H), 2.8 (m, 1H), 2.1-2.4 (m, 3H) 1.5-1.8 (m, 2H), 1.3, 1.27, 1.22 (s, 6H). Complicate ¹H NMR spectrum indicating the compound exits as a pair of rotomers at room temperature.

Mass Spectra (m/e): 602 (M+1).

Example 3

2-(cyclopropylsulfonyl)-3-{[4-(1-methyl-1-{[3-(trifluoromethyl)phenyl]sulfonyl}ethyl)piperidin-1-yl]carbonyl}-6-(trifluoromethyl)pyridine

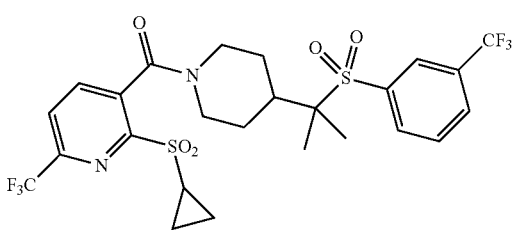

Step 1: magnesium bromide cyclopropanesulfinate

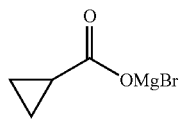

To 250 ml round bottom flask was added cyclopropylmagnesium bromide tetrahydrofuran solution (0.5 M, 25 ml, 12.5 mmol) and 20 ml tetrahydrofuran. The resulting solution was cooled to −78° C. Sulfor dioxide (SO$_2$) gas was bubbled through for 5 minutes. The resulting reaction mixture was allowed to warm up to room temperature over 30 minutes. The volatiles were removed under vacuum to give 3.5 g desired product as white solid (contains tetrahydrofuran solvent).

$^1$H-NMR (CD$_3$OD): δ1.95 (m, 1H), 0.8 (m, 2H), 0.65 (m, 2H).

Step 2: 2-(cyclopropylsulfonyl)-6-(trifluoromethyl) nicotinic acid

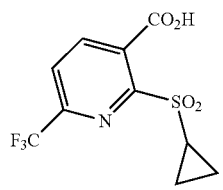

To a 100 ml round bottom flask was loaded magnesium bromide cyclopropanesulfinate (928 mg, 4.43 mmol), 2-chloro-6-(trifluoromethyl)nicotinic acid (250 mg, 1.11 mmol), CuI (844 mg, 4.43 mmol), NaOH (44.3 mg, 1.11 mmol), 20 ml dimethyl sulfoxide and 4 ml water. The resulting reaction mixture was flushed with nitrogen gas and heated at 120° C. for 18 hr. After cooling down to room temperature, the reaction mixture was diluted with 60 ml ethyl acetate and 60 ml water. It was filtered through a pad of celite, which was then rinsed with 20 ml ethyl acetate. The layers were separated from filtrates, and the organics were dried over sodium sulfate, filtered and concentrated. The residue was purified on reverse phase column eluted with water/acetonitrile gradient solvent to give desired product was white solid (152 mg, 0.52 mmol).

$^1$H-NMR (CD$_3$OD): δ8.43 (d, J=8.0 Hz, 1H), 8.18 (d, J=8.0 Hz, 1H), 3.14 (m, 1H), 1.31 (m, 2H), 1.17 (m, 1H).

Step 3: 2-(cyclopropylsulfonyl)-3-{[4-(1-methyl-1-{[3-(trifluoromethyl)phenyl]sulfonyl}ethyl)piperidin-1-yl]carbonyl}-6-(trifluoromethyl)pyridine

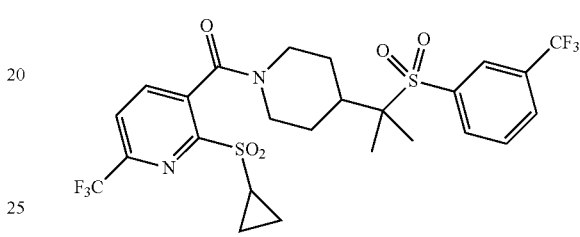

To a 50 ml round bottom flask was added 4-(1-methyl-1-{[3-(trifluoromethyl)phenyl]sulfonyl}ethyl)piperidine (1.64 g, 4.88 mmol), 2-(cyclopropylsulfonyl)-6-(trifluoromethyl)nicotinic acid (1.2 g, 4.06 mmol), Bop reagent (2.16 g, 4.88 mmol), diisopropylethyl amine (1.42 ml, 8.13 mmol) and 10 ml dimethylformamide. The resulting solution was stirred at room temperature 10 minutes. It was diluted with 60 ml NH$_4$Cl solution and extracted with 60 ml ethyl acetate. The organics were dried over sodium sulfate, filtered and concentrated. The sesidue was purified on silica gel column eluted with 2:1 ethyl acetate/hexane. The desired fraction was collected and concentrated. The residue was further purified on prep-TLC to give title compound as a white solid.

$^1$H-NMR (CDCl$_3$): δ8.14 (s, 1H), 8.1 (m, 1H), 7.95 (m, 3H), 7.75 (m, 1H), 4.8 (m, 1H), 3.4 (m, 1H), 3.2 (m, 1H), 3.0 (m, 1H), 2.8 (m, 1H), 1.4-2.4 (m, 5H), 1.29, 1.28, 1.27, 1.23 (s, 6H) 1.1 (m, 2H). Complicate $^1$H NMR spectrum indicating the compound exits as a pair of rotomers at room temperature.

Mass Spectra (m/e): 613 (M+1).

Example 4

1-[4-(cyclopropyloxy)-2,6-bis(methylsulfonyl)benzoyl]-4-(1-methyl-1-{[3-(trifluoromethyl)phenyl]sulfonyl}ethyl)piperidine

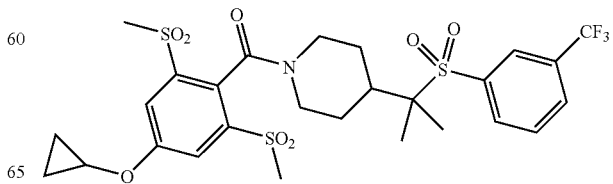

Step 1: 3,5-difluorophenyl vinyl ether

To a 100 ml round bottom flask was added 3,5-difluorophenol (3.85 g, 29.6 mmol), vinylacetate (5.1 g, 59.2 mmol), Na$_2$CO$_3$ (1.88 g, 17.8 mmol), chloro-1,5-cycooctadiene iridium (I) dimmer (199 mg, 0.296 mmol) and 10 ml toluene. The resulting reaction mixture was flushed with nitrogen and heated at 100° C. overnight. After cooling to room temperature, the reaction mixture was diluted with 60 ml hexane and washed with 60 ml water. The organics were dried over sodium sulfate, filtered through a pad of silica gel, rinsed with 60 ml hexane. The filtrates were concentrated to give 3.25 g desired product as colorless liquid.

$^1$H-NMR (CDCl$_3$): δ7.6 (m, 4H), 4.9 (dd, J=13.5, 1.8 Hz, 1H), 4.6 (m, 1H).

Step 2: cyclopropyl 3,5-difluorophenyl ether

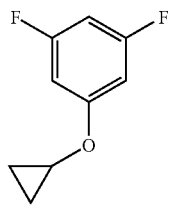

To a nitrogen flushed 250 ml round bottom flask equipped with magnetic stirring bar and septa was added 80 ml dichloromethane and Et$_2$Zn (7.18 g, 58.1 mmol). The resulting solution was cooled with ice bath. Trifluoroacetic acid (4.23 ml, 55 mmol) was added by a syringe slowly (septa was opened slightly to release pressure). The reaction mixture was stirred at 0° C. for 10 minutes after addition. Diiodomethane (4.88 ml, 60.4 mmol) was added by a syringe and the resulting reaction mixture was stirred at 0° C. for 10 minutes. A dichloromethane solution of 3,5-difluorophenyl vinyl ether (3.3 g, 21.1 mmol in 10 ml CH$_2$Cl$_2$) was added. The reaction mixture was allowed to warm up to room temperature over 30 minutes, then quenched by addition of 50 ml water and 50 ml 3N HCl. The layers were separated. The aqueous portion was extracted with 50 ml ether. The organics were combined, dried over sodium sulfate, filtered and concentrated. The residue was purified on silica gel column eluted with hexane to give 3.6 g desired product as light yellow liquid.

$^1$H-NMR (CDCl$_3$): δ6.6 (dd, J=9, 2.1 Hz, 2H), 6.45 (m, 1H), 3.73 (m, 1H), 0.82 (m, 4H).

Step 3: ethyl 4-(cyclopropyloxy)-2,6-difluorobenzoate

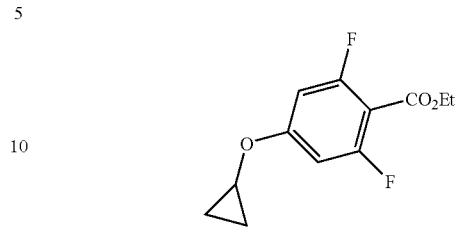

To a 250 ml round bottom flask was added cyclopropyl 3,5-difluorophenyl ether (3.6 g, 21.2 mmol) and 60 ml tetrahydrofuran. n-Butyllithium (nBuLi) (2.5 M, 8.9 ml, 22.2 mmol) was added via a syringe at −78° C. The resulting solution was stirred at −78° C. for 20 minutes. Ethylchloroformate (3.05 ml, 31.7 mmol) was added by a syringe. The resulting solution was left stirring for 5 more minutes. The reaction mixture was diluted with 100 ml ether and 60 ml brine. The layers were separated, and the organic portion was dried over sodium sulfate, filtered and concentrated. The crude product was purified on silica gel column eluted with hexane to 1:9 ethyl acetate/hexane gradient solvent to give 4.5 g desired product as yellow liquid.

$^1$H-NMR (CDCl$_3$): δ6.64 (dd, J=14.5, 3.6 Hz, 2H), 4.41 (q, J=7.1 Hz, 2H), 3.77 (m, 1H), 1.41 (t, J=7.1 Hz, 3H), 0.85 (m, 4H).

Step 4: 4-(cyclopropyloxy)-2,6-bis(methylthio)benzoic acid

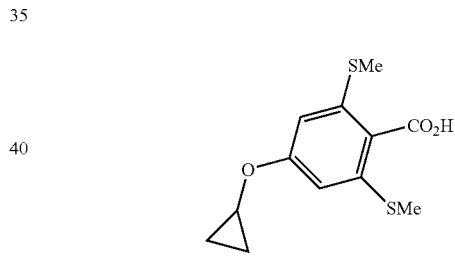

To a microwave heating vial was add ethyl 4-(cyclopropyloxy)-2,6-difluorobenzoate (1 g, 4.13 mmol) and DBU (2.18 ml, 14.5 mmol). The reaction mixture was cooled with dry ice acetone bath. Methanethiol (~1 ml) was condensed into the vial. The vial was sealed and the resulting reaction mixture was heated at 100° C. with microwave for 1 hour. The volatiles were removed by a stream of nitrogen. The residue was diluted with 60 ml ether, extracted with 2×30 ml 5% KOH. The aqueous portion was acidified with concentrated HCl to cause precipitation. The mixture was filtered and the precipitate was washed with 15 ml water. The resulting solid was air dried to give 0.37 g desired product as white solid. The organic portion was washed with 60 ml 1N HCl, dried over sodium sulfate, filtered and concentrated to give 0.78 g oil which contains mostly ethyl 4-(cyclopropyloxy)-2,6-bis(methylthio)benzoate. It was dissolved in 20 ml methanol and 3 ml water. LiOH (2 g) was added. The resulting reaction mixture was refluxed for 24 hours. The volatiles were removed, and the residue was dissolved in 40 ml water, washed with 30 ml ether, acidified with concentrated HCl to cause precipitation. It was filtered, washed with 20 ml water, air dried to give 0.52 g desired product as light yellow solid.

¹H-NMR (CDCl₃): δ6.84 (s, 2H), 3.8 (m, 1H), 2.48 (s, 6H), 0.83 (m, 4H).

Step 5: 1-[4-(cyclopropyloxy)-2,6-bis(methylthio) benzoyl]-4-(1-methyl-1-{[3-(trifluoromethyl)phenyl] sulfonyl}ethyl)piperidine

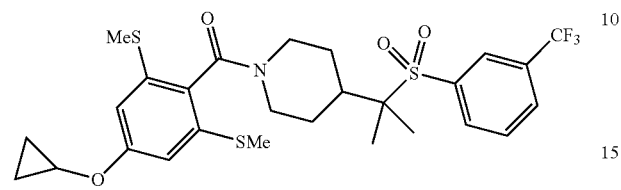

To a 16 ml vial was added 4-(cyclopropyloxy)-2,6-bis(methylthio)benzoic acid (375 mg, 1.39 mmol), 4-(1-methyl-1-{[3-(trifluoromethyl)phenyl]sulfonyl}ethyl)piperdine (465 mg, 1.39 mmol), Bop reagent (675 mg, 1.53 mmol), diisopropylethyl amine (1.21 ml, 6.93 mmol) and 4 ml dimethylformamide. The resulting solution was stirred at room temperature for 1 hour. It was diluted with 30 ml ethyl acetate, washed sequencially with 20 ml 1N HCl, 20 ml 5% KOH and 20 ml brine. The organics were dried over sodium sulfate, filtered and concentrated. The residue was purified on silica gel column eluted with 1:2 to 1:1 ethyl acetate/hexane to give desired product as sticky material.

Mass Spectra (m/e): 588 (M+1).

Step 6: 1-[4-(cyclopropyloxy)-2,6-bis(methylsulfonyl)benzoyl]-4-(1-methyl-1-{[3-(trifluoromethyl)phenyl]sulfonyl}ethyl)piperidine

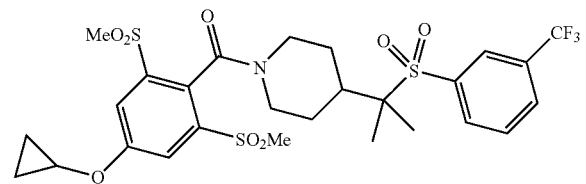

To a 100 ml round bottom flask was added 1-[4-(cyclopropyloxy)-2,6-bis(methylthio)benzoyl]-4-(1-methyl-1-{[3-(trifluoromethyl)phenyl]sulfonyl}ethyl)piperidine (460 mg, 0.783 mmol), meta-chloroperbenzoic acid (1.93 g, 7.83 mmol) and 30 ml methylene chloride. The resulting reaction mixture was heated at 45° C. for 18 h. After cooling to room temperature, the reaction mixture was washed with 40 ml saturated sodium carbonate and 20 ml sodium thiosulfate. The organics were dried over sodium sulfate, filtered and concentrated. The residue was purified on a reverse phase column eluted with water and acetonitrile gradient solvent. The fractions contain desired compound were collected and lyophilized to give the title compound as fluffy white solid.

¹H-NMR (CDCl₃): δ8.17 (d, J=7.5 Hz, 1H), 8.1 (m, 2H), 8.04 (m, 2H), 7.90 (t, J=7.8 Hz, 1H), 4.7 (m, 1H), 4.07 (m, 1H), 3.24, 3.19 (s, 6H), 3.05 (m, 1H), 3.15 (m, 1H), 2.75 (m, 1H), 2.15 (m, 1H), 1.8 (m, 1H), 1.65 (m, 1H), 1.28, 1.24 (s, 6H), 0.95 (m, 2H), 0.84 (m, 1H). Complicate ¹H NMR spectrum indicating the compound exits as a pair of rotomer at room temperature.

Mass Spectra (m/e): 651 (M+1).

Example 5

2-[(1-methyl-1-{1-[2-(methylsulfonyl)-4-(trifluoromethoxy)benzoyl]piperidin-4-yl}ethyl)sulfonyl]-6-(trifluoromethyl)pyridine

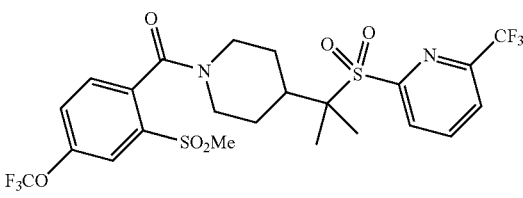

Step 1: tert-butyl 4-(1-mercaptoethyl)piperidine-1-carboxylate

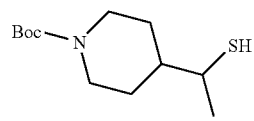

To a 500 ml round bottom flask was added tert-butyl 4-{1-[(methylsulfonyl)oxy]ethyl}piperidine-1-carboxylate (19 g, 61.8 mmol), potassium thioacetate (8.47 g, 74.2 mmol) and 90 ml dimethyl sulfoxide. The resulting reaction mixture was heated at 60° C. under nitrogen for 2 hours then at 45° C. for 18 hours. After cooling to room temperature, the reaction mixture was diluted with 300 ml ether, washed with 400 ml water and then 150 ml brine. The organics were dried over sodium sulfate, filtered and concentrated. The residue was purified on silica gel column eluted with 1:20 to 1:10 ethyl acetate/hexane to give 15 g tert-butyl 4-[1-(acetylthio)ethyl]piperidine-1-carboxylate as dark yellow sticky material. This material was dissolved in 100 ml MeOH. A solution of KOH (17.3 g, 309 mmol) in 150 ml water was added. The reaction mixture was flushed with nitrogen and stirred at 50° C. for 2 hours. After cooling to room temperature, the volume of reaction was reduced to 150 ml. Hexane (300 ml) was added. The layers were separated, and the aqueous portion was poured into an Erlenmyer flask with 250 ml saturated NH₄Cl, and pH of the mixture was adjusted to 7 by addition of 3N HCl. This solution was extracted with 250 ml ether. The extracts were washed with 100 ml brine, dried over sodium sulfate, filtered and concentrated. The residue was purified on silica gel column eluted with 1:20 to 1:9 ethyl acetate/hexane to give 8.3 g desire product as light yellow sticky material.

¹H-NMR (CDCl₃): δ4.2 (b, 2H), 2.9 (m, 1H), 2.7 (b, 2H), 1.8 (m, 2H) 1.49 (s, 9H), 1.37 (d, J=6.9 Hz, 3H), 1.3 (m, 2H).

Step 2: tert-butyl 4-(1-{[6-(trifluoromethyl)pyridin-2-yl]thio}ethyl)piperidine-1-carboxylate

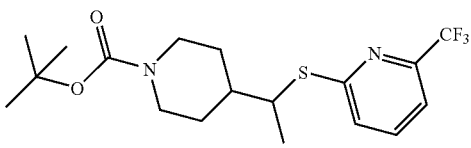

To a 16 ml vial was added tert-butyl 4-(1-mercaptoethyl) piperidine-1-carboxylate (500 mg, 2.04 mmol), 2-bromo-6-(trifluoromethyl)pyridine (460 mg, 2.04 mmol), Pd(dppf)Cl₂ (42 mg, 0.051 mmol) and Cs₂CO₃ (996 mg, 3.06 mmol) and 4 ml toluene. The vial was flushed with nitrogen, sealed and heated at 75° C. for 36 hours. After cooling to room temperature, the reaction mixture was diluted with 30 ml ether, and washed with 30 ml water. The organics were dried over sodium sulfate, filtered and concentrated. The residue was purified on silica gel column eluted with 1:9 to 1:4 ethyl acetate/hexane to give 750 mg desired product was light yellow oil.

¹H-NMR (CDCl₃): δ7.62 (t, J=7.8 Hz, 1H), 7.34 (d, J=7.3 Hz, 1H), 7.32 (d, J=7.3 Hz, 1H), 4.2 (b, 3H), 2.7 (b, 2H), 1.8 (b, 3H), 1.48 (s, 9H), 1.40 (d, J=7.3 Hz, 3H) 1.35 (m, 1H).

Mass Spectra (m/e): 391 (M+1).

Step 3: tert-butyl 4-(1-{[6-(trifluoromethyl)pyridin-2-yl]sulfonyl}ethyl)piperidine-1-carboxylate

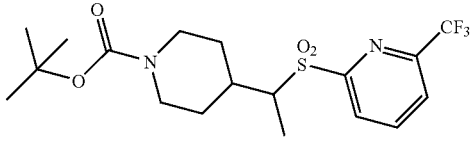

To a 100 ml round bottom flask was added tert-butyl 4-(1-{[6-(trifluoromethyl)pyridin-2-yl]thio}ethyl)piperidine-1-carboxylate (0.90 g, 2.31 mmol), meta-choroperbenzoic acid (MCPBA) (1.71 g, 6.91 mmol) and 20 ml dichloromethane. The resulting reaction mixture was stirred at room temperature for 2 hours. It was diluted with 50 ml ether, washed with 20 ml sodium carbonate and 20 ml sodium thiosulfate saturated solution. The organics were dried over sodium sulfate, filtered and concentrated. The residue was purified on silica gel column eluted with 1:4 to 1:2 ethyl acetate/hexane to give 0.78 g desired product as colorless sticky material.

¹H-NMR (CDCl₃): δ8.33 (d, J=7.8 Hz, 1H), 8.23 (t, J=7.8 Hz, 1H), 7.96 (d, J=8.0 Hz, 1H), 4.2 (b, 2H), 3.83 (m, 1H), 2.74 (b, 2H), 2.43 (m, 1H), 2.0 (b, 1H), 1.85 (m, 1H), 1.3-1.6 (m, 2H), 1.48 (s, 9H), 1.26 (d, J=7.3 Hz, 3H).

Step 4: tert-butyl 4-(1-methyl-1-{[6-(trifluoromethyl)pyridin-2-yl]sulfonyl}ethyl)piperidine-1-carboxylate

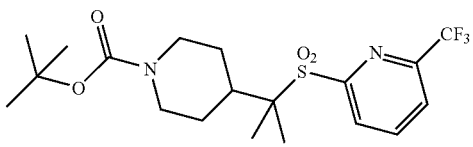

To a 50 ml round bottom flask was added tert-butyl 4-(1-{[6-(trifluoromethyl)pyridin-2-yl]sulfonyl}ethyl)piperidine-1-carboxylate (0.78 g, 1.85 mmol) and tetrahydrofuran (10 ml). The resulting solution was cooled with dry ice acetone bath. Sodium bis(trimethylsilyl)amide (NaHMDS) tetrahydrofuran solution (1M, 2.58 ml, 2.58 mmol) was added via a syringe. The resulting reaction solution was stirred at −78° C. for 10 minutes. MeI (0.173 ml, 2.77 mmol) was added. The reaction mixture was allowed to warm up to room temperature and quenched by addition of 50 ml saturated NH₄Cl solution. It was diluted with 30 ml ether. The layers were separated, and the organics were dried over sodium sulfate, filtered and concentrated. The residue was purified on silica gel column eluted with 1:4 to 1:2 ethyl acetate/hexane to give 0.806 g desired product (contains solvent).

¹H-NMR (CDCl₃): δ8.32 (d, J=7.8 Hz, 1H), 8.20 (t, J=7.9 Hz, 1H), 7.95 (d, J=7.7 Hz, 1H), 4.2 (b, 2H), 2.7 (b, 2H), 2.16 (m, 1H), 2.0 (b, 2H), 1.3-1.6 (m, 2H), 1.48 (s, 9H), 1.39 (s, 6H).

Mass Spectra (m/e): 437 (M+1).

Step 5: 2-[(1-methyl-1-piperidin-4-ylethyl)sulfonyl]-6-(trifluoromethyl)pyridine

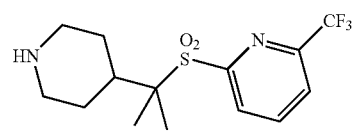

To a 25 ml round bottom flask was added tert-butyl 4-(1-methyl-1-{[6-(trifluoromethyl)pyridin-2-yl]sulfonyl}ethyl) piperidine-1-carboxylate (0.806 g, 1.85 mmol), trifluoroacetic acid (1.5 ml) and dichloromethane (5 ml). The resulting solution was stirred at room temperature for 1 hour. It was diluted with 50 ml ethyl acetate, washed with 50 ml 10% KOH and then 30 ml brine. The organics were dried over sodium sulfate, filtered and concentrated to give 0.33 g desired product as cyrstalline solid.

¹H-NMR (CDCl₃): δ8.33 (d, J=8.0 Hz, 1H), 8.20 (t, J=7.8 Hz, 1H), 7.96 (d, J=8.0 Hz, 1H), 3.17 (m, 2H), 2.64 (m, 2H), 2.15 (m, 1H), 2.0 (m, 2H), 1.45 (m, 2H), 1.42 (s, 6H).

Mass Spectra (m/e): 337 (M+1).

Step 6: 2-[(1-methyl-1-{1-[2-(methylsulfonyl)-4-(trifluoromethoxy)benzoyl]piperidin-4-yl}ethyl) sulfonyl]-6-(trifluoromethyl)pyridine

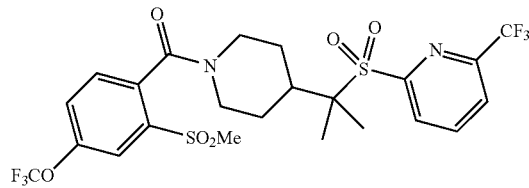

To a 10 ml vial was added 2-(methylsulfonyl)-4-(trifluoromethoxy)benzoic acid (16.9 mg, 0.059 mmol), 2-[(1-methyl-1-piperidin-4-ylethyl)sulfonyl]-6-(trifluoromethyl)pyridine (20 mg, 0.059 mmol), Bop reagent (31.6 mg, 0.071 mmol), diisopropylethyl amine (0.052 ml, 0.297 mmol) and 1 ml dimethylformamide. The resulting solution was stirred at room temperature for 1 hour. It was diluted with 1 m dimethyl sulfoxide, 0.5 ml water and 0.1 ml trifluoroacetic acid. This mixture was loaded on to reverse phase column directly and eluted with water acetonitrile gradient solvent to give the title compound as fluffy white solid after lyophilizing.

¹H-NMR (CDCl₃): δ8.4 (m, 2H), 8.16 (d, J=7.5 Hz, 1H), 7.94 (m, 1H), 7.7 (m, 1H), 7.6 (m, 1H), 4.8 (m, 1H), 3.7-1.5 (m, 8H), 3.31 3.25 (s, 3H), 1.41, 1.38, 1.37, 1.32 (s, 6H).

Complicate ¹H NMR spectrum indicating the compound exits as a pair of rotomers at room temperature.

Mass Spectra (m/e): 603 (M+1).

Example 6

1-[5-fluoro-2-(methylsulfonyl)benzoyl]-3-(1-methyl-1-{[3-(trifluoromethyl)phenyl]sulfonyl}ethyl)azetidine

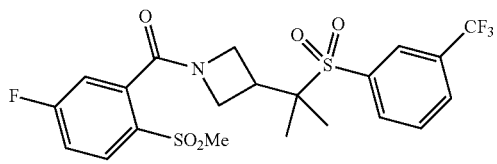

Step 1: tert-butyl 3-{[methoxy(methyl)amino]carbonyl}azetidine-1-carboxylate

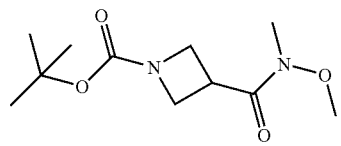

To a 100 ml round bottom flask was added 1-(tert-butoxycarbonyl)azetidine-3-carboxylic acid (3.75 g, 18.6 mmol) and 20 ml tetrahydrofuran, followed by CDI (3.63 g, 22.4 mmol). Vigorous gas evolution was observed. After gas evolution stopped, the reaction mixture was stirred at room temperature for additional 30 minutes. Methoxy(methyl)ammonium chloride (2.55 g, 26.1 mmol) was added, followed by diisopropylethyl amine (6.5 ml, 37.3 mmol). The resulting reaction mixture was stirred at room temperature overnight. It was diluted with 120 ml ether and washed with 60 ml saturated NH₄Cl. The organics were dried over sodium sulfate, filtered and concentrated. The residue was purified on silica gel column, eluted with 1:2 to 3:2 ethyl acetate/hexane to give 3.6 g desired product was colorless oil.

¹H-NMR (CDCl₃): δ4.17 (m, 2H), 4.08 (t, J=8.7 Hz, 2H), 3.69 (s, 3H), 3.5 (b, 1H), 3.24 (s, 3H), 1.47 (s, 9H).

Step 2: tert-butyl 3-acetylazetidine-1-carboxylate

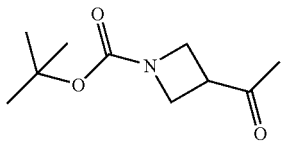

To a 100 ml round bottom flask was added tert-butyl 3-{[methoxy(methyl)amino]carbonyl}azetidine-1-carboxylate (2.6 g, 10.6 mmol) and 20 ml tetrahydrofuran. The resulting solution was cooled to 0° C. and methylmagnesium chloride tetrahydrofuran solution (4.3 ml, 3M, 12.8 mmol) was added by a syringe. The reaction mixture was stirred at 0° C. for 1 hour. It was diluted with 100 ml ether, and the resulting mixture was washed twice with 100 ml saturated ammonium chloride solution. The organics were dried over sodium sulfate, filtered and concentrated. The crude product was used for the next step without further purification.

¹H-NMR (CDCl₃): δ4.05 (m, 4H), 3.43 (m, 1H), 2.20 (s, 3H), 1.45 (s, 9H).

Step 3: tert-butyl 3-(1-hydroxyethyl)azetidine-1-carboxylate

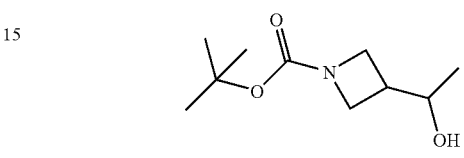

To a 100 ml round bottom flask was added tert-butyl 3-acetylazetidine-1-carboxylate (2.06, 10.3 mmol) and 30 ml MeOH. NaBH₄ (0.403 g, 10.6 mmol) was added in portions. The resulting reaction mixture was stirred at room temperature for 15 minutes. The volatiles were removed under vacuum. The residue was treated with 50 ml 10% KOH and extracted with 2×50 ml ethyl acetate. The organics were combined and dried over sodium sulfate, filtered and concentrated. The residue was purified on silica gel column eluted with 1:4 to 1:2 E/H to give 2.06 g desired product as colorless oil.

¹H-NMR (CDCl₃): δ3.95 (m, 2H), 3.83 (m, 1H), 3.65 (m, 1H), 2.5 (m, 1H), 1.45 (s, 9H) 1.17 (d, J=6.5 Hz, 3H).

Step 4: tert-butyl 3-(1-{[3-(trifluoromethyl)phenyl]thio}ethyl)azetidine-1-carboxylate

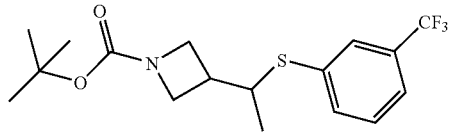

To 100 ml round bottom flask was added tert-butyl 3-(1-hydroxyethyl)azetidine-1-carboxylate (2.06 g, 10.2 mmol), triethylamine (4.2 ml, 30.7 mmol) and 40 ml dichloromethane. Methanesulfonyl chloride (0.955 ml, 12.3 mmol) was added at 0° C. The reaction mixture was allowed to warm up to room temperature and stirred for 1 hour. It was then diluted with 100 ml ether, washed with 2×50 ml saturated sodium carbonate solution. The organics were dried over sodium sulfate, filtered and concentrated. The residue was dissolved in 30 ml dimethylformamide. Potassium carbonate (3.75 g, 26.8 mmol) and 3-(trifluoromethyl)benzenethiol (1.91 g, 10.7 mmol) were added. The resulting reaction mixture was heated at 75° C. overnight. It was diluted with 120 ml ether, washed sequentially with 150 ml water, and 75 ml saturated sodium carbonate. The organics were dried over sodium sulfate, filtered and concentrated. The residue was purified on silica gel column eluted with hexane to 1:9 ethyl acetate/hexane to give 2.65 g desired product as colorless oil.

¹H-NMR (CDCl₃): δ7.68 (s, 1H), 7.61 (d, J=8.0 Hz, 1H), 7.55 (d, J=7.8 Hz, 1H), 7.47 (t, J=7.8 Hz, 1H), 4.0 (m, 2H), 3.80 (m, 1H), 3.7 (m, 1H), 3.15 (m, 1H), 2.6 (m, 1H), 1.47 (s, 9H) 1.30 (d, J=6.7 Hz, 3H).

Step 5: tert-butyl 3-(1-{[3-(trifluoromethyl)phenyl]sulfonyl}ethyl)azetidine-1-carboxylate

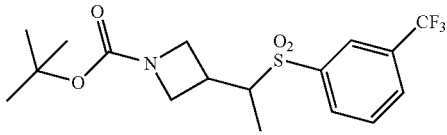

To 500 ml round bottom flask was added tert-butyl 3-(1-{[3-(trifluoromethyl)phenyl]thio}ethyl)azetidine-1-carboxylate (2.65 g, 7.33 mmol) and 150 ml MeOH. Oxone™ in 75 ml water (pH of the solution was adjusted to 3 with addition of potassium carbonate solution) was added. The resulting reaction mixture was stirred at room temperature for 2 hours. It was diluted with 100 ml ethyl acetate and filtered through a pad of celite. The volatiles were removed from the filtrate. The residue was partitioned between 100 ml ethyl acetate and 100 ml water. The organics were dried over sodium sulfate, filtered and concentrated. The residue was purified on silica gel column eluted with 1:4 to 1:2 ethyl acetate to give 2.5 g desired product was colorless sticky oil.

¹H-NMR (CDCl₃): δ8.17 (s, 1H), 8.11 (d, J=8.0 Hz, 1H), 7.99 (d, J=7.8 Hz, 1H), 7.79 (t, J=8.0 Hz, 1H), 4.05 (m, 2H), 3.90 (b, 1H), 3.75 (m, 1H), 3.4 (m, 1H), 2.95 (m, 1H), 1.46 (s, 9H) 1.29 (d, J=7.1 Hz, 3H).

Step 6: tert-butyl 3-(1-methyl-1-{[3-(trifluoromethyl)phenyl]sulfonyl}ethyl)azetidine-1-carboxylate

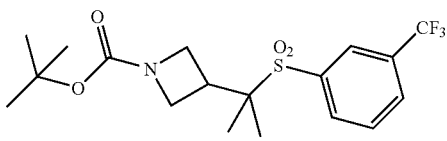

To a 100 ml round bottom flask was added was added tert-butyl 3-(1-{[3-(trifluoromethyl)phenyl]thio}ethyl)azetidine-1-carboxylate (1.82 g, 4.63 mmol) and 20 ml tetrahydrofuran. Sodium bis(trimethylsilyl)amide tetrahydrofuran solution (5.55 ml, 1M, 5.55 mmol) was added to this solution at −78° C. The resulting reaction solution was stirred at −78° C. for 5 minutes. The reaction mixture turned deep orange red immediately. Iodomethane was added dropwise via a syringe until reaction mixture turned to light yellow. More sodium bis(trimethylsilyl)amide tetrahydrofuran solution (2 ml, 1M, 2 mmol) was added, and the resulting reaction mixture was stirred at −78° C. for 5 minutes. More iodomethane (0.2 ml, 3.2 mmol) was added. After stirring at −78° C. for 10 minutes, it was quenched by addition of 30 ml saturated NH₄Cl. The reaction mixture was diluted with 60 ml ether and 30 ml water. The layers were separated, and the organics were dried over sodium sulfate, filtered and concentrated. The residue was purified on silica gel column eluted with 1:3 to 1:2 ethyl acetate/hexane to give 1.72 g desired product as colorless sticky oil.

¹H-NMR (CDCl₃): δ8.14 (s, 1H), 8.07 (d, J=8.3 Hz, 1H), 7.99 (d, J=7.5 Hz, 1H), 7.78 (t, J=7.8 Hz, 1H), 3.98 (m, 2H), 3.90 (b, 1H), 3.11 (m, 1H), 1.46 (s, 9H) 1.37 (s, 6H).

Step 7: 3-(1-methyl-1-{[3-(trifluoromethyl)phenyl]sulfonyl}ethyl)azetidine

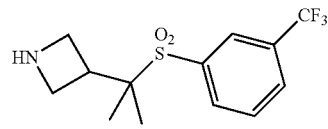

To a 100 ml round bottom flask equipped with a reflux condenser was added tert-butyl 3-(1-{[3-(trifluoromethyl)phenyl]sulfonyl}ethyl)azetidine-1-carboxylate (0.85 g, 2.09 mmol), ceric ammonium nitrate (1.37 g, 2.5 mmol) and 15 ml acetonitrile. The resulting reaction mixture was refluxed for 3 hours. The volatiles were removed. The residue was diluted with 60 ml ethyl acetate and 50 ml saturated sodium carbonate. It was filtered through a pad of celite. The organic portion from the filtrate was washed with 50 ml brine, dried over sodium sulfate, filtered and concentrated. The residue was redissolved in hexane/CH₂Cl₂ (9:1), filtered and concentrated to give 0.62 g yellow sticky solid. It is about 90% pure based on ¹H NMR spectra. It was used for next step without further purification.

¹H-NMR (CD₃OD): δ8.15 (d, J=8.4 Hz, 1H), 8.1 (m, 2H), 7.90 (m, 1H), 3.61 (t, J=8.8 Hz, 2H), 3.45 (t, J=8.9 Hz, 2H), 3.3 (m, 1H), 1.33 (s, 6H).

Step 8: 1-[5-fluoro-2-(methylsulfonyl)benzoyl]-3-(1-methyl-1-{[3-(trifluoromethyl)phenyl]sulfonyl}ethyl)azetidine

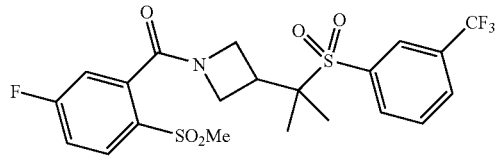

To a 10 ml vial was added 5-fluoro-2-(methylsulfonyl)benzoic acid (35.5 mg, 0.163 mmol), 3-(1-methyl-1-{[3-(trifluoromethyl)phenyl]sulfonyl}ethyl)azetidine (50 mg, 0.163 mmol), Bop reagent (79 mg, 0.179 mmol), diisopropylethyl amine (0.142 ml, 0.813 mmol) and 1 ml dimethylformamide. The resulting solution was stirred at room temperature for 1 hour. It was diluted with 1 m dimethyl sulfoxide, 0.5 ml water and 0.1 ml trifluoroacetic acid. This mixture was loaded on to reverse phase column directly eluted with water acetonitrile gradient solvent to give the title compound as a fluffy white solid after lyophilizing.

¹H-NMR (CD₃OD): δ8.15 (m, 4H), 7.90 (t, J=7.5 Hz, 1H), 7.45 (m, 1H), 7.37 (m, 1H), 4.15 (m, 1H), 4.05 (m, 1H), 3.97 (m, 1H), 3.91 (m, 1H), 3.35, 3.28 (s, 3H), 1.37, 1.31 (s, 6H). Complicate ¹H NMR spectrum indicating the compound exits as a pair of rotomer at room temperature.

Mass Spectra (m/e): 507 (M+1).

Example 7

3-[4-(1-methyl-1-{[3-(trifluoromethyl)phenyl]sulfonyl}ethyl)piperidin-1-yl]quinoline

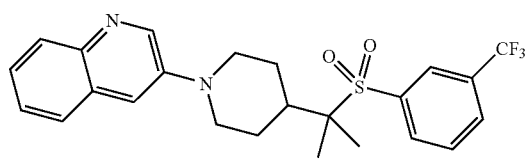

To a 10 ml vial was added 4-(1-methyl-1-{[3-(trifluoromethyl)phenyl]sulfonyl}ethyl)piperidine (30 mg, 0.089 mmol), quinolin-3-ylboronic acid (62 mg, 0.358 mmol), copper acetate (32.5 mg, 0.179 mmol), diisopropylethyl amine (0.049 ml, 0.358 mmol) and 1 ml tetrahydrofuran. The resulting reaction mixture was stirred at room temperature for one hour then 60° C. 3 hours. After aqueous work up, the crude product was purified on reverse phase column eluted with water/acetonitrile gradient solvent to give 24 mg desired product as fluffy white solid after lyophilizing.

$^1$H-NMR (CD$_3$OD): δ8.77 (s, 1H), 8.20 (d, J=8.0 Hz, 1H), 8.15 (s, 1H), 8.10 (d, J=7.7 Hz, 1H), 7.9 (m, 2H), 7.80 (d, J=7.5 Hz, 1H), 7.61 (s, 1H), 7.52 (m, 2H), 3.97 (m, 2H), 2.81 (m, 2H), 2.22 (m, 2H), 2.1 (m, 1H), 1.75 (m, 2H), 1.33 (s, 6H).

Mass Spectra (m/e): 463 (M+1).

Example 8

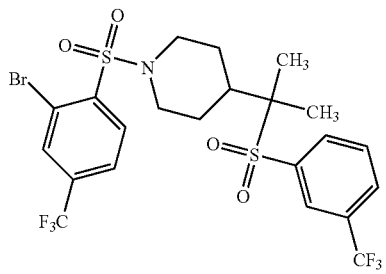

1-{[2-bromo-4-(trifluoromethyl)phenyl]sulfonyl}-4-(1-methyl-1-{[3-(trifluoromethyl)phenyl]sulfonyl}ethyl)piperidine To a 10 ml vial was loaded 4-(1-methyl-1-{[3-(trifluoromethyl)phenyl]sulfonyl}ethyl)piperidine (60 mg, 0.179 mmol), diisoprpoylethylamine (0.093 ml, 0.54 mmol), 2-bromo-4-(trifluoromethyl)benzenesulfonyl chloride (87 mg, 0.27 mmol), N,N-dimethylaminopyridine (4.4 mg, 0.036 mmol) and 1 ml methylene chloride. The resulting reaction solution was stirred at room temperature for one hour. It was diluted with 20 ml ethyl acetate, washed sequentially with 20 ml 1N HCl, 20 ml 10% KOH and 20 ml brine. Organics were dried over sodium sulfate, filtered and concentrated to give 91 mg white solid. A fraction of this crude product (20 mg) was further purified on a reverse phase column eluted with water/acetonitrile gradient solvent to give 16 mg desired product as fluffy white solid after lyophilizing.

$^1$H-NMR (CDCl$_3$): δ8.25 (d, J=8.0 Hz, 1H), 8.13 (s, 1H), 8.08 (d, J=8.0 Hz, 1H), 8.03 (s, 2H), 7.96 (d, J=8.2 Hz, 1H), 7.76 (m, 2H), 3.99 (d, J=10.8 Hz, 2H), 2.85 (t, J=12 Hz, 2H), 2.16 (m, 3H), 1.6 (m, 2H), 1.25 (s, 6H).

Mass Spectra (m/e): 622 (M+1).

Using the procedures described in EXAMPLES 1-8 with the appropriate modifications, reagents and substrates the following compounds of the current invention were prepared.

TABLE 1

| EXAMPLE # | STRUCTURE | CHEMICAL NAME | MASS SPECTRAL DATA m/e (M + H) |
|---|---|---|---|
| 9 | 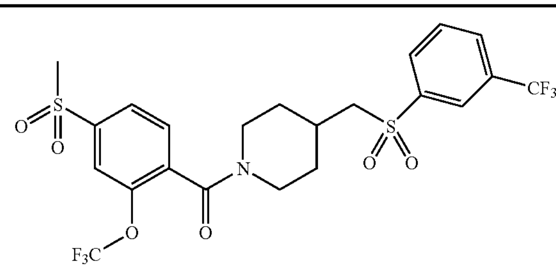 | 1-[4-(methylsulfonyl)-2-(trifluoromethoxy)benzoyl]-4-({[3-(trifluoromethyl)phenyl]sulfonyl}methyl)piperidine | 574 |
| 10 | 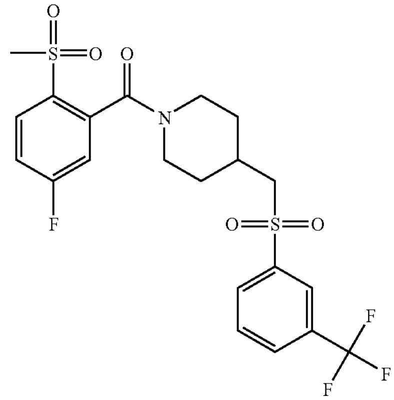 | 1-[5-fluoro-2-(methylsulfonyl)benzoyl]-4-({[3-(trifluoromethyl)phenyl]sulfonyl}methyl)piperidine | 508 |

TABLE 1-continued

| EXAMPLE # | STRUCTURE | CHEMICAL NAME | MASS SPECTRAL DATA m/e (M + H) |
|---|---|---|---|
| 11 | 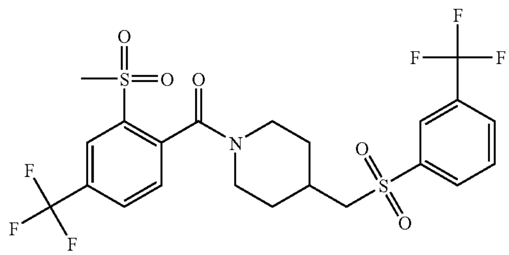 | 1-[2-(methylsulfonyl)-4-(trifluoromethyl)benzoyl]-4-({[3-(trifluoromethyl)-phenyl]sulfonyl}methyl)-piperidine | 558 |
| 12 | 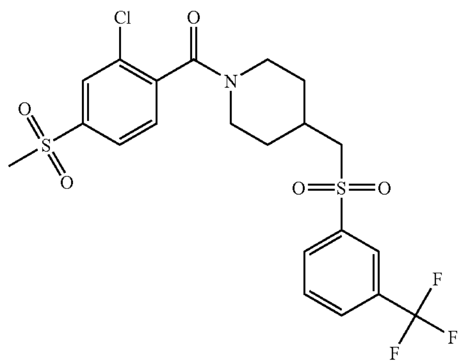 | 1-[2-chloro-4-(methylsulfonyl)benzoyl]-4-({[3-(trifluoromethyl)-phenyl]sulfonyl}methyl)piperidine | 524 |
| 13 | 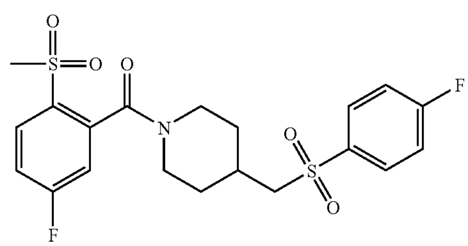 | 1-[5-fluoro-2-(methyl-sulfonyl)benzoyl]-4-({[4-fluorophenyl)sulfonyl]-methyl}piperdinehyl}piperidine | 458 |
| 14 | 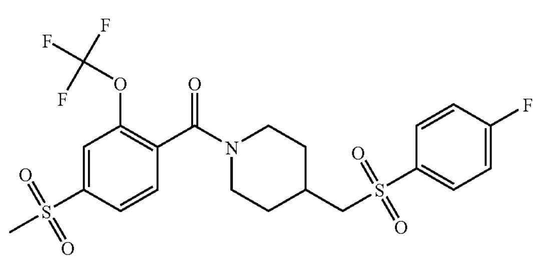 | 4-{[(4-fluorophenyl)-sulfonyl]methyl}-1-[4-(methylsulfonyl)-2-(trifluoromethoxy)benzoyl]piperidine | 524 |
| 15 | 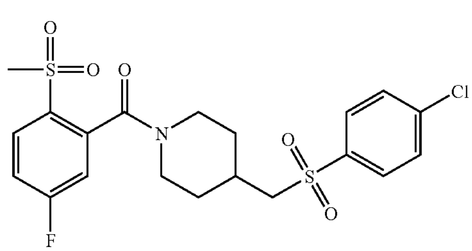 | 4-{[(4-chlorophenyl)-sulfonyl]methyl}-1-[5-fluoro-2-(methyl-sulfonyl)benzoyl]piperidine | 475 |

TABLE 1-continued

| EXAMPLE # | STRUCTURE | CHEMICAL NAME | MASS SPECTRAL DATA m/e (M + H) |
|---|---|---|---|
| 16 | 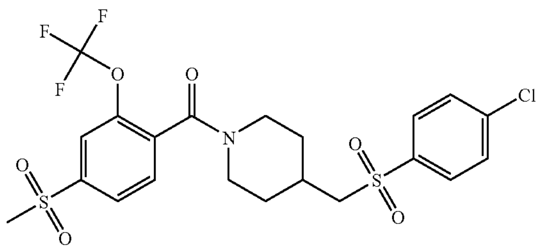 | 4-{[(4-chlorophenyl)sulfonyl]methyl}-1-[4-(methylsulfonyl)-2-(trifluoromethoxy)benzoyl]piperidine | 541 |
| 17 | 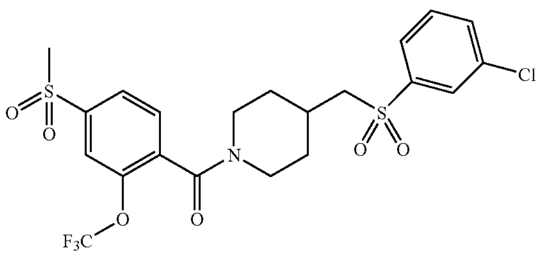 | 4-{[(3-chlorophenyl)sulfonyl]methyl}-1-[4-(methylsulfonyl)-2-(trifluoromethoxy)benzoyl]piperidine | 541 |
| 18 | 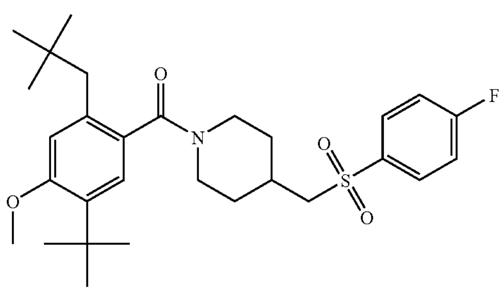 | 1-(3,5-di-tert-butyl-4-methoxybenzoyl)-4-{[(4-fluorophenyl)sulfonyl]methyl}piperidine | 504 |
| 19 | 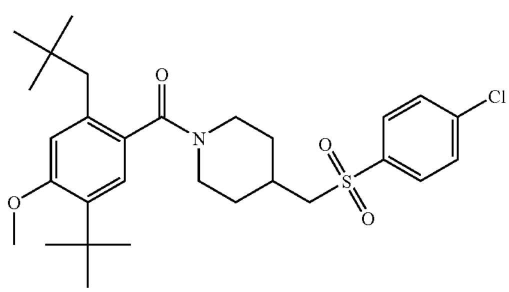 | 4-{[(4-chlorophenyl)sulfonyl]methyl}-1-(3,5-di-tert-butyl-4-methoxybenzoyl)piperidine | 520 |
| 20 | 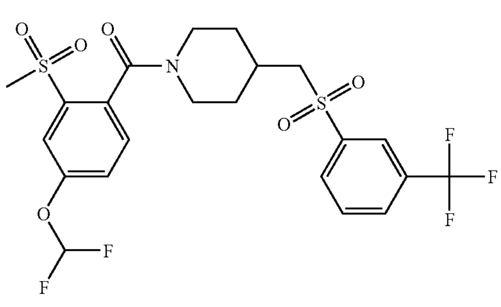 | 1-[4-(difluoromethoxy)-2-(methylsulfonyl)benzoyl]-4-({[3-(trifluoromethyl)-phenyl]sulfonyl}methyl)piperidine | 556 |

TABLE 1-continued

| EXAMPLE # | CHEMICAL NAME | MASS SPECTRAL DATA m/e (M + H) |
|---|---|---|
| 21 | 4-{[(4-fluorophenyl)sulfonyl]methyl}-1-[2-(methylsulfonyl)-4-(trifluoromethyl)benzoyl]piperidine | 508 |
| 22 | 1-[4-(difluoromethoxy)-2-(methylsulfonyl)benzoyl]-4-{[(4-fluorophenyl)sulfonyl]methyl}piperidine | 506 |
| 23 | 4-{[(4-chlorophenyl)sulfonyl]methyl}-1-[2-(methylsulfonyl)-4-(trifluoromethyl)benzoyl]piperidine | 524 |
| 24 | 4-{[(4-chlorophenyl)sulfonyl]methyl}-1-[4-(difluoromethoxy)-2-(methylsulfonyl)benzoyl]piperidine | 522 |
| 25 | 1-[2-(methylsulfonyl)-4-(trifluoromethoxy)benzoyl]-4-({{3-(trifluoromethyl)phenyl]sulfonyl}methyl)piperidine | 574 |

TABLE 1-continued

| EXAMPLE # | STRUCTURE | CHEMICAL NAME | MASS SPECTRAL DATA m/e (M + H) |
|---|---|---|---|
| 26 | 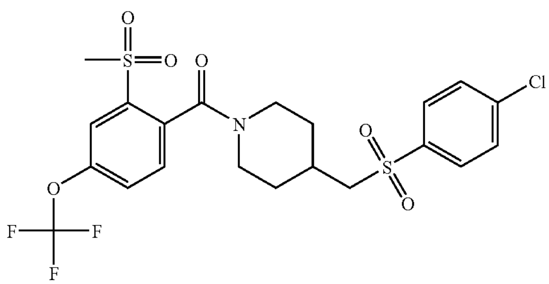 | 4-{[(4-chlorophenyl)sulfonyl]methyl}-1-[2-(methylsulfonyl)-4-(trifluoromethoxy)benzoyl]piperidine | 540 |
| 27 | 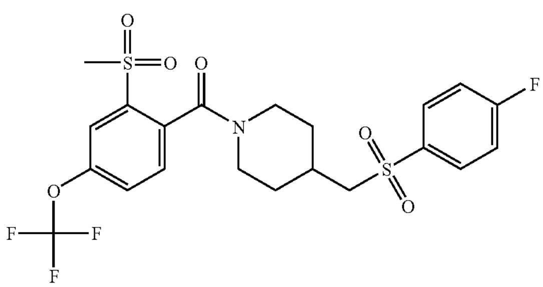 | 4-{[(4-fluorophenyl)sulfonyl]methyl}-1-[2-(methylsulfonyl)-4-(trifluoromethoxy)benzoyl]piperidine | 524 |

TABLE 2

| EXAMPLE # | STRUCTURE | CHEMICAL NAME | MASS SPECTRAL DATA m/e (M + H) |
|---|---|---|---|
| 28 | 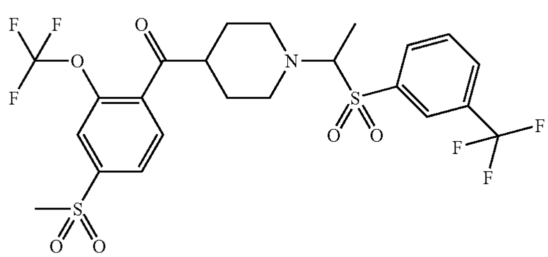 | 1-[4-(methylsulfonyl)-2-(trifluoromethoxy)benzoyl]-4-(1-{[3-(trifluoromethyl)phenyl]sulfonyl}ethyl)piperidine | 588 |
| 29 | 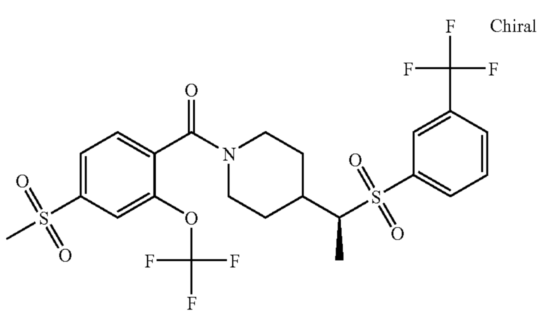 | 1-[4-(methylsulfonyl)-2-(trifluoromethoxy)benzoyl]-4-((1S)-1-{[3-(trifluoromethyl)phenyl]sulfonyl}ethyl)piperidine | 588 |

TABLE 2-continued

| EXAMPLE # | STRUCTURE | CHEMICAL NAME | MASS SPECTRAL DATA m/e (M + H) |
|---|---|---|---|
| 30 | 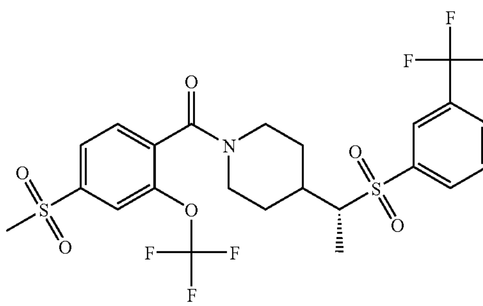 | 1-[4-(methylsulfonyl)-2-(trifluoromethoxy)benzoyl]-4-((1R)-1-{[3-(trifluoromethyl)phenyl]sulfonyl}ethyl)piperidine | 588 |
| 31 | 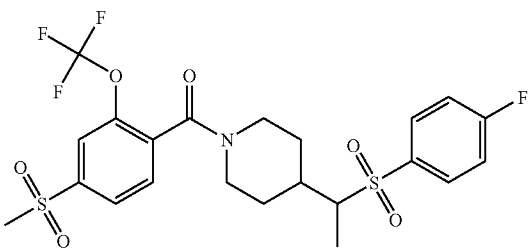 | 4-{1-[(4-fluorophenyl)sulfonyl]ethyl}-1-[4-(methylsulfonyl)-2-(trifluoromethoxy)benzoyl]piperidine | 538 |
| 32 | 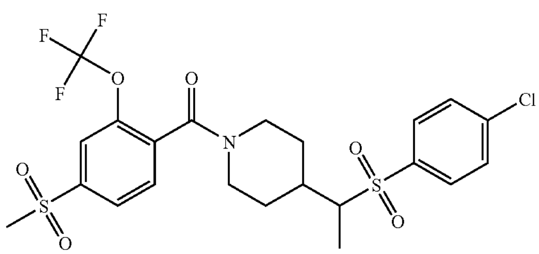 | 4-{1-[(4-chlorophenyl)sulfonyl]ethyl}-1-[4-(methylsulfonyl)-2-(trifluoromethoxy)benzoyl]piperidine | 555 |
| 33 | 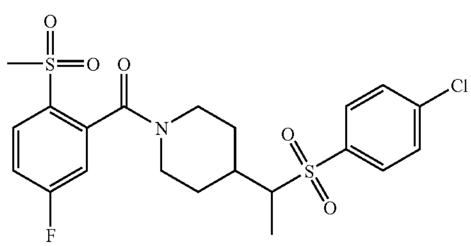 | 4-{1-[(4-chlorophenyl)sulfonyl]ethyl}-1-[5-fluoro-2-(methylsulfonyl)benzoyl]piperidine | 488 |
| 34 | 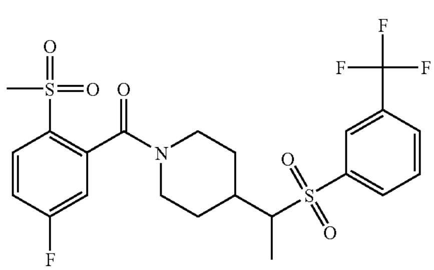 | 1-[5-fluoro-2-(methylsulfonyl)benzoyl]-4-(1-{[3-(trifluoromethyl)phenyl]sulfonyl}ethyl)piperidine | 522 |

TABLE 2-continued

| EXAMPLE # | STRUCTURE | CHEMICAL NAME | MASS SPECTRAL DATA m/e (M + H) |
|---|---|---|---|
| 35 | 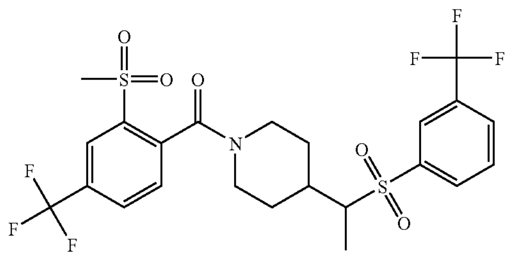 | 1-[2-(methylsulfonyl)-4-(trifluoromethyl)benzoyl]-4-(1-{[3-(trifluoromethyl)phenyl]sulfonyl}ethyl)piperidine | 572 |
| 36 | 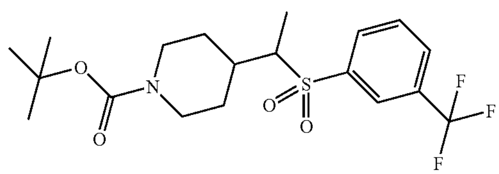 | tert-butyl4-(1-{[3-(trifluoromethyl)phenyl]sulfonyl}ethyl)piperidine-1-carboxylate | 422 |
| 37 | Chiral | 1-[2-(methylsulfonyl)-4-(trifluoromethoxy)benzoyl]-4-((1S)-1-{[3-(trifluoromethyl)phenyl]sulfonyl}ethyl)piperidine | 588 |
| 38 | Chiral | 1-[4-(difluoromethoxy)-2-(methylsulfonyl)benzoyl]-4-((1S)-1-{[3-(trifluoromethyl)phenyl]sulfonyl}ethyl)piperidine | 570 |
| 39 | Chiral | 1-[2-(methylsulfonyl)-4-(trifluoromethoxy)benzoyl]-4-((1R)-1-{[3-trifluoromethyl)phenyl]sulfonyl}ethyl)piperidine | 588 |

TABLE 2-continued

| EXAMPLE # | STRUCTURE | CHEMICAL NAME | MASS SPECTRAL DATA m/e (M + H) |
|---|---|---|---|
| 40 | 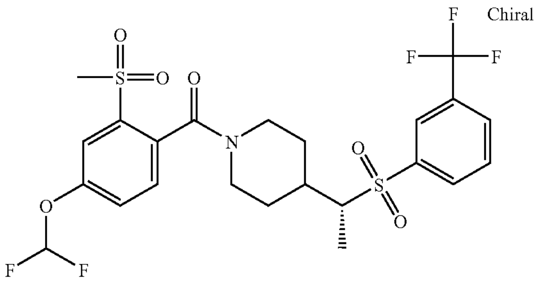 | 1-[4-(difluoromethoxy)-2-(methylsulfonyl)benzoyl]-4-((1R)-1-{[3-(trifluoromethyl)phenyl]sulfonyl}ethyl)piperidine | 570 |
| 41 | 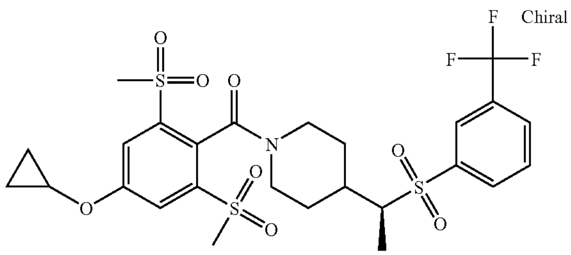 | 1-[4-(cyclopropyloxy)-2,6-bis(methylsulfonyl)benzoyl]-4-((1S)-1-{[3-(trifluoromethyl)phenyl]sulfonyl}ethyl)piperidine | 638 |
| 42 | 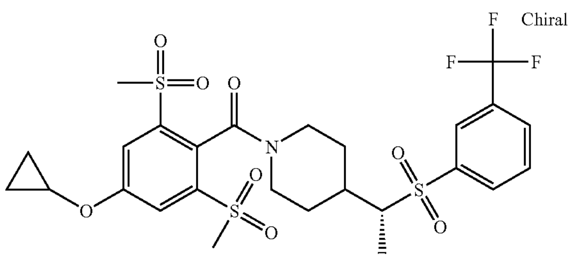 | 1-[4-(cyclopropyloxy)-2,6-bis(methylsulfonyl)benzoyl]-4-((1R)-1-{[3-(trifluoromethyl)phenyl]sulfonyl}ethyl)piperidine | 638 |
| 43 | 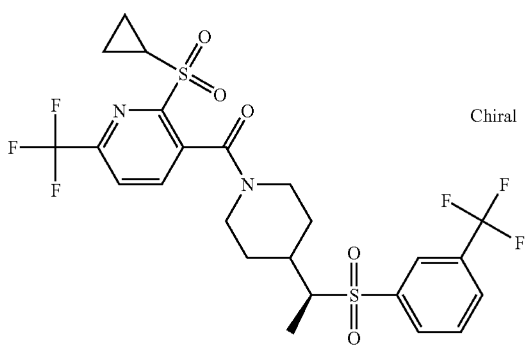 | 2-(cyclopropylsulfonyl)-6-(trifluoromethyl)-3-{[4-((1S)-1-{[3-(trifluoromethyl)phenyl]sulfonyl}ethyl)piperidin-1-yl]carbonyl}pyridine | 599 |
| 44 | 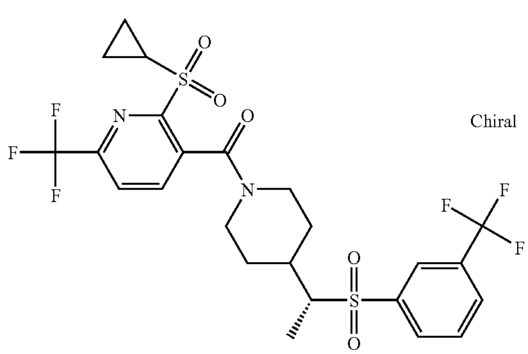 | 2-(cyclopropylsulfonyl)-6-(trifluoromethyl)-3-{[4-((1R)-1-{[3-(trifluoromethyl)phenyl]sulfonyl}ethyl)piperidin-1-yl]carbonyl}pyridine | 599 |

TABLE 2-continued

| EXAMPLE # | STRUCTURE | CHEMICAL NAME | MASS SPECTRAL DATA m/e (M + H) |
|---|---|---|---|
| 45 | 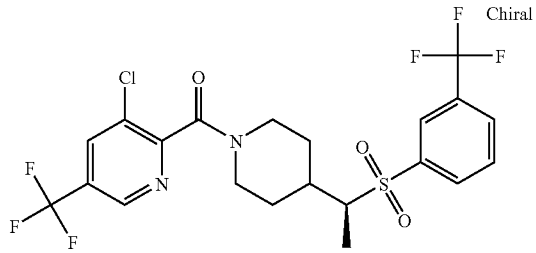 | 3-chloro-5-(trifluoromethyl)-2-{[4-((1S)-1-{[3-(trifluoromethyl)phenyl]sulfonyl}ethyl)piperidin-1-yl]carbonyl}pyridine | 529 |
| 46 | 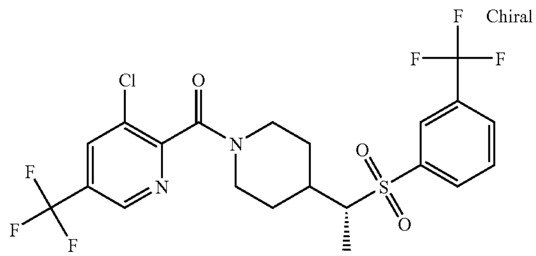 | 3-chloro-5-(trifluoromethyl)-2-{[4-((1S)-1-{[3-(trifluoromethyl)phenyl]sulfonyl}ethyl)piperidin-1-yl]carbonyl}pyridine | 529 |
| 47 | 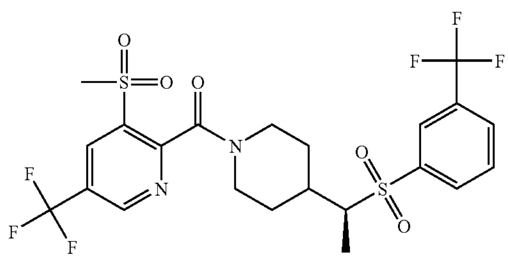 | 3-(methylsulfonyl)-5-(trifluoromethyl)-2-{[4-((1S)-1-{[3-(trifluoromethyl)phenyl]sulfonyl}ethyl)piperidin-1-yl]carbonyl}pyridine | 573 |
| 48 | 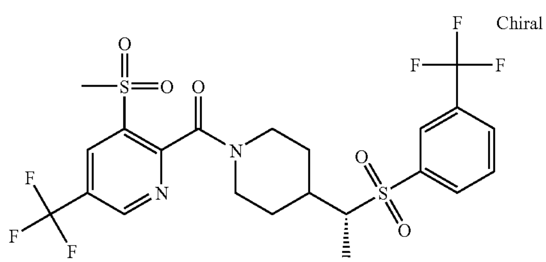 | 3-(methylsulfonyl)-5-(trifluoromethyl)-2-{[4-((1S)-1-{[3-(trifluoromethyl)phenyl]sulfonyl}ethyl)piperidin-1-yl]carbonyl}pyridine | 573 |
| 49 | 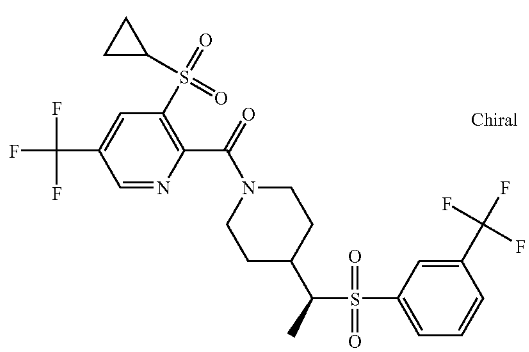 | 3-(cyclopropylsulfonyl)-5-(trifluoromethyl)-2-{[4-((1S)-1-{[3-(trifluoromethyl)phenyl]sulfonyl}ethyl)piperidin-1-yl]carbonyl}pyridine | 599 |

TABLE 2-continued

| EXAMPLE # | STRUCTURE | CHEMICAL NAME | MASS SPECTRAL DATA m/e (M + H) |
| --- | --- | --- | --- |
| 50 | Chiral | 3-(cyclopropylsulfonyl)-5-(trifluoromethyl)-2-{[4-((1S)-1-{[3-(trifluoromethyl)phenyl]sulfonyl}ethyl)piperidin-1-yl]carbonyl}pyridine | 599 |
| 51 | 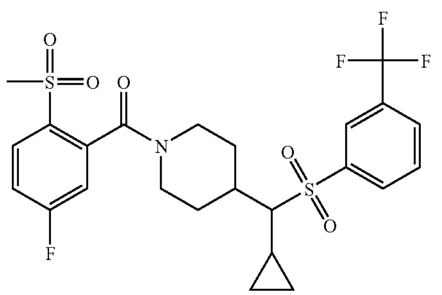 | 4-(cyclopropyl{[3-(trifluoromethyl)phenyl]sulfonyl}methyl)-1-[5-fluoro-2-(methylsulfonyl)benzoyl]piperidine | 548 |
| 52 | 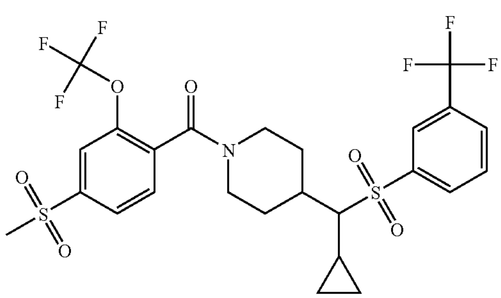 | 4-(cyclopropyl{[3-(trifluoromethyl)phenyl]sulfonyl}methyl)-1-[4-(methylsulfonyl)-2-(trifluoromethoxy)benzoyl]piperidine | 514 |

TABLE 3

| EXAMPLE # | STRUCTURE | CHEMICAL NAME | MASS SPECTRAL DATA m/e (M + H) |
| --- | --- | --- | --- |
| 53 | 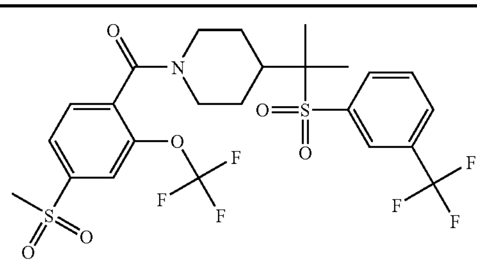 | 1-[4-(methylsulfonyl)-2-(trifluoromethoxy)benzoyl]-4-(1-methyl-1-{[3-(trifluoromethyl)phenyl]sulfonyl}ethyl)piperidine | 602 |

TABLE 3-continued

| EXAMPLE # | STRUCTURE | CHEMICAL NAME | MASS SPECTRAL DATA m/e (M + H) |
|---|---|---|---|
| 54 | 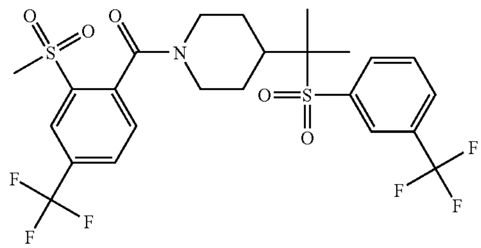 | 1-[2-(methylsulfonyl)-4-(trifluoromethyl)benzoyl]-4-(1-methyl-1-{[3-(trifluoromethyl)phenyl]sulfonyl}ethyl)piperidine | 586 |
| 55 | 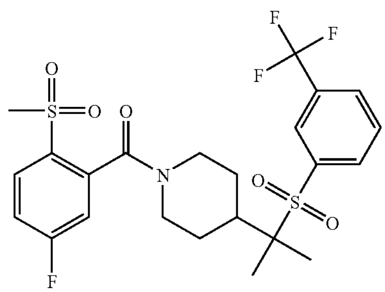 | 1-[5-fluoro-2-(methylsulfonyl)benzoyl]-4-(1-methyl-1-{[3-(trifluoromethyl)phenyl]sulfonyl}ethyl)piperidine | 536 |
| 56 | 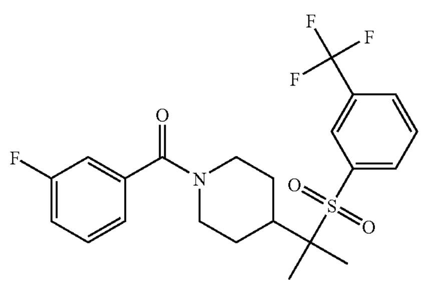 | 1-(3-fluorobenzoyl)-4-(1-methyl-1-{[3-(trifluoromethyl)phenyl]sulfonyl}ethyl)piperidine | 458 |
| 57 | 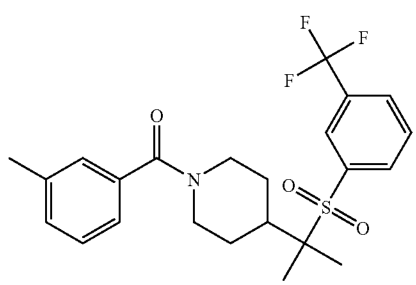 | 1-(3-methylbenzoyl)-4-(1-methyl-1-{[3-(trifluoromethyl)phenyl]sulfonyl}ethyl)piperidine | 454 |
| 58 | 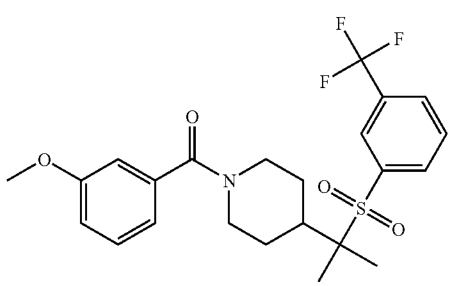 | 1-(3-methoxybenzoyl)-4-(1-methyl-1-{[3-(trifluoromethyl)phenyl]sulfonyl}ethyl)piperidine | 470 |

TABLE 3-continued

| EXAMPLE # | STRUCTURE | CHEMICAL NAME | MASS SPECTRAL DATA m/e (M + H) |
|---|---|---|---|
| 59 | 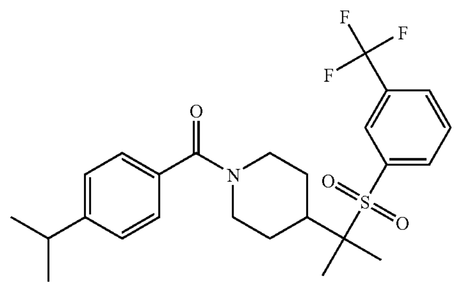 | 1-(4-isopropylbenzoyl)-4-(1-methyl-1-{[3-(trifluoromethyl)phenyl]sulfonyl}ethyl)piperidine | 482 |
| 60 | 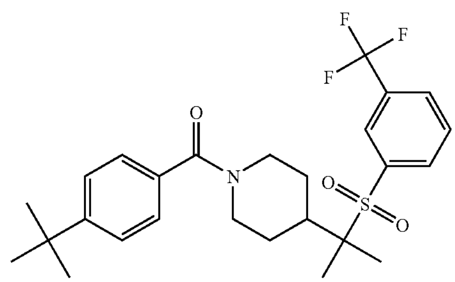 | 1-(4-tert-butylbenzoyl)-4-(1-methyl-1-{[3-(trifluoromethyl)phenyl]sulfonyl}ethyl)piperidine | 496 |
| 61 | 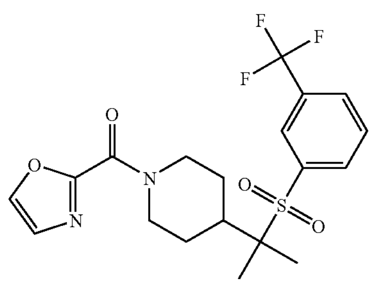 | 4-(1-methyl-1-{[3-(trifluoromethyl)phenyl]sulfonyl}ethyl)-1-(1,3-oxazol-2-ylcarbonyl)piperidine | 431 |
| 62 | 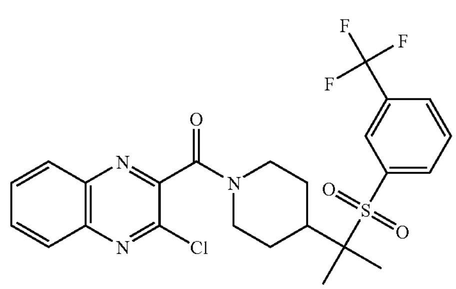 | 2-chloro-3-{[4-(1-methyl-1-{[3-(trifluoromethyl)phenyl]sulfonyl}ethyl)piperidin-1-yl]carbonyl}quinoxaline | 526 |
| 63 | 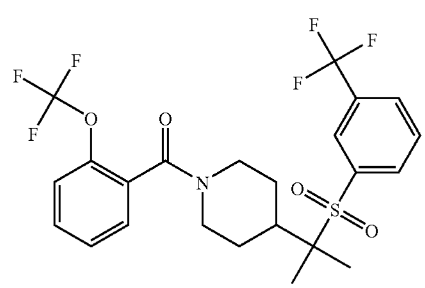 | 4-(1-methyl-1-{[3-(trifluoromethyl)phenyl]sulfonyl}ethyl)-1-[2-(trifluoromethoxy)benzoyl]piperidine | 524 |

TABLE 3-continued

| EXAMPLE # | STRUCTURE | CHEMICAL NAME | MASS SPECTRAL DATA m/e (M + H) |
|---|---|---|---|
| 64 | 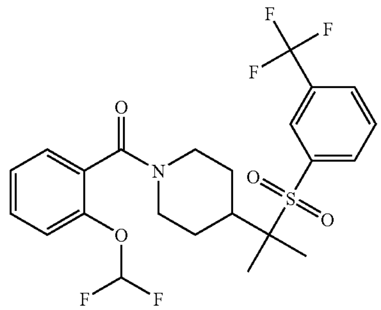 | 1-[2-(difluoromethoxy)benzoyl]-4-(1-methyl-1-{[3-(trifluoromethyl)phenyl]sulfonyl}ethyl)piperidine | 506 |
| 65 | 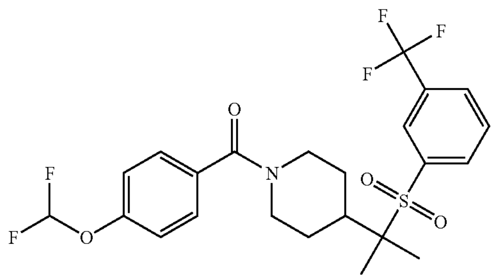 | 1-[4-(difluoromethoxy)benzoyl]-4-(1-methyl-1-{[3-(trifluoromethyl)phenyl]sulfonyl}ethyl)piperidine | 506 |
| 66 | 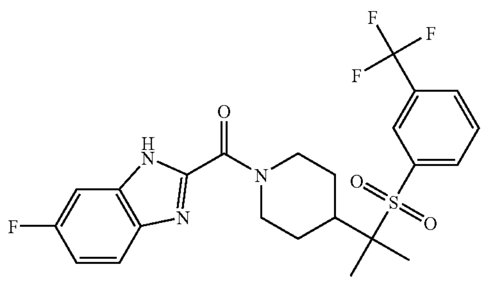 | 6-fluoro-2-{[4-(1-methyl-1-{[3-(trifluoromethyl)phenyl]sulfonyl}ethyl)piperidin-1-yl]carbonyl}-1H-benzimidazole | 498 |
| 67 | 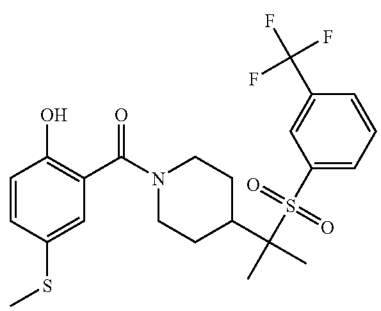 | 4-(methylthio)-2-{[4-(1-methyl-1-{[3-(trifluoromethyl)phenyl]sulfonyl}ethyl)piperidin-1-yl]carbonyl}phenol | 502 |
| 68 | 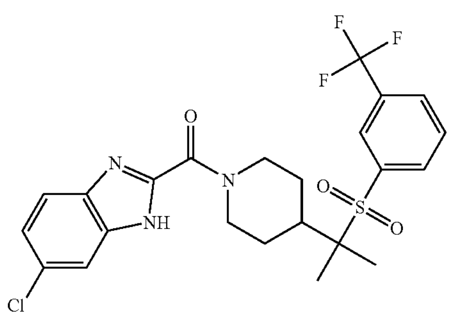 | 6-chloro-2-{[4-(1-methyl-1-{[3-(trifluoromethyl)phenyl]sulfonyl}ethyl)piperidin-1-yl]carbonyl}-1H-benzimidazole | 514 |

TABLE 3-continued

| EXAMPLE # | STRUCTURE | CHEMICAL NAME | MASS SPECTRAL DATA m/e (M + H) |
|---|---|---|---|
| 69 | 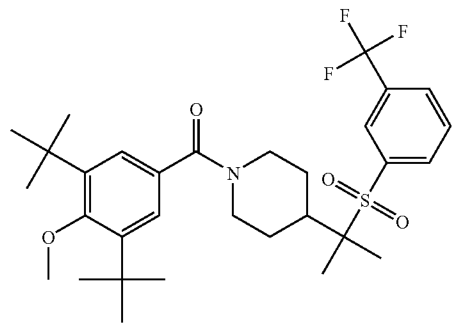 | 1-(3,5-di-tert-butyl-4-methoxybenzoyl)-4-(1-methyl-1-{[3-(trifluoromethyl)phenyl]sulfonyl}ethyl)piperidine | 582 |
| 70 | 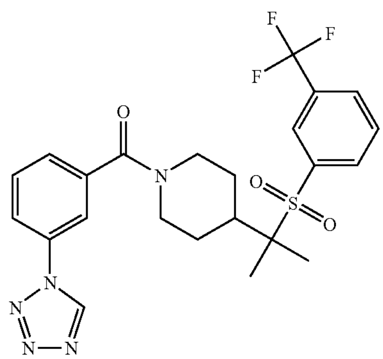 | 4-(1-methyl-1-{[3-(trifluoromethyl)phenyl]sulfonyl}ethyl)-1-[3-(1H-tetrazol-1-yl)benzoyl]piperidine | 508 |
| 71 | 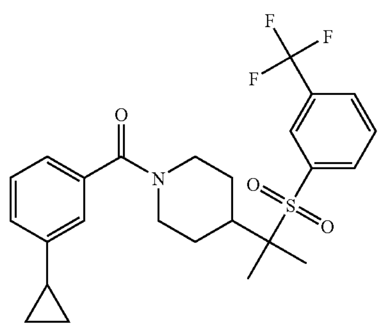 | 1-(3-cyclopropylbenzoyl)-4-(1-methyl-1-{[3-(trifluoromethyl)phenyl]sulfonyl}ethyl)piperidine | 480 |
| 72 | 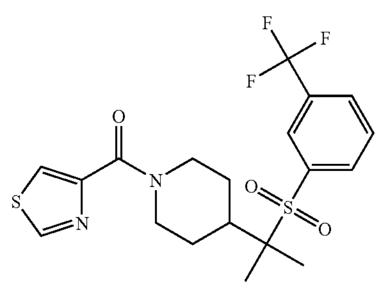 | 4-(1-methyl-1-{[3-(trifluoromethyl)phenyl]sulfonyl}ethyl)-1-(1,3-thiazol-4-ylcarbonyl)piperidine | 447 |

TABLE 3-continued

| EXAMPLE # | STRUCTURE | CHEMICAL NAME | MASS SPECTRAL DATA m/e (M + H) |
|---|---|---|---|
| 73 | 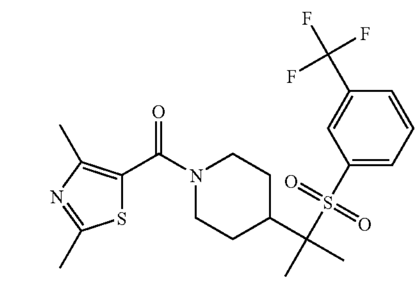 | 1-[(2,4-dimethyl-1,3-thiazol-5-yl)carbonyl]-4-(1-methyl-1-{[3-(trifluoromethyl)phenyl]sulfonyl}ethyl)piperidine | 475 |
| 74 | 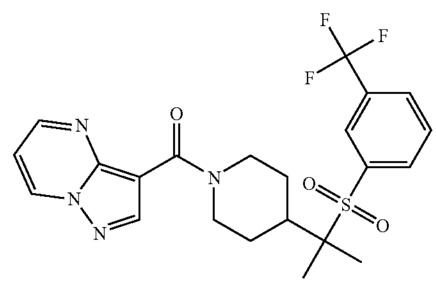 | 3-{[4-(1-methyl-1-{[3-(trifluoromethyl)phenyl]sulfonyl}ethyl)piperidin-1-yl]carbonyl}pyrazolo[1,5-a]pyrimidine | 481 |
| 75 | 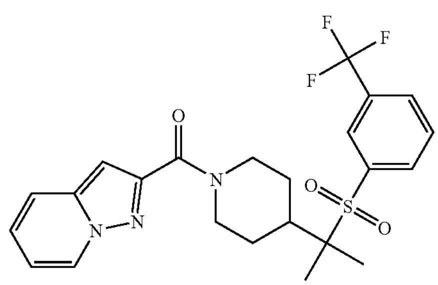 | 2-{[4-(1-methyl-1-{[3-(trifluoromethyl)phenyl]sulfonyl}ethyl)piperidin-1-yl]carbonyl}pyrazolo[1,5-a]pyridine | 480 |
| 76 | 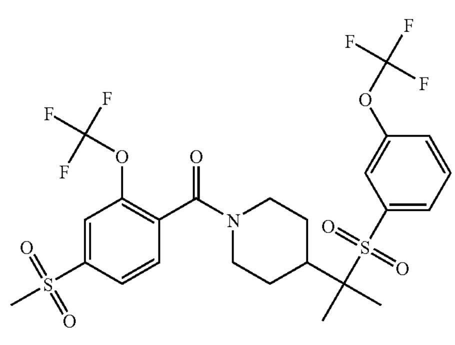 | 1-[4-(methylsulfonyl)-2-(trifluoromethoxy)benzoyl]-4-(1-methyl-1-{[3-(trifluoromethoxy)phenyl]sulfonyl}ethyl)piperidine | 618 |
| 77 | 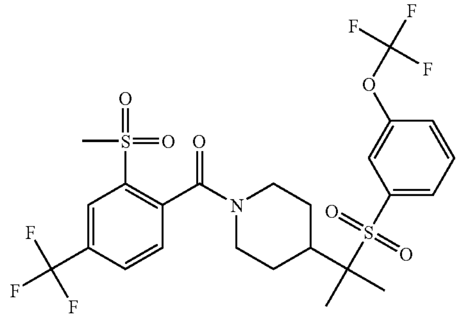 | 1-[2-(methylsulfonyl)-4-(trifluoromethyl)benzoyl]-4-(1-methyl-1-{[3-(trifluoromethoxy)phenyl]sulfonyl}ethyl)piperidine | 602 |

TABLE 3-continued

| EXAMPLE # | STRUCTURE | CHEMICAL NAME | MASS SPECTRAL DATA m/e (M + H) |
|---|---|---|---|
| 78 | 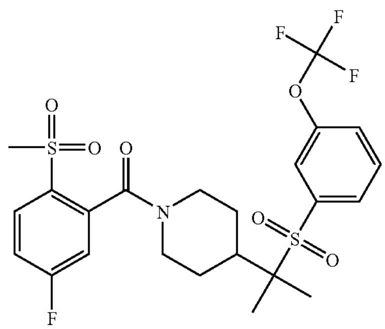 | 1-[5-fluoro-2-(methylsulfonyl)benzoyl]-4-(1-methyl-1-{[3-(trifluoromethoxy)phenyl]sulfonyl}ethyl)piperidine | 552 |
| 79 | 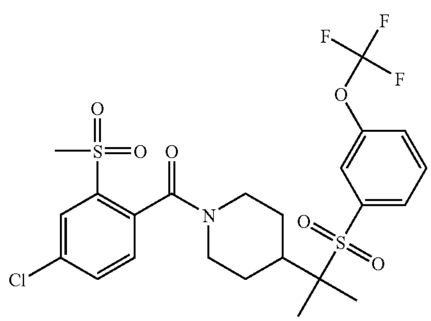 | 1-[4-chloro-2-(methylsulfonyl)benzoyl]-4-(1-methyl-1-{[3-(trifluoromethoxy)phenyl]sulfonyl}ethyl)piperidine | 569 |
| 80 | 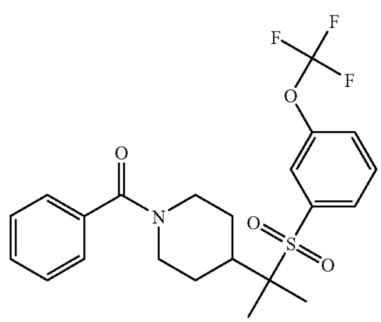 | 1-benzoyl-4-(1-methyl-1-{[3-(trifluoromethoxy)phenyl]sulfonyl}ethyl)piperidine | 456 |
| 81 | 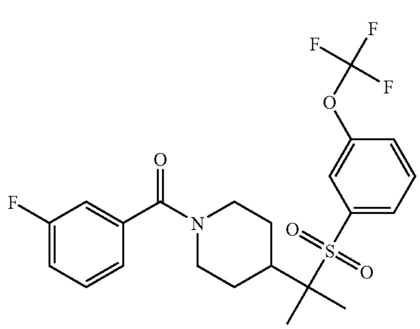 | 1-(3-fluorobenzoyl)-4-(1-methyl-1-{[3-(trifluoromethoxy)phenyl]sulfonyl}ethyl)piperidine | 474 |

TABLE 3-continued

| EXAMPLE # | STRUCTURE | CHEMICAL NAME | MASS SPECTRAL DATA m/e (M + H) |
|---|---|---|---|
| 82 | 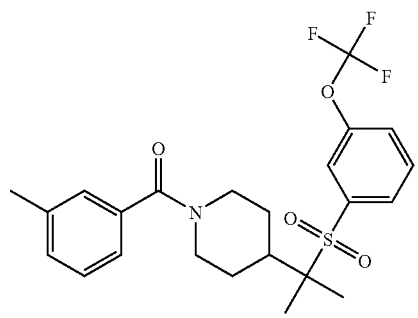 | 1-(3-methylbenzoyl)-4-(1-methyl-1-{[3-(trifluoromethoxy)phenyl]sulfonyl}ethyl)piperidine | 470 |
| 83 | 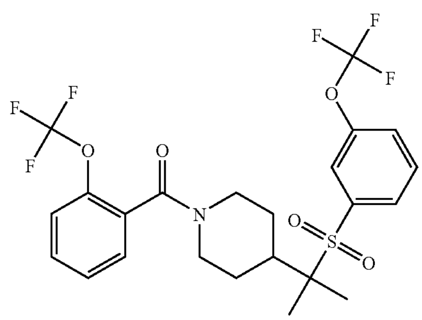 | 4-(1-methyl-1-{[3-(trifluoromethoxy)phenyl]sulfonyl}ethyl)-1-[2-(trifluoromethoxy)benzoyl]piperidine | 540 |
| 84 | 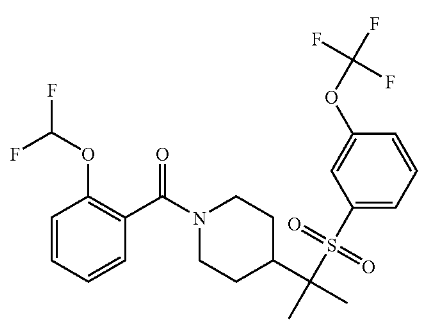 | 1-[2-(difluoromethoxy)benzoyl]-4-(1-methyl-1-{[3-(trifluoromethoxy)phenyl]sulfonyl}ethyl)piperidine | 522 |
| 85 | 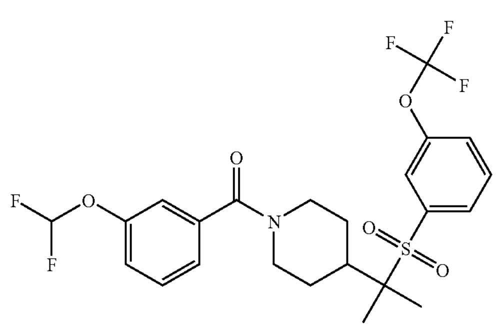 | 1-[3-(difluoromethoxy)benzoyl]-4-(1-methyl-1-{[3-(trifluoromethoxy)phenyl]sulfonyl}ethyl)piperidine | 522 |

TABLE 3-continued

| EXAMPLE # | STRUCTURE | CHEMICAL NAME | MASS SPECTRAL DATA m/e (M + H) |
|---|---|---|---|
| 86 | 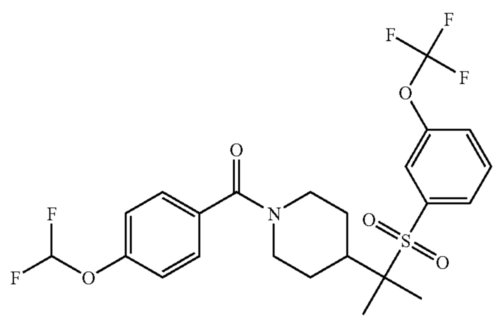 | 1-[4-(difluoromethoxy)benzoyl]-4-(1-methyl-1-{[3-(trifluoromethoxy)phenyl]sulfonyl}ethyl)piperidine | 522 |
| 87 | 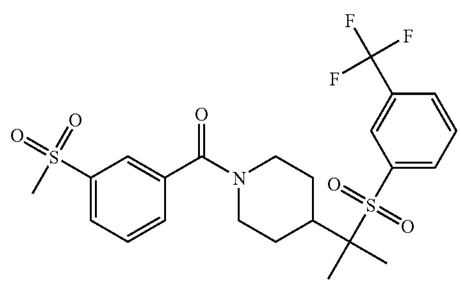 | 1-[3-(methylsulfonyl)benzoyl]-4-(1-methyl-1-{[3-(trifluoromethyl)phenyl]sulfonyl}ethyl)piperidine | 518 |
| 88 | 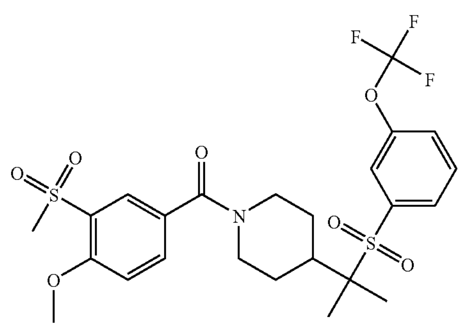 | 1-[4-methoxy-3-(methylsulfonyl)benzoyl]-4-(1-methyl-1-{[3-(trifluoromethoxy)phenyl]sulfonyl}ethyl)piperidine | 564 |
| 89 | 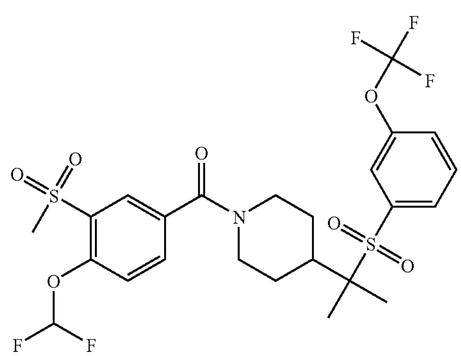 | 1-[4-(difluoromethoxy)-3-(methylsulfonyl)benzoyl]-4-(1-methyl-1-{[3-(trifluoromethoxy)phenyl]sulfonyl}ethyl)piperidine | 600 |

TABLE 3-continued

| EXAMPLE # | STRUCTURE | CHEMICAL NAME | MASS SPECTRAL DATA m/e (M + H) |
|---|---|---|---|
| 90 | 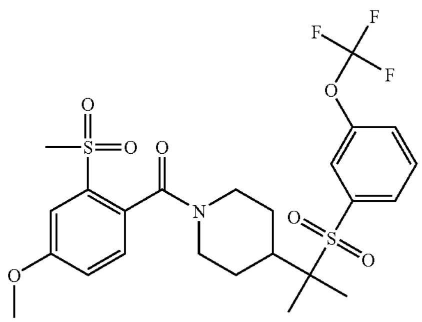 | 1-[4-methoxy-2-(methylsulfonyl)benzoyl]-4-(1-methyl-1-{[3-(trifluoromethoxy)phenyl]sulfonyl}ethyl)piperidine | 564 |
| 91 | 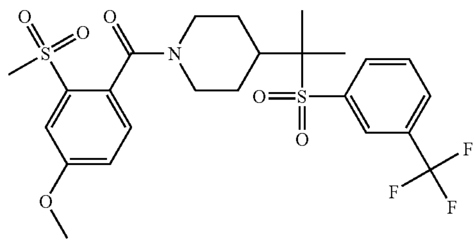 | 1-[4-methoxy-2-(methylsulfonyl)benzoyl]-4-(1-methyl-1-{[3-(trifluoromethyl)phenyl]sulfonyl}ethyl)piperidine | 548 |
| 92 | 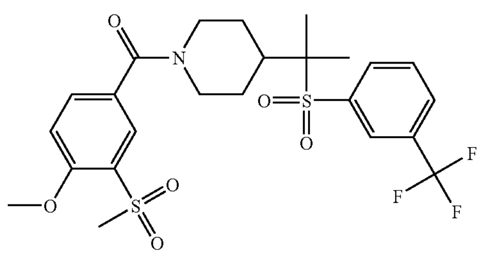 | 1-[4-methoxy-3-(methylsulfonyl)benzoyl]-4-(1-methyl-1-{[3-(trifluoromethyl)phenyl]sulfonyl}ethyl)piperidine | 548 |
| 93 | 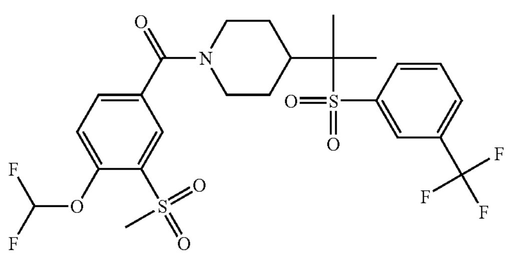 | 1-[4-(difluoromethoxy)-3-(methylsulfonyl)benzoyl]-4-(1-methyl-1-{[3-(trifluoromethyl)phenyl]sulfonyl}ethyl)piperidine | 584 |
| 94 | 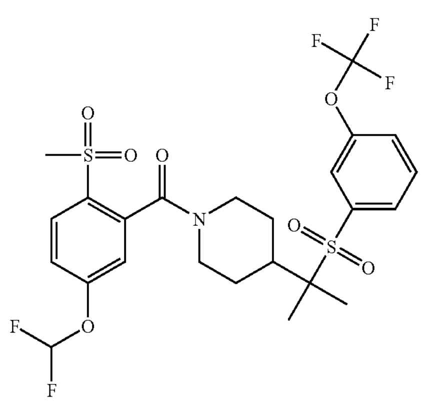 | 1-[5-(difluoromethoxy)-2-(methylsulfonyl)benzoyl]-4-(1-methyl-1-{[3-(trifluoromethoxy)phenyl]sulfonyl}ethyl)piperidine | 600 |

TABLE 3-continued

| EXAMPLE # | STRUCTURE | CHEMICAL NAME | MASS SPECTRAL DATA m/e (M + H) |
|---|---|---|---|
| 95 | 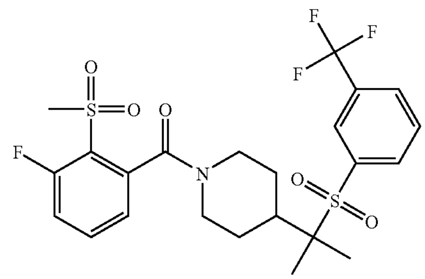 | 1-[3-fluoro-2-(methylsulfonyl)benzoyl]-4-(1-methyl-1-{[3-(trifluoromethyl)phenyl]sulfonyl}ethyl)piperidine | 536 |
| 96 | 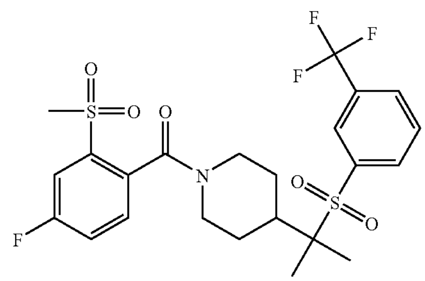 | 1-[4-fluoro-2-(methylsulfonyl)benzoyl]-4-(1-methyl-1-{[3-(trifluoromethyl)phenyl]sulfonyl}ethyl)piperidine | 536 |
| 97 | 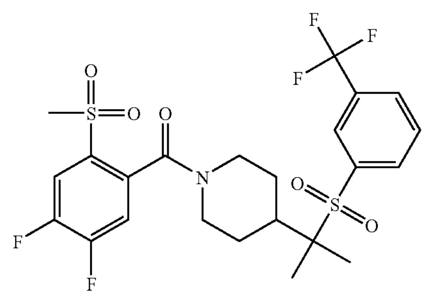 | 1-[4,5-difluoro-2-(methylsulfonyl)benzoyl]-4-(1-methyl-1-{[3-(trifluoromethyl)phenyl]sulfonyl}ethyl)piperidine | 554 |
| 98 | 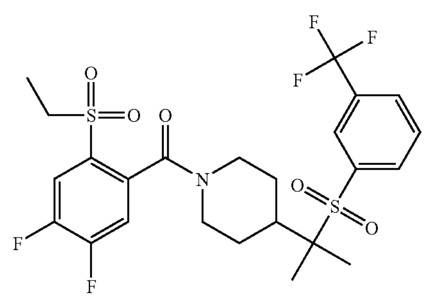 | 1-[2-(ethylsulfonyl)-4,5-difluorobenzoyl]-4-(1-methyl-1-{[3-(trifluoromethyl)phenyl]sulfonyl}ethyl)piperidine | 568 |
| 99 | 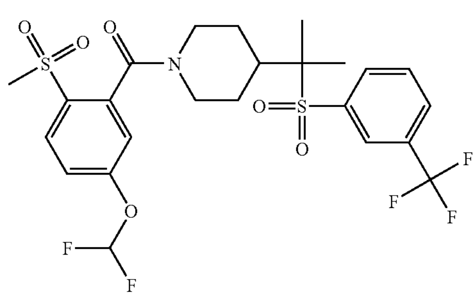 | 1-[5-(difluoromethoxy)-2-(methylsulfonyl)benzoyl]-4-(1-methyl-1-{[3-(trifluoromethyl)phenyl]sulfonyl}ethyl)piperidine | 584 |

TABLE 3-continued

| EXAMPLE # | STRUCTURE | CHEMICAL NAME | MASS SPECTRAL DATA m/e (M + H) |
|---|---|---|---|
| 100 | 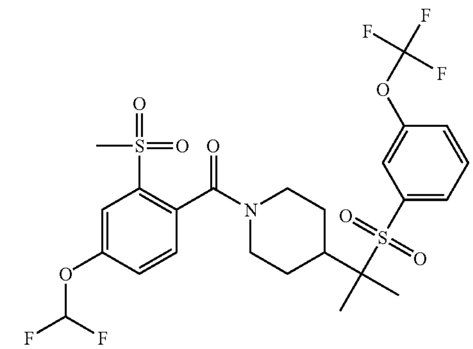 | 1-[4-(difluoromethoxy)-2-(methylsulfonyl)benzoyl]-4-(1-methyl-1-{[3-(trifluoromethoxy)phenyl]sulfonyl}ethyl)piperidine | 600 |
| 101 | 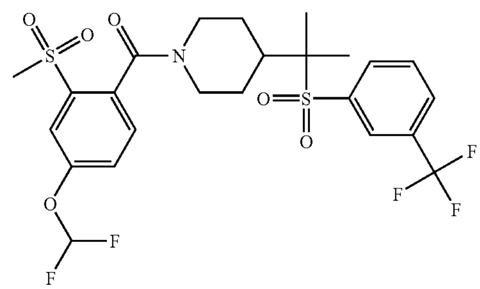 | 1-[4-(difluoromethoxy)-2-(methylsulfonyl)benzoyl]-4-(1-methyl-1-{[3-(trifluoromethyl)phenyl]sulfonyl}ethyl)piperidine | 584 |
| 102 | 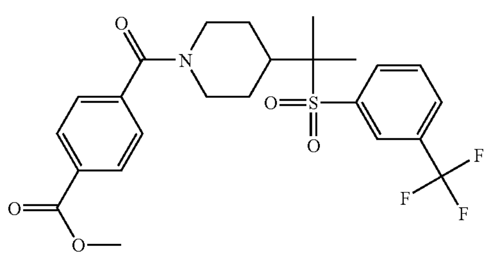 | Methyl 4-{[4-(1-methyl-1-{[3-(trifluoromethyl)phenyl]sulfonyl}ethyl)piperidin-1-yl]carbonyl}benzoate | 498 |
| 103 | 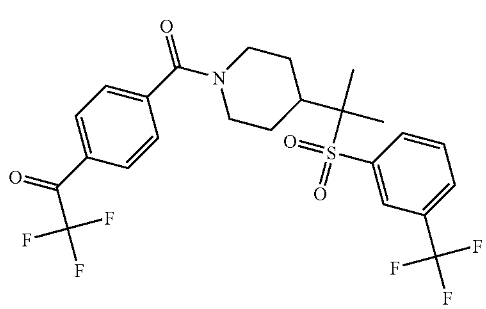 | 2,2,2-trifluoro-1-(4-{[4-(1-methyl-1-{[3-(trifluoromethyl)phenyl]sulfonyl}ethyl)piperidin-1-yl]carbonyl}phenyl)ethanone | 534 |
| 104 | 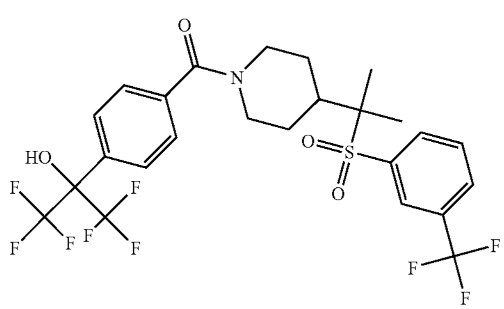 | 1,1,1,3,3,3-hexafluoro-2-(4-{[4-(1-methyl-1-{[3-(trifluoromethyl)phenyl]sulfonyl}ethyl)piperidin-1-yl]carbonyl}phenyl)propan-2-ol | 606 |

TABLE 3-continued

| EXAMPLE # | CHEMICAL NAME | MASS SPECTRAL DATA m/e (M + H) |
|---|---|---|
| 105 | N-methyl-4-{[4-(1-methyl-1-{[3-(trifluoromethyl)phenyl]sulfonyl}ethyl)piperidin-1-yl]carbonyl}benzamide | 497 |
| 106 | N-cyclopropyl-4-{[4-(1-methyl-1-{[3-(trifluoromethyl)phenyl]sulfonyl}ethyl)piperidin-1-yl]carbonyl}benzamide | 523 |
| 107 | N-tert-butyl)-4-{[4-(1-methyl-1-{[3-(trifluoromethyl)phenyl]sulfonyl}ethyl)piperidin-1-yl]carbonyl}benzamide | 539 |
| 108 | 1-[4-(azetidin-1-ylcarbonyl)benzoyl]-4-(1-methyl-1-{[3-(trifluoromethyl)phenyl]sulfonyl}ethyl)piperidine | 523 |
| 109 | 4-(1-methyl-1-{[3-(trifluoromethyl)phenyl]sulfonyl}ethyl)-1-[4-(pyrrolidin-1-ylcarbonyl)benzoyl]piperidine | 538 |

US 8,304,434 B2

TABLE 3-continued

| EXAMPLE # | STRUCTURE | CHEMICAL NAME | MASS SPECTRAL DATA m/e (M + H) |
|---|---|---|---|
| 110 | 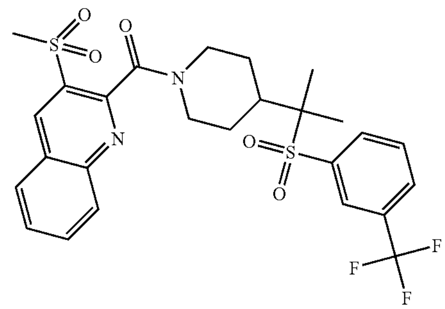 | 3-(methylsulfonyl)-2-{[4-(1-methyl-1-{[3-(trifluoromethyl)phenyl]sulfonyl}ethyl)piperidin-1-yl]carbonyl}quinoline | 569 |
| 111 | 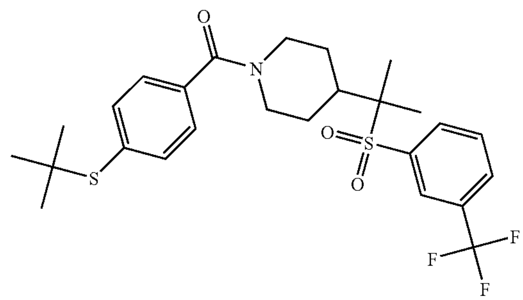 | 1-[4-(tert-butylthio)benzoyl]-4-(1-methyl-1-{[3-(trifluoromethyl)phenyl]sulfonyl}ethyl)piperidine | 528 |
| 112 | 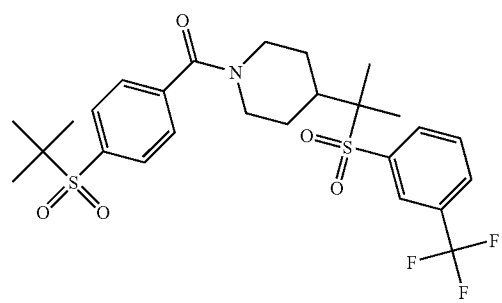 | 1-[4-(tert-butylsulfonyl)benzoyl]-4-(1-methyl-1-{[3-(trifluoromethyl)phenyl]sulfonyl}ethyl)piperidine | 560 |
| 113 | 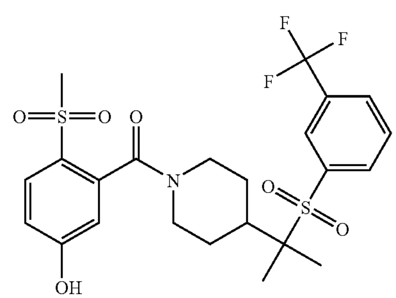 | 4-(methylsulfonyl)-3-{[4-(1-methyl-1-{[3-(trifluoromethyl)phenyl]sulfonyl}ethyl)piperidin-1-yl]carbonyl}phenol | 534 |
| 114 | 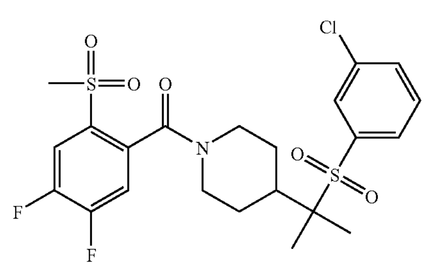 | 4-{1-[(3-chlorophenyl)sulfonyl]-1-methylethyl}-1-[4,5-difluoro-2-(methylsulfonyl)benzoyl]piperidine | 521 |

TABLE 3-continued

| EXAMPLE # | STRUCTURE | CHEMICAL NAME | MASS SPECTRAL DATA m/e (M + H) |
|---|---|---|---|
| 115 | 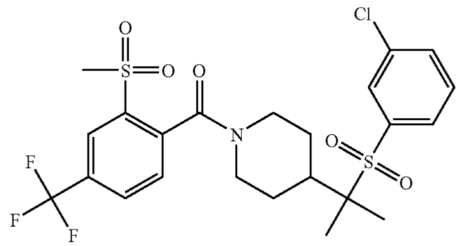 | 4-{1-[(3-chlorophenyl)sulfonyl]-1-methylethyl}-1-[2-(methylsulfonyl)-4-(trifluoromethyl)benzoyl]piperidine | 553 |
| 116 | 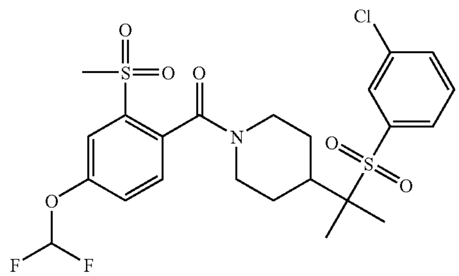 | 4-{1-[(3-chlorophenyl)sulfonyl]-1-methylethyl}-1-[4-(difluoromethoxy)-2-(methylsulfonyl)benzoyl]piperidine | 551 |
| 117 | 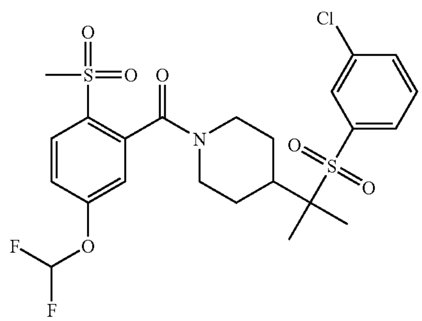 | 4-{1-[(3-chlorophenyl)sulfonyl]-1-methylethyl}-1-[5-(difluoromethoxy)-2-(methylsulfonyl)benzoyl]piperidine | 551 |
| 118 | 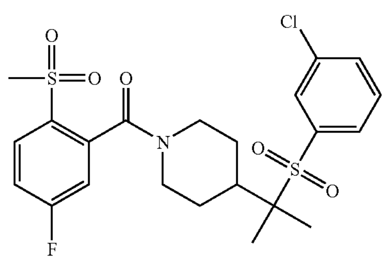 | 4-{1-[(3-chlorophenyl)sulfonyl]-1-methylethyl}-1-[5-fluoro-2-(methylsulfonyl)benzoyl]piperidine | 503 |
| 119 | 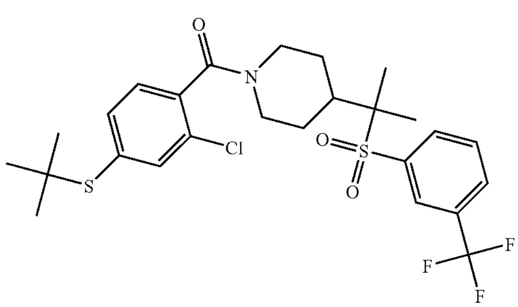 | 1-[4-(tert-butylthio)-2-chlorobenzoyl]-4-(1-methyl-1-{[3-(trifluoromethyl)phenyl]sulfonyl}ethyl)piperidine | 562 |

TABLE 3-continued

| EXAMPLE # | STRUCTURE | CHEMICAL NAME | MASS SPECTRAL DATA m/e (M + H) |
|---|---|---|---|
| 120 | 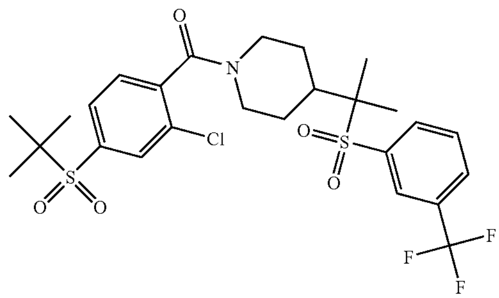 | 1-[4-(tert-butylsulfonyl)-2-chlorobenzoyl]-4-(1-methyl-1-{[3-(trifluoromethyl)phenyl]sulfonyl}ethyl)piperidine | 595 |
| 121 | 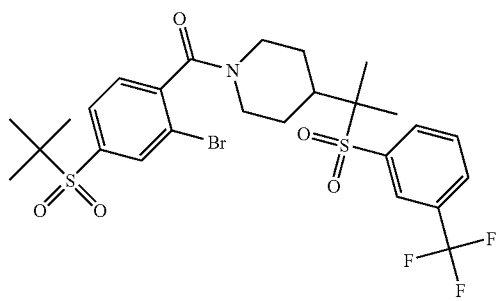 | 1-[2-bromo-4-(tert-butylsulfonyl)benzoyl]-4-(1-methyl-1-{[3-(trifluoromethyl)phenyl]sulfonyl}ethyl)piperidine | 639 |
| 122 | 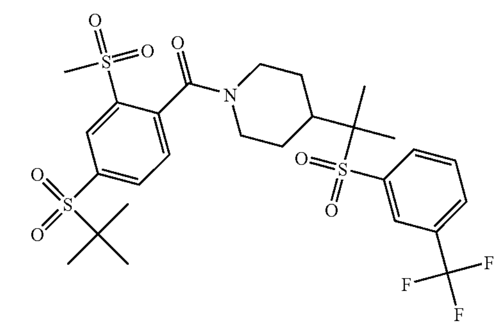 | 1-[4-(tert-butylsulfonyl)-2-(methylsulfonyl)benzoyl]-4-(1-methyl-1-{[3-(trifluoromethyl)phenyl]sulfonyl}ethyl)piperidine | 638 |
| 123 | 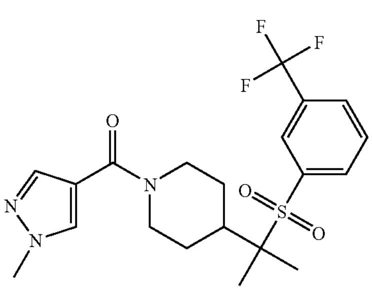 | 1-[(1-methyl-1H-pyrazol-4-yl)carbonyl]-4-(1-methyl-1-{[3-(trifluoromethyl)phenyl]sulfonyl}ethyl)piperidine | 444 |
| 124 | 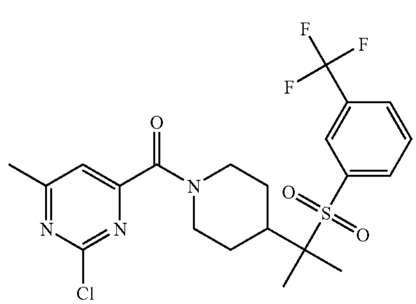 | 2-chloro-4-methyl-6-{[4-(1-methyl-1-{[3-(trifluoromethyl)phenyl]sulfonyl}ethyl)piperidin-1-yl]carbonyl}pyrimidine | 490 |

TABLE 3-continued

| EXAMPLE # | STRUCTURE | CHEMICAL NAME | MASS SPECTRAL DATA m/e (M + H) |
|---|---|---|---|
| 125 | 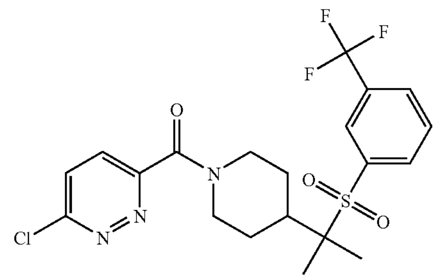 | 3-chloro-6-{[4-(1-methyl-1-{[3-(trifluoromethyl)phenyl]sulfonyl}ethyl)piperidin-1-yl]carbonyl}pyridazine | 476 |
| 126 | 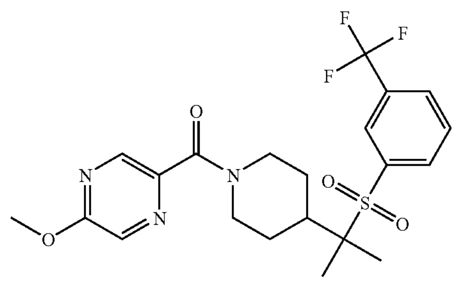 | 2-methoxy-5-{[4-(1-methyl-1-{[3-(trifluoromethyl)phenyl]sulfonyl}ethyl)piperidin-1-yl]carbonyl}pyrazine | 472 |
| 127 | 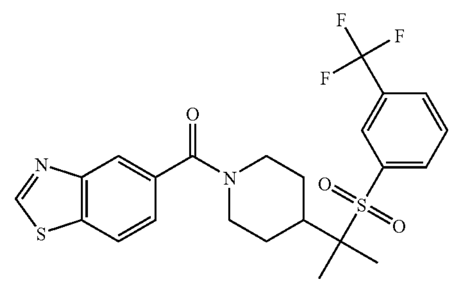 | 5-{[4-(1-methyl-1-{[3-(trifluoromethyl)phenyl]sulfonyl}ethyl)piperidin-1-yl]carbonyl}-1,3-benzothiazole | 497 |
| 128 | 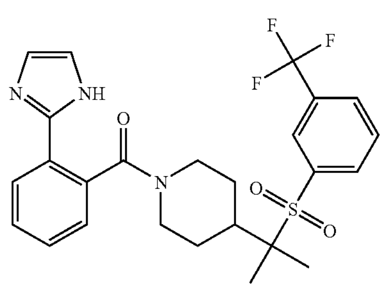 | 1-[2-(1H-imidazol-2-yl)benzoyl]-4-(1-methyl-1-{[3-(trifluoromethyl)phenyl]sulfonyl}ethyl)piperidine | 506 |
| 129 | 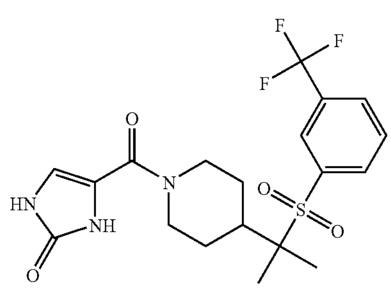 | 4-{[4-(1-methyl-1-{[3-(trifluoromethyl)phenyl]sulfonyl}ethyl)piperidin-1-yl]carbonyl}-1,3-dihydro-2H-imidazol-2-one | 446 |

TABLE 3-continued

| EXAMPLE # | STRUCTURE | CHEMICAL NAME | MASS SPECTRAL DATA m/e (M + H) |
|---|---|---|---|
| 130 | 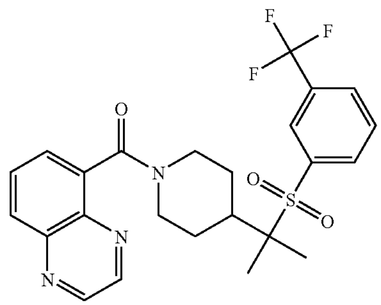 | 5-{[4-(1-methyl-1-{[3-(trifluoromethyl)phenyl]sulfonyl}ethyl)piperidin-1-yl]carbonyl}quinoxaline | 492 |
| 131 | 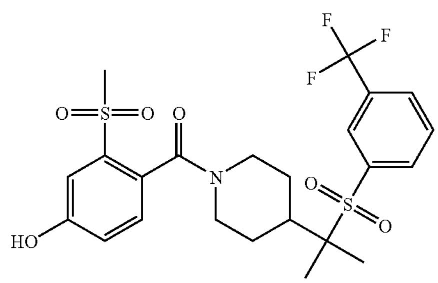 | 1-[4-hydroxy-2-(methylsulfonyl)benzoyl]-4-[1-methyl-1-[[3-(trifluoromethyl)phenyl]sulfonyl]ethyl]piperidine | 534 |
| 132 | 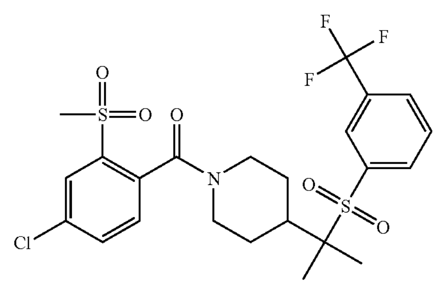 | 1-[4-chloro-2-(methylsulfonyl)benzoyl]-4-(1-methyl-1-{[3-(trifluoromethyl)phenyl]sulfonyl}ethyl)piperidine | 553 |
| 133 | 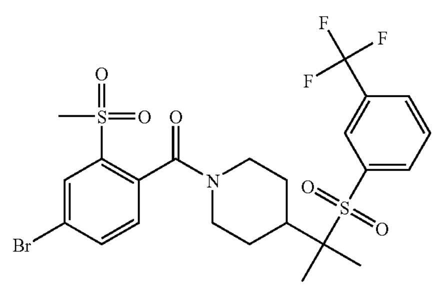 | 1-[4-bromo-2-(methylsulfonyl)benzoyl]-4-(1-methyl-1-{[3-(trifluoromethyl)phenyl]sulfonyl}ethyl)piperidine | 597 |
| 134 | 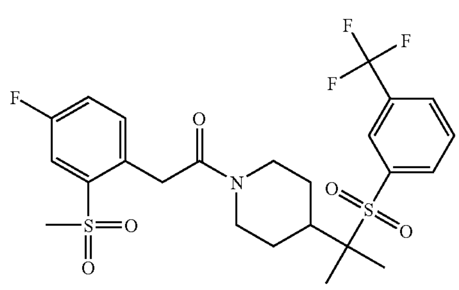 | 1-{[4-fluoro-2-(methylsulfonyl)phenyl]acetyl}-4-(1-methyl-1-{[3-(trifluoromethyl)phenyl]sulfonyl}ethyl)piperidine | 550 |

TABLE 3-continued

| EXAMPLE # | STRUCTURE | CHEMICAL NAME | MASS SPECTRAL DATA m/e (M + H) |
|---|---|---|---|
| 135 | 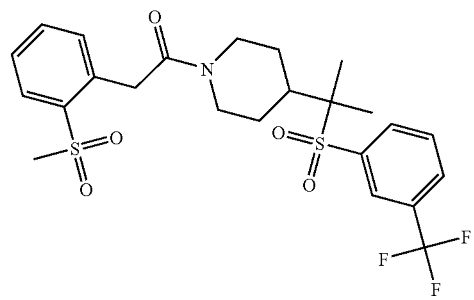 | 1-{[2-(methylsulfonyl)phenyl]acetyl}-4-(1-methyl-1-{[3-(trifluoromethyl)phenyl]sulfonyl}ethyl)piperidine | 532 |
| 136 | 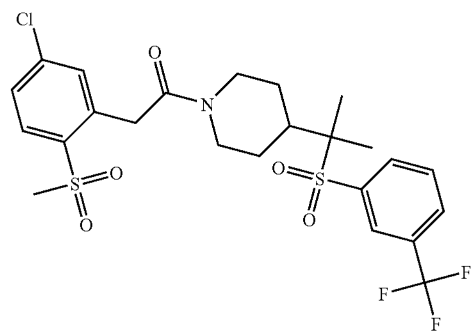 | 1-{[5-chloro-2-(methylsulfonyl)phenyl]acetyl}-4-(1-methyl-1-{[3-(trifluoromethyl)phenyl]sulfonyl}ethyl)piperidine | 567 |
| 137 | 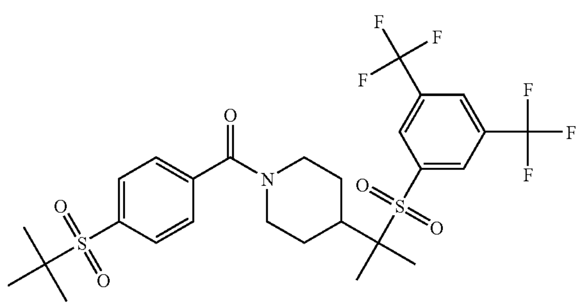 | 4-(1-{[3,5-bis(trifluoromethyl)phenyl]sulfonyl}-1-methylethyl)-1-[4-(tert-butylsulfonyl)benzoyl]piperidine | 628 |
| 138 | 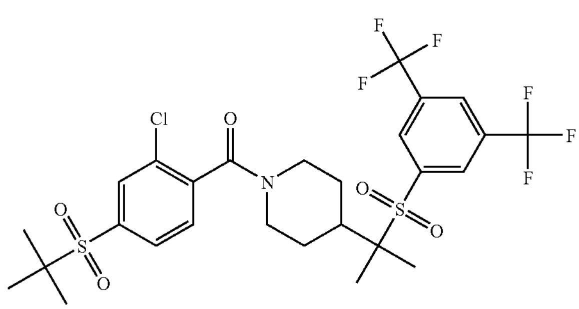 | 4-(1-{[3,5-bis(trifluoromethyl)phenyl]sulfonyl}-1-methylethyl)-1-[4-(tert-butylsulfonyl)-2-chlorobenzoyl]piperidine | 663 |
| 139 | 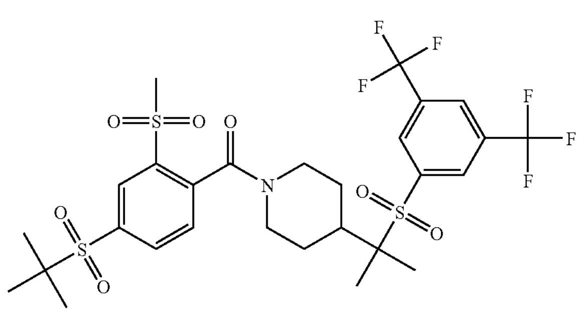 | 4-(1-{[3,5-bis(trifluoromethyl)phenyl]sulfonyl}-1-methylethyl)-1-[4-(tert-butylsulfonyl)-2-(methylsulfonyl)benzoyl]piperidine | 706 |

TABLE 3-continued

| EXAMPLE # | STRUCTURE | CHEMICAL NAME | MASS SPECTRAL DATA m/e (M + H) |
|---|---|---|---|
| 140 | 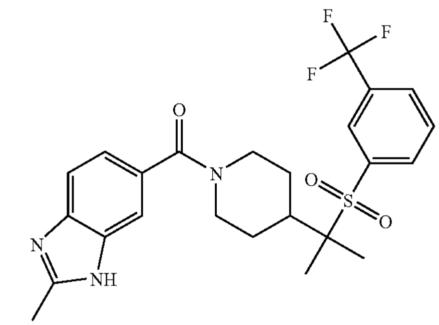 | 2-methyl-6-{[4-(1-methyl-1-{[3-(trifluoromethyl)phenyl]sulfonyl}ethyl)piperidin-1-yl]carbonyl}-1H-benzimidazole | 494 |
| 141 | 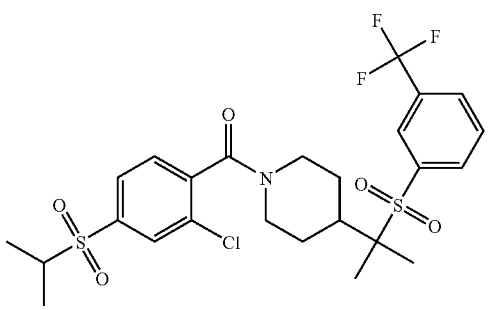 | 1-[2-chloro-4-(isopropylsulfonyl)benzoyl]-4-(1-methyl-1-{[3-(trifluoromethyl)phenyl]sulfonyl}ethyl)piperidine | 581 |
| 142 | 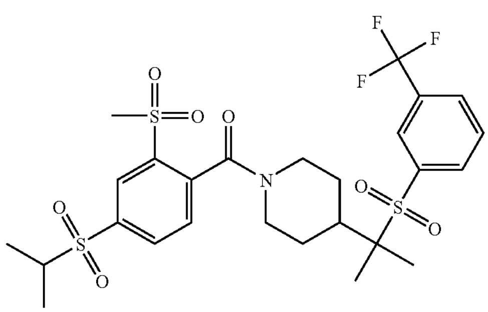 | 1-[4-(isopropylsulfonyl)-2-(methylsulfonyl)benzoyl]-4-(1-methyl-1-{[3-(trifluoromethyl)phenyl]sulfonyl}ethyl)piperidine | 624 |
| 143 | 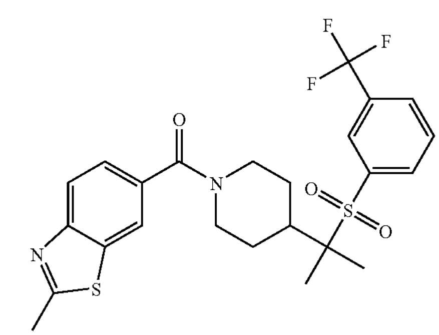 | 2-methyl-6-{[4-(1-methyl-1-{[3-(trifluoromethyl)phenyl]sulfonyl}ethyl)piperidin-1-yl]carbonyl}-1,3-benzothiazole | 511 |

TABLE 3-continued

| EXAMPLE # | STRUCTURE | CHEMICAL NAME | MASS SPECTRAL DATA m/e (M + H) |
|---|---|---|---|
| 144 | 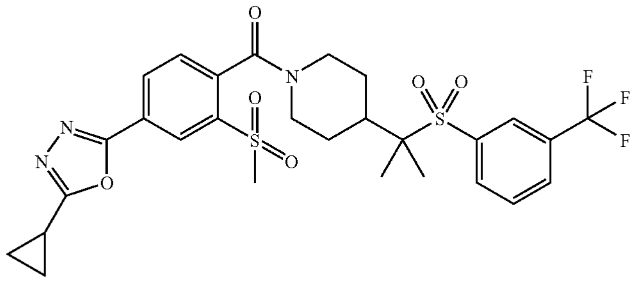 | 1-[4-(5-cyclopropyl-1,3,4-oxadiazol-2-yl)-2-(methylsulfonyl)benzoyl]-4-(1-methyl-1-{[3-(trifluoromethyl)phenyl]sulfonyl}ethyl)piperidine | 626 |
| 145 | 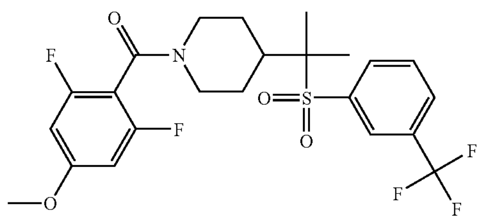 | 1-(2,6-difluoro-4-methoxybenzoyl)-4-(1-methyl-1-{[3-(trifluoromethyl)phenyl]sulfonyl}ethyl)piperidine | 506 |
| 146 | 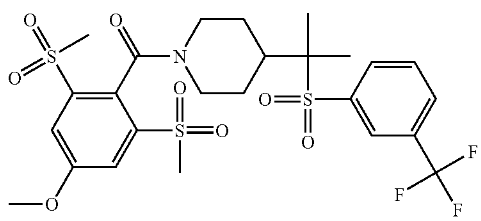 | 1-[4-methoxy-2,6-bis(methylsulfonyl)benzoyl]-4-(1-methyl-1-{[3-(trifluoromethyl)phenyl]sulfonyl}ethyl)piperidine | 626 |
| 147 | 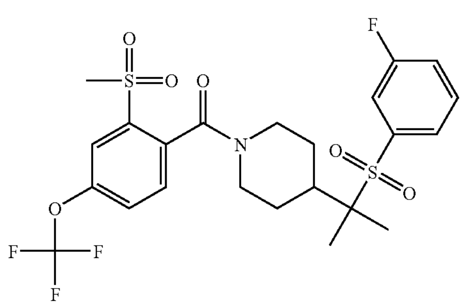 | 4-{1-[(3-fluorophenyl)sulfonyl]-1-methylethyl}-1-[2-(methylsulfonyl)-4-(trifluoromethoxy)benzoyl]piperidine | 552 |
| 148 | 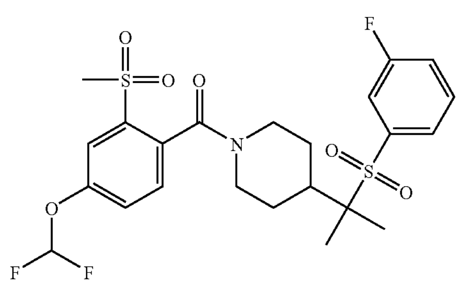 | 1-[4-(difluoromethoxy)-2-(methylsulfonyl)benzoyl]-4-{1-[(3-fluorophenyl)sulfonyl]-1-methylethyl}piperidine | 534 |

TABLE 3-continued

| EXAMPLE # | STRUCTURE | CHEMICAL NAME | MASS SPECTRAL DATA m/e (M + H) |
|---|---|---|---|
| 149 | 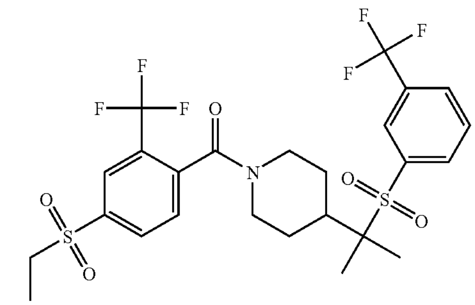 | 1-[4-(ethylsulfonyl)-2-(trifluoromethyl)benzoyl]-4-(1-methyl-1-{[3-(trifluoromethyl)phenyl]sulfonyl}ethyl)piperidine | 600 |
| 150 | 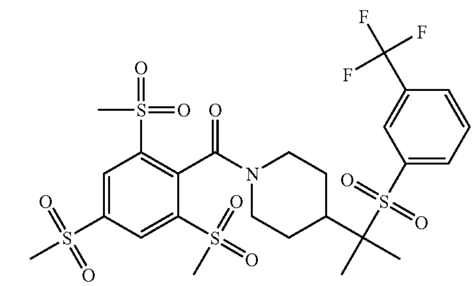 | 4-(1-methyl-1-{[3-(trifluoromethyl)phenyl]sulfonyl}ethyl)-1-[2,4,6-tris(methylsulfonyl)benzoyl]piperidine | 674 |
| 151 | 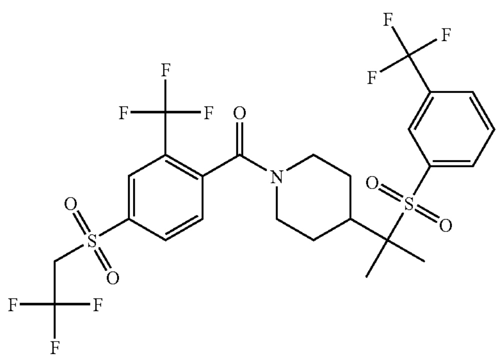 | 4-(1-methyl-1-{[3-(trifluoromethyl)phenyl]sulfonyl}ethyl)-1-[4-[(2,2,2-trifluoroethyl)sulfonyl]-2-(trifluoromethyl)benzoyl]piperidine | 654 |
| 152 | 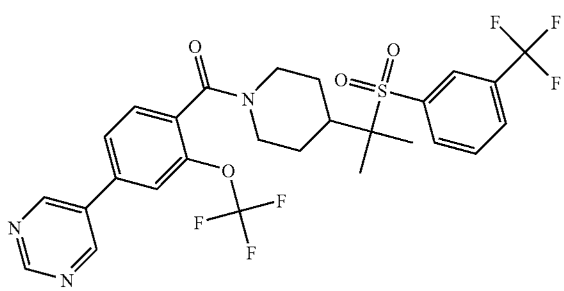 | 5-[4-{[4-(1-methyl-1-{[3-(trifluoromethyl)phenyl]sulfonyl}ethyl)piperidin-1-yl]carbonyl}-3-(trifluoromethoxy)phenyl]pyrimidine | 602 |
| 153 | 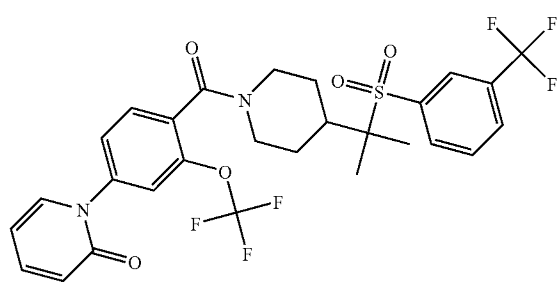 | 1-[4-{[4-(1-methyl-1-{[3-(trifluoromethyl)phenyl]sulfonyl}ethyl)piperid1-[4-{[4-(1-methyl-1-{[3-(trifluoromethyl)phenyl]sulfonyl}ethyl)piperidin-2(1H)-one | 617 |

TABLE 3-continued

| EXAMPLE # | STRUCTURE | CHEMICAL NAME | MASS SPECTRAL DATA m/e (M + H) |
|---|---|---|---|
| 154 | 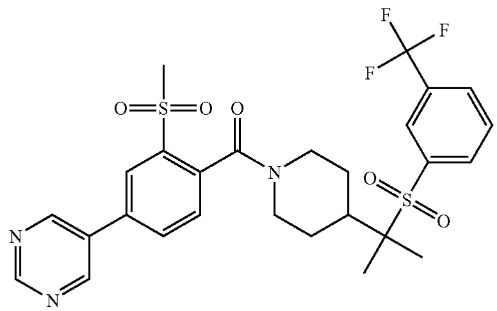 | 5-(3-(methylsulfonyl)-4-{[4-(1-methyl-1-{[3-(trifluoromethyl)phenyl]sulfonyl}ethyl)piperidin-1-yl]carbonyl}phenyl)pyrimidine | 596 |
| 155 | 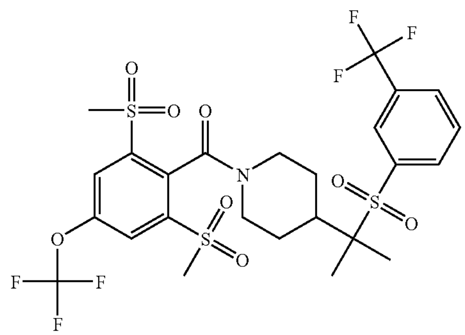 | 1-[2,6-bis(methylsulfonyl)-4-(trifluoromethoxy)benzoyl]-4-(1-methyl-1-{[3-(trifluoromethyl)phenyl]sulfonyl}ethyl)piperidine | 680 |
| 156 | 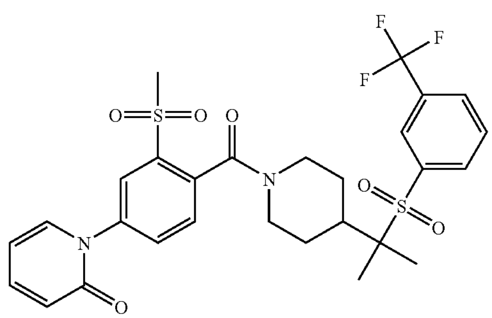 | 1-(3-(methylsulfonyl)-4-{[4-(1-methyl-1-{[3-(trifluoromethyl)phenyl]sulfonyl}ethyl)piperidin-1-yl]carbonyl}phenyl)pyridin-2(1H)-one | 611 |
| 157 | 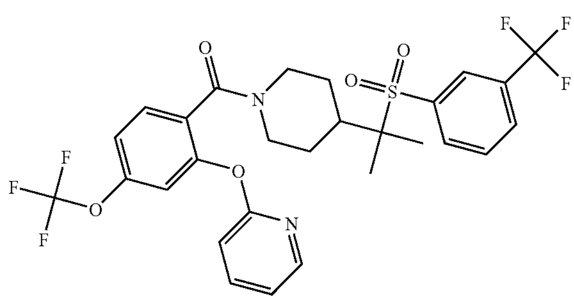 | 2-[2-{[4-(1-methyl-1-{[3-(trifluoromethyl)phenyl]sulfonyl}ethyl)piperidin-1-yl]carbonyl}-5-(trifluoromethoxy)phenoxy]pyridine | 617 |
| 158 | 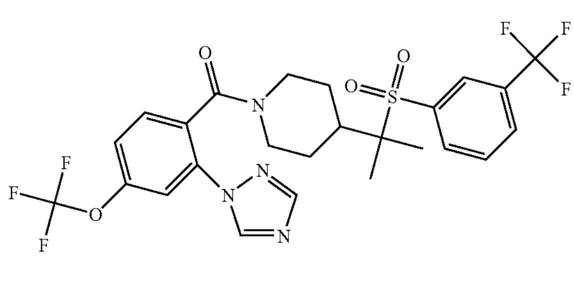 | 4-(1-methyl-1-{[3-(trifluoromethyl)phenyl]sulfonyl}ethyl)-1-[2-(1H-1,2,4-triazol-1-yl)-4-(trifluoromethoxy)benzoyl]piperidine | 591 |

TABLE 3-continued

| EXAMPLE # | STRUCTURE | CHEMICAL NAME | MASS SPECTRAL DATA m/e (M + H) |
|---|---|---|---|
| 159 | 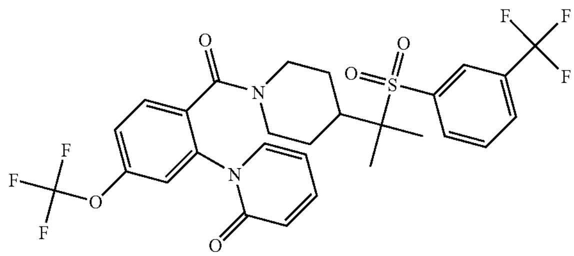 | 1-[2-{[4-(1-methyl-1-{[3-(trifluoromethyl)phenyl]sulfonyl}ethyl)piperidin-1-yl]carbonyl}-5-(trifluoromethoxy)phenyl]pyridin-2(1H)-one | 617 |
| 160 | 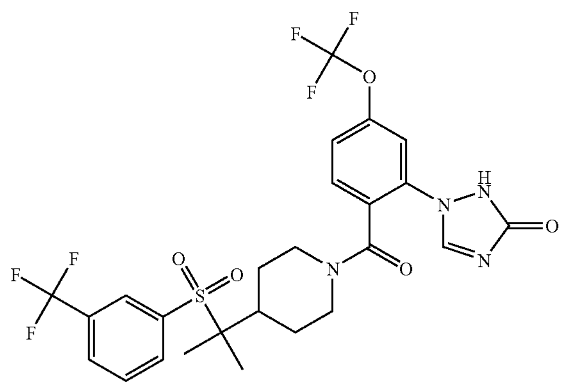 | 1-[2-{[4-(1-methyl-1-{[3-(trifluoromethyl)phenyl]sulfonyl}ethyl)piperidin-1-yl]carbonyl}-5-(trifluoromethoxy)phenyl]-1,2-dihydro-3H-1,2,4-triazol-3-one | 607 |
| 161 | 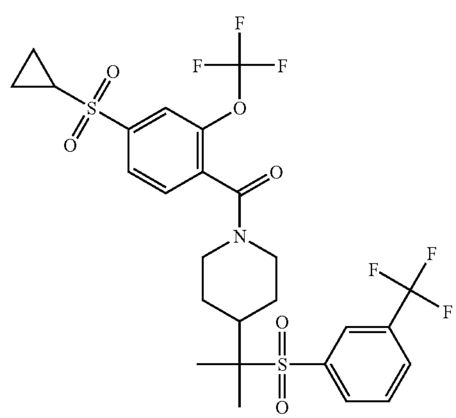 | 1-[4-(cyclopropylsulfonyl)-2-(trifluoromethoxy)benzoyl]-4-(1-methyl-1-{[3-(trifluoromethyl)phenyl]sulfonyl}ethyl)piperidine | 628 |
| 162 | 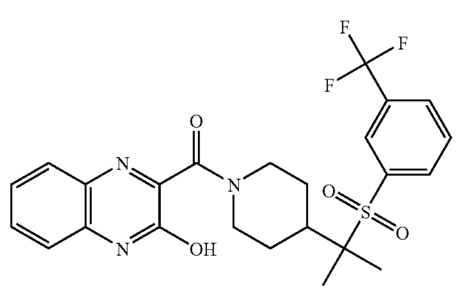 | 3-{[4-(1-methyl-1-{[3-(trifluoromethyl)phenyl]sulfonyl}ethyl)piperidin-1-yl]carbonyl}quinoxalin-2-ol | 508 |

TABLE 3-continued

| EXAMPLE # | STRUCTURE | CHEMICAL NAME | MASS SPECTRAL DATA m/e (M + H) |
|---|---|---|---|
| 163 | 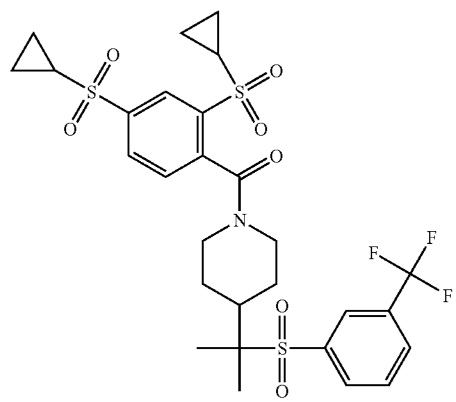 | 1-[2,4-bis(cyclopropylsulfonyl)benzoyl]-4-(1-methyl-1-{[3-(trifluoromethyl)phenyl]sulfonyl}ethyl)piperidine | 648 |
| 164 | 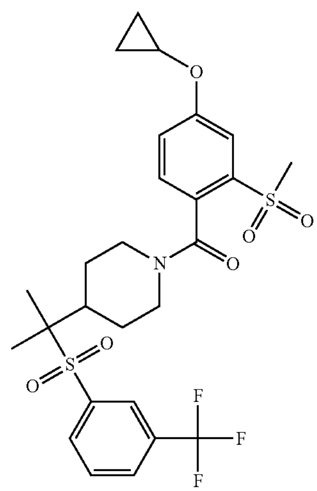 | 1-[4-(cyclopropyloxy)-2-(methylsulfonyl)benzoyl]-4-(1-methyl-1-{[3-(trifluoromethyl)phenyl]sulfonyl}ethyl)piperidine | 574 |
| 165 | 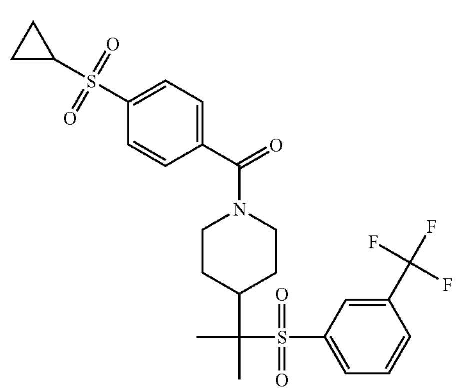 | 1-[4-(cyclopropylsulfonyl)benzoyl]-4-(1-methyl-1-{[3-(trifluoromethyl)phenyl]sulfonyl}ethyl)piperidine | 544 |

TABLE 3-continued

| EXAMPLE # | STRUCTURE | CHEMICAL NAME | MASS SPECTRAL DATA m/e (M + H) |
|---|---|---|---|
| 166 | 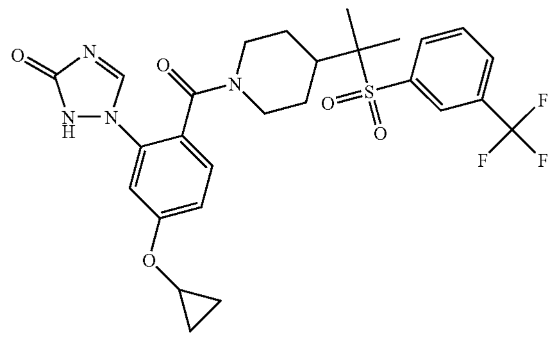 | 1-(5-(cyclopropyloxy)-2-{[4-(1-methyl-1-{[3-(trifluoromethyl)phenyl]sulfonyl}ethyl)piperidin-1-yl]carbonyl}phenyl)-1,2-dihydro-3H-1,2,4-triazol-3-one | 579 |
| 167 | 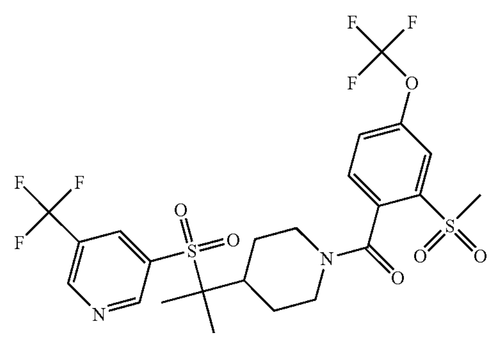 | 3-[(1-methyl-1-{1-[2-(methylsulfonyl)-4-(trifluoromethoxy)benzoyl]piperidin-4-yl}ethyl)sulfonyl]-5-(trifluoromethyl)pyridine | 603 |
| 168 | 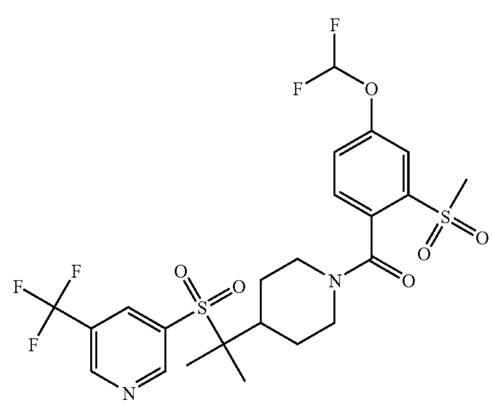 | 3-[(1-{1-{4-(difluoromethoxy)-2-(methylsulfonyl)benzoyl]piperidin-4-yl}-1-methylethyl)sulfonyl]-5-(trifluoromethyl)pyridine | 585 |
| 169 | 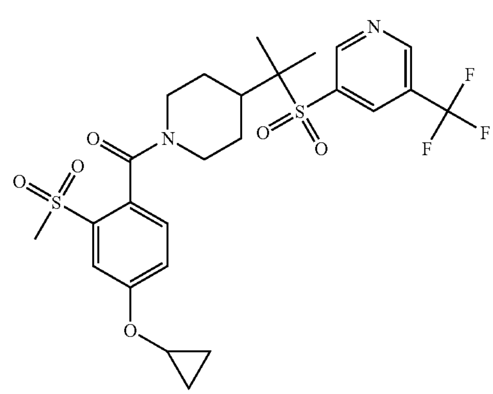 | 3-[(1-{1-[4-(cyclopropyloxy)-2-(methylsulfonyl)benzoyl]piperidin-4-yl}-1-methylethyl)sulfonyl]-5-(trifluoromethyl)pyridine | 575 |

TABLE 3-continued

| EXAMPLE # | STRUCTURE | CHEMICAL NAME | MASS SPECTRAL DATA m/e (M + H) |
|---|---|---|---|
| 170 | 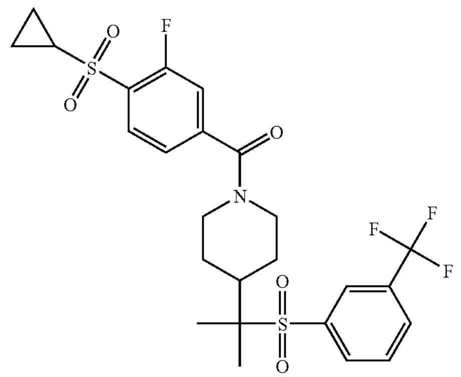 | 1-[4-(cyclopropylsulfonyl)-3-fluorobenzoyl]-4-(1-methyl-1-{[3-(trifluoromethyl)phenyl]sulfonyl}ethyl)piperidine | 562 |
| 171 | 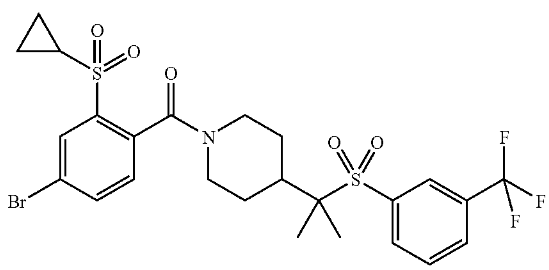 | 1-[4-bromo-2-(cyclopropylsulfonyl)benzoyl]-4-(1-methyl-1-{[3-(trifluoromethyl)phenyl]sulfonyl}ethyl)piperidine | 623 |
| 172 | 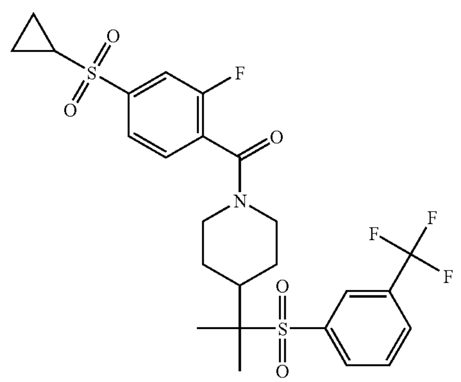 | 1-[4-(cyclopropylsulfonyl)-2-fluorobenzoyl]-4-(1-methyl-1-{[3-(trifluoromethyl)phenyl]sulfonyl}ethyl)piperidine | 562 |
| 173 | 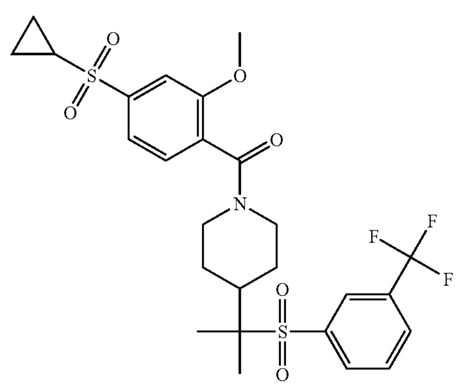 | 1-[4-(cyclopropylsulfonyl)-2-methoxybenzoyl]-4-(1-methyl-1-{[3-(trifluoromethyl)phenyl]sulfonyl}ethyl)piperidine | 574 |

TABLE 3-continued

| EXAMPLE # | STRUCTURE | CHEMICAL NAME | MASS SPECTRAL DATA m/e (M + H) |
|---|---|---|---|
| 174 | 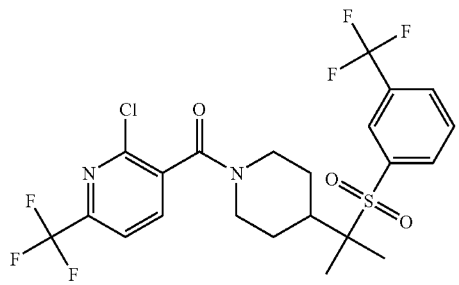 | 2-chloro-3-{[4-(1-methyl-1-{[3-(trifluoromethyl)phenyl]sulfonyl}ethyl)piperidin-1-yl]carbonyl}-6-(trifluoromethyl)pyridine | 543 |
| 175 | 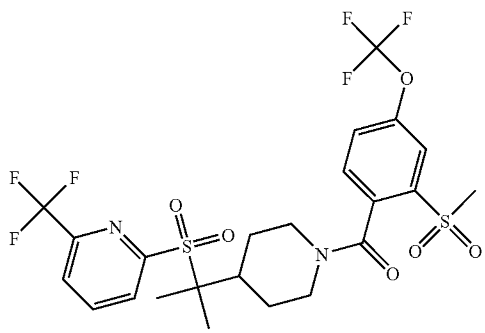 | 2-[(1-methyl-1-{1-[2-(methylsulfonyl)-4-(trifluoromethoxy)benzoyl]piperidin-4-yl}ethyl)sulfonyl]-6-(trifluoromethyl)pyridine | 603 |
| 176 | 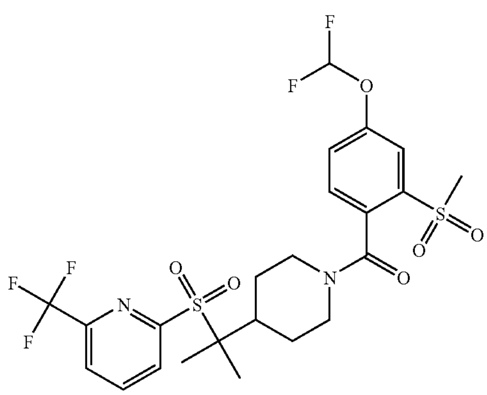 | 2-[(1-{1-[4-(difluoromethoxy)-2-(methylsulfonyl)benzoyl]piperidin-4-yl}-1-methylethyl)sulfonyl]-6-(trifluoromethyl)pyridine | 585 |
| 177 | 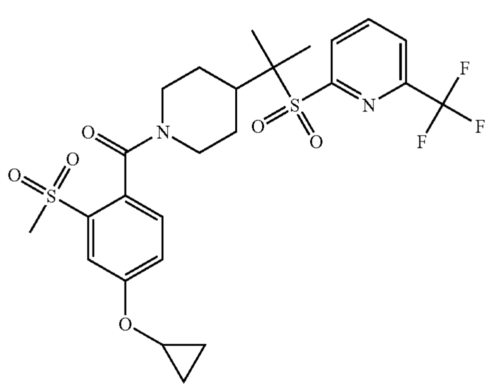 | 2-[(1-{1-[4-(cyclopropyloxy)-2-(methylsulfonyl)benzoyl]piperidin-4-yl}-1-methylethyl)sulfonyl]-6-(trifluoromethyl)pyridine | 575 |

TABLE 3-continued

| EXAMPLE # | STRUCTURE | CHEMICAL NAME | MASS SPECTRAL DATA m/e (M + H) |
|---|---|---|---|
| 178 | 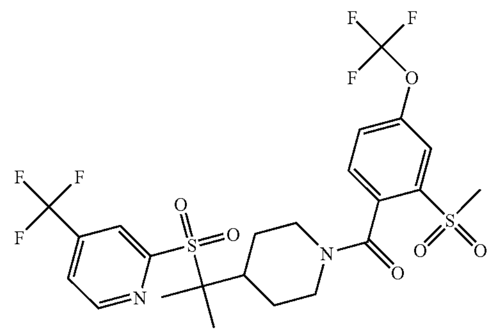 | 2-[(1-methyl-1-{1-[2-(methylsulfonyl)-4-(trifluoromethoxy)benzoyl]piperidin-4-yl}ethyl)sulfonyl]-4-(trifluoromethyl)pyridine | 603 |
| 179 | 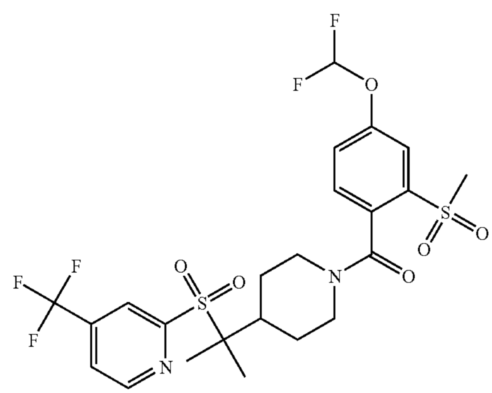 | 2-[(1-{1-[4-(difluoromethoxy)-2-(methylsulfonyl)benzoyl]piperidin-4-yl}-1-methylethyl)sulfonyl]-4-(trifluoromethyl)pyridine | 585 |
| 180 | 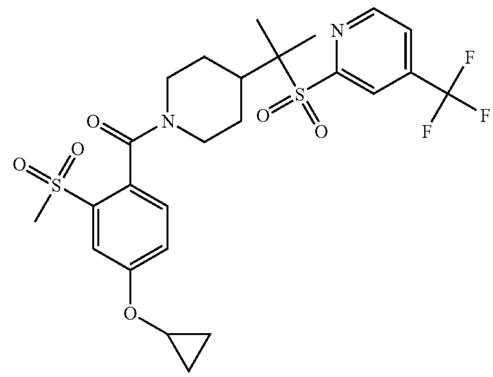 | 2-[(1-{1-[4-(cyclopropyloxy)-2-(methylsulfonyl)benzoyl]piperidin-4-yl}-1-methylethyl)sulfonyl]-4-(trifluoromethyl)pyridine | 575 |
| 181 | 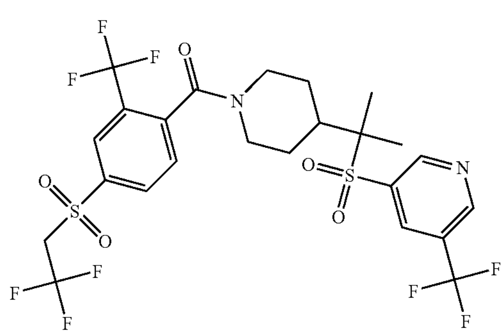 | 3-[(1-methyl-1-{1-[4-[(2,2,2-trifluoroethyl)sulfonyl]-2-(trifluoromethyl)benzoyl]piperidin-4-yl}ethyl)sulfonyl]-5-(trifluoromethyl)pyridine | 655 |

TABLE 3-continued

| EXAMPLE # | STRUCTURE | CHEMICAL NAME | MASS SPECTRAL DATA m/e (M + H) |
|---|---|---|---|
| 182 | 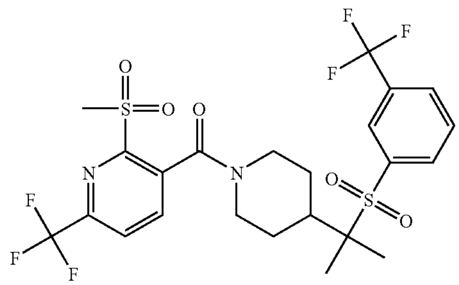 | 2-(methylsulfonyl)-3-{[4-(1-methyl-1-{[3-(trifluoromethyl)phenyl]sulfonyl}ethyl)piperidin-1-yl]carbonyl}-6-(trifluoromethyl)pyridine | 587 |
| 183 | 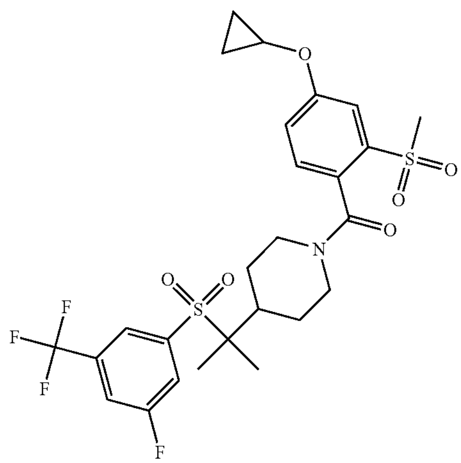 | 1-[4-(cyclopropyloxy)-2-(methylsulfonyl)benzoyl]-4-(1-{[3-fluoro-5-(trifluoromethyl)phenyl]sulfonyl}-1-methylethyl)piperidine | 592 |
| 184 | 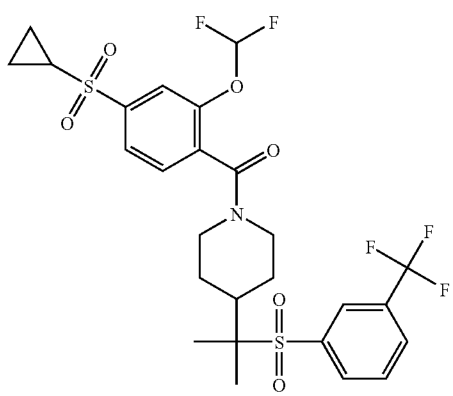 | 1-[4-(cyclopropylsulfonyl)-2-(difluoromethoxy)benzoyl]-4-(1-methyl-1-{[3-(trifluoromethyl)phenyl]sulfonyl}ethyl)piperidine | 610 |
| 185 | 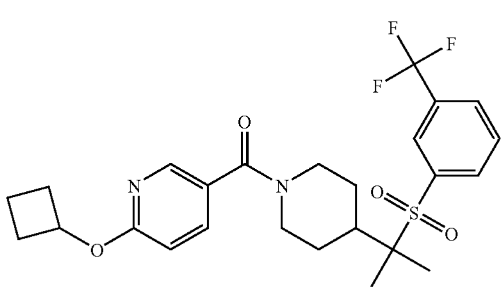 | 2-(cyclobutyloxy)-5-{[4-(1-methyl-1-{[3-(trifluoromethyl)phenyl]sulfonyl}ethyl)piperidin-1-yl]carbonyl}pyridine | 511 |

TABLE 3-continued

| EXAMPLE # | STRUCTURE | CHEMICAL NAME | MASS SPECTRAL DATA m/e (M + H) |
|---|---|---|---|
| 186 | 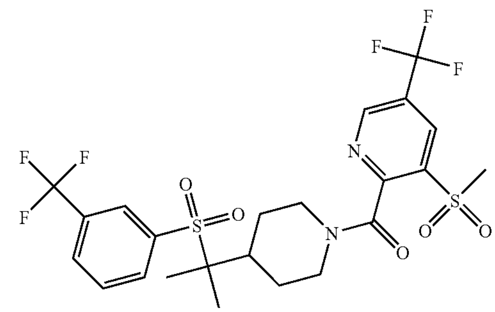 | 3-(methylsulfonyl)-2-{[4-(1-methyl-1-{[3-(trifluoromethyl)phenyl]sulfonyl}ethyl)piperidin-1-yl]carbonyl}-5-(trifluoromethyl)pyridine | 587 |
| 187 | 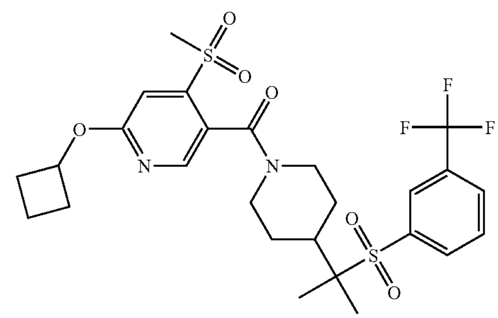 | 2-(cyclobutyloxy)-4-(methylsulfonyl)-5-{[4-(1-methyl-1-{[3-(trifluoromethyl)phenyl]sulfonyl}ethyl)piperidin-1-yl]carbonyl}pyridine | 589 |
| 188 | 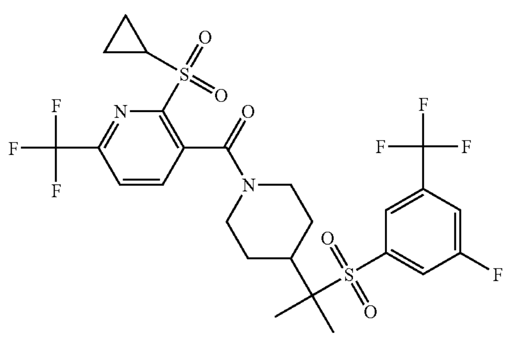 | 2-(cyclopropylsulfonyl)-3-{[4-(1-{[3-fluoro-5-(trifluoromethyl)phenyl]sulfonyl}-1-methylethyl)piperidin-1-yl]carbonyl}-6-(trifluoromethyl)pyridine | 631 |
| 189 | 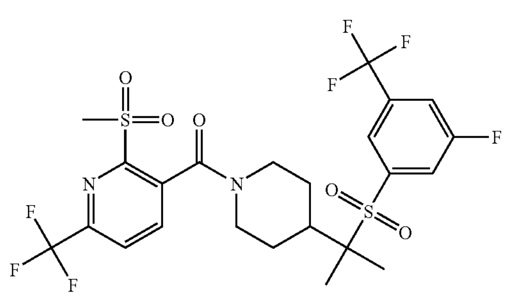 | 3-{[4-(1-{[3-fluoro-5-(trifluoromethyl)phenyl]sulfonyl}-1-methylethyl)piperidin-1-yl]carbonyl}-2-(methylsulfonyl)-6-(trifluoromethyl)pyridine | 605 |

TABLE 3-continued

| EXAMPLE # | STRUCTURE | CHEMICAL NAME | MASS SPECTRAL DATA m/e (M + H) |
|---|---|---|---|
| 190 | 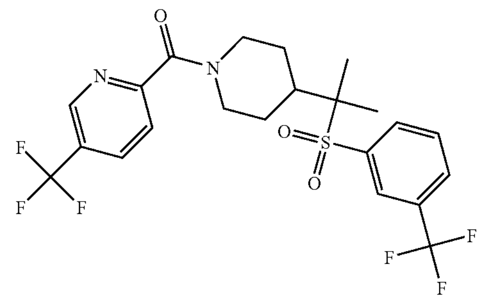 | 2-{[4-(1-methyl-1-{[3-(trifluoromethyl)phenyl]sulfonyl}ethyl)piperidin-1-yl]carbonyl}-5-(trifluoromethyl)pyridine | 509 |
| 191 | 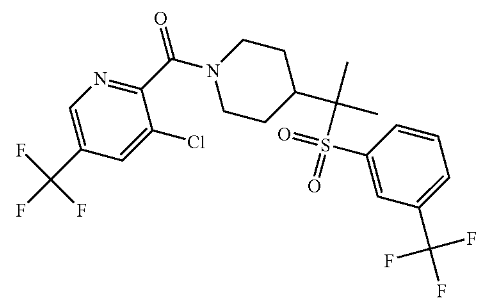 | 3-chloro-2-{[4-(1-methyl-1-{[3-(trifluoromethyl)phenyl]sulfonyl}ethyl)piperidin-1-yl]carbonyl}-5-(trifluoromethyl)pyridine | 543 |
| 192 | 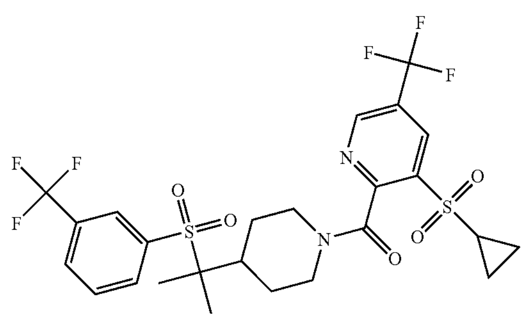 | 3-(cyclopropylsulfonyl)-2-{[4-(1-methyl-1-{[3-(trifluoromethyl)phenyl]sulfonyl}ethyl)piperidin-1-yl]carbonyl}-5-(trifluoromethyl)pyridine | 613 |
| 193 | 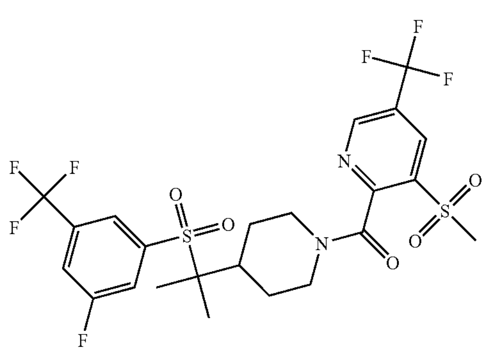 | 2-{[4-(1-{[3-fluoro-5-(trifluoromethyl)phenyl]sulfonyl}-1-methylethyl)piperidin-1-yl]carbonyl}-3-(methylsulfonyl)-5-(trifluoromethyl)pyridine | 605 |

TABLE 3-continued

| EXAMPLE # | STRUCTURE | CHEMICAL NAME | MASS SPECTRAL DATA m/e (M + H) |
|---|---|---|---|
| 194 | 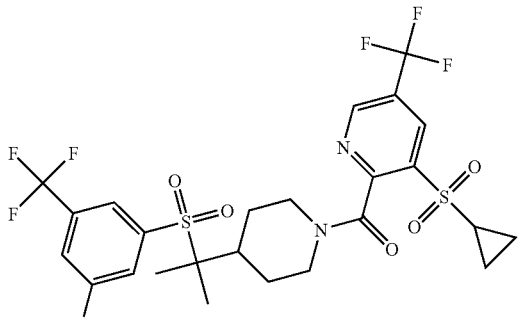 | | 631 |
| 195 | 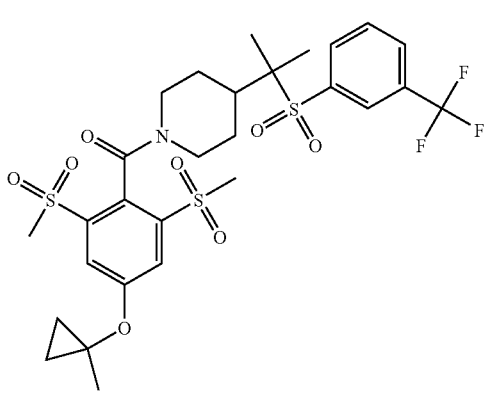 | 1-[4-[(1-methylcyclopropyl)oxy]-2,6-bis(methylsulfonyl)benzoyl]-4-(1-methyl-1-{[3-(trifluoromethyl)phenyl]sulfonyl}ethyl)piperidine | 666 |
| 196 | 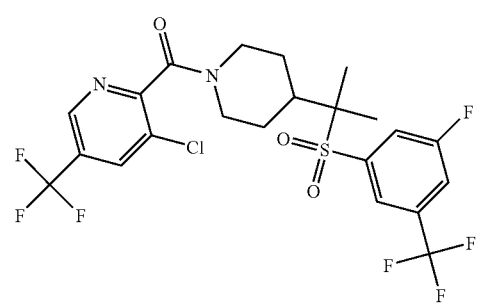 | 3-chloro-2-{[4-(1-{[3-fluoro-5-(trifluoromethyl)phenyl]sulfonyl}-1-methylethyl)piperidin-1-yl]carbonyl}-5-(trifluoromethyl)pyridine | 561 |
| 197 | 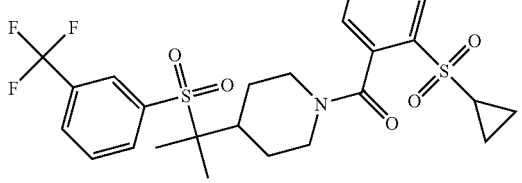 | 1-[2-(cyclopropylsulfonyl)-4-(trifluoromethoxy)benzoyl]-4-(1-methyl-1-{[3-(trifluoromethyl)phenyl]sulfonyl}ethyl)piperidine | 528 |

TABLE 3-continued

| EXAMPLE # | STRUCTURE | CHEMICAL NAME | MASS SPECTRAL DATA m/e (M + H) |
|---|---|---|---|
| 198 | 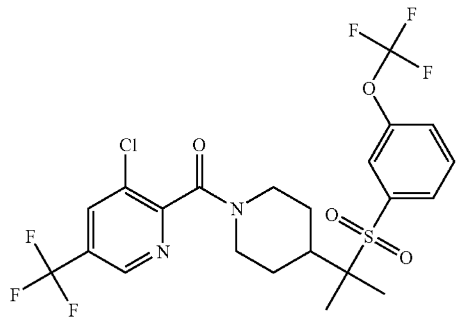 | 3-chloro-2-{[4-(1-methyl-1-{[3-(trifluoromethoxy)phenyl]sulfonyl}ethyl) piperidin-1-yl]carbonyl}-5-(trifluoromethyl)pyridine | 559 |
| 199 | 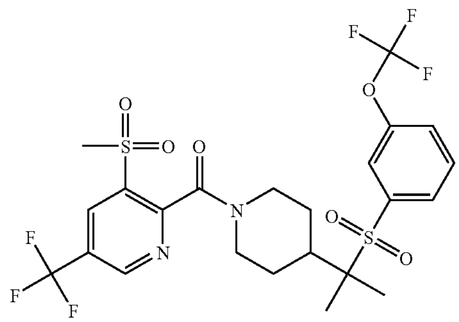 | 3-(methylsulfonyl)-2-{[4-(1-methyl-1-{[3-(trifluoromethoxy)phenyl]sulfonyl}ethyl)piperidin-1-yl]carbonyl}-5-(trifluoromethyl)pyridine | 603 |
| 200 | 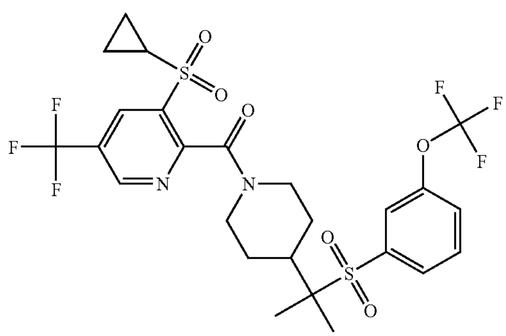 | 3-(cyclopropylsulfonyl)-2-{[4-(1-methyl-1-{[3-(trifluoromethoxy)phenyl]sulfonyl}ethyl)piperidin-1-yl]carbonyl}-5-(trifluoromethyl)pyridine | 629 |
| 201 | 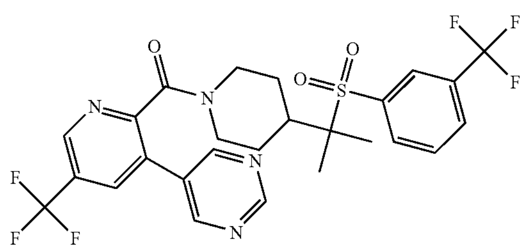 | 5-[2-{[4-(1-methyl-1-{[3-(trifluoromethyl)phenyl]sulfonyl}ethyl)piperidin-1-yl]carbonyl}-5-(trifluoromethyl)pyridin-3-yl]pyrimidine | 587 |
| 202 | 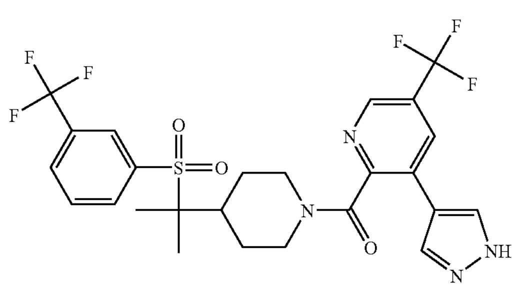 | 2-{[4-(1-methyl-1-{[3-(trifluoromethyl)phenyl]sulfonyl}ethyl)piperidin-1-yl]carbonyl}-3-(1H-pyrazol-4-yl)-5-(trifluoromethyl)pyridine | 575 |

TABLE 3-continued

| EXAMPLE # | STRUCTURE | CHEMICAL NAME | MASS SPECTRAL DATA m/e (M + H) |
|---|---|---|---|
| 203 | 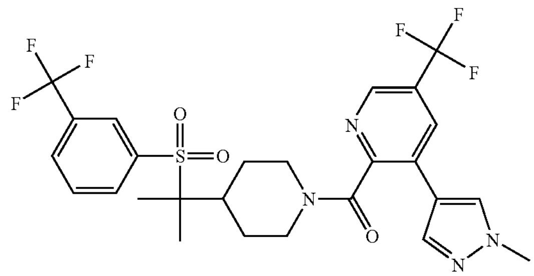 | 3-(1-methyl-1H-pyrazol-4-yl)-2-{[4-(1-methyl-1-{[3-(trifluoromethyl)phenyl]sulfonyl}ethyl)piperidin-1-yl]carbonyl}-5-(trifluoromethyl)pyridine | 589 |
| 204 | 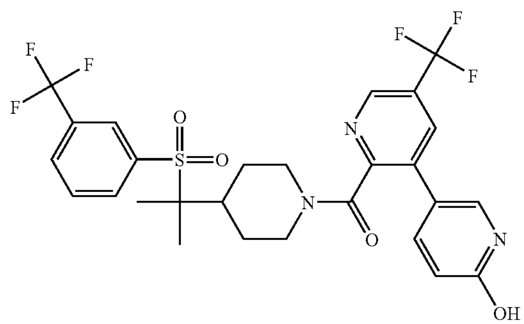 | 2'-{[4-(1-methyl-1-{[3-(trifluoromethyl)phenyl]sulfonyl}ethyl)piperidin-1-yl]carbonyl}-5'-(trifluoromethyl)-3,3'-bipyridin-6-ol | 602 |
| 205 | 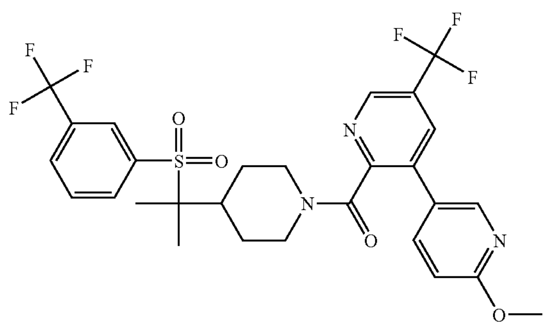 | 6'-methoxy-2-{[4-(1-methyl-1-{[3-(trifluoromethyl)phenyl]sulfonyl}ethyl)piperidin-1-yl]carbonyl}-5-(trifluoromethyl)-3,3'-bipyridine | 616 |
| 206 | 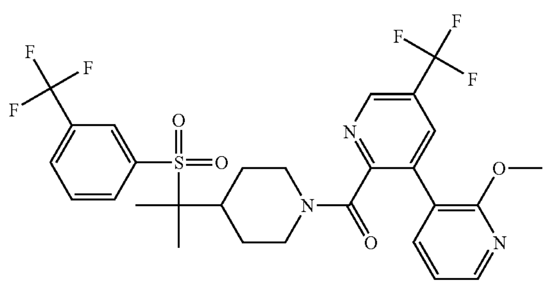 | 2'-methoxy-2-{[4-(1-methyl-1-{[3-(trifluoromethyl)phenyl]sulfonyl}ethyl)piperidin-1-yl]carbonyl}-5-(trifluoromethyl)-3,3'-bipyridine | 616 |
| 207 | 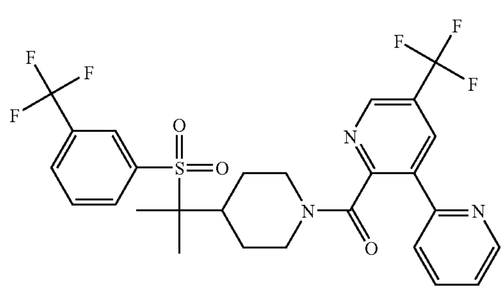 | 2'-{[4-(1-methyl-1-{[3-(trifluoromethyl)phenyl]sulfonyl}ethyl)piperidin-1-yl]carbonyl}-5'-(trifluoromethyl)-2,3'-bipyridine | 586 |

TABLE 3-continued

| EXAMPLE # | CHEMICAL NAME | MASS SPECTRAL DATA m/e (M + H) |
|---|---|---|
| 208 | 2-{[4-(1-methyl-1-{[3-(trifluoromethyl)phenyl]sulfonyl}ethyl)piperidin-1-yl]carbonyl}-5-(trifluoromethyl)-3,4'-bipyridine | 586 |
| 209 | 6-methyl-2'-{[4-(1-methyl-1-{[3-(trifluoromethyl)phenyl]sulfonyl}ethyl)piperidin-1-yl]carbonyl}-5'-(trifluoromethyl)-2,3'-bipyridine | 600 |
| 210 | 2-{[4-(1-methyl-1-{[3-(trifluoromethyl)phenyl]sulfonyl}ethyl)piperidin-1-yl]carbonyl}-5-(trifluoromethyl)nicotinonitrile | 534 |
| 211 | 3-(ethylsulfonyl)-2-{[4-(1-methyl-1-{[3-(trifluoromethyl)phenyl]sulfonyl}ethyl)piperidin-1-yl]carbonyl}-5-(trifluoromethyl)pyridine | 601 |
| 212 | 2-{[4-(1-{[3-(difluoromethoxy)phenyl]sulfonyl}-1-methylethyl)piperidin-1-yl]carbonyl}-3-(ethylsulfonyl)-5-(trifluoromethyl)pyridine | 599 |

TABLE 3-continued

| EXAMPLE # | STRUCTURE | CHEMICAL NAME | MASS SPECTRAL DATA m/e (M + H) |
|---|---|---|---|
| 213 | 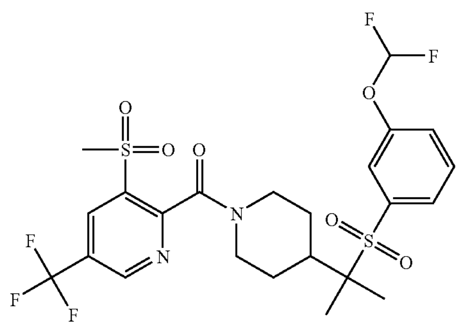 | 2-{[4-(1-{[3-(difluoromethoxy)phenyl]sulfonyl}-1-methylethyl)piperidin-1-yl]carbonyl}-3-(methylsulfonyl)-5-(trifluoromethyl)pyridine | 585 |
| 214 | 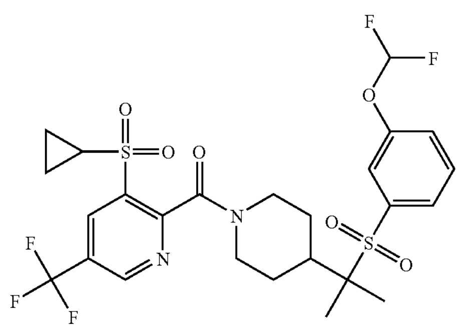 | 3-(cyclopropylsulfonyl)-2-{[4-(1-{[3-(difluoromethoxy)phenyl]sulfonyl}-1-methylethyl)piperidin-1-yl]carbonyl}-5-(trifluoromethyl)pyridine | 611 |

TABLE 4

| EXAMPLE # | STRUCTURE | CHEMICAL NAME | MASS SPECTRAL DATA m/e (M + H) |
|---|---|---|---|
| 215 | 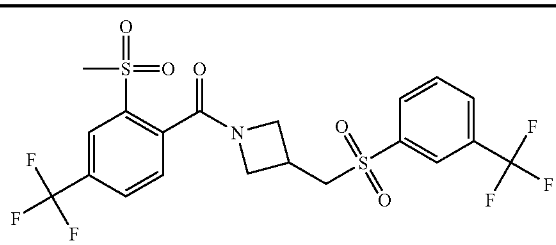 | 1-[2-(methylsulfonyl)-4-(trifluoromethyl)benzoyl]-3-({[3-(trifluoromethyl)phenyl]sulfonyl}methyl)azetidine | 530 |
| 216 | 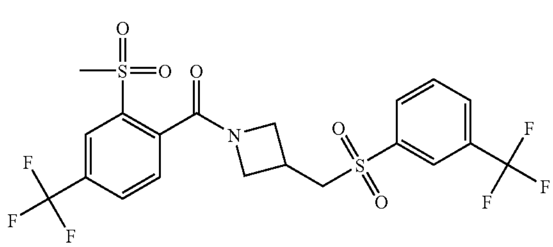 | 1-[2-(methylsulfonyl)-4-(trifluoromethyl)benzoyl]-3-({[3-(trifluoromethyl)phenyl]sulfonyl}methyl)azetidine | 496 |

TABLE 4-continued

| EXAMPLE # | STRUCTURE | CHEMICAL NAME | MASS SPECTRAL DATA m/e (M + H) |
|---|---|---|---|
| 217 | 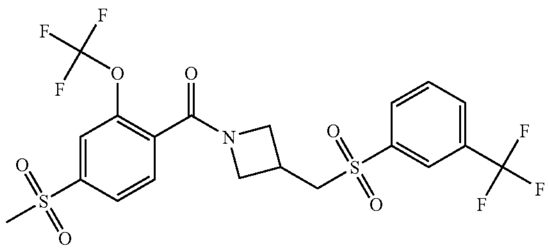 | 1-[4-(methylsulfonyl)-2-(trifluoromethoxy)benzoyl]-3-({[3-(trifluoromethyl)phenyl]sulfonyl}methyl)azetidine | 546 |
| 218 | 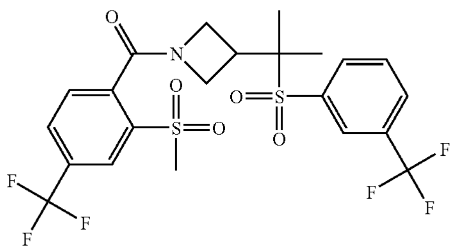 | 1-[2-(methylsulfonyl)-4-(trifluoromethyl)benzoyl]-3-(1-methyl-1-{[3-(trifluoromethyl)phenyl]sulfonyl}ethyl)azetidine | 558 |
| 219 | 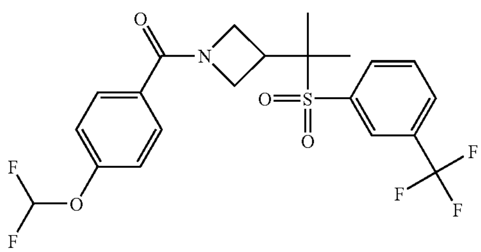 | 1-[4-(difluoromethoxy)benzoyl]-3-(1-methyl-1-{[3-(trifluoromethyl)phenyl]sulfonyl}ethyl)azetidine | 478 |
| 220 | 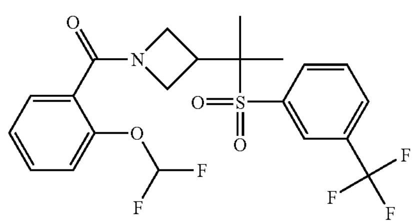 | 1-[2-(difluoromethoxy)benzoyl]-3-(1-methyl-1-{[3-(trifluoromethyl)phenyl]sulfonyl}ethyl)azetidine | 478 |
| 221 | 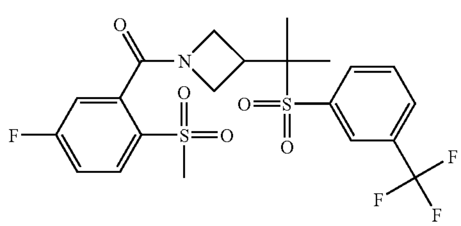 | 1-[5-fluoro-2-(methylsulfonyl)benzoyl]-3-(1-methyl-1-{[3-(trifluoromethyl)phenyl]sulfonyl}ethyl)azetidine | 508 |
| 222 | 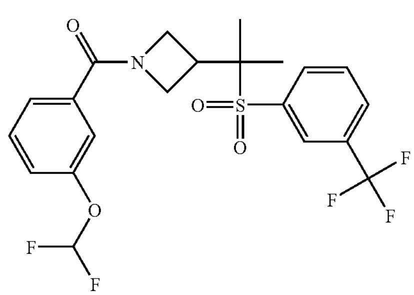 | 1-[3-(difluoromethoxy)benzoyl]-3-(1-methyl-1-{[3-(trifluoromethyl)phenyl]sulfonyl}ethyl)azetidine | 478 |

TABLE 4-continued

| EXAMPLE # | STRUCTURE | CHEMICAL NAME | MASS SPECTRAL DATA m/e (M + H) |
|---|---|---|---|
| 223 | 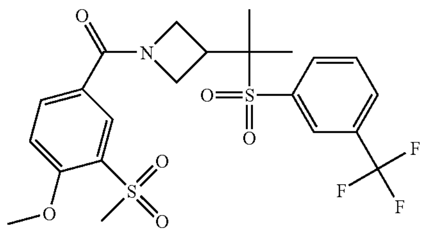 | 1-[4-methoxy-3-(methylsulfonyl)benzoyl]-3-(1-methyl-1-{[3-(trifluoromethyl)phenyl]sulfonyl}ethyl) azetidine | 520 |
| 224 | 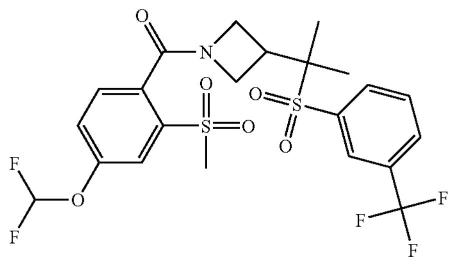 | 1-[4-(difluoromethoxy)-2-(methylsulfonyl)benzoyl]-3-(1-methyl-1-{[3-(trifluoromethyl)phenyl]sulfonyl}ethyl) azetidine | 556 |
| 225 | 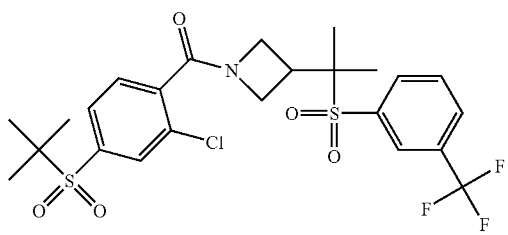 | 1-[4-(tert-butylsulfonyl)-2-chlorobenzoyl]-3-(1-methyl-1-{[3-(trifluoromethyl)phenyl]sulfonyl}ethyl) azetidine | 567 |
| 226 | 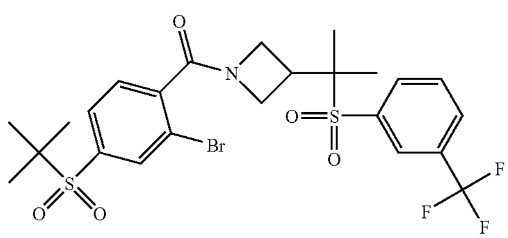 | 1-[2-bromo-4-(tert-butylsulfonyl)benzoyl]-3-(1-methyl-1-{[3-(trifluoromethyl)phenyl]sulfonyl}ethyl) azetidine | 611 |
| 227 | 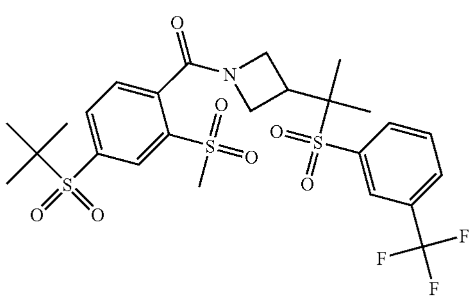 | 1-[4-(tert-butylsulfonyl)-2-(methylsulfonyl)benzoyl]-3-(1-methyl-1-{[3-(trifluoromethyl)phenyl]sulfonyl}ethyl) azetidine | 610 |
| 228 | 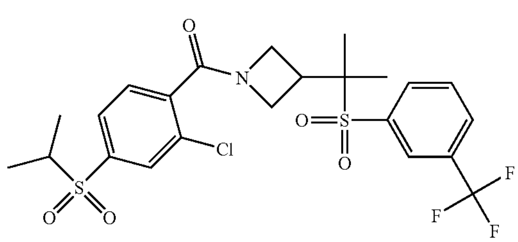 | 1-[2-chloro-4-(isopropylsulfonyl)benzoyl]-3-(1-methyl-1-{[3-(trifluoromethyl)phenyl]sulfonyl}ethyl) azetidine | 553 |

TABLE 4-continued

| EXAMPLE # | STRUCTURE | CHEMICAL NAME | MASS SPECTRAL DATA m/e (M + H) |
|---|---|---|---|
| 229 | 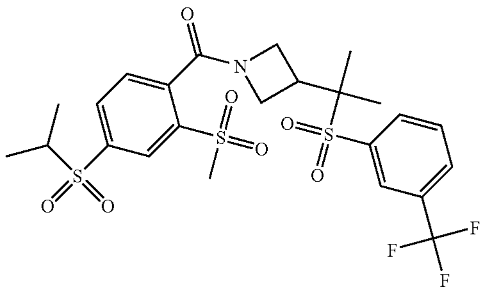 | 1-[4-(isopropylsulfonyl)-2-(methylsulfonyl)benzoyl]-3-(1-methyl-1-{[3-(trifluoromethyl)phenyl]sulfonyl}ethyl)azetidine | 596 |
| 230 | 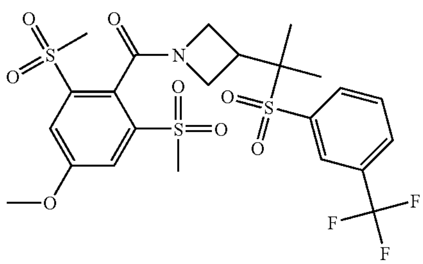 | 1-[4-methoxy-2,6-bis(methylsulfonyl)benzoyl]-3-(1-methyl-1-{[3-(trifluoromethyl)phenyl]sulfonyl}ethyl)azetidine | 598 |
| 231 | 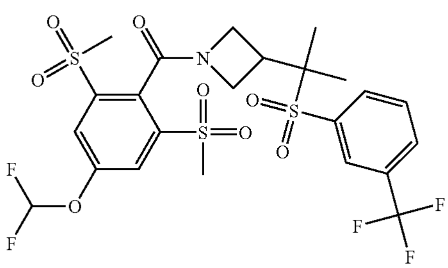 | 1-[4-(difluoromethoxy)-2,6-bis(methylsulfonyl)benzoyl]-3-(1-methyl-1-{[3-(trifluoromethyl)phenyl]sulfonyl}ethyl)azetidine | 634 |
| 232 | 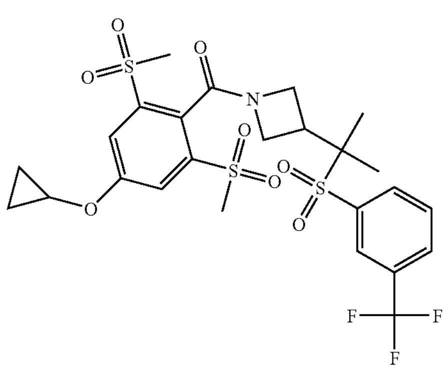 | 1-[4-(cyclopropyloxy)-2,6-bis(methylsulfonyl)benzoyl]-3-(1-methyl-1-{[3-(trifluoromethyl)phenyl]sulfonyl}ethyl)azetidine | 624 |

TABLE 4-continued

| EXAMPLE # | STRUCTURE | CHEMICAL NAME | MASS SPECTRAL DATA m/e (M + H) |
|---|---|---|---|
| 233 | 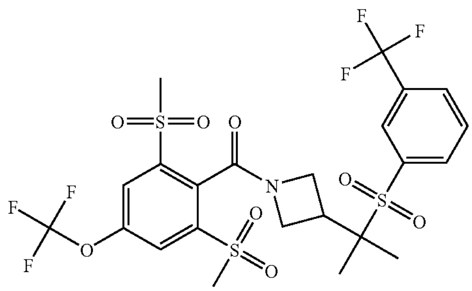 | 1-[2,6-bis(methylsulfonyl)-4-(trifluoromethoxy)benzoyl]-3-(1-methyl-1-{[3-(trifluoromethyl)phenyl]sulfonyl}ethyl)azetidine | 652 |
| 234 | Chiral | (3R)-1-[4-(cyclopropyloxy)-2-(methylsulfonyl)benzoyl]-3-(1-methyl-1-{[3-(trifluoromethyl)phenyl]sulfonyl}ethyl)pyrrolidine | 560 |
| 235 | Chiral | (3R)-1-[4-(cyclopropyloxy)-2,6-bis(methylsulfonyl)benzoyl]-3-(1-methyl-1-{[3-(trifluoromethyl)phenyl]sulfonyl}ethyl)pyrrolidine | 638 |
| 236 | Chiral | (3R)-1-[4-(cyclopropylsulfonyl)-2-methoxybenzoyl]-3-(1-methyl-1-{[3-(trifluoromethyl)phenyl]sulfonyl}ethyl)pyrrolidine | 560 |

TABLE 5

| EXAMPLE # | STRUCTURE | CHEMICAL NAME | MASS SPECTRAL DATA m/e (M + H) |
|---|---|---|---|
| 237 | 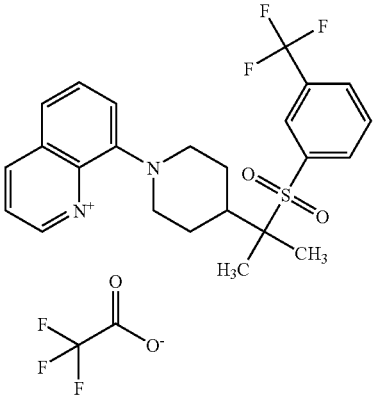 | 8-[4-(1-methyl-1-{[3-(trifluoromethyl)phenyl]sulfonyl}ethyl)piperidin-1-yl]quinolinium trifluoroacetate | 463 |
| 238 | 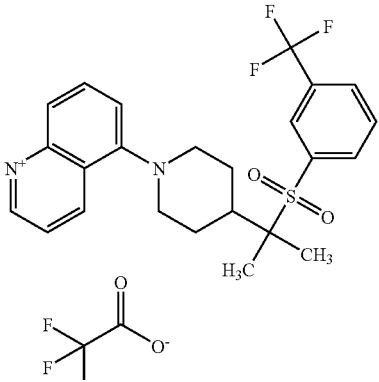 | 5-[4-(1-methyl-1-{[3-(trifluoromethyl)phenyl]sulfonyl}ethyl)piperidin-1-yl]quinolinium trifluoroacetate | 463 |
| 239 | 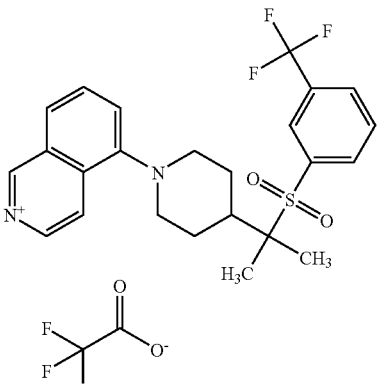 | 5-[4-(1-methyl-1-{[3-(trifluoromethyl)phenyl]sulfonyl}ethyl)piperidin-1-yl]isoquinolinium trifluoroacetate | 463 |
| 240 | 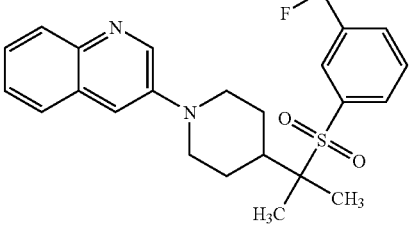 | 3-[4-(1-methyl-1-{[3-(trifluoromethyl)phenyl]sulfonyl}ethyl)piperidin-1-yl]quinoline | 463 |

TABLE 5-continued

| EXAMPLE # | STRUCTURE | CHEMICAL NAME | MASS SPECTRAL DATA m/e (M + H) |
|---|---|---|---|
| 241 | 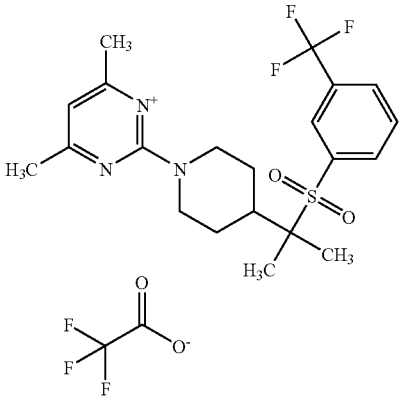 | 4,6-dimethyl-2-[4-(1-methyl-1-{[3-(trifluoromethyl)phenyl]sulfonyl}ethyl)piperidin-1-yl]pyrimidin-1-ium trifluoroacetate | 443 |
| 242 | 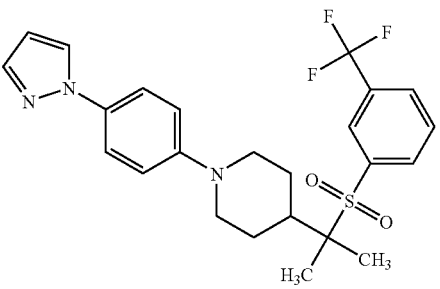 | 4-(1-methyl-1-{[3-(trifluoromethyl)phenyl]sulfonyl}ethyl)-1-[4-(1H-pyrazol-1-yl)phenyl]piperidine | 478 |
| 243 | 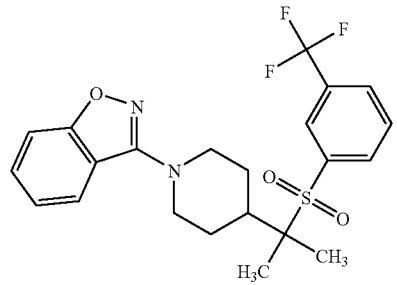 | 3-[4-(1-methyl-1-{[3-(trifluoromethyl)phenyl]sulfonyl}ethyl)piperidin-1-yl]-1,2-benzisoxazole | 453 |
| 244 | 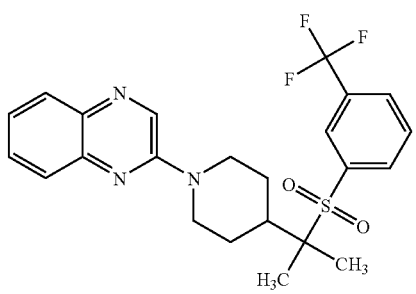 | 2-[4-(1-methyl-1-{[3-(trifluoromethyl)phenyl]sulfonyl}ethyl)piperidin-1-yl]quinoxaline | 464 |

TABLE 5-continued

| EXAMPLE # | STRUCTURE | CHEMICAL NAME | MASS SPECTRAL DATA m/e (M + H) |
|---|---|---|---|
| 245 | 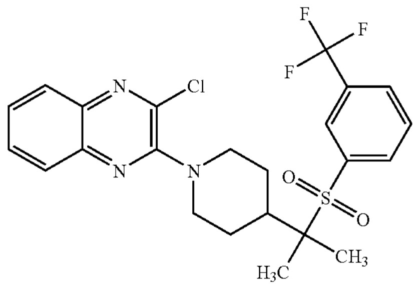 | 2-chloro-3-[4-(1-methyl-1-{[3-(trifluoromethyl)phenyl]sulfonyl}ethyl)piperidin-1-yl]quinoxaline | 497 |
| 246 | 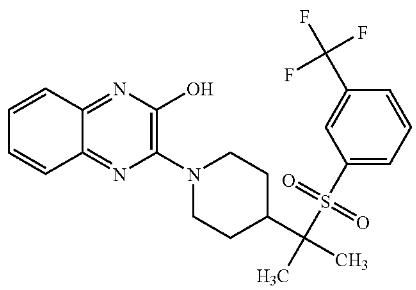 | 3-[4-(1-methyl-1-{[3-(trifluoromethyl)phenyl]sulfonyl}ethyl)piperidin-1-yl]quinoxalin-2-ol | 480 |
| 247 | 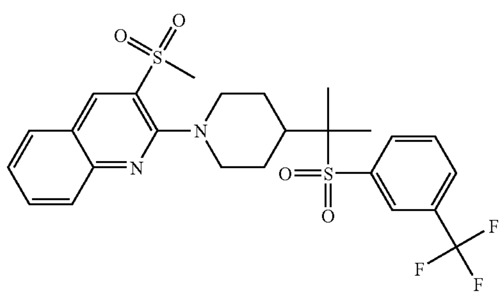 | 3-(methylsulfonyl)-2-[4-(1-methyl-1-{[3-(trifluoromethyl)phenyl]sulfonyl}ethyl)piperidin-1-yl]quinoline | 540 |
| 248 | 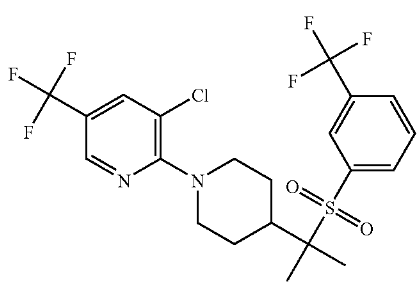 | 3-(methylsulfonyl)-2-[4-(1-methyl-1-{[3-(trifluoromethyl)phenyl]sulfonyl}ethyl)piperidin-1-yl]quinoline | 514 |
| 249 | 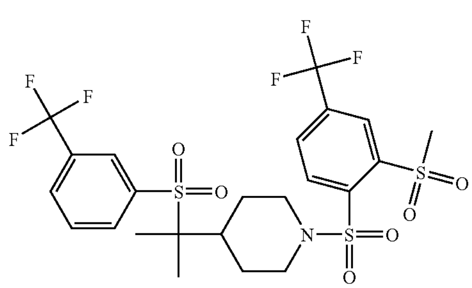 | 1-{[2-(methylsulfonyl)-4-(trifluoromethyl)phenyl]sulfonyl}-4-(1-methyl-1-{[3-(trifluoromethyl)phenyl]sulfonyl}ethyl)piperidine | 622 |

TABLE 5-continued

| EXAMPLE # | STRUCTURE | CHEMICAL NAME | MASS SPECTRAL DATA m/e (M + H) |
|---|---|---|---|
| 250 | 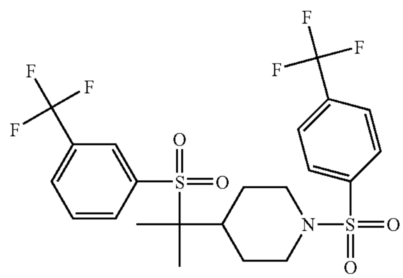 | 4-(1-methyl-1-{[3-(trifluoromethyl)phenyl]sulfonyl}ethyl)-1-{[4-(trifluoromethyl)phenyl]sulfonyl}piperidine | 544 |

TABLE 6

| EXAMPLE # | STRUCTURE | CHEMICAL NAME | MASS SPECTRAL DATA m/e (M + H) |
|---|---|---|---|
| 251 | 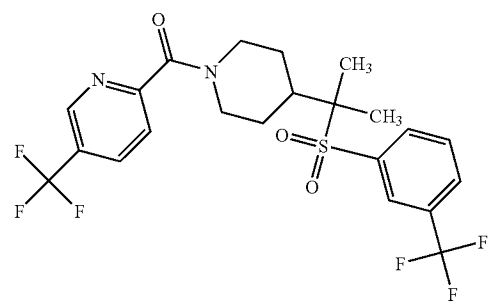 | 2-{[4-(1-methyl-1-{[3-(trifluoromethyl)phenyl]sulfonyl}ethyl)piperidin-1-yl]carbonyl}-5-(trifluoromethyl)pyridine | 509 |
| 252 | 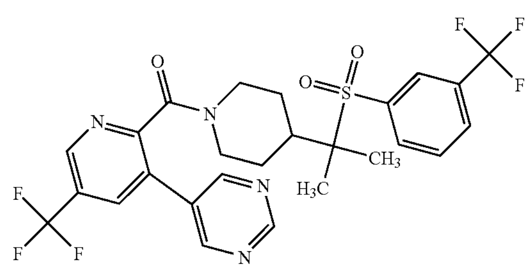 | 5-[2-{[4-(1-methyl-1-{[3-(trifluoromethyl)phenyl]sulfonyl}ethyl)piperidin-1-yl]carbonyl}-5-(trifluoromethyl)pyridin-3-yl]pyrimidine | 587 |
| 253 | 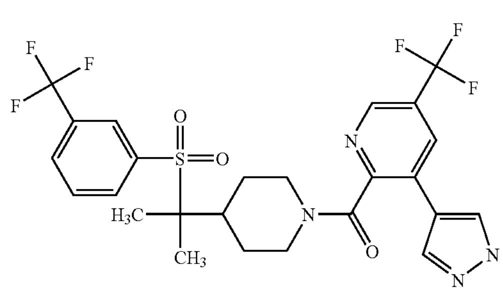 | 2-{[4-(1-methyl-1-{[3-(trifluoromethyl)phenyl]sulfonyl}ethyl)piperidin-1-yl]carbonyl}-3-(1H-pyrazol-4-yl)-5-(trifluoromethyl)pyridine | 575 |

TABLE 6-continued

| EXAMPLE # | STRUCTURE | CHEMICAL NAME | MASS SPECTRAL DATA m/e (M + H) |
|---|---|---|---|
| 254 | 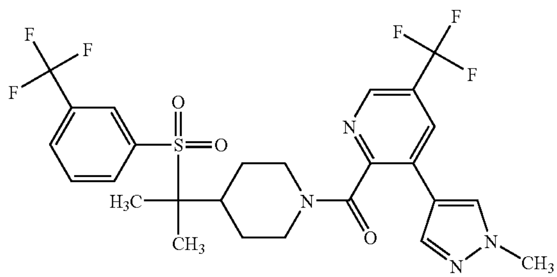 | 3-(1-methyl-1H-pyrazol-4-yl)-2-{[4-(1-methyl-1-{[3-(trifluoromethyl)phenyl]sulfonyl ethyl)piperidin-1-yl]carbonyl}-5-(trifluoromethyl)pyridine | 589 |
| 255 | 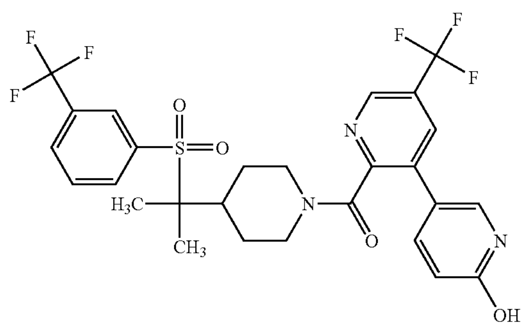 | 2'-{[4-(1-methyl-1-{[3-(trifluoromethyl)phenyl]sulfonyl}ethyl)piperidin-1-yl]carbonyl}-5'-(trifluoromethyl)-3,3'-bipyridin-6-ol | 602 |
| 256 | 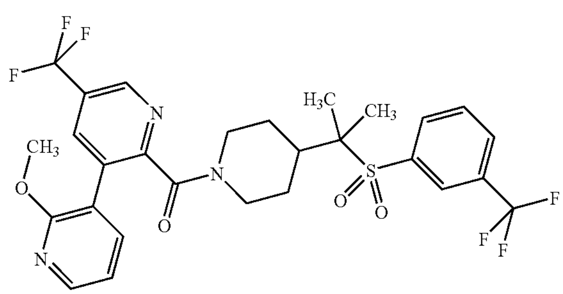 | 2'-methoxy-2-{[4-(1-methyl-1-{[3-(trifluoromethyl)phenyl]sulfonyl}ethyl)piperidin-1-yl]carbonyl}-5-(trifluoromethyl)-3,3'-bipyridine | 616 |
| 257 | 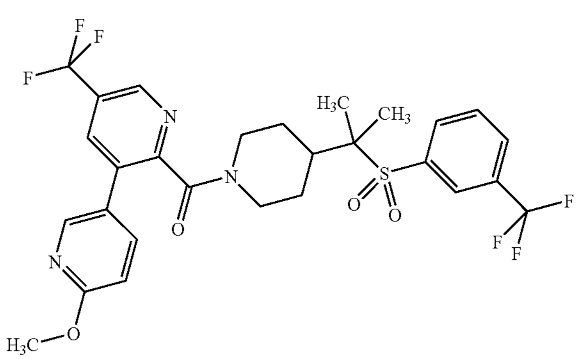 | 6'-methoxy-2-{[4-(1-methyl-1-{[3-(trifluoromethyl)phenyl]sulfonyl}ethyl)piperidin-1-yl]carbonyl}-5-(trifluoromethyl)-3,3'-bipyridine | 616 |

TABLE 6-continued

| EXAMPLE # | STRUCTURE | CHEMICAL NAME | MASS SPECTRAL DATA m/e (M + H) |
|---|---|---|---|
| 258 | 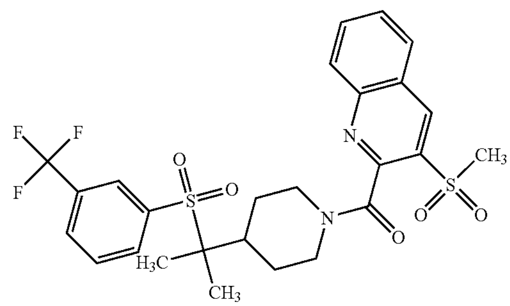 | 3-(methylsulfonyl)-2-{[4-(1-methyl-1-{[3(trifluoromethyl)phenyl]sulfonyl}ethyl)piperidin-1-yl]carbonyl}quinoline | 569 |
| 259 | 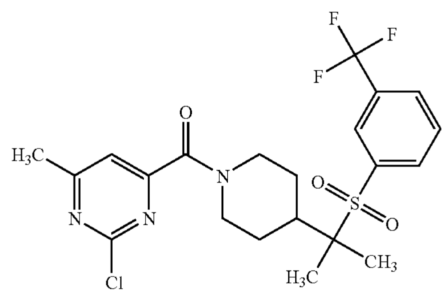 | 2-chloro-4-methyl-6-{[4-(1-methyl-1-{[3-(trifluoromethyl)phenyl]sulfonyl}ethyl)piperidin-1-yl]carbonyl}pyrimidine | 490 |
| 260 | 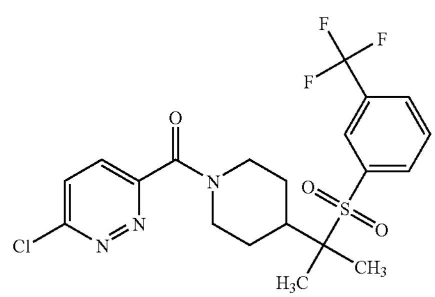 | 3-chloro-6-{[4-(1-methyl-1-{[3-(trifluoromethyl)phenyl]sulfonyl}ethyl)piperidin-1-yl]carbonyl}pyridazine | 476 |
| 261 | 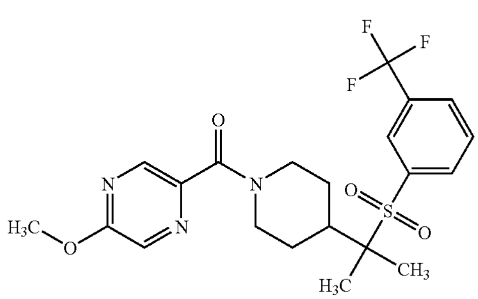 | 2-methoxy-5-{[4-(1-methyl-1-{[3-(trifluoromethyl)phenyl]sulfonyl}ethyl) piperidin-1-yl]carbonyl}pyrazine | 472 |
| 262 | 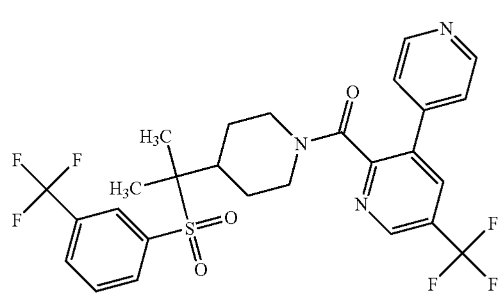 | 2-{[4-(1-methyl-1-{[3-(trifluoromethyl)phenyl]sulfonyl}ethyl)piperidin-1-yl]carbonyl}-5-(trifluoromethyl)-3,4'-bipyridine | 586 |

TABLE 6-continued

| EXAMPLE # | STRUCTURE | CHEMICAL NAME | MASS SPECTRAL DATA m/e (M + H) |
|---|---|---|---|
| 263 | 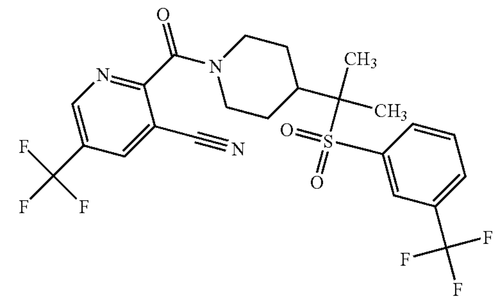 | 2-{[4-(1-methyl-1-{[3-(trifluoromethyl)phenyl]sulfonyl}ethyl)piperidin-1-yl]carbonyl}-5-(trifluoromethyl)nicotinonitrile | 534 |
| 264 | 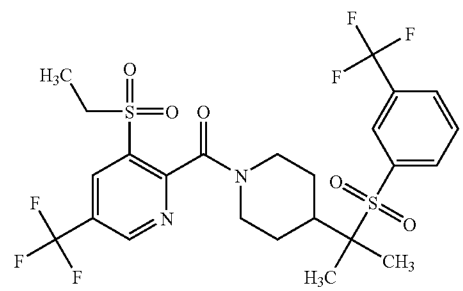 | 3-(ethylsulfonyl)-2-{[4-(1-methyl-1-{[3(trifluoromethyl)phenyl]sulfonyl}ethyl)piperidin-1-yl]carbonyl}-5-(trifluoromethyl)pyridine | 601 |
| 265 | 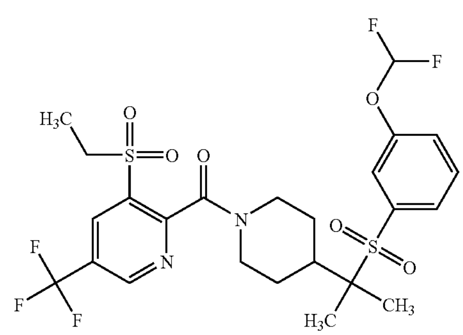 | 2-{[4-(1-{[3-(difluoromethoxy)phenyl]sulfonyl}-1-methylethyl)piperidin-1-yl]carbonyl}-3-(ethylsulfonyl)-5-(trifluoromethyl)pyridine | 599 |
| 266 | 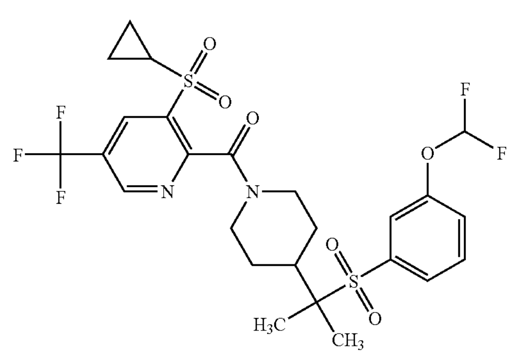 | 3-(cyclopropylsulfonyl)-2-{[4-(1-{[3-(difluoromethoxy)phenyl]sulfonyl}-1-methylethyl)piperidin-1-yl]carbonyl}-5-(trifluoromethyl)pyridine | 611 |

TABLE 6-continued

| EXAMPLE # | STRUCTURE | CHEMICAL NAME | MASS SPECTRAL DATA m/e (M + H) |
|---|---|---|---|
| 267 | 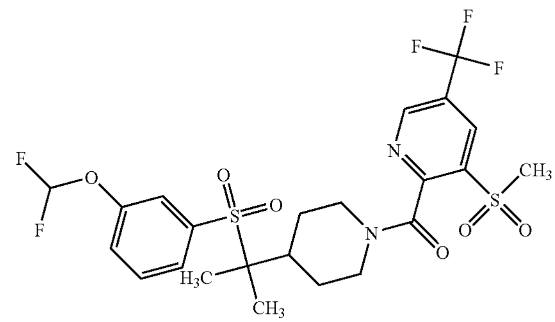 | 2-{[4-(1-{[3-(difluoromethoxy)phenyl]sulfonyl}-1-methyl ethyl)piperidin-1-yl]carbonyl}-3-(methylsulfonyl)-5-(trifluoromethyl)pyridine | 585 |
| 268 | 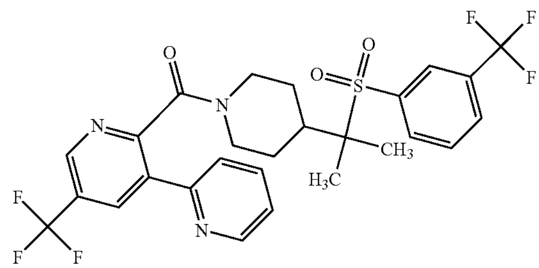 | 2'-{[4-(1-methyl-1-{[3-(trifluoromethyl)phenyl]sulfonyl}ethyl)piperidin-1-yl]carbonyl}-5'-(trifluoromethyl)-2,3'-bipyridine | 586 |
| 269 | 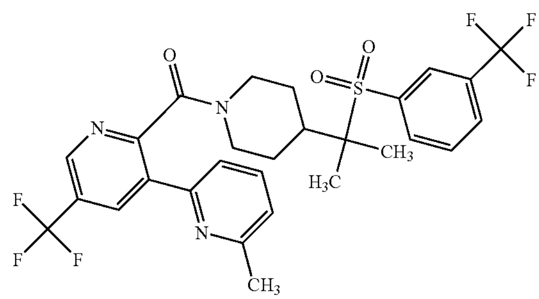 | 6-methyl-2'-{[4-(1-methyl-1-{[3-(trifluoromethyl)phenyl]sulfonyl}ethyl)piperidin-1-yl]carbonyl}-5'-(trifluoromethyl)-2,3'-bipyridine | 600 |
| 270 | 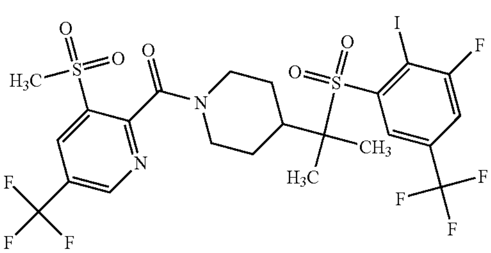 | 2-{[4-(1-{[3-fluoro-2-iodo-5-(trifluoromethyl)phenyl]sulfonyl}-1-methylethyl)piperidin-1-yl]carbonyl}-3-(methylsulfonyl)-5-(trifluoromethyl)pyridine | 731 |
| 271 | 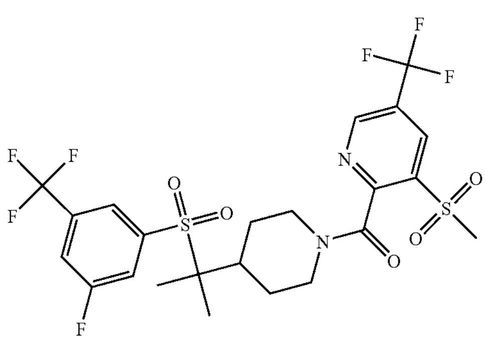 | 2-{[4-(1-{[3-fluoro-5-(trifluoromethyl)phenyl]sulfonyl]}-1-methylethyl)piperidin-1-yl]carbonyl}-3-(methylsulfonyl)-5-(trifluoromethyl)pyridine | 605 |

TABLE 6-continued

| EXAMPLE # | STRUCTURE | CHEMICAL NAME | MASS SPECTRAL DATA m/e (M + H) |
|---|---|---|---|
| 272 | Chiral | tert-butyl{(1S)-1-benzyl-2-[4-(1-methyl-1-{[3-(trifluoromethyl)phenyl]sulfonyl}ethyl)piperidin-1-yl]-2-oxoethyl}carbamate | 583 |
| 273 | 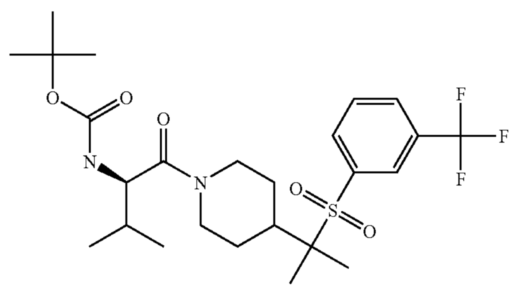 | tert-butyl{(1S))-2-methyl-1-{[4-(1-methyl-1-{[3-(trifluoromethyl)phenyl]sulfonyl}ethyl)piperidin-1-yl]carbonyl}propyl)carbamate | 535 |
| 274 | 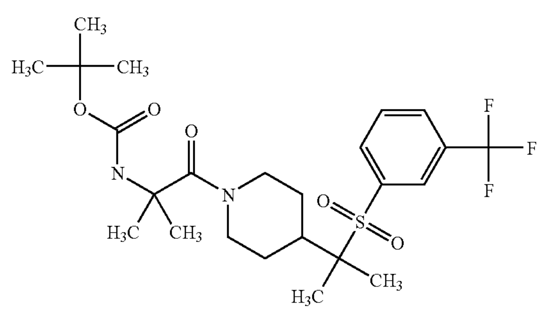 | tert-butyl{1,1-dimethyl-2-[4-(1-methyl-1-{[3-(trifluoromethyl)phenyl]sulfonyl}ethyl)piperidin-1-yl]-2-oxoethyl}carbamate | 521 |
| 275 | 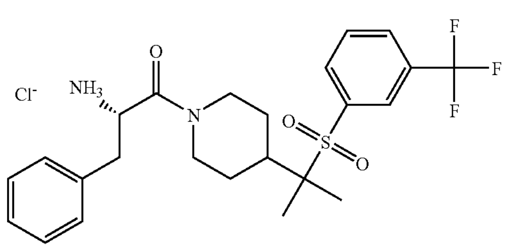 | (2S)-1-[4-(1-methyl-1-{[3-(trifluoromethyl)phenyl]sulfonyl}ethyl)piperidin-1-yl]-1-oxo-3-phenylpropan-2-aminium chloride | 483 |
| 276 | 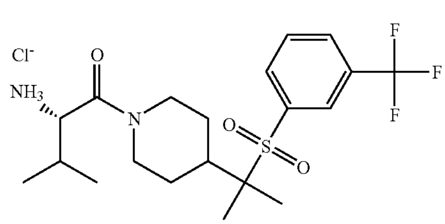 | (2S)-3-methyl-1-[4-(1-methyl-1-{[3-(trifluoromethyl)phenyl]sulfonyl}ethyl)piperidin-1-yl]-1-oxobutan-2-aminium chloride | 435 |

TABLE 6-continued

| EXAMPLE # | STRUCTURE | CHEMICAL NAME | MASS SPECTRAL DATA m/e (M + H) |
|---|---|---|---|
| 277 | 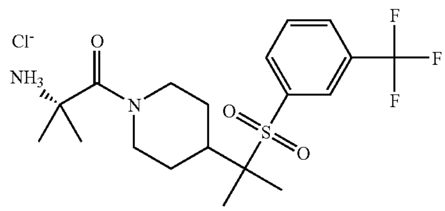 | 2-methyl-1-[4-(1-methyl-1-{[3-(trifluoromethyl)phenyl]sulfonyl}ethyl)piperidin-1-yl]-1-oxopropan-2-aminium chloride | 421 |
| 278 | 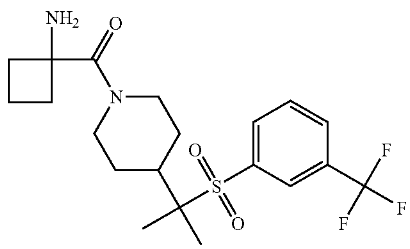 | 1-{[4-(1-methyl-1-{[3-(trifluoromethyl)phenyl]sulfonyl}ethyl)piperidin-1-yl]carbonyl}cyclobutanamine | 433 |
| 279 | 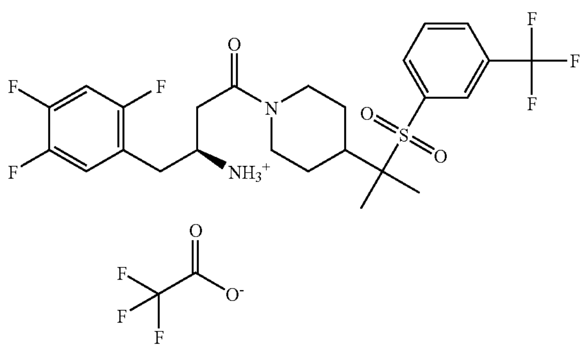 | (2R)-4-[4-(1-methyl-1-{[3-(trifluoromethyl)phenyl]sulfonyl}ethyl)piperidin-1-yl]-4-oxo-1-(2,4,5-trifluorophenyl)butan-2-aminiumtrifluoroacetate | 551 |
| 280 | 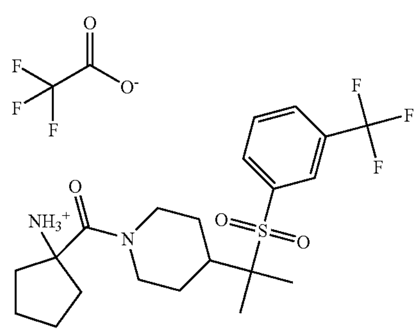 | 1-{[4-(1-methyl-1-{[3-(trifluoromethyl)phenyl]sulfonyl}ethyl)piperidin-1-yl]carbonyl}cyclopentanaminium trifluoroacetate | 447 |
| 281 | 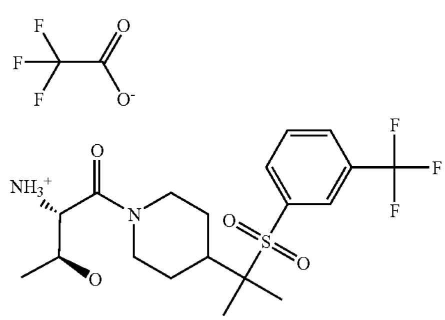 | (2S,3R)-3-hydroxy-1-[4-(1-methyl-1-{[3-(trifluoromethyl)phenyl]sulfonyl}ethyl)piperidin-1-yl]-1-oxobutan-2-aminium trifluoroacetate | 437 |

US 8,304,434 B2

165 166

TABLE 6-continued

| EXAMPLE # | STRUCTURE | CHEMICAL NAME | MASS SPECTRAL DATA m/e (M + H) |
|---|---|---|---|
| 282 | 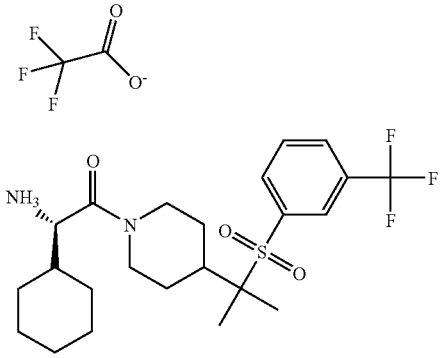 | (1S)-1-cyclohexyl-2-[4-(1-methyl-1-([3-(trifluoromethyl)phenyl]sulfonyl}ethyl)piperidin-1-yl]-2-oxoethanaminium trifluoroacetate | 475 |
| 283 | 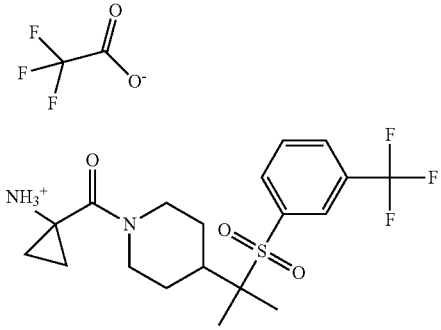 | 1-{[4-(1-methyl-1-{[3-(trifluoromethyl)phenyl]sulfonyl}ethyl)piperidin-1-yl]carbonyl}cyclopropanaminium trifluoroacetate | 419 |
| 284 | 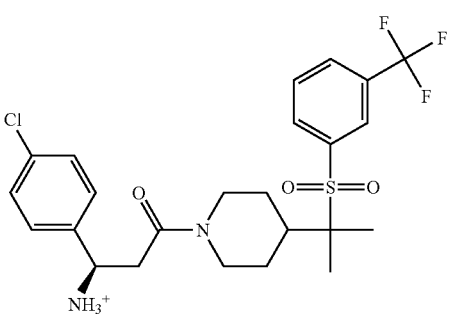 | (R)-1-(4-chlorophenyl)-3-[4-(1-methyl-1-{[3-(trifluoromethyl)phenyl]sulfonyl}ethyl)piperidin-1-yl]-3-oxopropan-1-aminium trifluoroacetate | 517 |
| 285 | 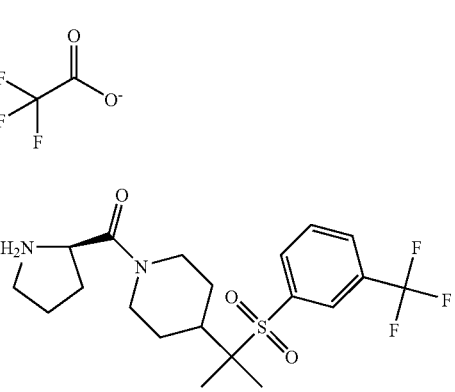 | (2S)-2-{[4-(1-methyl-1-{[3-(trifluoromethyl)phenyl]sulfonyl}ethyl)piperidin-1-yl]carbonyl}pyrrolidinium trifluoroacetate | 433 |

TABLE 6-continued

| EXAMPLE # | STRUCTURE | CHEMICAL NAME | MASS SPECTRAL DATA m/e (M + H) |
|---|---|---|---|
| 286 | 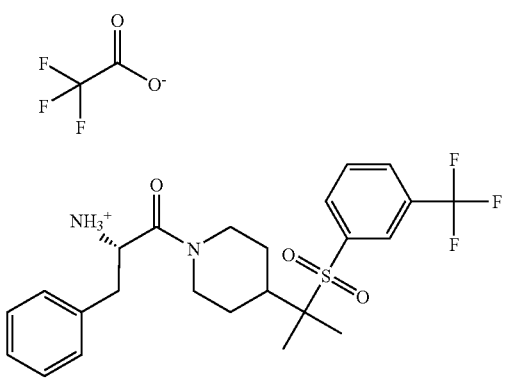 | (2R)-1-[4-(1-methyl-1-{[3-(trifluoromethyl)phenyl]sulfonyl}ethyl)piperidin-1-yl]-1-oxo-3-phenylpropan-2-aminium trifluoroacetate | 483 |
| 287 | 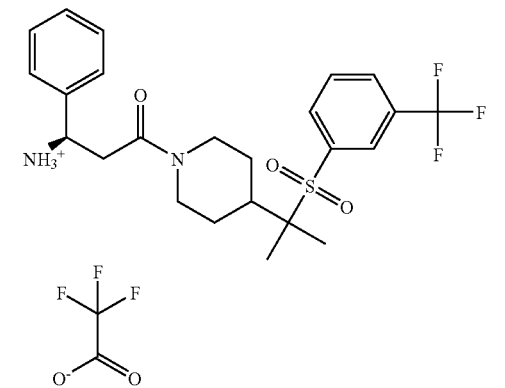 | (1R)-3-[4-(1-methyl-1-{[3-(trifluoromethyl)phenyl]sulfonyl}ethyl)piperidin-1-yl]-3-oxo-1-phenylpropan-1-aminium trifluoroacetate | 483 |
| 288 | 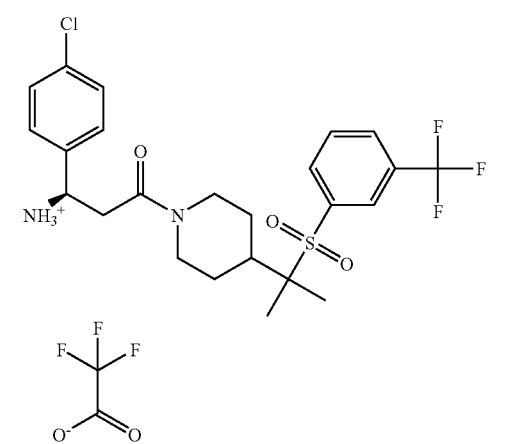 | (1S)-1-(4-chlorophenyl)-3-[4-(1-methyl-1-{[3-(trifluoromethyl)phenyl]sulfonyl}ethyl)piperidin-1-yl]-3-oxopropan-1-aminium trifluoroacetate | 517 |

TABLE 6-continued

| EXAMPLE # | STRUCTURE | CHEMICAL NAME | MASS SPECTRAL DATA m/e (M + H) |
|---|---|---|---|
| 289 | 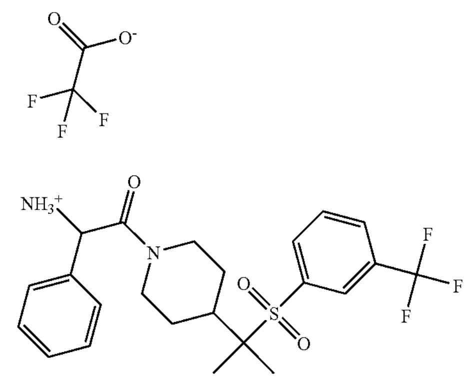 | (1R)-2-[4-(1-methyl-1-{[3-(trifluoromethyl)phenyl]sulfonyl}ethyl)piperidin-1-yl]-2-oxo-1-phenylethanaminium trifluoroacetate | 469 |
| 290 | 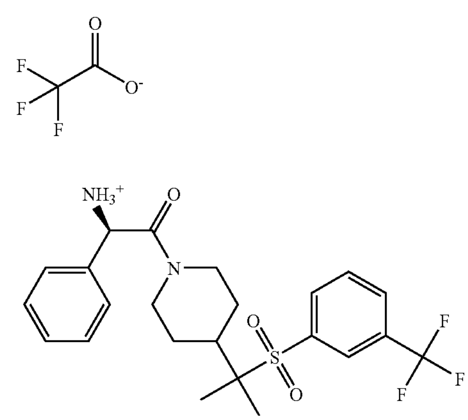 | (1S)-2-[4-(1-methyl-1-{[3-(trifluoromethyl)phenyl]sulfonyl}ethyl)piperidin-1-yl]-2-oxo-1-phenylethanaminium trifluoroacetate | 469 |
| 291 | 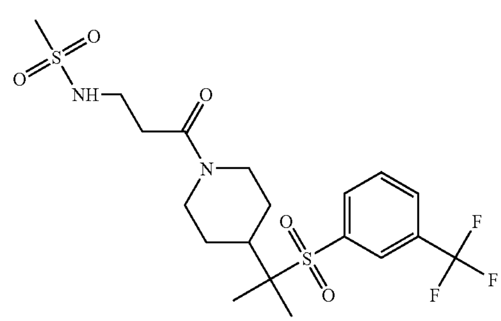 | N-{3-[4-(1-methyl-1-{[3-(trifluoromethyl)phenyl]sulfonyl}ethyl)piperidin-1-yl]-3-oxopropyl}methanesulfonamide | 485 |
| 292 | 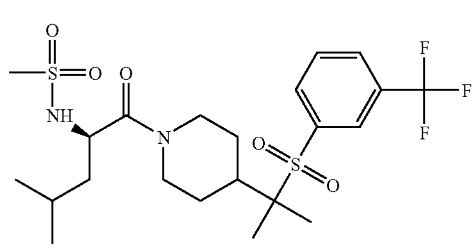 | N-((1S)-3-methyl-1-{[4-(1-methyl-1-{[3-(trifluoromethyl)phenyl]sulfonyl}ethyl)piperidin-1-yl]carbonyl}butyl)methanesulfonamide | 526 |

TABLE 6-continued

| EXAMPLE # | STRUCTURE | CHEMICAL NAME | MASS SPECTRAL DATA m/e (M + H) |
|---|---|---|---|
| 293 | 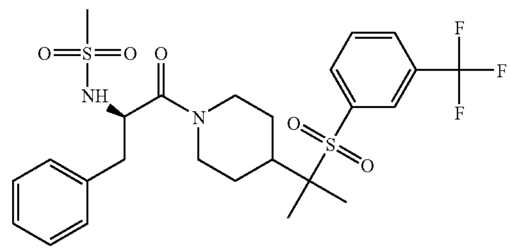 | N-{(1S-1-benzyl-2-[4-(1-methyl-1-{[3-(trifluoromethyl)phenyl]sulfonyl}ethyl)piperidin-1-yl]-2-oxoethyl}methanesulfonamide | 561 |
| 294 | 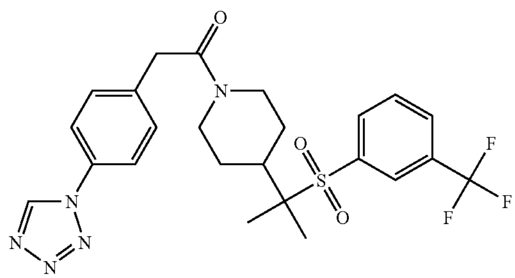 | 4-(1-methyl-1-{[3-(trifluoromethyl)phenyl]sulfonyl}ethyl)-1-{[4-(1H-tetrazol-1-yl)phenyl]acetyl}piperidine | 522 |
| 295 | 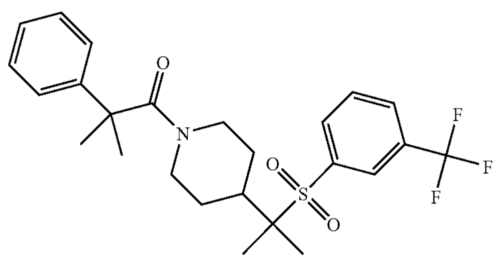 | 1-(2-methyl-2-phenylpropanoyl)-4-(1-methyl-1-{[3-(trifluoromethyl)phenyl]sulfonyl}ethyl)piperidine | 482 |
| 297 | 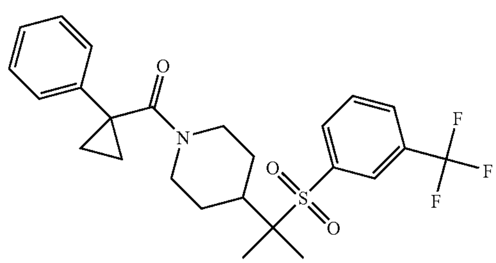 | 4-(1-methyl-1-{[3-(trifluoromethyl)phenyl]sulfonyl}ethyl)-1-[(1-phenylcyclopropyl)carbonyl]piperidine | 480 |
| 298 | 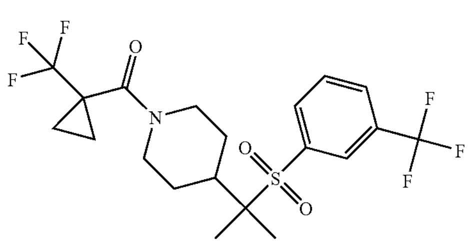 | 4-(1-methyl-1-{[3-(trifluoromethyl)phenyl]sulfonyl}ethyl)-1-{[1-(trifluoromethyl)cyclopropyl]carbonyl}piperidine | 472 |

TABLE 6-continued

| EXAMPLE # | STRUCTURE | CHEMICAL NAME | MASS SPECTRAL DATA m/e (M + H) |
|---|---|---|---|
| 299 | 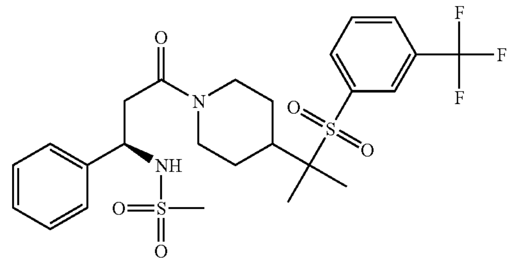 | N-{(1)-3-[4-(1-methyl-1-{[3-(trifluoromethyl)phenyl]sulfonyl}ethyl)piperidin-1-yl]-3-oxo-1-phenylpropyl}methanesulfonamide | 561 |
| 300 | 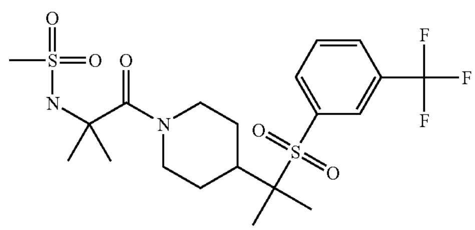 | N-{1,1-dimethyl-2-[4-(1-methyl-1-{[3-(trifluoromethyl)phenyl]sulfonyl}ethyl)piperidin-1-yl]-2-oxoethyl}methanesulfonamide | 499 |
| 301 | 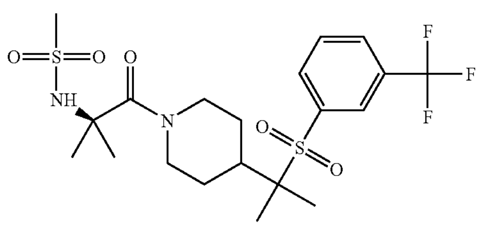 | N-((1S)-2-methyl-1-{[4-(1-methyl-1-{[3-(trifluoromethyl)phenyl]sulfonyl}ethyl)piperidin-1-yl]carbonyl}propyl)methanesulfonamide | 513 |
| 302 | 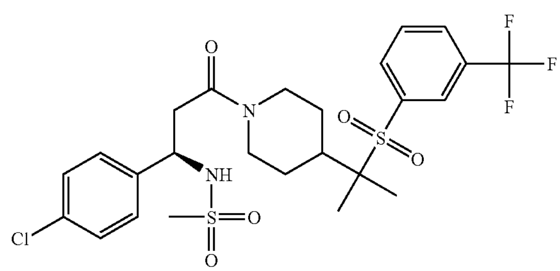 | N-{(1S)-1-(4-chlorophenyl)-3-[4-(1-methyl-1-{[3-(trifluoromethyl)phenyl]sulfonyl}ethyl)piperidin-1-yl]-3-oxopropyl}methanesulfonamide | 595 |
| 303 | 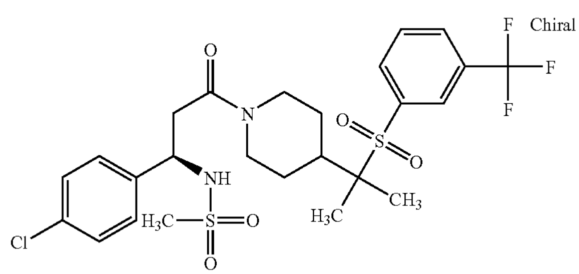 | N-{(1R)-1-(4-chlorophenyl)-3-[4-(1-methyl-1-{[3-(trifluoromethyl)phenyl]sulfonyl}ethyl)piperidin-1-yl]-3-oxopropyl}methanesulfonamide | 595 |

TABLE 6-continued

| EXAMPLE # | STRUCTURE | CHEMICAL NAME | MASS SPECTRAL DATA m/e (M + H) |
|---|---|---|---|
| 304 | 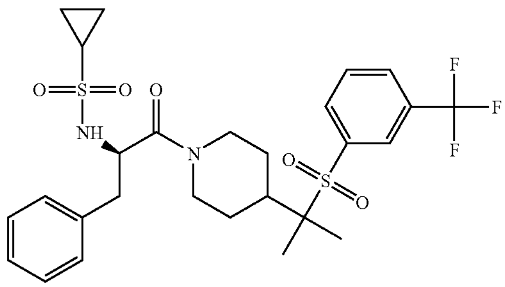 | N-{(1S)-1-benzyl-2-[4-(1-methyl-1-{[3-(trifluoromethyl)phenyl]sulfonyl}ethyl)piperidin-1-yl]-2-oxoethyl}cyclopropanesulfonamide | 587 |
| 305 | 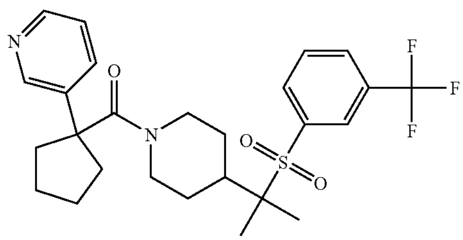 | 3-(1-{[4-(1-methyl-1-{[3-(trifluoromethyl)phenyl]sulfonyl}ethyl)piperidin-1-yl]carbonyl}cyclopentyl)pyridine | 509 |
| 306 | 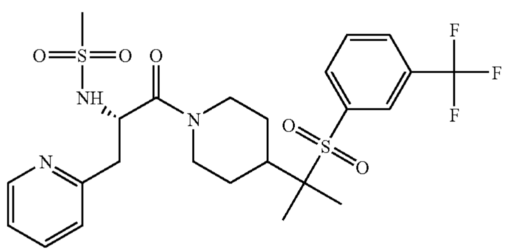 | N-[(1S)-2-[4-(1-methyl-1-{[3-(trifluoromethyl)phenyl]sulfonyl}ethyl)piperidin-1-yl]-2-oxo-1-(pyridin-2-ylmethyl)ethyl]methanesulfonamide | 562 |
| 307 | 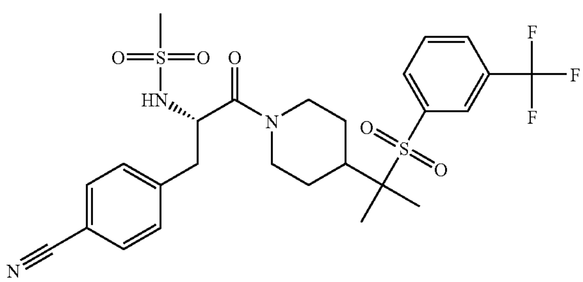 | N-{(1S)-1-(4-cyanobenzyl)-2-[4-(1-methyl-1-{[3-(trifluoromethyl)phenyl]sulfonyl}ethyl)piperidin-1-yl]-2-oxoethyl}methanesulfonamide | 586 |
| 308 | 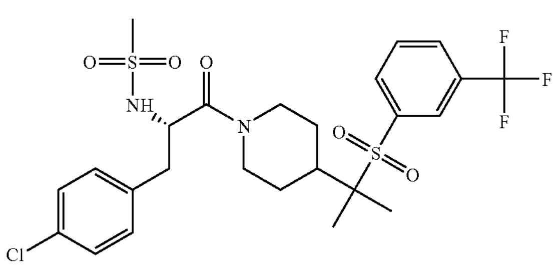 | N-{(1S)-1-(4-chlorobenzyl)-2-[4-(1-methyl-1-{[3-(trifluoromethyl)phenyl]sulfonyl}ethyl)piperidin-1-yl]-2-oxoethyl}methanesulfonamide | 595 |

TABLE 6-continued

| EXAMPLE # | STRUCTURE | CHEMICAL NAME | MASS SPECTRAL DATA m/e (M + H) |
|---|---|---|---|
| 309 | 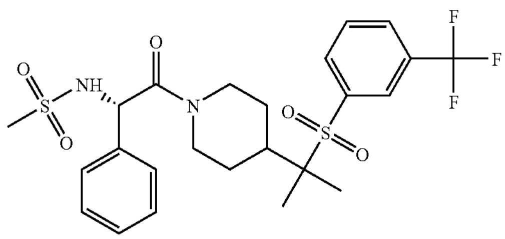 | N-{(1S)-2-[4-(1-methyl-1-{[3-(trifluoromethyl)phenyl]sulfonyl}ethyl)piperidin-1-yl]-2-oxo-1-phenylethyl}methanesulfonamide | 547 |
| 310 | 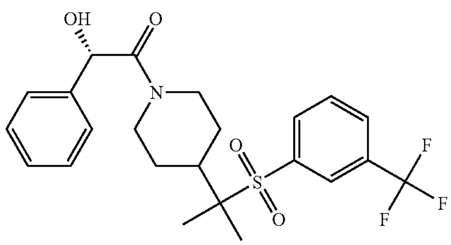 | (1S)-2-[4-(1-methyl-1-{[3-(trifluoromethyl)phenyl]sulfonyl}ethyl)piperidin-1-yl]-2-oxo-1-phenylethanol | 470 |
| 311 | 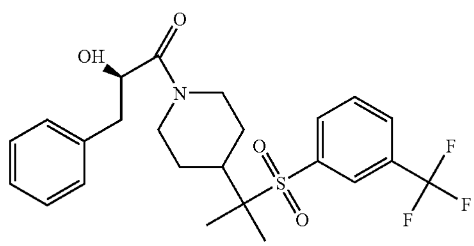 | (2R)-1-[4-(1-methyl-1-{[3-(trifluoromethyl)phenyl]sulfonyl}ethyl)piperidin-1-yl]-1-oxo-3-phenylpropan-2-ol | 484 |
| 312 | 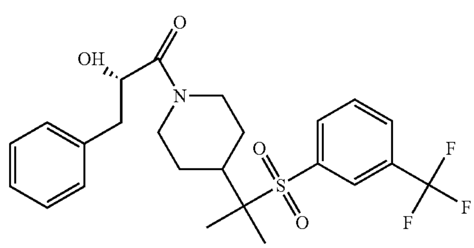 | (2S)-1-[4-(1-methyl-1-([3-(trifluoromethyl)phenyl]sulfonyl}ethyl)piperidin-1-yl]-1-oxo-3-phenylpropan-2-ol | 484 |
| 313 | 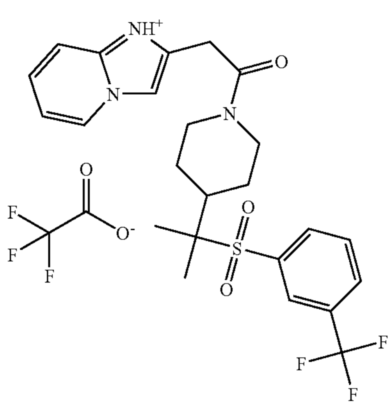 | 2-{2-[4-(1-methyl-1-{[3-(trifluoromethyl)phenyl]sulfonyl}ethyl)piperidin-1-yl]-2-oxoethyl}imidazo[1,2-a]pyridin-1-ium trifluoroacetate | 494 |

TABLE 6-continued

| EXAMPLE # | STRUCTURE | CHEMICAL NAME | MASS SPECTRAL DATA m/e (M + H) |
|---|---|---|---|
| 314 | 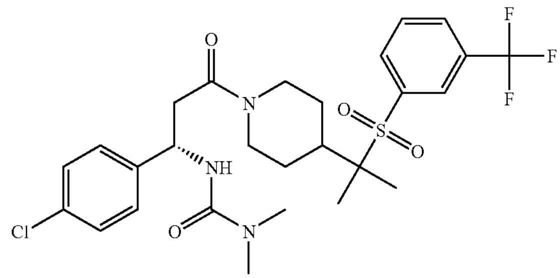 | N'-{(1S)-1-(4-chlorophenyl)-3-[4-(1-methyl-1-{[3-(trifluoromethyl)phenyl]sulfonyl}ethyl)piperidin-1-yl]-3-oxopropyl}-N,N-dimethylurea | 588 |
| 315 | 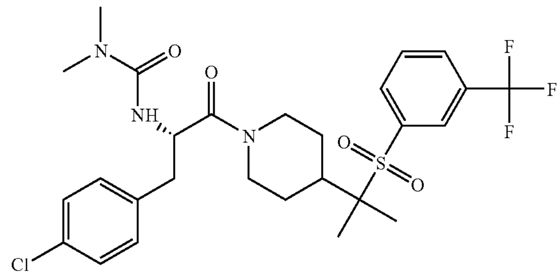 | N'-{(1S)-1-(4-chlorobenzyl)-2-[4-(1-methyl-1-{[3-(trifluoromethyl)phenyl]sulfonyl}ethyl)piperidin-1-yl]-2-oxoethyl}-N,N-dimethylurea | 588 |
| 316 | 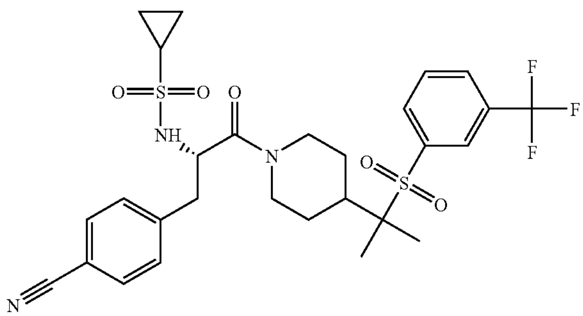 | N-{(1S)-1-(4-cyanobenzyl)-2-[4-(1-methyl-1-{[3-(trifluoromethyl)phenyl]sulfonyl}ethyl)piperidin-1-yl]-2-oxoethyl}cyclopropanesulfonamide | 612 |
| 317 | 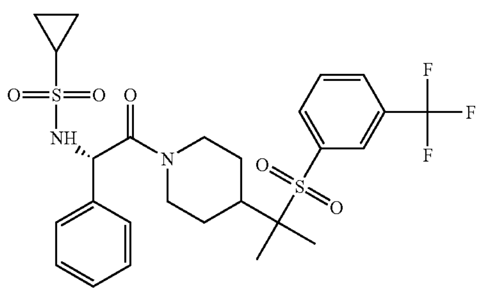 | N-{(1S)-2-[4-(1-methyl-1-{[3-(trifluoromethyl)phenyl]sulfonyl}ethyl)piperidin-1-yl]-2-oxo-1-phenylethyl}cyclopropanesulfonamide | 573 |
| 318 | 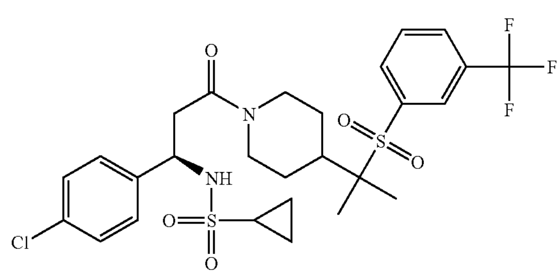 | N-{(1R)-1-(4-chlorophenyl)-3-[4-(1-methyl-1-{[3-(trifluoromethyl)phenyl]sulfonyl}ethyl)piperidin-1-yl]-3-oxopropyl}cyclopropanesulfonamide | 622 |

TABLE 6-continued

| EXAMPLE # | STRUCTURE | CHEMICAL NAME | MASS SPECTRAL DATA m/e (M + H) |
|---|---|---|---|
| 319 | 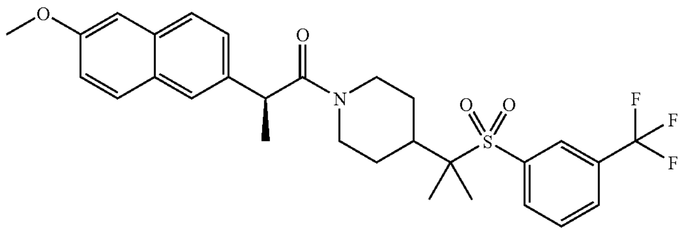 | 1-[(2S)-2-(6-methoxy-2-naphthyl)propanoyl]-4-(1-methyl-1-{[3-(trifluoromethyl)phenyl]sulfonyl}ethyl)piperidine | 548 |
| 320 | 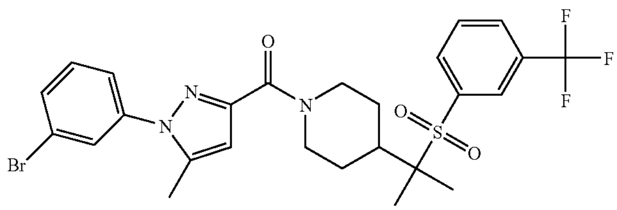 | 1-{[1-(3-bromophenyl)-5-methyl-1H-pyrazol-3-yl]carbonyl}-4-(1-methyl-1-{[3-(trifluoromethyl)phenyl]sulfonyl}ethyl)piperidine | 598 |
| 321 | 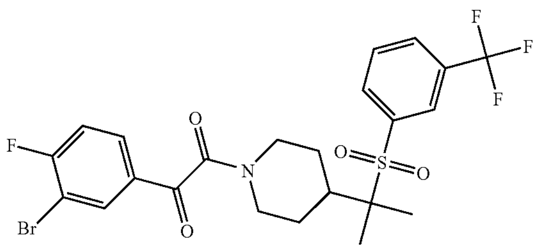 | 1-(3-bromo-4-fluorophenyl)-2-[4-(1-methyl-1-{[3-(trifluoromethyl)phenyl]sulfonyl}ethyl)piperidin-1-yl]-2-oxoethanone | 564 |
| 322 | 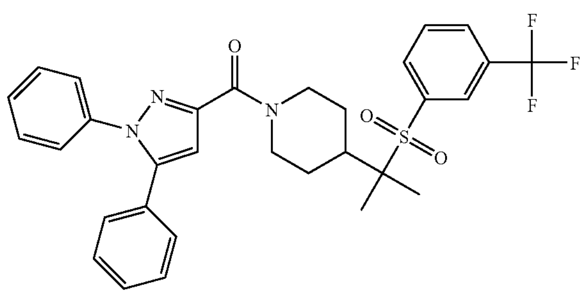 | 1-[(1,5-diphenyl-1H-pyrazol-3-yl)carbonyl]-4-(1-methyl-1-{[3-(trifluoromethyl)phenyl]sulfonyl}ethyl)piperidine | 582 |
| 323 | 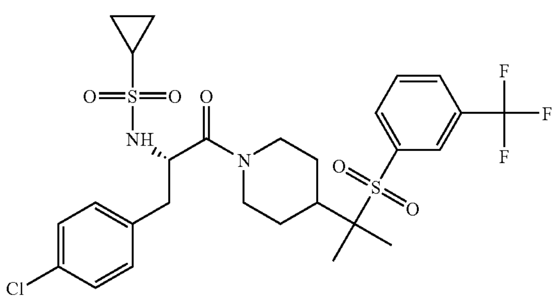 | N-{(1S)-1-(4-chlorobenzyl)-2-[4-(1-methyl-1-{[3-(trifluoromethyl)phenyl]sulfonyl}ethyl)piperidin-1-yl]-2-oxoethyl}cyclopropanesulfonamide | 621 |
| 324 | 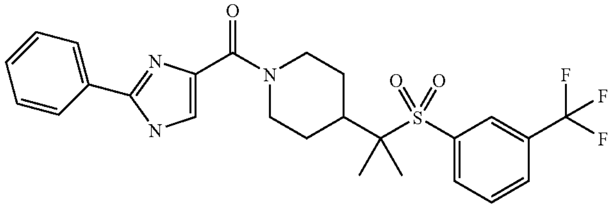 | 4-(1-methyl-1-{[3-(trifluoromethyl)phenyl]sulfonyl}ethyl)-1-[(2-phenyl-1H-imidazol-4-yl)carbonyl]piperidine | 506 |

TABLE 6-continued

| EXAMPLE # | STRUCTURE | CHEMICAL NAME | MASS SPECTRAL DATA m/e (M + H) |
|---|---|---|---|
| 325 | 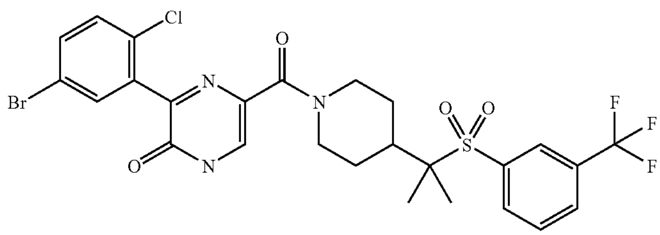 | 3-(5-bromo-2-chlorophenyl)-5-{[4-(1-methyl-1-{[3-(trifluoromethyl)phenyl]sulfonyl}ethyl)piperidin-1-yl]carbonyl}pyrazin-2(1H)-one | 647 |
| 326 | 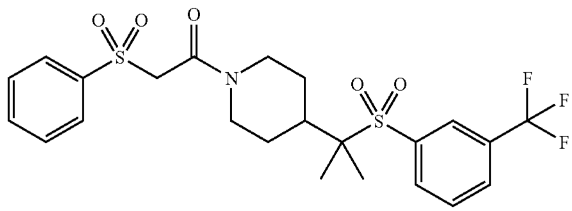 | 4-(1-methyl-1-{[3-(trifluoromethyl)phenyl]sulfonyl}ethyl)-1-[(phenylsulfonyl)acetyl]piperidine | 518 |
| 327 | 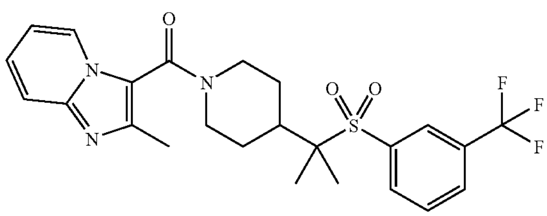 | 2-methyl-3-{[4-(1-methyl-1-{[3-(trifluoromethyl)phenyl]sulfonyl}ethyl)piperidin-1-yl]carbonyl}imidazo[1,2-a]pyridine | 494 |
| 328 | 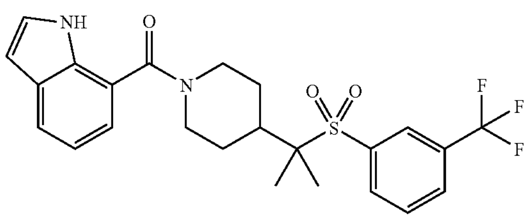 | 7-{[4-(1-methyl-1-{[3-(trifluoromethyl)phenyl]sulfonyl}ethyl)piperidin-1-yl]carbonyl}-1H-indole | 479 |
| 329 | 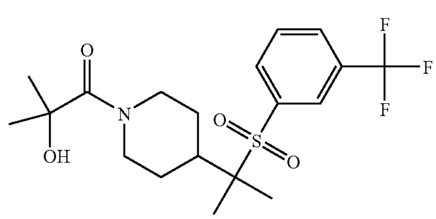 | 2-methyl-1-[4-(1-methyl-1-{[3-(trifluoromethyl)phenyl]sulfonyl}ethyl)piperidin-1-yl]-1-oxopropan-2-ol | 422 |
| 330 | 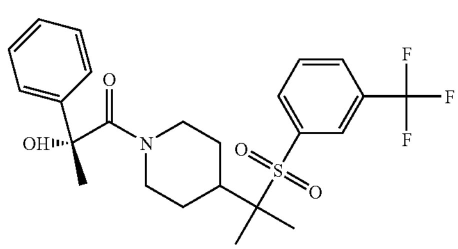 | (2R)-1-[4-(1-methyl-1-{[3-(trifluoromethyl)phenyl]sulfonyl}ethyl)piperidin-1-yl]-1-oxo-2-phenylpropan-2-ol | 484 |

TABLE 6-continued

| EXAMPLE # | CHEMICAL NAME | MASS SPECTRAL DATA m/e (M + H) |
|---|---|---|
| 331 | (2S)-1-[4-(1-methyl-1-{[3-(trifluoromethyl)phenyl]sulfonyl}ethyl)piperidin-1-yl]-1-oxo-2-phenylpropan-2-ol | 484 |
| 332 | (2R)-2-(4-tert-butylphenyl)-1-[4-(1-methyl-1-{[3-(trifluoromethyl)phenyl]sulfonyl}ethyl)piperidin-1-yl]-1-oxopropan-2-ol | 540 |
| 333 | 2-methyl-3-{[4-(1-methyl-1-{[3-(trifluoromethyl)phenyl]sulfonyl}ethyl)piperidin-1-yl]carbonyl}imidazo[1,2-a]pyridin-1-ium chloride | 494 |
| 334 | (2S)-3-(4-chlorophenyl)-1-[4-(1-methyl-1-{[3-(trifluoromethyl)phenyl]sulfonyl}ethyl)piperidin-1-yl]-1-oxopropan-2-ol | 518 |
| 335 | 2,2-dimethyl-3-[4-(1-methyl-1-{[3-(trifluoromethyl)phenyl]sulfonyl}ethyl)piperidin-1-yl]-3-oxo-1-phenylpropan-1-ol | 512 |
| 336 | (2R)-2-(3-chlorophenyl)-1-[4-(1-methyl-1-{[3-(trifluoromethyl)phenyl]sulfonyl}ethyl)piperidin-1-yl]-1-oxopropan-2-ol | 518 |

TABLE 6-continued

| EXAMPLE # | STRUCTURE | CHEMICAL NAME | MASS SPECTRAL DATA m/e (M + H) |
|---|---|---|---|
| 337 | 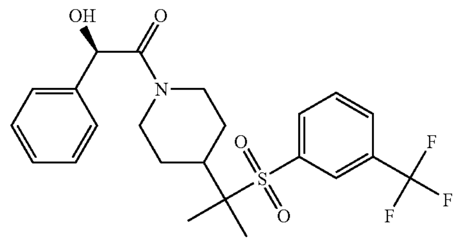 | (1R)-2-[4-(1-methyl-1-{[3-(trifluoromethyl)phenyl]sulfonyl}ethyl)piperidin-1-yl]-2-oxo-1-phenylethanol | 470 |
| 338 | 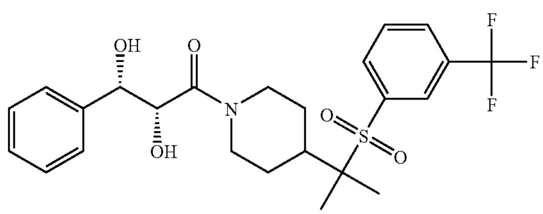 | (1S,2R)-3-[4-(1-methyl-1-{[3-(trifluoromethyl)phenyl]sulfonyl}ethyl)piperidin-1-yl]-3-oxo-1-phenylpropane-1,2-diol | 500 |
| 339 | 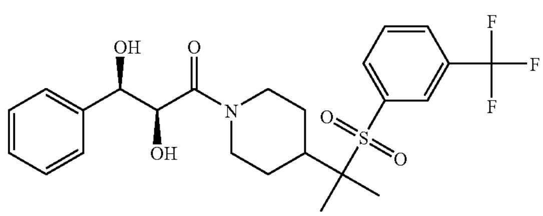 | (1R,2S)-3-[4-(1-methyl-1-{[3-(trifluoromethyl)phenyl]sulfonyl}ethyl)piperidin-1-yl]-3-oxo-1-phenylpropane-1,2-diol | 500 |
| 340 | 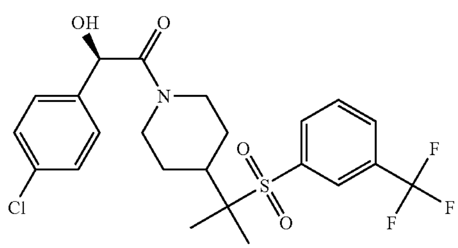 | (1R)-1-(4-chlorophenyl)-2-[4-(1-methyl-1-{[3-(trifluoromethyl)phenyl]sulfonyl}ethyl)piperidin-1-yl]-2-oxoethanol | 504 |
| 341 | 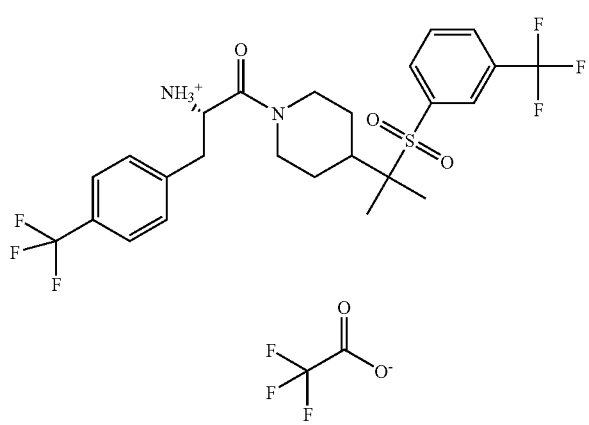 | (2S)-1-[4-(1-methyl-1-{[3-(trifluoromethyl)phenyl]sulfonyl}ethyl)piperidin-1-yl]-1-oxo-3-[4-(trifluoromethyl)phenyl]propan-2-aminiumtrifluoroacetate | 552 |

TABLE 6-continued

| EXAMPLE # | STRUCTURE | CHEMICAL NAME | MASS SPECTRAL DATA m/e (M + H) |
|---|---|---|---|
| 342 | 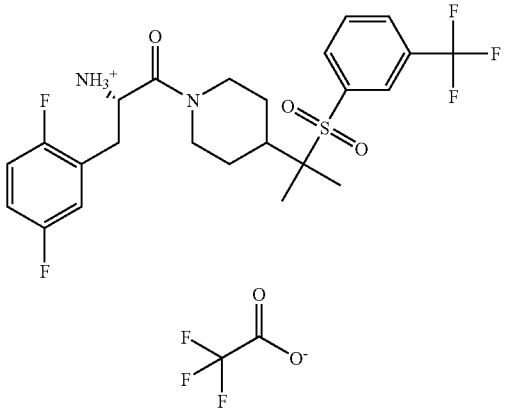 | (2S)-3-(2,5-difluorophenyl)-1-[4-(1-methyl-1-{[3-(trifluoromethyl)phenyl]sulfonyl}ethyl)piperidin-1-yl]-1-oxopropan-2-aminium trifluoroacetate | 519 |
| 343 | 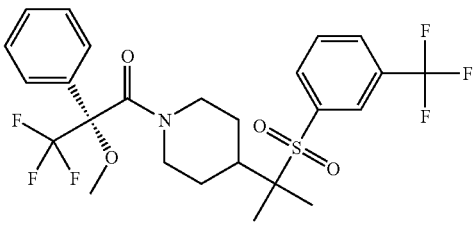 | 4-(1-methyl-1-{[3-(trifluoromethyl)phenyl]sulfonyl}ethyl)-1-[(2R)-3,3,3-trifluoro-2-methoxy-2-phenylpropanoyl]piperidine | 552 |
| 344 | 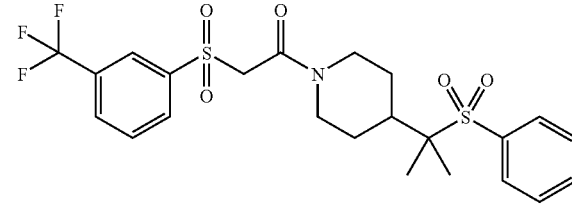 | 4-(1-methyl-1-{[3-(trifluoromethyl)phenyl]sulfonyl}ethyl)-1-({[3-(trifluoromethyl)phenyl]sulfonyl}acetyl)piperidineuoromethyl)phenyl]sulfonyl}acetyl)piperidine | 586 |
| 345 | 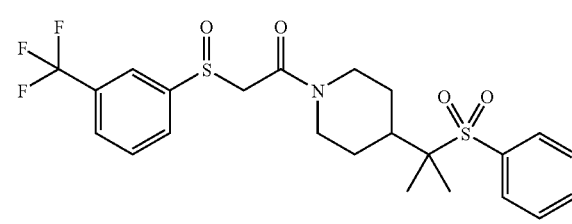 | 4-(1-methyl-1-{[3-(trifluoromethyl)phenyl]sulfonyl}ethyl)-1-({[3-(trifluoromethyl)phenyl]sulfinyl}acetyl)piperidine | 570 |
| 346 | 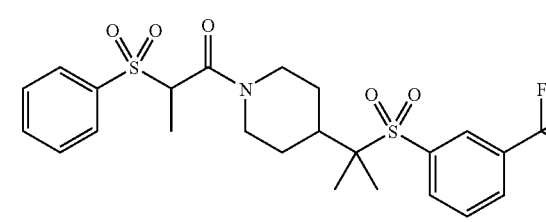 | 4-(1-methyl-1-{[3-(trifluoromethyl)phenyl]sulfonyl}ethyl)-1-[2-(phenylsulfonyl)propanoyl]piperidine | 532 |
| 347 | 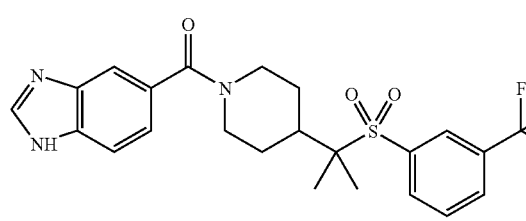 | 5-{[4-(1-methyl-1-{[3-(trifluoromethyl)phenyl]sulfonyl}ethyl)piperidin-1-yl]carbonyl}-1H-benzimidazole | 480 |

TABLE 6-continued

| EXAMPLE # | STRUCTURE | CHEMICAL NAME | MASS SPECTRAL DATA m/e (M + H) |
|---|---|---|---|
| 348 | 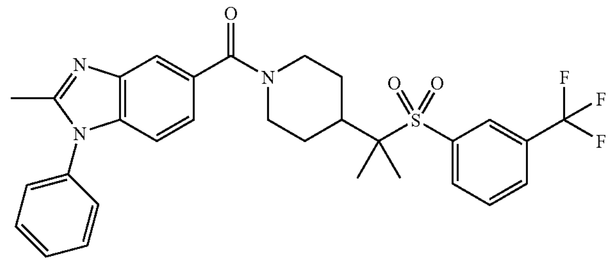 | 2-methyl-5-{[4-(1-methyl-1-{[3-(trifluoromethyl)phenyl]sulfonyl}ethyl)piperidin-1-yl]carbonyl}-1-phenyl-1H-benzimidazole | 570 |
| 349 | 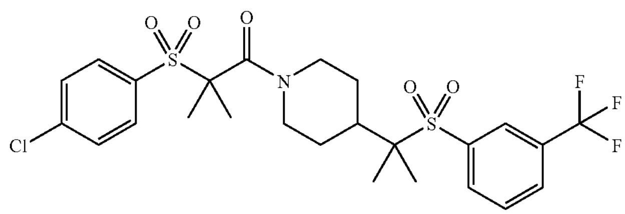 | 1-{2-[(4-chlorophenyl)sulfonyl]-2-methylpropanoyl}-4-(1-methyl-1-{[3-(trifluoromethyl)phenyl]sulfonyl}ethyl)piperidine | 580 |
| 350 | 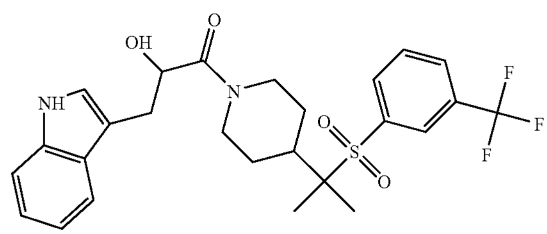 | 3-(1H-indol-3-yl)-1-[4-(1-methyl-1-{[3-(trifluoromethyl)phenyl]sulfonyl}ethyl)piperidin-1-yl]-1-oxopropan-2-ol | 523 |
| 351 | 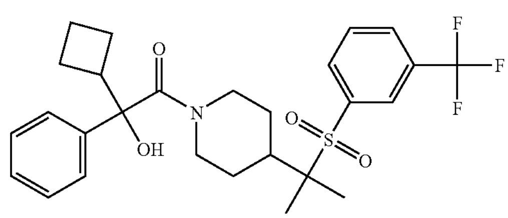 | 1-cyclobutyl-2-[4-(1-methyl-1-{[3-(trifluoromethyl)phenyl]sulfonyl}ethyl)piperidin-1-yl]-2-oxo-1-phenylethanol | 524 |
| 352 | 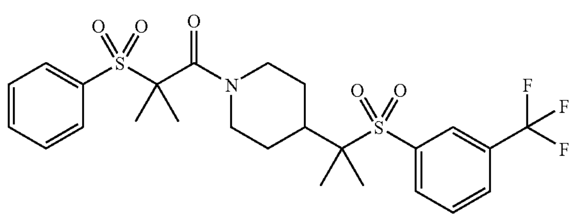 | 1-[2-methyl-2-(phenylsulfonyl)propanoyl]-4-(1-methyl-1-{[3-(trifluoromethyl)phenyl]sulfonyl}ethyl)piperidine | 546 |
| 353 | 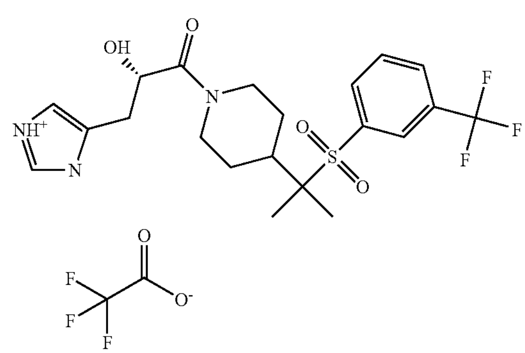 | 5-{(2S)-2-hydroxy-3-[4-(1-methyl-1-{[3-(trifluoromethyl)phenyl]sulfonyl}ethyl)piperidin-1-yl]-3-oxopropyl}-1H-imidazol-3-ium trifluoroacetate | 474 |

TABLE 6-continued

| EXAMPLE # | STRUCTURE | CHEMICAL NAME | MASS SPECTRAL DATA m/e (M + H) |
|---|---|---|---|
| 354 | 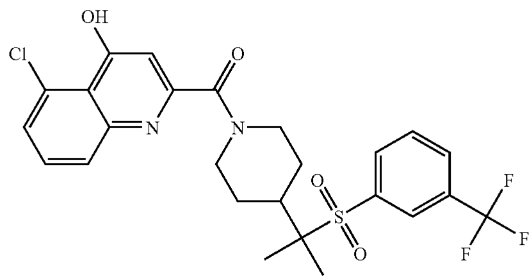 | 5-chloro-2-{[4-(1-methyl-1-{[3-(trifluoromethyl)phenyl]sulfonyl}ethyl)piperidin-1-yl]carbonyl}quinolin-4-ol | 541 |
| 355 | 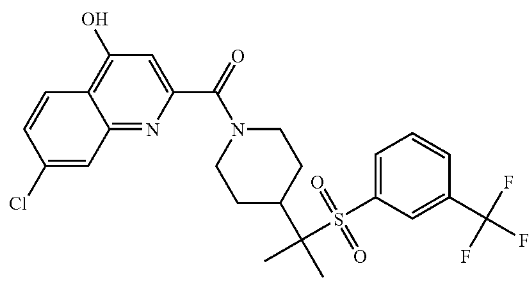 | 7-chloro-2-{[4-(1-methyl-1-{[3-(trifluoromethyl)phenyl]sulfonyl}ethyl)piperidin-1-yl]carbonyl}quinolin-4-ol | 541 |
| 356 | 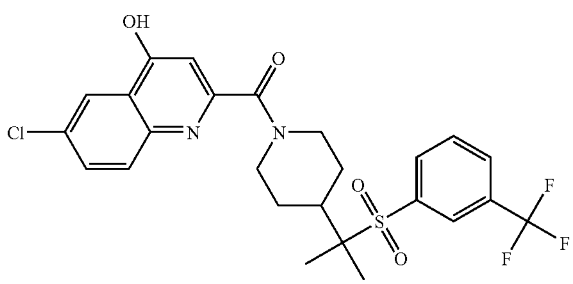 | 6-chloro-2-{[4-(1-methyl-1-{[3-(trifluoromethyl)phenyl]sulfonyl}ethyl)piperidin-1-yl]carbonyl}quinolin-4-ol | 541 |
| 357 | 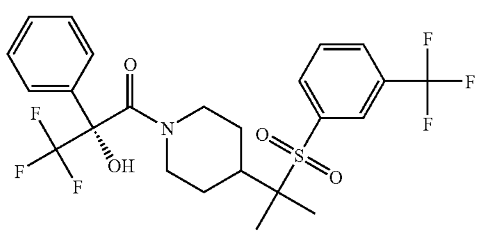 | (2R)-1,1,1-trifluoro-3-[4-(1-methyl-1-{[3-(trifluoromethyl)phenyl]sulfonyl}ethyl)piperidin-1-yl]-3-oxo-2-phenylpropan-2-ol | 538 |
| 358 | 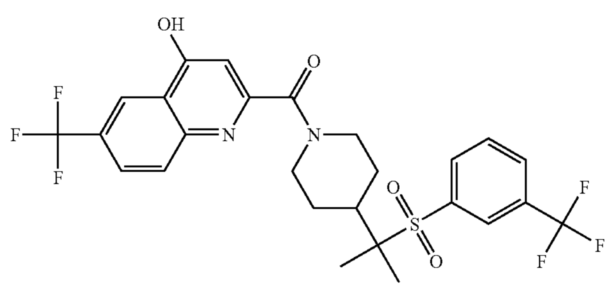 | 2-{[4-(1-methyl-1-{[3-(trifluoromethyl)phenyl]sulfonyl}ethyl)piperidin-1-yl]carbonyl}-6-(trifluoromethyl)quinolin-4-ol | 575 |

TABLE 6-continued

| EXAMPLE # | CHEMICAL NAME | MASS SPECTRAL DATA m/e (M + H) |
|---|---|---|
| 359 | (2R)-3-(1H-indol-3-yl)-1-[4-(1-methyl-1-{[3-(trifluoromethyl)phenyl]sulfonyl}ethyl)piperidin-1-yl]-1-oxopropan-2-amine | 522 |
| 360 | 4-(1-methyl-1-{[3-(trifluoromethyl)phenyl]sulfonyl}ethyl)-1-(2-methyl-2-{[3-(trifluoromethyl)phenyl]sulfonyl}propanoyl)piperidine | 614 |
| 361 | 1-(3-chlorobenzoyl)-4-(1-methyl-1-{[3-(trifluoromethyl)phenyl]sulfonyl}ethyl)piperidine | 474 |
| 362 | 2-{1,1-dimethyl-2-[4-(1-methyl-1-{[3-(trifluoromethyl)phenyl]sulfonyl}ethyl)piperidin-1-yl]-2-oxoethoxy}-5-(trifluoromethyl)pyridine | 567 |
| 363 | 6-chloro-3-{[4-(1-methyl-1-{[3-(trifluoromethyl)phenyl]sulfonyl}ethyl)piperidin-1-yl]carbonyl}quinolin-4-ol | 541 |
| 364 | 6-fluoro-3-{[4-(1-methyl-1-{[3-(trifluoromethyl)phenyl]sulfonyl}ethyl)piperidin-1-yl]carbonyl}quinolin-4-ol | 525 |

TABLE 6-continued

| EXAMPLE # | STRUCTURE | CHEMICAL NAME | MASS SPECTRAL DATA m/e (M + H) |
|---|---|---|---|
| 365 | 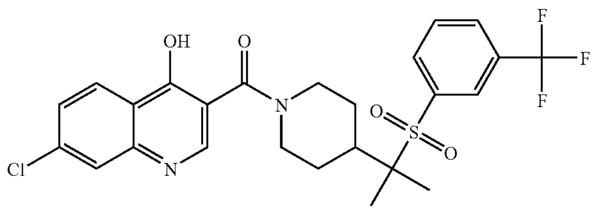 | 7-chloro-3-{[4-(1-methyl-1-{[3-(trifluoromethyl)phenyl]sulfonyl}ethyl)piperidin-1-yl]carbonyl}quinolin-4-ol | 541 |
| 366 | 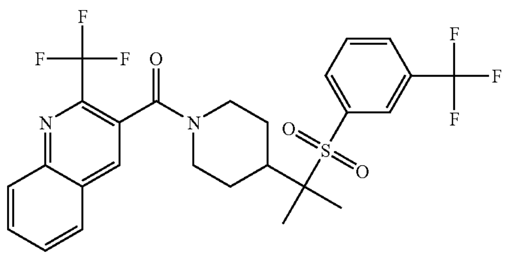 | 3-{[4-(1-methyl-1-{[3-(trifluoromethyl)phenyl]sulfonyl}ethyl)piperidin-1-yl]carbonyl}-2-(trifluoromethyl)quinoline | 559 |
| 367 | 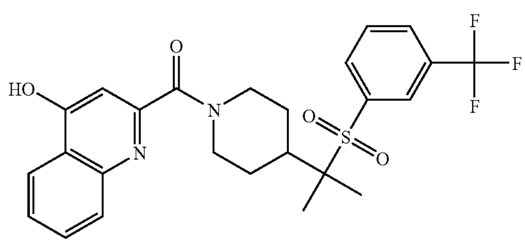 | 2-{[4-(1-methyl-1-{[3-(trifluoromethyl)phenyl]sulfonyl}ethyl)piperidin-1-yl]carbonyl}quinolin-4-ol | 507 |
| 368 | 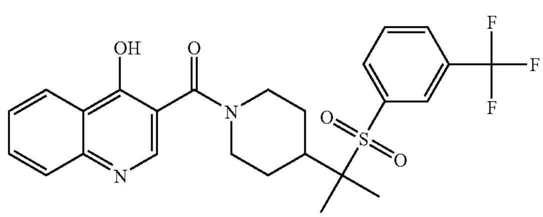 | 3-{[4-(1-methyl-1-{[3-(trifluoromethyl)phenyl]sulfonyl}ethyl)piperidin-1-yl]carbonyl}quinolin-4-ol | 507 |
| 369 | 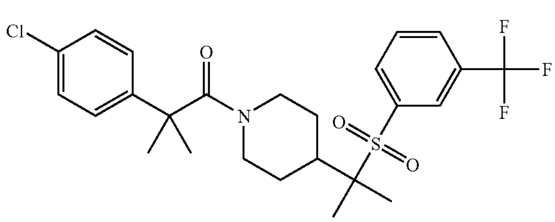 | 1-[2-(4-chlorophenyl)-2-methylpropanoyl]-4-(1-methyl-1-{[3-(trifluoromethyl)phenyl]sulfonyl)ethyl)piperidine | 516 |
| 370 | 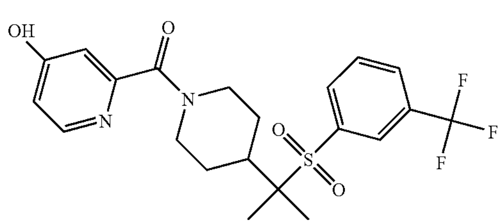 | 2-{[4-(1-methyl-1-{[3-(trifluoromethyl)phenyl]sulfonyl}ethyl)piperidin-1-yl]carbonyl}pyridin-4-ol | 457 |

TABLE 6-continued

| EXAMPLE # | STRUCTURE | CHEMICAL NAME | MASS SPECTRAL DATA m/e (M + H) |
|---|---|---|---|
| 371 | 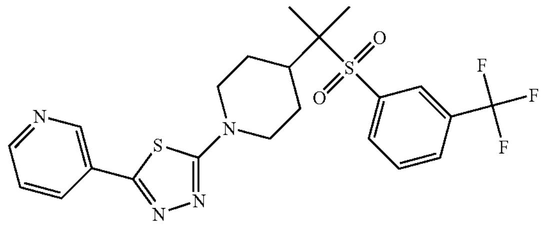 | 3-{5-[4-(1-methyl-1-{[3-(trifluoromethyl)phenyl]sulfonyl}ethyl)piperidin-1-yl]-1,3,4-thiadiazol-2-yl}pyridine | 497 |
| 372 | 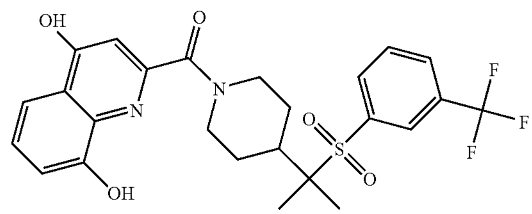 | 2-{[4-(1-methyl-1-{[3-(trifluoromethyl)phenyl]sulfonyl}ethyl)piperidin-1-yl]carbonyl}quinoline-4,8-diol | 523 |
| 373 | 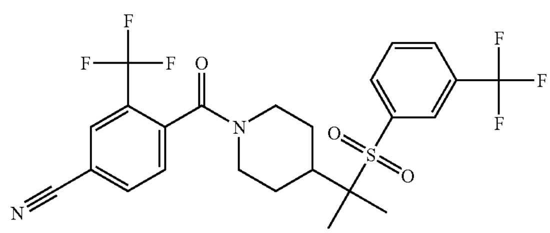 | 4-{[4-(1-methyl-1-{[3-(trifluoromethyl)phenyl]sulfonyl}ethyl)piperidin-1-yl]carbonyl}-3-(trifluoromethyl)benzonitrile | 533 |
| 374 | 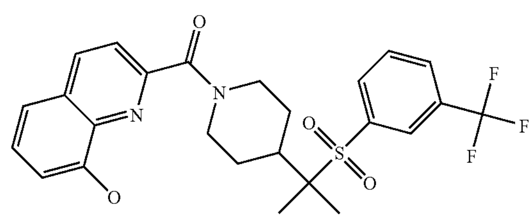 | 2-{[4-(1-methyl-1-{[3-(trifluoromethyl)phenyl]sulfonyl}ethyl)piperidin-1-yl]carbonyl}quinolin-8-ol | 507 |
| 375 | 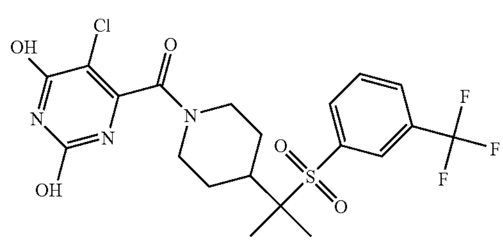 | 5-chloro-6-{[4-(1-methyl-1-{[3-(trifluoromethyl)phenyl]sulfonyl}ethyl)piperidin-1-yl]carbonyl}pyrimidine-2,4-diol | 508 |
| 376 | 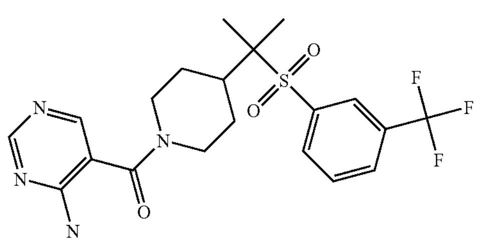 | 5-{[4-(1-methyl-1-{[3-(trifluoromethyl)phenyl]sulfonyl}ethyl)piperidin-1-yl]carbonyl}pyrimidin-4-amine | 457 |

TABLE 6-continued

| EXAMPLE # | STRUCTURE | CHEMICAL NAME | MASS SPECTRAL DATA m/e (M + H) |
|---|---|---|---|
| 377 | 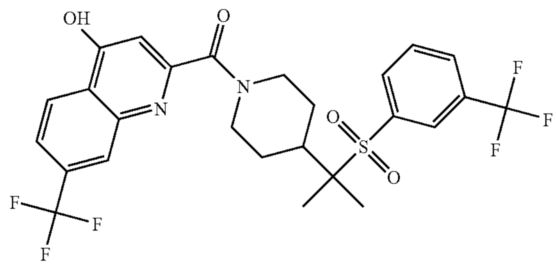 | 2-{[4-(1-methyl-1-{[3-(trifluoromethyl)phenyl]sulfonyl}ethyl)piperidin-1-yl]carbonyl}-7-(trifluoromethyl)quinolin-4-ol | 575 |
| 378 | 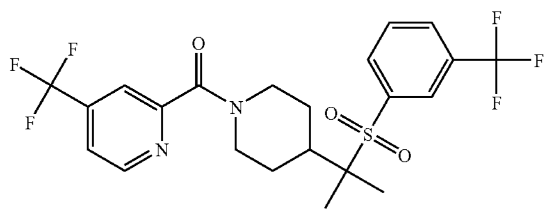 | 2-{[4-(1-methyl-1-{[3-(trifluoromethyl)phenyl]sulfonyl}ethyl)piperidin-1-yl]carbonyl}-4-(trifluoromethyl)pyridine | 509 |
| 379 | 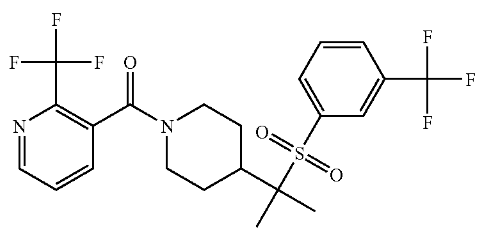 | 3-{[4-(1-methyl-1-{[3-(trifluoromethyl)phenyl]sulfonyl}ethyl)piperidin-1-yl]carbonyl}-2-(trifluoromethyl)pyridine | 509 |
| 380 | 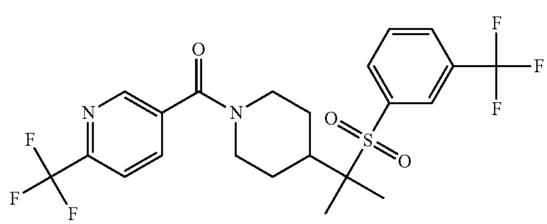 | 5-{[4-(1-methyl-1-{[3-(trifluoromethyl)phenyl]sulfonyl}ethyl)piperidin-1-yl]carbonyl}-2-(trifluoromethyl)pyridine | 509 |
| 381 | 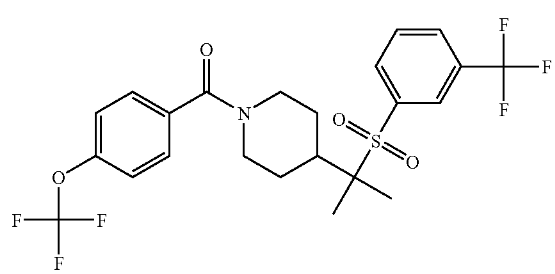 | 4-(1-methyl-1-{[4-(trifluoromethyl)phenyl]sulfonyl}ethyl)-1-[3-(trifluoromethoxy)benzoyl]piperidine | 524 |
| 382 | 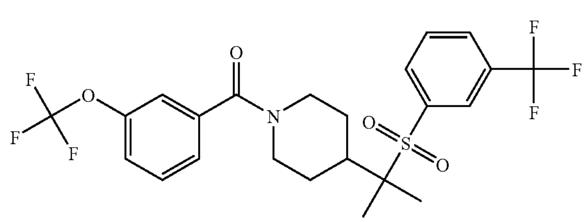 | 4-(1-methyl-1-{[3-(trifluoromethyl)phenyl]sulfonyl}ethyl)-1-[3-(trifluoromethoxy)benzoyl]piperidine | 524 |

TABLE 6-continued

| EXAMPLE # | STRUCTURE | CHEMICAL NAME | MASS SPECTRAL DATA m/e (M + H) |
|---|---|---|---|
| 383 | 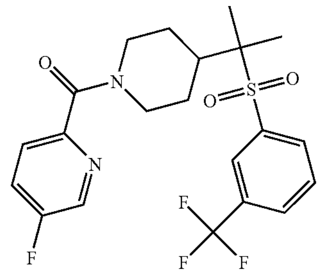 | 5-fluoro-2-{[4-(1-methyl-1-{[3-(trifluoromethyl)phenyl]sulfonyl}ethyl)piperidin-1-yl]carbonyl}pyridine | 459 |
| 384 | 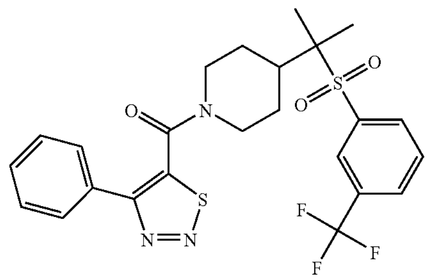 | 1-[(4-phenyl-1,2,3-thiadiazol-5-yl)carbonyl]-4-(1-methyl-1-{[3-(trifluoromethyl)phenyl]sulfonyl}ethyl)piperidine | 524 |
| 385 | 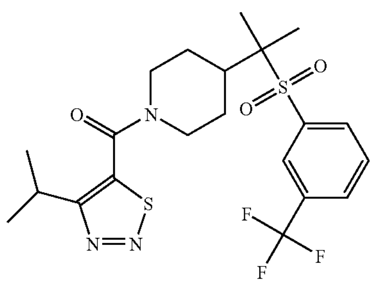 | 1-[(4-isopropyl-1,2,3-thiadiazol-5-yl)carbonyl]-4-(1-methyl-1-{[3-(trifluoromethyl)phenyl]sulfonyl}ethyl)piperidine | 490 |
| 386 | 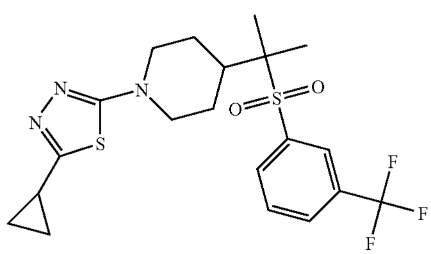 | 1-(5-cyclopropyl-1,3,4-thiadiazol-2-yl)-4-(1-methyl-1-{[3-(trifluoromethyl)phenyl]sulfonyl}ethyl)piperidine | 460 |
| 387 | 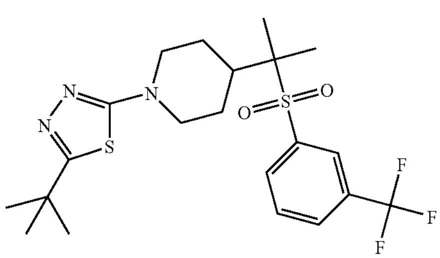 | 1-(5-tert-butyl-1,3,4-thiadiazol-2-yl)-4-(1-methyl-1-{[3-(trifluoromethyl)phenyl]sulfonyl}ethyl)piperidine | 476 |

TABLE 6-continued

| EXAMPLE # | STRUCTURE | CHEMICAL NAME | MASS SPECTRAL DATA m/e (M + H) |
|---|---|---|---|
| 388 | 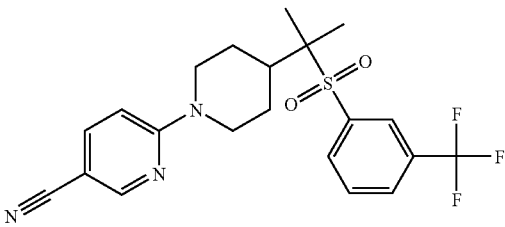 | 6-[4-(1-methyl-1-{[3-(trifluoromethyl)phenyl]sulfonyl}ethyl)piperidin-1-yl]nicotinonitrile | 438 |
| 389 | 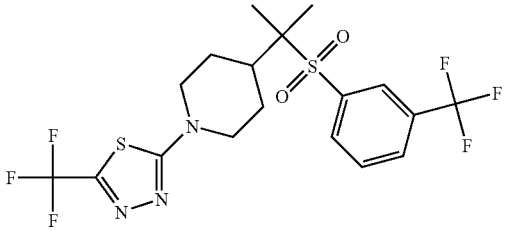 | 4-(1-methyl-1-{[3-(trifluoromethyl)phenyl]sulfonyl}ethyl)-1-[5-(trifluoromethyl)-1,3,4-thiadiazol-2-yl]piperidine | 488 |
| 390 | 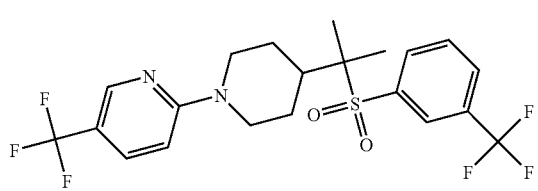 | 2-[4-(1-methyl-1-{[3-(trifluoromethyl)phenyl]sulfonyl}ethyl)piperidin-1-yl]-5-(trifluoromethyl)pyridine | 481 |
| 391 | 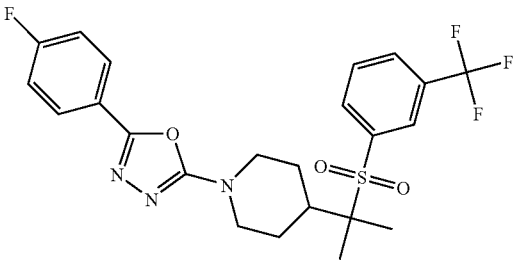 | 1-[5-(4-fluorophenyl)-1,3,4-oxadiazol-2-yl]-4-(1-methyl-1-{[3-(trifluoromethyl)phenyl]sulfonyl}ethyl)piperidine | 498 |
| 392 | 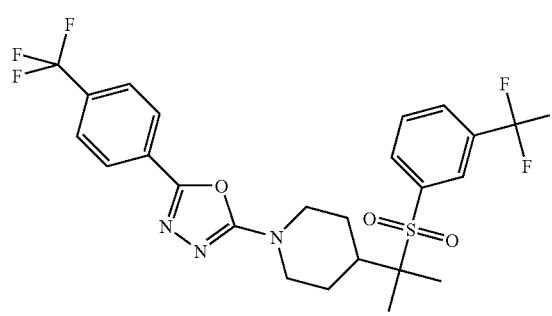 | 4-(1-methyl-1-{[3-(trifluoromethyl)phenyl]sulfonyl}ethyl)-1-{5-[4-(trifluoromethyl)phenyl]-1,3,4-oxadiazol-2-yl}piperidine | 548 |
| 393 | 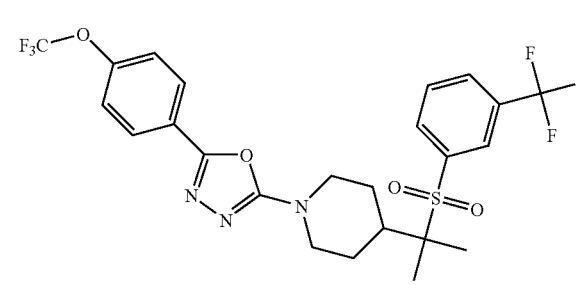 | 4-(1-methyl-1-{[3-(trifluoromethyl)phenyl]sulfonyl}ethyl)-1-{5-[4-(trifluoromethoxy)phenyl]-1,3,4-oxadiazol-2-yl}piperidine | 563 |

TABLE 6-continued

| EXAMPLE # | STRUCTURE | CHEMICAL NAME | MASS SPECTRAL DATA m/e (M + H) |
|---|---|---|---|
| 394 | 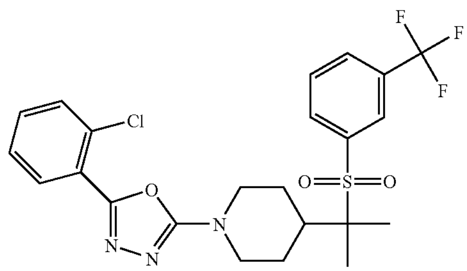 | 1-[5-(2-chlorophenyl)-1,3,4-oxadiazol-2-yl]-4-(1-methyl-1-{[3-(trifluoromethyl)phenyl]sulfonyl}ethyl)piperidine | 514 |
| 395 | 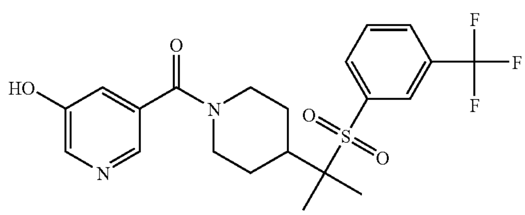 | 5-{[4-(1-methyl-1-{[3-(trifluoromethyl)phenyl]sulfonyl}ethyl)piperidin-1-yl]carbonyl}pyridin-3-ol | 457 |
| 396 | 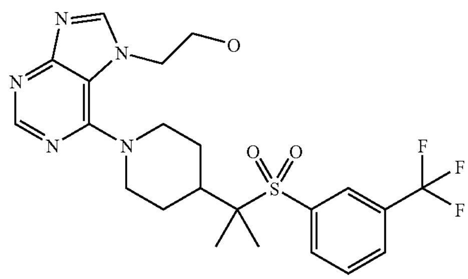 | 2-{6-[4-(1-methyl-1-{[3-(trifluoromethyl)phenyl]sulfonyl}ethyl)piperidin-1-yl]-7H-purin-7-yl}ethanol | 498 |
| 397 | 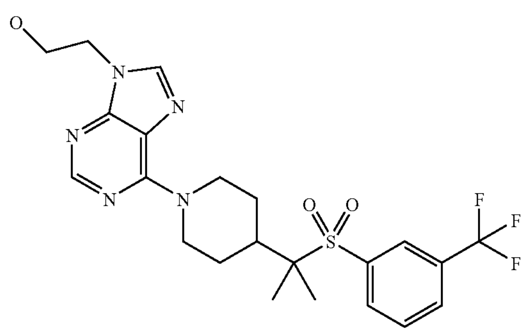 | 2-{6-[4-(1-methyl-1-{[3-(trifluoromethyl)phenyl]sulfonyl}ethyl)piperidin-1-yl]-9H-purin-9-yl}ethanol | 498 |
| 398 | 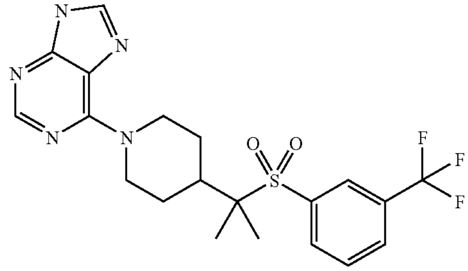 | 6-[4-(1-methyl-1-{[3-(trifluoromethyl)phenyl]sulfonyl}ethyl)piperidin-1-yl]-9H-purine | 454 |

TABLE 6-continued

| EXAMPLE # | STRUCTURE | CHEMICAL NAME | MASS SPECTRAL DATA m/e (M + H) |
|---|---|---|---|
| 399 | 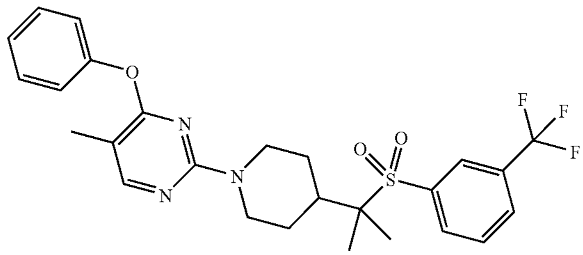 | 5-methyl-2-[4-(1-methyl-1-{[3-(trifluoromethyl)phenyl]sulfonyl}ethyl)piperidin-1-yl]-4-phenoxypyrimidine | 520 |
| 400 | 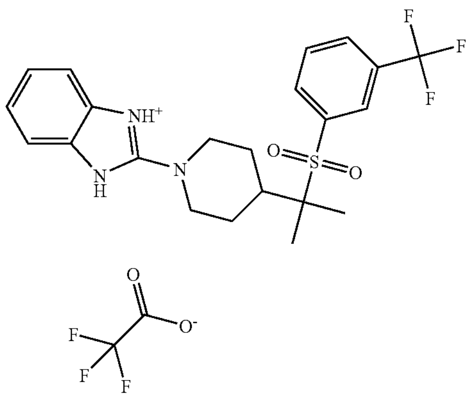 | 2-[4-(1-methyl-1-{[3-(trifluoromethyl)phenyl]sulfonyl}ethyl)piperidin-1-yl]-1H-benzimidazol-3-ium trifluoroacetate | 452 |
| 401 | 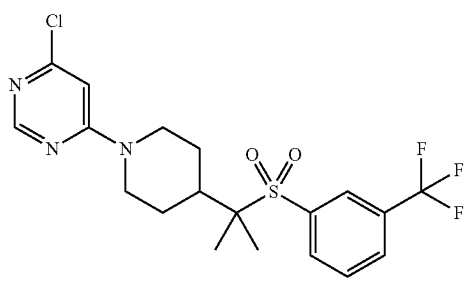 | 4-chloro-6-[4-(1-methyl-1-{[3-(trifluoromethyl)phenyl]sulfonyl}ethyl)piperidin-1-yl]pyrimidine | 448 |
| 402 | 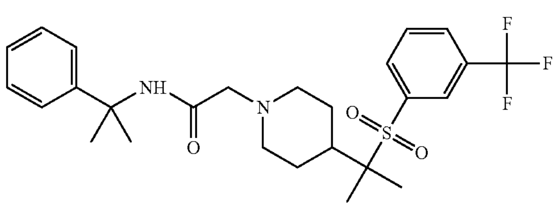 | N-(1-methyl-1-phenylethyl)-2-[4-(1-methyl-1-{[3-(trifluoromethyl)phenyl]sulfonyl}ethyl)piperidin-1-yl]acetamide | 511 |
| 403 | 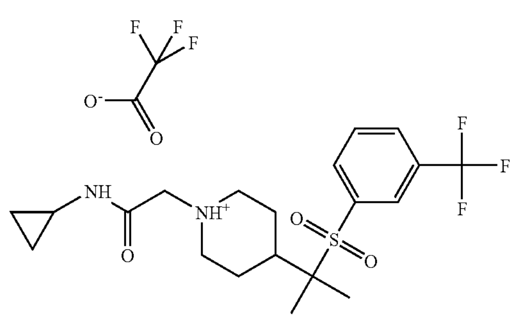 | 1-[2-(cyclopropylamino)-2-oxoethyl]-4-(1-methyl-1-{[3-(trifluoromethyl)phenyl]sulfonyl}ethyl)piperidinium trifluoroacetate | 433 |

TABLE 6-continued

| EXAMPLE # | STRUCTURE | CHEMICAL NAME | MASS SPECTRAL DATA m/e (M + H) |
|---|---|---|---|
| 404 | 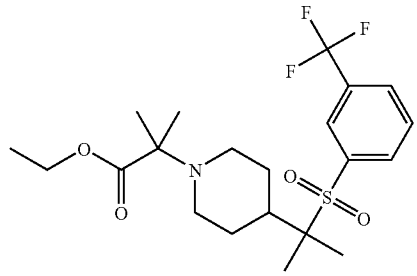 | ethyl 2-methyl-2-[4-(1-methyl-1-{[3-(trifluoromethyl)phenyl]sulfonyl}ethyl)piperidin-1-yl]propanoate | 450 |
| 405 | 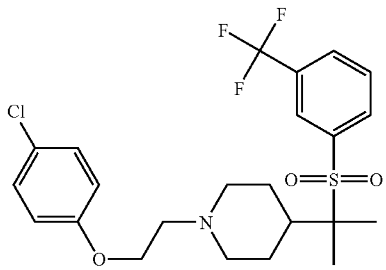 | 1-[2-(4-chlorophenoxy)ethyl]-4-(1-methyl-1-{[3-(trifluoromethyl)phenyl]sulfonyl}ethyl)piperidine | 490 |
| 406 | 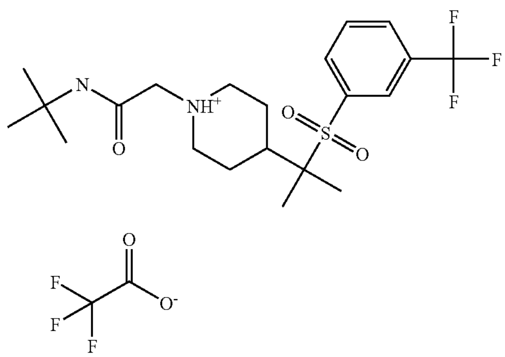 | 1-[2-(tert-butylamino)-2-oxoethyl]-4-(1-methyl-1-{[3-(trifluoromethyl)phenyl]sulfonyl}ethyl)piperidinium trifluoroacetate | 449 |

The compounds of this invention were evaluated using the various assays described above. The data for a representative set of compounds of this invention obtained using the Assay Example 1 is provided in Table 7.

TABLE 7

| STRUCTURE | CaV2.2 IC$_{50}$ (micromolar) |
|---|---|
| 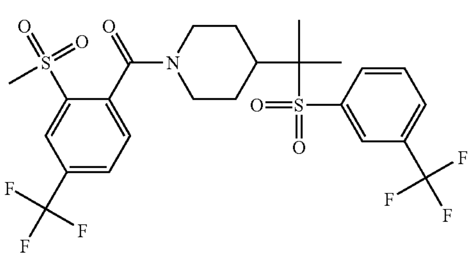 | 0.15 |

TABLE 7-continued

| STRUCTURE | CaV2.2 IC$_{50}$ (micromolar) |
|---|---|
| 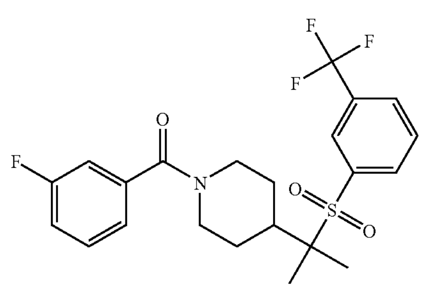 | 0.83 |

TABLE 7-continued

| STRUCTURE | CaV2.2 IC$_{50}$ (micromolar) |
|---|---|
| 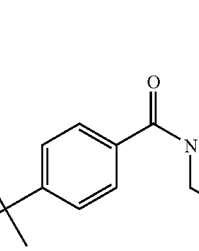 | 0.49 |
| 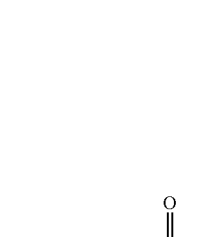 | 0.79 |
| 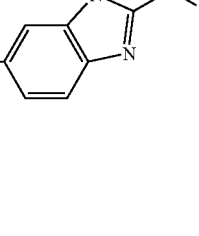 | 1.4 |
| 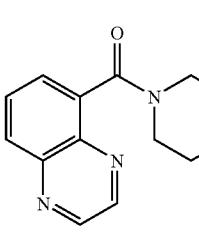 | 0.49 Chiral |
| 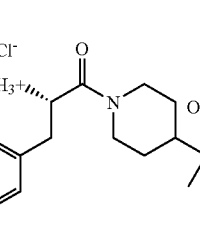 | 1.17 |

TABLE 7-continued

| STRUCTURE | CaV2.2 IC$_{50}$ (micromolar) |
|---|---|
| 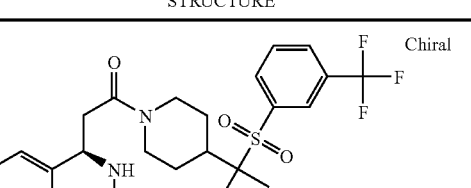 | 0.36 Chiral |
| 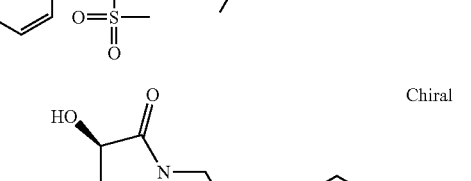 | 0.51 Chiral |
| 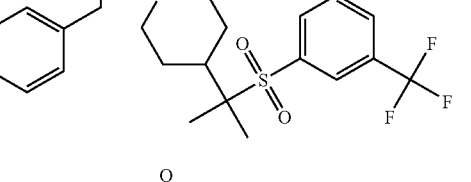 | 1.39 |

What is claimed is:

1. A compound of formula Ia:

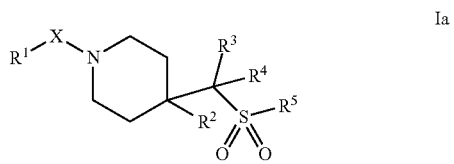

Ia and pharmaceutically acceptable salts thereof and individual enantiomers and diastereomers thereof wherein:

X is C=O;

$R^1$ is H, $C_{1-6}$-alkyl, $C_{3-7}$-cycloalkyl, $OR^{10}$, $C(O)R^{10}$, $(CH_2)_nC_{5-10}$ heterocycle, $(CH_2)_nC_{6-10}$ aryl, $(CH_2)_nC_{5-10}$ heteroaryl, fused aryl or fused heteroaryl, wherein said alkyl, cycloalkyl, heterocycle, aryl and heteroaryl is optionally substituted with one to three groups of $R^a$;

$R^2$ is H, $C_{1-4}$ alkyl and $C_{1-4}$-perfluoroalkyl, $C_{3-5}$-cycloalkyl, $C_{6-10}$ aryl, $C_{5-10}$ heteroaryl, F, Cl, CN, $NR^{10}R^{11}$, wherein said alkyl, cycloalkyl, aryl and heteroaryl is optionally substituted with one to three groups of $R^a$;

$R^3$ and $R^4$ are each and independently selected from H, or $C_{1-6}$ alkyl, $C_{1-4}$-perfluoroalkyl, $C_{3-7}$-cycloalkyl, $C_{6-10}$ aryl, $C_{5-10}$ heteroaryl, F, Cl, CN, $OR^{10}$, $NR^{10}R^{11}$, $SO_2R^{10}$, $SO_2NR^{10}R^{11}$, $CO_2R^{10}$, $CONHR^{10}$, $CONR^{10}R^{11}$, or $R^3$ and $R^4$ join to form a 3-7 member carbocyclic or heterocyclic ring, wherein said alkyl, cycloalkyl, heterocycle, aryl and heteroaryl is optionally substituted with one to three groups of $R^a$;

R⁵ is $C_{6-10}$ aryl, $C_{5-10}$ heteroaryl, $C_{3-7}$ cycloalkyl, $C_{5-10}$ heterocycle, wherein said cycloalkyl, heterocycle, aryl and heteroaryl is optionally substituted with one to three groups of $R^a$;

$R^{10}$ and $R^{11}$ are each and independently selected from H, or $C_{1-6}$alkyl, $(CH_2)_nC_{1-4}$-fluoroalkyl, $C_{3-7}$cycloalkyl, $C_{6-10}$ aryl, $C_{5-10}$ heteroaryl, or $R^{10}$ and $R^{11}$ join to form a 3-7 member carbocyclic or heterocyclic ring with the atom to which they are attached;

said alkyl, aryl, or heteroaryl optionally substituted with 1 to 3 groups of $R^a$, n represents 0 to 6, and $R^a$ represents $C_{1-6}$ alkyl, $C_{3-7}$ cycloalkyl, $C_{1-4}$-fluoroalkyl, $C_{6-10}$ aryl, $C_{5-10}$ heteroaryl, halogen, CN, —$OCF_3$, —$OCHF_2$, —$C(O)CF_3$, —$C(OR^{10})(CF_3)_2$, $SR^{10}$, —$OR^{10}$, $NR^{10}R^{11}$, $SOR^{10}$, $SO_2R^{10}$, $NR^{10}COR^{11}$, $NR^{10}COOR^{11}$, $NR^{10}CONR^{10}R^{11}$, $NR^{10}SO_2NR^{10}R^{11}$, $SO_2NR^{10}R^{11}$, $NR^{10}SO_2R^{11}$, $CO_2R^{10}$, $CONR^{10}R^{11}$, said aryl and heteroaryl optionally substituted with 1 to 3 groups of $C_{1-6}$ alkyl, $C_{3-7}$ cycloalkyl, halogen, $CF_3$, CN or $OR^{10}$; with the proviso that the compound of formula I cannot be 4-[[[4-[[5-[2-(2-Aminobenzothiazol-6-yl)vinyl]pyrimidin-2-yl]amino]phenyl]sulfonyl]-methyl] piperidine-1-carboxylic acid tert-butyl ester; 4-[[[4-[(5-Vinylpyrimidin-2-yl)amino]phenyl]sulfonyl]methyl] piperidine-1-carboxylic acid tert-butyl ester; Piperidinecarboxylic acid, 4-[[[4-[[5-[(1E)-2-(3-methoxyphenyl)ethenyl]-2-pyrimidinyl]amino]phenyl]sulfonyl]methyl]-, 1,1-dimethylethyl ester; 4-[[(4-Bromophenyl)sulfonyl]methyl]piperidine-1-carboxylic acid tert-butyl ester; Piperidinecarboxylic acid, 4-[[(4-fluorophenyl)sulfonyl]methyl]; Piperidinecarboxylic acid, 4-[[(2-fluorophenyl)sulfonyl]methyl]-, 1,1-dimethylethyl ester; Piperidinecarboxylic acid, 3-hydroxy-4-[[[4-(methylthio)phenyl]sulfonyl]methyl]-, 1,1-dimethylethyl ester, (3R,4S); tert-Butyl 4-[(4-chlorobenzenesulfonyl)(2,5-difluorophenyl)methyl]piperidine-1-carboxylate; 4-[[(4-Fluorophenyl)sulfonyl]methyl]-1-piperidinecarboxylate hydrochloride; tert-Butyl 4-[[(4-fluorophenyl)sulfonyl] methyl]-1-piperidinecarboxylate; or Piperidine, 1-(bromoacetyl)-4-[[(4-methylphenyl)sulfonyl]methyl]; or the compound of formula I is not piperidinyl-1-(bromoacetyl-4-[[4-methylphenyl)sulfonyl]methyl], or benzonitrilyl-4-[4-[[(4-fluorophenyl)sulfonyl]methyl]-4-hydroxy-1-piperidinyl]-2-(trifluoromethyl).

2. The compound according to claim 1 wherein $R^1$ is $(CH_2)_nC_{5-10}$ heterocycle, $(CH_2)_nC_{6-10}$ aryl, $(CH_2)_nC_{5-10}$ heteroaryl, fused aryl or fused heteroaryl, and $R^5$ is $C_{6-10}$ aryl, $C_{5-10}$ heteroaryl, or $C_{5-10}$ heterocycle, wherein said heterocycle, aryl and heteroaryl is optionally substituted with one to three groups of $R^a$.

3. The compound according to claim 2 wherein $R^1(CH_2)_n$ $C_{6-10}$ aryl.

4. The compound according to claim 2 wherein $R^1$ is $(CH_2)_n C_{5-10}$ heteroaryl.

5. The compound according to claim 1 wherein both $R^3$ and $R^4$ are H or $CH_3$, or one of $R^3$ and $R^4$ is H and the other is $CH_3$, and $R^1$ and $R^5$ are independently phenyl, or pyridyl optionally substituted with 1 to 3 groups of $R^a$.

6. A compound which is:

1-benzoyl-4-(1-methyl-1-{[3-(trifluoromethyl)phenyl] sulfonyl}ethyl)piperidine;

tert-butyl 4-(1-{[3-(trifluoromethyl)phenyl] sulfonyl}ethyl)piperidine-1-carboxylate;

tert-butyl 4-(1-methyl-1-{[3-(trifluoromethyl)phenyl] sulfonyl}ethyl)piperidine-1-carboxylate;

1-benzoyl-4-(1-methyl-1-{[3-(trifluoromethyl)phenyl] sulfonyl}ethyl)piperidine;

1-[2-(methylsulfonyl)-4-(trifluoromethoxy)benzoyl]-4-(1-methyl-1-{[3-(trifluoromethyl)phenyl] sulfonyl}ethyl)piperidine;

2-(cyclopropylsulfonyl)-3-{[4-(1-methyl-1-{[3-(trifluoromethyl)phenyl]sulfonyl}-ethyl)piperidin-1-yl]carbonyl}-6-(trifluoromethyl)pyridine;

1-[4-(cyclopropyloxy)-2,6-bis(methylsulfonyl)benzoyl]-4-(1-methyl-1-{[3-(trifluoromethyl)phenyl] sulfonyl}ethyl)piperidine;

1-[4-(cyclopropyloxy)-2,6-bis(methylthio)benzoyl]-4-(1-methyl-1-{[3-(trifluoromethyl)-phenyl]sulfonyl}ethyl) piperidine;

2-[(1-methyl-1-{1-[2-(methylsulfonyl)-4-(trifluoromethoxy)benzoyl]piperidin-4-yl}ethyl)sulfonyl]-6-(trifluoromethyl)pyridine;

tert-butyl 4-(1-methyl-1-{[6-(trifluoromethyl)pyridin-2-yl]sulfonyl}ethyl)piperidine-1-carboxylate;

1-[4-(methylsulfonyl)-2-(trifluoromethoxy)benzoyl]-4-({[3-(trifluoromethyl)-phenyl]sulfonyl}methyl)-piperidine;

1-[5-fluoro-2-(methylsulfonyl)benzoyl]-4-({[3-(trifluoromethyl)-phenyl]sulfonyl}methyl)-piperidine;

1-[2-(methylsulfonyl)-4-(trifluoromethyl)benzoyl]-4-({[3-(trifluoromethyl)-phenyl]sulfonyl}methyl)piperidine;

1-[2-chloro-4-(methylsulfonyl)benzoyl]-4-({[3-(trifluoromethyl)-phenyl]sulfonyl}methyl)piperidine;

1-[5-fluoro-2-(methyl-sulfonyl)benzoyl]-4-{[(4-fluorophenyl)sulfonyl]-methyl}piperidinehyl}piperidine;

4-{[(4-fluorophenyl)-sulfonyl]methyl}-1-[4-(methylsulfonyl)-2-(trifluoromethoxy)benzoyl]piperidine;

4-{[(4-chlorophenyl)-sulfonyl]methyl}-1-[5-fluoro-2-(methylsulfonyl)benzoyl]piperidine;

4-{[(4-chlorophenyl)sulfonyl]methyl}-1-[4-(methylsulfonyl)-2-(trifluoromethoxy)benzoyl]-piperidine;

4-{[(3-chlorophenyl)sulfonyl]methyl}-1-[4-(methylsulfonyl)-2-(trifluoromethoxy)benzoyl]piperidine;

1-(3,5-di-tert-butyl-4-methoxybenzoyl)-4-{[(4-fluorophenyl)sulfonyl]methyl}piperidine;

4-{[(4-chlorophenyl)sulfonyl]methyl}-1-(3,5-di-tert-butyl-4-methoxybenzoyl)piperidine;

1-[4-(difluoromethoxy)-2-(methylsulfonyl)benzoyl]-4-({[3-(trifluoromethyl)-phenyl]sulfonyl}methyl)piperidine;

4-{[(4-fluorophenyl)-sulfonyl]methyl}-1-[2-(methylsulfonyl)-4-(trifluoromethoxy)benzoyl]piperidine;

1-[4-(difluoromethoxy)-2-(methylsulfonyl)benzoyl]-4-{[(4-fluorophenyl)sulfonyl]methyl}piperidine;

4-{[(4-chlorophenyl)sulfonyl]methyl}-1-[2-(methylsulfonyl)-4-(trifluoromethoxy)benzoyl]piperidine;

4-{[(4-chlorophenyl)sulfonyl]methyl}-1-[4-(difluoromethoxy)-2-(methylsulfonyl)benzoyl]piperidine;

1-[2-(methylsulfonyl)-4-(trifluoromethoxy)benzoyl]-4-({[3-(trifluoromethyl)phenyl]sulfonyl}methyl)piperidine;

4-{[(4-chlorophenyl)sulfonyl]methyl}-1-[2-(methylsulfonyl)-4-(trifluoromethoxy)benzoyl]piperidine;

4-{[(4-fluorophenyl)sulfonyl]methyl}-1-[2-(methylsulfonyl)-4-(trifluoromethoxy)benzoyl]piperidine;

1-[4-(methylsulfonyl)-2-(trifluoromethoxy)benzoyl]-4-(1-{[3-(trifluoromethyl)phenyl]-sulfonyl}ethyl)piperidine;

1-[4-(methylsulfonyl)-2-(trifluoromethoxy)benzoyl]-4-((1S)-1-{[3-(trifluoromethyl)phenyl]-sulfonyl}ethyl) piperidine;

1-[4-(methylsulfonyl)-2-(trifluoromethoxy)benzoyl]-4-
((1R)-1-{[3-(trifluoromethyl)phenyl]-sulfonyl}ethyl)
piperidine;
4-{1-[(4-fluorophenyl)sulfonyl]ethyl}-1-[4-(methylsulfonyl)-2-(trifluoromethoxy)benzoyl]-piperidine;
4-{1-[(4-chlorophenyl)sulfonyl]ethyl}-1-[4-(methylsulfonyl)-2-(trifluoromethoxy)benzoyl]-piperidine;
4-{1-[(4-chlorophenyl)sulfonyl]ethyl}-1-[5-fluoro-2-(methylsulfonyl)benzoyl]piperidine;
1-[5-fluoro-2-(methylsulfonyl)benzoyl]-4-(1-{[3-(trifluoromethyl)phenyl]sulfonyl}ethyl)-piperidine;
1-[2-(methylsulfonyl)-4-(trifluoromethyl)benzoyl]-4-(1-{[3-(trifluoromethyl)phenyl]sulfonyl}-ethyl)piperidine;
tert-butyl-4-(1-{[3-(trifluoromethyl)phenyl]sulfonyl}ethyl)piperidine-1-carboxylate;
1-[2-(methylsulfonyl)-4-(trifluoromethoxy)benzoyl]-4-((1S)-1-{[3-(trifluoromethyl)phenyl]-sulfonyl}ethyl)piperidine;
1-[4-(difluoromethoxy)-2-(methylsulfonyl)benzoyl]-4-((1S)-1-{[3-(trifluoromethyl)phenyl]-sulfonyl}ethyl)piperidine;
1-[2-(methylsulfonyl)-4-(trifluoromethoxy)benzoyl]-4-((1R)-1-{[3-(trifluoromethyl)phenyl]-sulfonyl}ethyl)piperidine;
1-[4-(difluoromethoxy)-2-(methylsulfonyl)benzoyl]-4-((1R)-1-{[3-(trifluoromethyl)phenyl]-sulfonyl}ethyl)piperidine;
1-[4-(cyclopropyloxy)-2,6-bis(methylsulfonyl)benzoyl]-4-((1S)-1-{[3-(trifluoromethyl)phenyl]-sulfonyl}ethyl)piperidine;
1-[4-(cyclopropyloxy)-2,6-bis(methylsulfonyl)benzoyl]-4-((1R)-1-{[3-(trifluoromethyl)phenyl]-sulfonyl}ethyl)piperidine;
2-(cyclopropylsulfonyl)-6-(trifluoromethyl)-3-{[4-((1S)-1-{[3-(trifluoromethyl)phenyl]-sulfonyl}ethyl)piperidin-1-yl]carbonyl}pyridine;
2-(cyclopropylsulfonyl)-6-(trifluoromethyl)-3-{[4-((1R)-1-{[3-(trifluoromethyl)phenyl]sulfonyl}-ethyl)piperidin-1-yl]carbonyl}pyridine;
3-chloro-5-(trifluoromethyl)-2-{[4-((1S)-1-{[3-(trifluoromethyl)phenyl]sulfonyl}ethyl)piperidin-1-yl]carbonyl}pyridine;
3-chloro-5-(trifluoromethyl)-2-{[4-((1S)-1-{[3-(trifluoromethyl)phenyl]sulfonyl}ethyl)piperidin-1-yl]carbonyl}pyridine;
3-(methylsulfonyl)-5-(trifluoromethyl)-2-{[4-((1S)-1-{[3-(trifluoromethyl)phenyl]sulfonyl}-ethyl)piperidin-1-yl]carbonyl}pyridine;
3-(methylsulfonyl)-5-(trifluoromethyl)-2-{[4-((1S)-1-{[3-(trifluoromethyl)phenyl]sulfonyl}-ethyl)piperidin-1-yl]carbonyl}pyridine;
3-(cyclopropylsulfonyl)-5-(trifluoromethyl)-2-{[4-((1S)-1-{[3-(trifluoromethyl)phenyl]sulfonyl}-ethyl)piperidin-1-yl]carbonyl}pyridine;
3-(cyclopropylsulfonyl)-5-(trifluoromethyl)-2-{[4-((1S)-1-{[3-(trifluoromethyl)phenyl]-sulfonyl}ethyl)piperidin-1-yl]carbonyl}pyridine;
4-(cyclopropyl{[3-(trifluoromethyl)phenyl]sulfonyl}methyl)-1-[5-fluoro-2-(methylsulfonyl)-benzoyl]piperidine;
4-(cyclopropyl{[3-(trifluoromethyl)phenyl]sulfonyl}methyl)-1-[4-(methylsulfonyl)-2-(trifluoromethoxy)benzoyl]piperidine;
1-[4-(methylsulfonyl)-2-(trifluoromethoxy)benzoyl]-4-(1-methyl-1-{[3-(trifluoromethyl)phenyl]-sulfonyl}ethyl)piperidine;
1-[2-(methylsulfonyl)-4-(trifluoromethyl)benzoyl]-4-(1-methyl-1-{[3-(trifluoromethyl)phenyl]-sulfonyl}ethyl)piperidine;
1-[5-fluoro-2-(methylsulfonyl)benzoyl]-4-(1-methyl-1-{[3-(trifluoromethyl)phenyl]-sulfonyl}ethyl)piperidine;
1-(3-fluorobenzoyl)-4-(1-methyl-1-{[3-(trifluoromethyl)phenyl]sulfonyl}ethyl)piperidine;
1-(3-methylbenzoyl)-4-(1-methyl-1-{[3-(trifluoromethyl)phenyl]sulfonyl}ethyl)piperidine;
1-(3-methoxybenzoyl)-4-(1-methyl-1-{[3-(trifluoromethyl)phenyl]sulfonyl}ethyl)piperidine;
1-(4-isopropylbenzoyl)-4-(1-methyl-1-{[3-(trifluoromethyl)phenyl]sulfonyl}ethyl)piperidine;
1-(4-tert-butylbenzoyl)-4-(1-methyl-1-{[3-(trifluoromethyl)phenyl]sulfonyl}ethyl)piperidine;
4-(1-methyl-1-{[3-(trifluoromethyl)phenyl]sulfonyl}ethyl)-1-(1,3-oxazol-2-ylcarbonyl)piperidine;
2-chloro-3-{[4-(1-methyl-1-{[3-(trifluoromethyl)phenyl]sulfonyl}ethyl)piperidin-1-yl]carbonyl}quinoxaline;
4-(1-methyl-1-{[3-(trifluoromethyl)phenyl]sulfonyl}ethyl)-1-[2-(trifluoromethoxy)benzoyl]-piperidine;
1-[2-(difluoromethoxy)benzoyl]-4-(1-methyl-1-{[3-(trifluoromethyl)phenyl]sulfonyl}-ethyl)piperidine;
1-[4-(difluoromethoxy)benzoyl]-4-(1-methyl-1-{[3-(trifluoromethyl)phenyl]sulfonyl}-ethyl)piperidine;
6-fluoro-2-{[4-(1-methyl-1-{[3-(trifluoromethyl)phenyl]sulfonyl}ethyl)piperidin-1-yl]carbonyl}-1H-benzimidazole;
4-(methylthio)-2-{[4-(1-methyl-1-{[3-(trifluoromethyl)phenyl]sulfonyl}ethyl)piperidin-1-yl]carbonyl}phenol;
6-chloro-2-{[4-(1-methyl-1-{[3-(trifluoromethyl)phenyl]sulfonyl}ethyl)piperidin-1-yl]carbonyl}-1H-benzimidazole;
1-(3,5-di-tert-butyl-4-methoxybenzoyl)-4-(1-methyl-1-{[3-(trifluoromethyl)phenyl]sulfonyl}-ethyl)piperidine;
4-(1-methyl-1-{[3-(trifluoromethyl)phenyl]sulfonyl}ethyl)-1-[3-(1H-tetrazol-1-yl)benzoyl]piperidine;
1-(3-cyclopropylbenzoyl)-4-(1-methyl-1-{[3-(trifluoromethyl)phenyl]sulfonyl}ethyl)piperidine;
4-(1-methyl-1-{[3-(trifluoromethyl)phenyl]sulfonyl}ethyl)-1-(1,3-thiazol-4-ylcarbonyl)piperidine;
1-[(2,4-dimethyl-1,3-thiazol-5-yl)carbonyl]-4-(1-methyl-1-{[3-(trifluoromethyl)phenyl]sulfonyl}-ethyl)piperidine;
3-{[4-(1-methyl-1-{[3-(trifluoromethyl)phenyl]sulfonyl}ethyl)piperidin-1-yl]carbonyl}pyrazolo-[1,5-a]pyrimidine;
2-{[4-(1-methyl-1-{[3-(trifluoromethyl)phenyl]sulfonyl}ethyl)piperidin-1-yl]carbonyl}pyrazolo-[1,5-a]pyridine;
1-[4-(methylsulfonyl)-2-(trifluoromethoxy)benzoyl]-4-(1-methyl-1-{[3-(trifluoromethoxy)-phenyl]sulfonyl}ethyl)piperidine;
1-[2-(methylsulfonyl)-4-(trifluoromethyl)benzoyl]-4-(1-methyl-1-{[3-(trifluoromethoxy)phenyl]-sulfonyl}ethyl)piperidine;
1-[5-fluoro-2-(methylsulfonyl)benzoyl]-4-(1-methyl-1-{[3-(trifluoromethoxy)phenyl]-sulfonyl}ethyl)piperidine;
1-[4-chloro-2-(methylsulfonyl)benzoyl]-4-(1-methyl-1-{[3-(trifluoromethoxy)phenyl]sulfonyl}-ethyl)piperidine;

1-benzoyl-4-(1-methyl-1-{[3-(trifluoromethoxy)phenyl]sulfonyl}ethyl)piperidine;
1-(3-fluorobenzoyl)-4-(1-methyl-1-{[3-(trifluoromethoxy)phenyl]sulfonyl}ethyl)piperidine;
1-(3-methylbenzoyl)-4-(1-methyl-1-{[3-(trifluoromethoxy)phenyl]sulfonyl}ethyl)piperidine;
4-(1-methyl-1-{[3-(trifluoromethoxy)phenyl]sulfonyl}ethyl)-1-[2-(trifluoromethoxy)benzoyl]-piperidine;
1-[2-(difluoromethoxy)benzoyl]-4-(1-methyl-1-{[3-(trifluoromethoxy)phenyl]sulfonyl}ethyl)-piperidine;
1-[3-(difluoromethoxy)benzoyl]-4-(1-methyl-1-{[3-(trifluoromethoxy)phenyl]sulfonyl}ethyl)-piperidine;
1-[4-(difluoromethoxy)benzoyl]-4-(1-methyl-1-{[3-(trifluoromethoxy)phenyl]sulfonyl}ethyl)-piperidine;
1-[3-(methylsulfonyl)benzoyl]-4-(1-methyl-1-{[3-(trifluoromethyl)phenyl]sulfonyl}ethyl)-piperidine;
1-[4-methoxy-3-(methylsulfonyl)benzoyl]-4-(1-methyl-1-{[3-(trifluoromethoxy)phenyl]-sulfonyl}ethyl)piperidine;
1-[4-(difluoromethoxy)-3-(methylsulfonyl)benzoyl]-4-(1-methyl-1-{[3-(trifluoromethoxy)-phenyl]sulfonyl}ethyl)piperidine;
1-[4-methoxy-2-(methylsulfonyl)benzoyl]-4-(1-methyl-1-{[3-(trifluoromethoxy)phenyl]-sulfonyl}ethyl)piperidine;
1-[4-methoxy-2-(methylsulfonyl)benzoyl]-4-(1-methyl-1-{[3-(trifluoromethyl)phenyl]sulfonyl}-ethyl)piperidine;
1-[4-methoxy-3-(methylsulfonyl)benzoyl]-4-(1-methyl-1-{[3-(trifluoromethyl)phenyl]-sulfonyl}ethyl)piperidine;
1-[4-(difluoromethoxy)-3-(methylsulfonyl)benzoyl]-4-(1-methyl-1-{[3-(trifluoromethyl)phenyl]-sulfonyl}ethyl)piperidine;
1-[5-(difluoromethoxy)-2-(methylsulfonyl)benzoyl]-4-(1-methyl-1-{[3-(trifluoromethoxy)-phenyl]sulfonyl}ethyl)piperidine;
1-[3-fluoro-2-(methylsulfonyl)benzoyl]-4-(1-methyl-1-{[3-(trifluoromethyl)phenyl]-sulfonyl}ethyl)piperidine;
1-[4-fluoro-2-(methylsulfonyl)benzoyl]-4-(1-methyl-1-{[3-(trifluoromethyl)phenyl]-sulfonyl}ethyl)piperidine;
1-[4,5-difluoro-2-(methylsulfonyl)benzoyl]-4-(1-methyl-1-{[3-(trifluoromethyl)phenyl]-sulfonyl}ethyl)piperidine;
1-[2-(ethylsulfonyl)-4,5-difluorobenzoyl]-4-(1-methyl-1-{[3-(trifluoromethyl)phenyl]-sulfonyl}ethyl)piperidine;
1-[5-(difluoromethoxy)-2-(methylsulfonyl)benzoyl]-4-(1-methyl-1-{[3-(trifluoromethyl)-phenyl]sulfonyl}ethyl)piperidine;
1-[4-(difluoromethoxy)-2-(methylsulfonyl)benzoyl]-4-(1-methyl-1-{[3-(trifluoromethoxy)-phenyl]sulfonyl}ethyl)piperidine;
1-[4-(difluoromethoxy)-2-(methylsulfonyl)benzoyl]-4-(1-methyl-1-{[3-(trifluoromethyl)-phenyl]sulfonyl}ethyl)piperidine;
Methyl 4-{[4-(1-methyl-1-{[3-(trifluoromethyl)phenyl]sulfonyl}ethyl)piperidin-1-yl]carbonyl}benzoate;
2,2,2-trifluoro-1-(4-{[4-(1-methyl-1-{[3-(trifluoromethyl)phenyl]sulfonyl}ethyl)piperidin-1-yl]carbonyl}phenyl)ethanone;
1,1,1,3,3,3-hexafluoro-2-(4-{[4-(1-methyl-1-{[3-(trifluoromethyl)phenyl]sulfonyl}-ethyl)piperidin-1-yl]carbonyl}phenyl)propan-2-ol;
N-methyl-4-{[4-(1-methyl-1-{[3-(trifluoromethyl)phenyl]sulfonyl}ethyl)piperidin-1-yl]carbonyl}benzamide;
N-cyclopropyl-4-{[4-(1-methyl-1-{[3-(trifluoromethyl)phenyl]sulfonyl}ethyl)piperidin-1-yl]carbonyl}benzamide;
N-tert-butyl-4-{[4-(1-methyl-1-{[3-(trifluoromethyl)phenyl]sulfonyl}ethyl)piperidin-1-yl]carbonyl}benzamide;
1-[4-(azetidin-1-ylcarbonyl)benzoyl]-4-(1-methyl-1-{[3-(trifluoromethyl)phenyl]sulfonyl}ethyl)-piperidine;
4-(1-methyl-1-{[3-(trifluoromethyl)phenyl]sulfonyl}ethyl)-1-[4-(pyrrolidin-1-ylcarbonyl)benzoyl]piperidine;
3-(methylsulfonyl)-2-{[4-(1-methyl-1-{[3-(trifluoromethyl)phenyl]sulfonyl}ethyl)piperidin-1-yl]carbonyl}quinoline;
1-[4-(tert-butylthio)benzoyl]-4-(1-methyl-1-{[3-(trifluoromethyl)phenyl]sulfonyl}ethyl)-piperidine;
1-[4-(tert-butylsulfonyl)benzoyl]-4-(1-methyl-1-{[3-(trifluoromethyl)phenyl]sulfonyl}ethyl)-piperidine;
4-(methylsulfonyl)-3-{[4-(1-methyl-1-{[3-(trifluoromethyl)phenyl]sulfonyl}ethyl)piperidin-1-yl]carbonyl}phenol;
4-{1-[(3-chlorophenyl)sulfonyl]-1-methylethyl}-1-[4,5-difluoro-2-(methylsulfonyl)benzoyl]-piperidine;
4-{1-[(3-chlorophenyl)sulfonyl]-1-methylethyl}-1-[2-(methylsulfonyl)-4-(trifluoromethyl)-benzoyl]piperidine;
4-{1-[(3-chlorophenyl)sulfonyl]-1-methylethyl}-1-[4-(difluoromethoxy)-2-(methylsulfonyl)-benzoyl]piperidine;
4-{1-[(3-chlorophenyl)sulfonyl]-1-methylethyl}-1-[5-(difluoromethoxy)-2-(methylsulfonyl)-benzoyl]piperidine;
4-{1-[(3-chlorophenyl)sulfonyl]-1-methylethyl}-1-[5-fluoro-2-(methylsulfonyl)-benzoyl]piperidine;
1-[4-(tert-butylthio)-2-chlorobenzoyl]-4-(1-methyl-1-{[3-(trifluoromethyl)phenyl]sulfonyl}-ethyl)piperidine;
1-[4-(tert-butylsulfonyl)-2-chlorobenzoyl]-4-(1-methyl-1-{[3-(trifluoromethyl)phenyl]-sulfonyl}ethyl)piperidine;
1-[2-bromo-4-(tert-butylsulfonyl)benzoyl]-4-(1-methyl-1-{[3-(trifluoromethyl)phenyl]sulfonyl}-ethyl)piperidine;
1-[4-(tert-butylsulfonyl)-2-(methylsulfonyl)benzoyl]-4-(1-methyl-1-{[3-(trifluoromethyl)phenyl]-sulfonyl}ethyl)piperidine;
1-[(1-methyl-1H-pyrazol-4-yl)carbonyl]-4-(1-methyl-1-{[3-(trifluoromethyl)phenyl]-sulfonyl}ethyl)piperidine;
2-chloro-4-methyl-6-{[4-(1-methyl-1-{[3-(trifluoromethyl)phenyl]sulfonyl}ethyl)piperidin-1-yl]carbonyl}pyrimidine;
3-chloro-6-{[4-(1-methyl-1-{[3-(trifluoromethyl)phenyl]sulfonyl}ethyl)piperidin-1-yl]carbonyl}pyridazine;
2-methoxy-5-{[4-(1-methyl-1-{[3-(trifluoromethyl)phenyl]sulfonyl}ethyl)piperidin-1-yl]carbonyl}pyrazine;
5-{[4-(1-methyl-1-{[3-(trifluoromethyl)phenyl]sulfonyl}ethyl)piperidin-1-yl]carbonyl}-1,3-benzothiazole;
1-[2-(1H-imidazol-2-yl)benzoyl]-4-(1-methyl-1-{[3-(trifluoromethyl)phenyl]sulfonyl}ethyl)-piperidine;
4-{[4-(1-methyl-1-{[3-(trifluoromethyl)phenyl]sulfonyl}ethyl)piperidin-1-yl]carbonyl}-1,3-dihydro-2H-imidazol-2-one;

5-{[4-(1-methyl-1-{[3-(trifluoromethyl)phenyl]
sulfonyl}ethyl)piperidin-1-yl]carbonyl}-quinoxaline;
1-[4-hydroxy-2-(methylsulfonyl)benzoyl]-4-[1-methyl-1-
[[3-(trifluoromethyl)phenyl]-sulfonyl]ethyl]piperidine;
1-[4-chloro-2-(methylsulfonyl)benzoyl]-4-(1-methyl-1-
{[3-(trifluoromethyl)phenyl]-sulfonyl}ethyl)piperi-
dine;
1-[4-bromo-2-(methylsulfonyl)benzoyl]-4-(1-methyl-1-
{[3-(trifluoromethyl)phenyl]-sulfonyl}ethyl)piperi-
dine;
1-{[4-fluoro-2-(methylsulfonyl)phenyl]acetyl}-4-(1-me-
thyl-1-{[3-(trifluoromethyl)phenyl]-sulfonyl}ethyl)pi-
peridine;
1-{[2-(methylsulfonyl)phenyl]acetyl}-4-(1-methyl-1-{[3-
(trifluoromethyl)phenyl]-sulfonyl}ethyl)piperidine;
1-{[5-chloro-2-(methylsulfonyl)phenyl]acetyl}-4-(1-me-
thyl-1-{[3-(trifluoromethyl)phenyl]-sulfonyl}ethyl)pi-
peridine;
4-(1-{[3,5-bis(trifluoromethyl)phenyl]sulfonyl}-1-meth-
ylethyl)-1-[4-(tert-butylsulfonyl)benzoyl]-piperidine;
4-(1-{[3,5-bis(trifluoromethyl)phenyl]sulfonyl}-1-meth-
ylethyl)-1-[4-(tert-butylsulfonyl)-2-chlorobenzoyl]pip-
eridine;
4-(1-{[3,5-bis(trifluoromethyl)phenyl]sulfonyl}-1-meth-
ylethyl)-1-[4-(tert-butylsulfonyl)-2-(methylsulfonyl)
benzoyl]piperidine;
2-methyl-6-{[4-(1-methyl-1-{[3-(trifluoromethyl)phenyl]
sulfonyl}ethyl)piperidin-1-yl]carbonyl}-1H-benzimi-
dazole;
1-[2-chloro-4-(isopropylsulfonyl)benzoyl]-4-(1-methyl-
1-{[3-(trifluoromethyl)phenyl]sulfonyl}-ethyl)piperi-
dine;
1-[4-(isopropylsulfonyl)-2-(methylsulfonyl)benzoyl]-4-
[1-methyl-1-{[3-(trifluoromethyl)phenyl]-
sulfonyl}ethyl]piperidine;
2-methyl-6-{[4-(1-methyl-1-{[3-(trifluoromethyl)phenyl]
sulfonyl}ethyl)piperidin-1-yl]carbonyl}-1,3-ben-
zothiazole;
1-[4-(5-cyclopropyl-1,3,4-oxadiazol-2-yl)-2-(methylsul-
fonyl)benzoyl]-4-(1-methyl-1-{[3-(trifluoromethyl)
phenyl]sulfonyl}ethyl)piperidine;
1-(2,6-difluoro-4-methoxybenzoyl)-4-(1-methyl-1-{[3-
(trifluoromethyl)phenyl]sulfonyl}-ethyl)piperidine;
1-[4-methoxy-2,6-bis(methylsulfonyl)benzoyl]-4-(1-me-
thyl-1-{[3-(trifluoromethyl)phenyl]sulfonyl}ethyl)pi-
peridine;
4-{1-[(3-fluorophenyl)sulfonyl]-1-methylethyl}-1-[2-
(methylsulfonyl)-4-(trifluoromethoxy)-benzoyl]piperi-
dine;
1-[4-(difluoromethoxy)-2-(methylsulfonyl)benzoyl]-4-
{1-[(3-fluorophenyl)sulfonyl]-1-
methylethyl}piperidine;
1-[4-(ethylsulfonyl)-2-(trifluoromethoxy)benzoyl]-4-(1-
methyl-1-{[3-(trifluoromethyl)phenyl]-sulfonyl}ethyl)
piperidine;
4-(1-methyl-1-{[3-(trifluoromethyl)phenyl]
sulfonyl}ethyl)-1-[2,4,6-tris(methylsulfonyl)-benzoyl]
piperidine;
4-(1-methyl-1-{[3-(trifluoromethyl)phenyl]
sulfonyl}ethyl)-1-[4-[(2,2,2-trifluoroethyl)sulfonyl]-2-
(trifluoromethyl)benzoyl]piperidine;
5-[4-{[4-(1-methyl-1-{[3-(trifluoromethyl)phenyl]
sulfonyl}ethyl)piperidin-1-yl]carbonyl}-3-(trifluo-
romethoxy)phenyl]pyrimidine;

1-[4-{[4-(1-methyl-1-{[3-(trifluoromethyl)phenyl]
sulfonyl}ethyl)piperid1-[4-{[4-(1-methyl-1-{[3-(trif-
luoromethyl)phenyl]sulfonyl}ethyl)piperidin-2(1H)-
one;
5-(3-(methylsulfonyl)-4-{[4-(1-methyl-1-{[3-(trifluo-
romethyl)phenyl]sulfonyl}ethyl)piperidin-1-yl]
carbonyl}phenyl)pyrimidine;
1-[2,6-bis(methylsulfonyl)-4-(trifluoromethoxy)ben-
zoyl]-4-(1-methyl-1-{[3-(trifluoromethyl)phenyl]
sulfonyl}ethyl)piperidine;
1-(3-(methylsulfonyl)-4-{[4-(1-methyl-1-{[3-(trifluo-
romethyl)phenyl]sulfonyl}ethyl)piperidin-1-yl]
carbonyl}phenyl)pyridin-2(1H)-one;
2-[2-{[4-(1-methyl-1-{[3-(trifluoromethyl)phenyl]
sulfonyl}ethyl)piperidin-1-yl]carbonyl}-5-(trifluo-
romethoxy)phenoxy]pyridine;
4-(1-methyl-1-{[3-(trifluoromethyl)phenyl]
sulfonyl}ethyl)-1-[2-(1H-1,2,4-triazol-1-yl)-4-(trifluo-
romethoxy)benzoyl]piperidine;
1-[2-{[4-(1-methyl-1-{[3-(trifluoromethyl)phenyl]
sulfonyl}ethyl)piperidin-1-yl]carbonyl}-5-(trifluo-
romethoxy)phenyl]pyridin-2(1H)-one;
1-[2-{[4-(1-methyl-1-{[3-(trifluoromethyl)phenyl]
sulfonyl}ethyl)piperidin-1-yl]carbonyl}-5-(trifluo-
romethoxy)phenyl]-1,2-dihydro-3H-1,2,4-triazol-3-
one;
1-[4-(cyclopropylsulfonyl)-2-(trifluoromethoxy)ben-
zoyl]-4-(1-methyl-1-{[3-(trifluoromethyl)-phenyl]
sulfonyl}ethyl)piperidine;
3-{[4-(1-methyl-1-{[3-(trifluoromethyl)phenyl]
sulfonyl}ethyl)piperidin-1-yl]carbonyl}quinoxalin-2-
ol;
1-[2,4-bis(cyclopropylsulfonyl)benzoyl]-4-(1-methyl-1-
{[3-(trifluoromethyl)phenyl]-sulfonyl}ethyl)piperi-
dine;
1-[4-(cyclopropyloxy)-2-(methylsulfonyl)benzoyl]-4-(1-
methyl-1-{[3-(trifluoromethyl)phenyl]-sulfonyl}ethyl)
piperidine;
1-[4-(cyclopropylsulfonyl)benzoyl]-4-(1-methyl-1-{[3-
(trifluoromethyl)phenyl]sulfonyl}-ethyl)piperidine;
1-(5-(cyclopropyloxy)-2-{[4-(1-methyl-1-{[3-(trifluo-
romethyl)phenyl]sulfonyl}ethyl)piperidin-1-yl]
carbonyl}phenyl)-1,2-dihydro-3H-1,2,4-triazol-3-one;
3-[(1-methyl-1-{1-[2-(methylsulfonyl)-4-(trifluo-
romethoxy)benzoyl]piperidin-4-yl}ethyl)sulfonyl]-5-
(trifluoromethyl)pyridine;
3-[(1-{1-[4-(difluoromethoxy)-2-(methylsulfonyl)ben-
zoyl]piperidin-4-yl}-1-methylethyl)sulfonyl]-5-(trif-
luoromethyl)pyridine;
3-[(1-{1-[4-(cyclopropyloxy)-2-(methylsulfonyl)ben-
zoyl]piperidin-4-yl}-1-methylethyl)-sulfonyl]-5-(trif-
luoromethyl)pyridine;
1-[4-(cyclopropylsulfonyl)-3-fluorobenzoyl]-4-(1-me-
thyl-1-{[3-(trifluoromethyl)phenyl]-sulfonyl}ethyl)pi-
peridine;
1-[4-bromo-2-(cyclopropylsulfonyl)benzoyl]-4-(1-me-
thyl-1-{[3-(trifluoromethyl)phenyl]-sulfonyl}ethyl)pi-
peridine;
1-[4-(cyclopropylsulfonyl)-2-fluorobenzoyl]-4-(1-me-
thyl-1-{[3-(trifluoromethyl)phenyl]-sulfonyl}ethyl)pi-
peridine;
1-[4-(cyclopropylsulfonyl)-2-methoxybenzoyl]-4-(1-me-
thyl-1-{[3-(trifluoromethyl)phenyl]-sulfonyl}ethyl)pi-
peridine;
2-chloro-3-{[4-(1-methyl-1-{[3-(trifluoromethyl)phenyl]
sulfonyl}ethyl)piperidin-1-yl]carbonyl}-6-(trifluorom-
ethyl)pyridine;

2-[(1-methyl-1-{1-[2-(methylsulfonyl)-4-(trifluoromethoxy)benzoyl]piperidin-4-yl}ethyl)sulfonyl]-6-(trifluoromethyl)pyridine;
2-[(1-{1-[4-(difluoromethoxy)-2-(methylsulfonyl)benzoyl]piperidin-4-yl}-1-methylethyl)sulfonyl]-6-(trifluoromethyl)pyridine;
2-[(1-{1-[4-(cyclopropyloxy)-2-(methylsulfonyl)benzoyl]piperidin-4-yl}-1-methylethyl)sulfonyl]-6-(trifluoromethyl)pyridine;
2-[(1-methyl-1-{1-[2-(methylsulfonyl)-4-(trifluoromethoxy)benzoyl]piperidin-4-yl}ethyl)sulfonyl]-4-(trifluoromethyl)pyridine;
2-[(1-{1-[4-(difluoromethoxy)-2-(methylsulfonyl)benzoyl]piperidin-4-yl}-1-methylethyl)sulfonyl]-4-(trifluoromethyl)pyridine;
2-[(1-{1-[4-(cyclopropyloxy)-2-(methylsulfonyl)benzoyl]piperidin-4-yl}-1-methylethyl)sulfonyl]-4-(trifluoromethyl)pyridine;
3-[(1-methyl-1-{1-[4-[(2,2,2-trifluoroethyl)sulfonyl]-2-(trifluoromethyl)benzoyl]piperidin-4-yl}ethyl)sulfonyl]-5-(trifluoromethyl)pyridine;
2-(methylsulfonyl)-3-{[4-(1-methyl-1-{[3-(trifluoromethyl)phenyl]sulfonyl}ethyl)piperidin-1-yl]carbonyl}-6-(trifluoromethyl)pyridine;
1-[4-(cyclopropyloxy)-2-(methylsulfonyl)benzoyl]-4-(1-{[3-fluoro-5-(trifluoromethyl)phenyl]sulfonyl}-1-methylethyl)piperidine;
1-[4-(cyclopropylsulfonyl)-2-(difluoromethoxy)benzoyl]-4-(1-methyl-1-{[3-(trifluoromethyl)phenyl]sulfonyl}ethyl)piperidine;
2-(cyclobutyloxy)-5-{[4-(1-methyl-1-{[3-(trifluoromethyl)phenyl]sulfonyl}ethyl)piperidin-1-yl]carbonyl}pyridine;
3-(methylsulfonyl)-2-{[4-(1-methyl-1-{[3-(trifluoromethyl)phenyl]sulfonyl}ethyl)piperidin-1-yl]carbonyl}-5-(trifluoromethyl)pyridine;
2-(cyclobutyloxy)-4-(methylsulfonyl)-5-{[4-(1-methyl-1-{[3-(trifluoromethyl)phenyl]sulfonyl}-ethyl)piperidin-1-yl]carbonyl}pyridine;
2-(cyclopropylsulfonyl)-3-{[4-(1-{[3-fluoro-5-(trifluoromethyl)phenyl]sulfonyl}-1-methylethyl)piperidin-1-yl]carbonyl}-6-(trifluoromethyl)pyridine;
3-{[4-(1-{[3-fluoro-5-(trifluoromethyl)phenyl]sulfonyl}-1-methylethyl)piperidin-1-yl]carbonyl}-2-(methylsulfonyl)-6-(trifluoromethyl)pyridine;
2-{[4-(1-methyl-1-{[3-(trifluoromethyl)phenyl]sulfonyl}ethyl)piperidin-1-yl]carbonyl}-5-(trifluoromethyl)pyridine;
3-chloro-2-{[4-(1-methyl-1-{[3-(trifluoromethyl)phenyl]sulfonyl}ethyl)piperidin-1-yl]carbonyl}-5-(trifluoromethyl)pyridine;
3-(cyclopropylsulfonyl)-2-{[4-(1-methyl-1-{[3-(trifluoromethyl)phenyl]sulfonyl}ethyl)piperidin-1-yl]carbonyl}-5-(trifluoromethyl)pyridine;
2-{[4-(1-{[3-fluoro-5-(trifluoromethyl)phenyl]sulfonyl}-1-methylethyl)piperidin-1-yl]carbonyl}-3-(methylsulfonyl)-5-(trifluoromethyl)pyridine;
3-(cyclopropylsulfonyl)-2-{[4-(1-{[3-fluoro-5-(trifluoromethyl)phenyl]sulfonyl}-1-methylethyl)piperidin-1-yl]carbonyl}-5-(trifluoromethyl)pyridine;
1-[4-[(1-methylcyclopropyl)oxy]-2,6-bis(methylsulfonyl)benzoyl]-4-(1-methyl-1-{[3-(trifluoromethyl)phenyl]sulfonyl}ethyl)piperidine;
3-chloro-2-{[4-(1-{[3-fluoro-5-(trifluoromethyl)phenyl]sulfonyl}-1-methylethyl)piperidin-1-yl]carbonyl}-5-(trifluoromethyl)pyridine;

1-[2-(cyclopropylsulfonyl)-4-(trifluoromethoxy)benzoyl]-4-(1-methyl-1-{[3-(trifluoromethyl)phenyl]sulfonyl}ethyl)piperidine;
3-chloro-2-{[4-(1-methyl-1-{[3-(trifluoromethoxy)phenyl]sulfonyl}ethyl)piperidin-1-yl]carbonyl}-5-(trifluoromethyl)pyridine;
3-(methylsulfonyl)-2-{[4-(1-methyl-1-{[3-(trifluoromethoxy)phenyl]sulfonyl}ethyl)piperidin-1-yl]carbonyl}-5-(trifluoromethyl)pyridine;
3-(cyclopropylsulfonyl)-2-{[4-(1-methyl-1-{[3-(trifluoromethoxy)phenyl]sulfonyl}ethyl)piperidin-1-yl]carbonyl}-5-(trifluoromethyl)pyridine;
5-[2-{[4-(1-methyl-1-{[3-(trifluoromethyl)phenyl]sulfonyl}ethyl)piperidin-1-yl]carbonyl}-5-(trifluoromethyl)pyridin-3-yl]pyrimidine;
2-{[4-(1-methyl-1-{[3-(trifluoromethyl)phenyl]sulfonyl}ethyl)piperidin-1-yl]carbonyl}-3-(1H-pyrazol-4-yl)-5-(trifluoromethyl)pyridine;
3-(1-methyl-1H-pyrazol-4-yl)-2-{[4-(1-methyl-1-{[3-(trifluoromethyl)phenyl]sulfonyl}ethyl)-piperidin-1-yl]carbonyl}-5-(trifluoromethyl)pyridine;
2'-{[4-(1-methyl-1-{[3-(trifluoromethyl)phenyl]sulfonyl}ethyl)piperidin-1-yl]carbonyl}-5'-(trifluoromethyl)-3,3'-bipyridin-6-ol;
6'-methoxy-2-{[4-(1-methyl-1-{[3-(trifluoromethyl)phenyl]sulfonyl}ethyl)piperidin-1-yl]carbonyl}-5-(trifluoromethyl)-3,3'-bipyridine;
2'-methoxy-2-{[4-(1-methyl-1-{[3-(trifluoromethyl)phenyl]sulfonyl}ethyl)piperidin-1-yl]carbonyl}-5-(trifluoromethyl)-3,3'-bipyridine;
2'-{[4-(1-methyl-1-{[3-(trifluoromethyl)phenyl]sulfonyl}ethyl)piperidin-1-yl]carbonyl}-5'-(trifluoromethyl)-2,3'-bipyridine;
2-{[4-(1-methyl-1-{[3-(trifluoromethyl)phenyl]sulfonyl}ethyl)piperidin-1-yl]carbonyl}-5-(trifluoromethyl)-3,4'-bipyridine;
6-methyl-2'-{[4-(1-methyl-1-{[3-(trifluoromethyl)phenyl]sulfonyl}ethyl)piperidin-1-yl]carbonyl}-5'-(trifluoromethyl)-2,3'-bipyridine;
2-{[4-(1-methyl-1-{[3-(trifluoromethyl)phenyl]sulfonyl}ethyl)piperidin-1-yl]carbonyl}-5-(trifluoromethyl)nicotinonitrile;
3-(ethylsulfonyl)-2-{[4-(1-methyl-1-{[3-(trifluoromethyl)phenyl]sulfonyl}ethyl)piperidin-1-yl]carbonyl}-5-(trifluoromethyl)pyridine;
2-{[4-(1-{[3-(difluoromethoxy)phenyl]sulfonyl}-1-methylethyl)piperidin-1-yl]carbonyl}-3-(ethylsulfonyl)-5-(trifluoromethyl)pyridine;
2-{[4-(1-{[3-(difluoromethoxy)phenyl]sulfonyl}-1-methylethyl)piperidin-1-yl]carbonyl}-3-(methylsulfonyl)-5-(trifluoromethyl)pyridine;
3-(cyclopropylsulfonyl)-2-{[4-(1-{[3-(difluoromethoxy)phenyl]sulfonyl}-1-methylethyl)-piperidin-1-yl]carbonyl}-5-(trifluoromethyl)pyridine;
2-{[4-(1-methyl-1-{[3-(trifluoromethyl)phenyl]sulfonyl}ethyl)piperidin-1-yl]carbonyl}-5-(trifluoromethyl)pyridine;
5-[2-{[4-(1-methyl-1-{[3-(trifluoromethyl)phenyl]sulfonyl}ethyl)piperidin-1-yl]carbonyl}-5-(trifluoromethyl)pyridin-3-yl]pyrimidine;
2-{[4-(1-methyl-1-{[3-(trifluoromethyl)phenyl]sulfonyl}ethyl)piperidin-1-yl]carbonyl}-3-(1H-pyrazol-4-yl)-5-(trifluoromethyl)pyridine;
3-(1-methyl-1H-pyrazol-4-yl)-2-{[4-(1-methyl-1-{[3-(trifluoromethyl)phenyl]sulfonyl ethyl)piperidin-1-yl]carbonyl}-5-(trifluoromethyl)pyridine;

2'-{[4-(1-methyl-1-{[3-(trifluoromethyl)phenyl]
  sulfonyl}ethyl)piperidin-1-yl]carbonyl}-5'-(trifluo-
  romethyl)-3,3'-bipyridin-6-ol;
2'-methoxy-2-{[4-(1-methyl-1-{[3-(trifluoromethyl)phe-
  nyl]sulfonyl}ethyl)piperidin-1-yl]carbonyl}-5-(trifluo-
  romethyl)-3,3'-bipyridine;
6'-methoxy-2-{[4-(1-methyl-1-{[3-(trifluoromethyl)phe-
  nyl]sulfonyl}ethyl)piperidin-1-yl]carbonyl}-5-(trifluo-
  romethyl)-3,3'-bipyridine;
3-(methylsulfonyl)-2-{[4-(1-methyl-1-{[3 (trifluorom-
  ethyl)phenyl]sulfonyl]-ethyl)piperidin-1-yl]
  carbonyl}quinoline;
2-chloro-4-methyl-6-{[4-(1-methyl-1-{[3-(trifluorom-
  ethyl)phenyl]sulfonyl}ethyl)piperidin-1-yl]
  carbonyl}pyrimidine;
3-chloro-6-{[4-(1-methyl-1-{[3-(trifluoromethyl)phenyl]
  sulfonyl}ethyl)piperidin-1-yl]carbonyl}pyridazine;
2-methoxy-5-{[4-(1-methyl-1-{[3-(trifluoromethyl)phe-
  nyl]sulfonyl}ethyl)piperidin-1-yl]carbonyl}pyrazine;
2-{[4-(1-methyl-1-{[3-(trifluoromethyl)phenyl]
  sulfonyl}ethyl)piperidin-1-yl]carbonyl}-5-(trifluorom-
  ethyl)-3,4'-bipyridine;
2-{[4-(1-methyl-1-{[3-(trifluoromethyl)phenyl]
  sulfonyl}ethyl)piperidin-1-yl]carbonyl}-5-(trifluorom-
  ethyl)nicotinonitrile;
3-(ethylsulfonyl)-2-{[4-(1-methyl-1-{[3 (trifluoromethyl)
  phenyl]sulfonyl}ethyl)piperidin-1-yl]carbonyl}-5-(tri-
  fluoromethyl)pyridine;
2-{[4-(1-{[3-(difluoromethoxy)phenyl]sulfonyl}-1-meth-
  ylethyl)piperidin-1-yl]carbonyl}-3-(ethylsulfonyl)-5-
  (trifluoromethyl)pyridine;
3-(cyclopropylsulfonyl)-2-{[4-(1-{[3-(difluoromethoxy)
  phenyl]sulfonyl}-1-methylethyl)piperidin-1-yl]carbo-
  nyl}-5-(trifluoromethyl)pyridine;
2-{[4-(1-{[3-(difluoromethoxy)phenyl]sulfonyl}-1-me-
  thyl ethyl)piperidin-1-yl]carbonyl}-3-(methylsulfo-
  nyl)-5-(trifluoromethyl)pyridine;
2'-{[4-(1-methyl-1-{[3-(trifluoromethyl)phenyl]
  sulfonyl}ethyl)piperidin-1-yl]carbonyl}-5'-(trifluo-
  romethyl)-2,3'-bipyridine;
6-methyl-2'-{[4-(1-methyl-1-{[3-(trifluoromethyl)phe-
  nyl]sulfonyl}ethyl)piperidin-1-yl]carbonyl}-5'-(trif-
  luoromethyl)-2,3'-bipyridine;
2-{[4-(1-{[3-fluoro-2-iodo-5-(trifluoromethyl)phenyl]
  sulfonyl}-1-methylethyl)piperidin-1-yl]carbonyl}-3-
  (methylsulfonyl)-5-(trifluoromethyl)pyridine;
2-{[4-(1-{[3-fluoro-5-(trifluoromethyl)phenyl]sulfonyl}-
  1-methylethyl)piperidin-1-yl]carbonyl}-3-(methylsul-
  fonyl)-5-(trifluoromethyl)pyridine;
tert-butyl{(1S)-1-benzyl-2-[4-(1-methyl-1-{[3-(trifluo-
  romethyl)phenyl]sulfonyl}ethyl)piperidin-1-yl]-2-
  oxoethyl}carbamate;
tert-butyl{(1S))-2-methyl-1-{[4-(1-methyl-1-{[3-(trifluo-
  romethyl)phenyl]sulfonyl}ethyl)piperidin-1-yl]
  carbonyl}propyl)carbamate;
tert-butyl{1,1-dimethyl-2-[4-(1-methyl-1-{[3-(trifluo-
  romethyl)phenyl]sulfonyl}ethyl)piperidin-1-yl]-2-
  oxoethyl}carbamate;
(2S)-1-[4-(1-methyl-1-{[3-(trifluoromethyl)phenyl]
  sulfonyl}ethyl)piperidin-1-yl]-1-oxo-3-phenylpropan-
  2-aminium chloride;
(2S)-3-methyl-1-[4-(1-methyl-1-{[3-(trifluoromethyl)
  phenyl]sulfonyl}ethyl)piperidin-1-yl]-1-oxobutan-2-
  aminium chloride;
2-methyl-1-[4-(1-methyl-1-{[3-(trifluoromethyl)phenyl]
  sulfonyl}ethyl)piperidin-1-yl]-1-oxopropan-2-
  aminium chloride;

1-{[4-(1-methyl-1-{[3-(trifluoromethyl)phenyl]
  sulfonyl}ethyl)piperidin-1-yl]
  carbonyl}cyclobutanamine;
(1S)-1-cyclohexyl-2-[4-(1-methyl-1-{[3-(trifluorom-
  ethyl)phenyl]sulfonyl}ethyl)piperidin-1-yl]-2-oxoetha-
  naminium trifluoroacetate;
1-{[4-(1-methyl-1-{[3-(trifluoromethyl)phenyl]
  sulfonyl}ethyl)piperidin-1-yl]
  carbonyl}cyclopropanaminium trifluoroacetate;
(R)-1-(4-chlorophenyl)-3-[4-(1-methyl-1-{[3-(trifluo-
  romethyl)phenyl]sulfonyl}ethyl)piperidin-1-yl]-3-oxo-
  propan-1-aminium trifluoroacetate;
(2S)-2-{[4-(1-methyl-1-{[3-(trifluoromethyl)phenyl]
  sulfonyl}ethyl)piperidin-1-yl]carbonyl}pyrrolidinium
  trifluoroacetate;
(2R)-1-[4-(1-methyl-1-{[3-(trifluoromethyl)phenyl]
  sulfonyl}ethyl)piperidin-1-yl]-1-oxo-3-phenylpropan-
  2-aminium trifluoroacetate;
(1R)-3-[4-(1-methyl-1-{[3-(trifluoromethyl)phenyl]
  sulfonyl}ethyl)piperidin-1-yl]-3-oxo-1-phenylpropan-
  1-aminium trifluoroacetate;
(1S)-1-(4-chlorophenyl)-3-[4-(1-methyl-1-{[3-(trifluo-
  romethyl)phenyl]sulfonyl}ethyl)piperidin-1-yl]-3-oxo-
  propan-1-aminium trifluoroacetate;
(1R)-2-[4-(1-methyl-1-{[3-(trifluoromethyl)phenyl]
  sulfonyl}ethyl)piperidin-1-yl]-2-oxo-1-phenyletha-
  naminium trifluoroacetate;
(1S)-2-[4-(1-methyl-1-{[3-(trifluoromethyl)phenyl]
  sulfonyl}ethyl)piperidin-1-yl]-2-oxo-1-phenyletha-
  naminium trifluoroacetate;
N-{3-[4-(1-methyl-1-{[3-(trifluoromethyl)phenyl]
  sulfonyl}ethyl)piperidin-1-yl]-3-oxopropyl}methane
  sulfonamide;
N-((1S)-3-methyl-1-{[4-(1-methyl-1-{[3-(trifluorom-
  ethyl)phenyl]sulfonyl}ethyl)piperidin-1-yl]
  carbonyl}butyl)methanesulfonamide;
N-{(1S-1-benzyl-2-[4-(1-methyl-1-{[3-(trifluoromethyl)
  phenyl]sulfonyl}ethyl)piperidin-1-yl]-2-
  oxoethyl}methanesulfonamide;
4-(1-methyl-1-{[3-(trifluoromethyl)phenyl]
  sulfonyl}ethyl)-1-{[4-(1H-tetrazol-1-yl)phenyl]
  acetyl}piperidine;
1-(2-methyl-2-phenylpropanoyl)-4-(1-methyl-1-{[3-(trif-
  luoromethyl)phenyl]sulfonyl}ethyl)piperidine;
4-(1-methyl-1-{[3-(trifluoromethyl)phenyl]
  sulfonyl}ethyl)-1-[(1-phenylcyclopropyl)carbonyl]pip-
  eridine;
4-(1-methyl-1-{[3-(trifluoromethyl)phenyl]
  sulfonyl}ethyl)-1-{[1-(trifluoromethyl)cyclopropyl]-
  carbonyl}piperidine;
N-{(1)-3-[4-(1-methyl-1-{[3-(trifluoromethyl)phenyl]
  sulfonyl}ethyl)piperidin-1-yl]-3-oxo-1-
  phenylpropyl}methanesulfonamide;
N-{1,1-dimethyl-2-[4-(1-methyl-1-{[3-(trifluoromethyl)
  phenyl]sulfonyl}ethyl)piperidin-1-yl]-2-oxo
  ethyl}methanesulfonamide;
N-((1S)-2-methyl-1-{[4-(1-methyl-1-{[3-(trifluorom-
  ethyl)phenyl]sulfonyl}ethyl)piperidin-1-yl]
  carbonyl}propyl)methanesulfonamide;
N-{(1S)-1-(4-chlorophenyl)-3-[4-(1-methyl-1-{[3-(trif-
  luoromethyl)phenyl]sulfonyl}ethyl)piperidin-1-yl]-3-
  oxopropyl}methanesulfonamide;
N-{(1R)-1-(4-chlorophenyl)-3-[4-(1-methyl-1-{[3-(trif-
  luoromethyl)phenyl]sulfonyl}ethyl)piperidin-1-yl]-3-
  oxopropyl}methanesulfonamide;

N-{(1S)-1-benzyl-2-[4-(1-methyl-1-{[3-(trifluoromethyl) phenyl]sulfonyl}ethyl)piperidin-1-yl]-2-oxoethyl}cyclopropanesulfonamide;

3-(1-{[4-(1-methyl-1-{[3-(trifluoromethyl)phenyl] sulfonyl}ethyl)piperidin-1-yl]carbonyl}cyclopentyl) pyridine;

N-[(1S)-2-[4-(1-methyl-1-{[3-(trifluoromethyl)phenyl] sulfonyl}ethyl)piperidin-1-yl]-2-oxo-1-(pyridin-2-yl-methyl)ethyl]methanesulfonamide;

N-{(1S)-1-(4-cyanobenzyl)-2-[4-(1-methyl-1-{[3-(trifluoromethyl)phenyl]sulfonyl]-ethyl)piperidin-1-yl]-2-oxoethyl}methanesulfonamide;

N-{(1S)-1-(4-chlorobenzyl)-2-[4-(1-methyl-1-{[3-(trifluoromethyl)phenyl]sulfonyl}ethyl)-piperidin-1-yl]-2-oxoethyl}methanesulfonamide;

N-{(1S)-2-[4-(1-methyl-1-{[3-(trifluoromethyl)phenyl] sulfonyl}ethyl)piperidin-1-yl]-2-oxo-1-phenylethyl}methanesulfonamide;

(1S)-2-[4-(1-methyl-1-{[3-(trifluoromethyl)phenyl] sulfonyl}ethyl)piperidin-1-yl]-2-oxo-1-phenylethanol;

(2R)-1-[4-(1-methyl-1-{[3-(trifluoromethyl)phenyl] sulfonyl}ethyl)piperidin-1-yl]-1-oxo-3-phenylpropan-2-ol;

(2S)-1-[4-(1-methyl-1-{[3-(trifluoromethyl)phenyl] sulfonyl}ethyl)piperidin-1-yl]-1-oxo-3-phenylpropan-2-ol;

2-{2-[4-(1-methyl-1-{[3-(trifluoromethyl)phenyl] sulfonyl}ethyl)piperidin-1-yl]-2-oxoethyl}imidazo[1,2-a]pyridin-1-ium trifluoroacetate;

N'-{(1S)-1-(4-chlorophenyl)-3-[4-(1-methyl-1-{[3-(trifluoromethyl)phenyl]sulfonyl}ethyl)piperidin-1-yl]-3-oxopropyl}-N,N-dimethylurea;

N'-{(1S)-1-(4-chlorobenzyl)-2-[4-(1-methyl-1-{[3-(trifluoromethyl)phenyl]sulfonyl]-ethyl)piperidin-1-yl]-2-oxoethyl}-N,N-dimethylurea;

N-{(1S)-1-(4-cyanobenzyl)-2-[4-(1-methyl-1-{[3-(trifluoromethyl)phenyl]sulfonyl}ethyl)piperidin-1-yl]-2-oxoethyl}cyclopropanesulfonamide;

N-{(1S)-2-[4-(1-methyl-1-{[3-(trifluoromethyl)phenyl] sulfonyl}ethyl)piperidin-1-yl]-2-oxo-1-phenylethyl}cyclopropanesulfonamide;

N-{(1R)-1-(4-chlorophenyl)-3-[4-(1-methyl-1-{[3-(trifluoromethyl)phenyl]sulfonyl}ethyl)piperidin-1-yl]-3-oxopropyl}cyclopropanesulfonamide;

1-[(2S)-2-(6-methoxy-2-naphthyl)propanoyl]-4-(1-methyl-1-{[3-(trifluoromethyl)phenyl]-sulfonyl}ethyl)piperidine;

1-{[1-(3-bromophenyl)-5-methyl-1H-pyrazol-3-yl]carbonyl}-4-(1-methyl-1-{[3-(trifluoromethyl)phenyl] sulfonyl}ethyl)piperidine;

1-(3-bromo-4-fluorophenyl)-2-[4-(1-methyl-1-{[3-(trifluoromethyl)phenyl]sulfonyl}ethyl)piperidin-1-yl]-2-oxoethanone;

1-[(1,5-diphenyl-1H-pyrazol-3-yl)carbonyl]-4-(1-methyl-1-{[3-(trifluoromethyl)phenyl]-sulfonyl}ethyl)piperidine;

N-{(1S)-1-(4-chlorobenzyl)-2-[4-(1-methyl-1-{[3-(trifluoromethyl)phenyl]sulfonyl}ethyl)piperidin-1-yl]-2-oxoethyl}cyclopropanesulfonamide;

4-(1-methyl-1-{[3-(trifluoromethyl)phenyl] sulfonyl}ethyl)-1-[(2-phenyl-1H-imidazol-4-yl)carbonyl]piperidine;

3-(5-bromo-2-chlorophenyl)-5-{[4-(1-methyl-1-{[3-(trifluoromethyl)phenyl]sulfonyl}ethyl)piperidin-1-yl]carbonyl}pyrazin-2(1H)-one;

4-(1-methyl-1-{[3-(trifluoromethyl)phenyl] sulfonyl}ethyl)-1-[(phenylsulfonyl)acetyl]piperidine;

2-methyl-3-{[4-(1-methyl-1-{[3-(trifluoromethyl)phenyl] sulfonyl}ethyl)piperidin-1-yl]carbonyl}imidazo[1,2-a]pyridine;

7-{[4-(1-methyl-1-{[3-(trifluoromethyl)phenyl] sulfonyl}ethyl)piperidin-1-yl]carbonyl}-1H-indole;

2-methyl-1-[4-(1-methyl-1-{[3-(trifluoromethyl)phenyl] sulfonyl}ethyl)piperidin-1-yl]-1-oxopropan-2-ol;

(2R)-1-[4-(1-methyl-1-{[3-(trifluoromethyl)phenyl] sulfonyl}ethyl)piperidin-1-yl]-1-oxo-2-phenylpropan-2-ol;

(2S)-1-[4-(1-methyl-1-{[3-(trifluoromethyl)phenyl] sulfonyl}ethyl)piperidin-1-yl]-1-oxo-2-phenylpropan-2-ol;

(2R)-2-(4-tert-butylphenyl)-1-[4-(1-methyl-1-{[3-(trifluoromethyl)phenyl]sulfonyl}-ethyl)piperidin-1-yl]-1-oxopropan-2-ol;

2-methyl-3-{[4-(1-methyl-1-{[3-(trifluoromethyl)phenyl] sulfonyl}ethyl)piperidin-1-yl]carbonyl}imidazo[1,2-a]pyridin-1-ium chloride;

(2S)-3-(4-chlorophenyl)-1-[4-(1-methyl-1-{[3-(trifluoromethyl)phenyl]sulfonyl}ethyl)piperidin-1-yl]-1-oxopropan-2-ol;

2,2-dimethyl-3-[4-(1-methyl-1-{[3-(trifluoromethyl)phenyl]sulfonyl}ethyl)piperidin-1-yl]-3-oxo-1-phenylpropan-1-ol;

(2R)-2-(3-chlorophenyl)-1-[4-(1-methyl-1-{[3-(trifluoromethyl)phenyl]sulfonyl}ethyl)piperidin-1-yl]-1-oxopropan-2-ol;

(1R)-2-[4-(1-methyl-1-{[3-(trifluoromethyl)phenyl] sulfonyl}ethyl)piperidin-1-yl]-2-oxo-1-phenylethanol;

(1S,2R)-3-[4-(1-methyl-1-{[3-(trifluoromethyl)phenyl] sulfonyl}ethyl)piperidin-1-yl]-3-oxo-1-phenylpropane-1,2-diol;

(1R,2S)-3-[4-(1-methyl-1-{[3-(trifluoromethyl)phenyl] sulfonyl}ethyl)piperidin-1-yl]-3-oxo-1-phenylpropane-1,2-diol;

(1R)-1-(4-chlorophenyl)-2-[4-(1-methyl-1-{[3-(trifluoromethyl)phenyl]sulfonyl}ethyl)piperidin-1-yl]-2-oxoethanol;

(2S)-1-[4-(1-methyl-1-{[3-(trifluoromethyl)phenyl] sulfonyl}ethyl)piperidin-1-yl]-1-oxo-3-[4-(trifluoromethyl)phenyl]propan-2-aminiumtrifluoroacetate;

(2S)-3-(2,5-difluorophenyl)-1-[4-(1-methyl-1-{[3-(trifluoromethyl)phenyl]sulfonyl}ethyl)-piperidin-1-yl]-1-oxopropan-2-aminium trifluoroacetate;

4-(1-methyl-1-{[3-(trifluoromethyl)phenyl] sulfonyl}ethyl)-1-[(2R)-3,3,3-trifluoro-2-methoxy-2-phenylpropanoyl]piperidine;

4-(1-methyl-1-{[3-(trifluoromethyl)phenyl] sulfonyl}ethyl)-1-({[3-(trifluoromethyl)phenyl]-sulfonyl}acetyl)piperidineuoromethyl)phenyl] sulfonyl}acetyl)piperidine;

4-(1-methyl-1-{[3-(trifluoromethyl)phenyl] sulfonyl}ethyl)-1-({[3-(trifluoromethyl)phenyl]-sulfinyl}acetyl)piperidine;

4-(1-methyl-1-{[3-(trifluoromethyl)phenyl] sulfonyl}ethyl)-1-[2-(phenylsulfonyl)propanoyl]piperidine;

5-{[4-(1-methyl-1-{[3-(trifluoromethyl)phenyl] sulfonyl}ethyl)piperidin-1-yl]carbonyl}-1H-benzimidazole;

2-methyl-5-{[4-(1-methyl-1-{[3-(trifluoromethyl)phenyl] sulfonyl}ethyl)piperidin-1-yl]carbonyl}-1-phenyl-1H-benzimidazole;

1-{2-[(4-chlorophenyl)sulfonyl]-2-methylpropanoyl}-4-(1-methyl-1-{[3-(trifluoromethyl)phenyl]-sulfonyl}ethyl)piperidine;

3-(1H-indol-3-yl)-1-[4-(1-methyl-1-{[3-(trifluoromethyl)phenyl]sulfonyl}ethyl)piperidin-1-yl]-1-oxopropan-2-ol;

1-cyclobutyl-2-[4-(1-methyl-1-{[3-(trifluoromethyl)phenyl]sulfonyl}ethyl)piperidin-1-yl]-2-oxo-1-phenylethanol;

1-[2-methyl-2-(phenylsulfonyl)propanoyl]-4-(1-methyl-1-{[3-(trifluoromethyl)phenyl]-sulfonyl}ethyl)piperidine;

5-{(2S)-2-hydroxy-3-[4-(1-methyl-1-{[3-(trifluoromethyl)phenyl]sulfonyl}ethyl)piperidin-1-yl]-3-oxopropyl}-1H-imidazol-3-ium trifluoroacetate;

5-chloro-2-{[4-(1-methyl-1-{[3-(trifluoromethyl)phenyl]sulfonyl}ethyl)piperidin-1-yl]carbonyl}quinolin-4-ol;

7-chloro-2-{[4-(1-methyl-1-{[3-(trifluoromethyl)phenyl]sulfonyl}ethyl)piperidin-1-yl]carbonyl}quinolin-4-ol;

6-chloro-2-{[4-(1-methyl-1-{[3-(trifluoromethyl)phenyl]sulfonyl}ethyl)piperidin-1-yl]carbonyl}quinolin-4-ol;

(2R)-1,1,1-trifluoro-3-[4-(1-methyl-1-{[3-(trifluoromethyl)phenyl]sulfonyl}ethyl)piperidin-1-yl]-3-oxo-2-phenylpropan-2-ol;

2-{[4-(1-methyl-1-{[3-(trifluoromethyl)phenyl]sulfonyl}ethyl)piperidin-1-yl]carbonyl}-6-(trifluoromethyl)quinolin-4-ol;

(2R)-3-(1H-indol-3-yl)-1-[4-(1-methyl-1-{[3-(trifluoromethyl)phenyl]sulfonyl}ethyl)piperidin-1-yl]-1-oxopropan-2-amine;

4-(1-methyl-1-{[3-(trifluoromethyl)phenyl]sulfonyl}ethyl)-1-(2-methyl-2-{[3-(trifluoromethyl)phenyl]-sulfonyl}propanoyl)piperidine;

1-(3-chlorobenzoyl)-4-(1-methyl-1-{[3-(trifluoromethyl)phenyl]sulfonyl}ethyl)piperidine;

2-{1,1-dimethyl-2-[4-(1-methyl-1-{[3-(trifluoromethyl)phenyl]sulfonyl}ethyl)piperidin-1-yl]-2-oxoethoxy}-5-(trifluoromethyl)pyridine;

6-chloro-3-{[4-(1-methyl-1-{[3-(trifluoromethyl)phenyl]sulfonyl}ethyl)piperidin-1-yl]carbonyl}quinolin-4-ol;

7-chloro-3-{[4-(1-methyl-1-{[3-(trifluoromethyl)phenyl]sulfonyl}ethyl)piperidin-1-yl]carbonyl}quinolin-4-ol;

3-{[4-(1-methyl-1-{[3-(trifluoromethyl)phenyl]sulfonyl}ethyl)piperidin-1-yl]carbonyl}-2-(trifluoromethyl)quinoline;

2-{[4-(1-methyl-1-{[3-(trifluoromethyl)phenyl]sulfonyl}ethyl)piperidin-1-yl]carbonyl}quinolin-4-ol;

3-{[4-(1-methyl-1-{[3-(trifluoromethyl)phenyl]sulfonyl}ethyl)piperidin-1-yl]carbonyl}quinolin-4-ol;

1-[2-(4-chlorophenyl)-2-methylpropanoyl]-4-(1-methyl-1-{[3-(trifluoromethyl)phenyl]-sulfonyl}ethyl)piperidine;

2-{[4-(1-methyl-1-{[3-(trifluoromethyl)phenyl]sulfonyl}ethyl)piperidin-1-yl]carbonyl}pyridin-4-ol;

3-{5-[4-(1-methyl-1-{[3-(trifluoromethyl)phenyl]sulfonyl}ethyl)piperidin-1-yl]-1,3,4-thiadiazol-2-yl}pyridine;

2-{[4-(1-methyl-1-{[3-(trifluoromethyl)phenyl]sulfonyl}ethyl)piperidin-1-yl]carbonyl}quinoline-4,8-diol;

4-{[4-(1-methyl-1-{[3-(trifluoromethyl)phenyl]sulfonyl}ethyl)piperidin-1-yl]carbonyl}-3-(trifluoromethyl)benzonitrile;

2-{[4-(1-methyl-1-{[3-(trifluoromethyl)phenyl]sulfonyl}ethyl)piperidin-1-yl]carbonyl}quinolin-8-ol;

5-chloro-6-{[4-(1-methyl-1-{[3-(trifluoromethyl)phenyl]sulfonyl}ethyl)piperidin-1-yl]carbonyl}pyrimidine-2,4-diol;

5-{[4-(1-methyl-1-{[3-(trifluoromethyl)phenyl]sulfonyl}ethyl)piperidin-1-yl]carbonyl}pyrimidin-4-amine;

2-{[4-(1-methyl-1-{[3-(trifluoromethyl)phenyl]sulfonyl}ethyl)piperidin-1-yl]carbonyl}-7-(trifluoromethyl)quinolin-4-ol;

2-{[4-(1-methyl-1-{[3-(trifluoromethyl)phenyl]sulfonyl}ethyl)piperidin-1-yl]carbonyl}-4-(trifluoromethyl)pyridine;

3-{[4-(1-methyl-1-{[3-(trifluoromethyl)phenyl]sulfonyl}ethyl)piperidin-1-yl]carbonyl}-2-(trifluoromethyl)pyridine;

5-{[4-(1-methyl-1-{[3-(trifluoromethyl)phenyl]sulfonyl}ethyl)piperidin-1-yl]carbonyl}-2-(trifluoromethyl)pyridine;

4-(1-methyl-1-{[4-(trifluoromethyl)phenyl]sulfonyl}ethyl)-1-[3-(trifluoromethoxy)benzoyl]piperidine;

4-(1-methyl-1-{[3-(trifluoromethyl)phenyl]sulfonyl}ethyl)-1-[3-(trifluoromethoxy)benzoyl]piperidine;

5-fluoro-2-{[4-(1-methyl-1-{[3-(trifluoromethyl)phenyl]sulfonyl}ethyl)piperidin-1-yl]carbonyl}pyridine;

1-[(4-phenyl-1,2,3-thiadiazol-5-yl)carbonyl]-4-(1-methyl-1-{[3-(trifluoromethyl)phenyl]sulfonyl}-ethyl)piperidine;

1-[(4-isopropyl-1,2,3-thiadiazol-5-yl)carbonyl]-4-(1-methyl-1-{[3-(trifluoromethyl)phenyl]-sulfonyl}ethyl)piperidine;

5-{[4-(1-methyl-1-{[3-(trifluoromethyl)phenyl]sulfonyl}ethyl)piperidin-1-yl]carbonyl}pyridin-3-ol;

1-[2-(tert-butylamino)-2-oxoethyl]-4-(1-methyl-1-{[3-(trifluoromethyl)phenyl]sulfonyl}-ethyl)piperidinium trifluoroacetate;

1-{[4-(1-methyl-1-{[3-(trifluoromethyl)phenyl]sulfonyl}ethyl)piperidin-1-yl]carbonyl}cyclobutanamine;

(2R)-4-[4-(1-methyl-1-{[3-(trifluoromethyl)phenyl]sulfonyl}ethyl)piperidin-1-yl]-4-oxo-1-(2,4,5-trifluorophenyl)butan-2-aminiumtrifluoroacetate;

1-{[4-(1-methyl-1-{[3-(trifluoromethyl)phenyl]sulfonyl}ethyl)piperidin-1-yl]carbonyl}-cyclopentanaminium trifluoroacetate;

(2S,3R)-3-hydroxy-1-[4-(1-methyl-1-{[3-(trifluoromethyl)phenyl]sulfonyl}ethyl)piperidin-1-yl]-1-oxobutan-2-aminium trifluoroacetate;

or pharmaceutically acceptable salts thereof and individual enantiomers and diastereomers thereof.

7. A compound according to claim 6 which is:

2-{[4-(1-{[3-fluoro-5-(trifluoromethyl)phenyl]sulfonyl}-1-methylethyl)piperidin-1-yl]carbonyl}-3-(methylsulfonyl)-5-(trifluoromethyl)pyridine;

3-(methylsulfonyl)-2-{[4-(1-methyl-1-{[3-(trifluoromethoxy)phenyl]sulfonyl}-ethyl)piperidin-1-yl]carbonyl}-5-(trifluoromethyl)pyridine;

3-(ethylsulfonyl)-2-{[4-(1-methyl-1-{[3-(trifluoromethyl)phenyl]sulfonyl}-ethyl)piperidin-1-yl]carbonyl}-5-(trifluoromethyl)pyridine;

2-{[4-(1-{[3-(difluoromethoxy)phenyl]sulfonyl}-1-methylethyl)piperidin-1-yl]carbonyl}-3-(ethylsulfonyl)-5-(trifluoromethyl)pyridine;

2-{[4-(1-{[3-(difluoromethoxy)phenyl]sulfonyl}-1-methylethyl)piperidin-1-yl]carbonyl}-3-(methylsulfonyl)-5-(trifluoromethyl)pyridine;

4-{1-[(3-chlorophenyl)sulfonyl]-1-methylethyl}-1-[5-fluoro-2-(methylsulfonyl)benzoyl]-piperidine;

1-[4-chloro-2-(methylsulfonyl)benzoyl]-4-(1-methyl-1-{[3-(trifluoromethyl)phenyl]-sulfonyl}ethyl)piperidine;

1-[4-bromo-2-(methylsulfonyl)benzoyl]-4-(1-methyl-1-{[3-(trifluoromethyl)phenyl]-sulfonyl}ethyl)piperidine;

1-{[4-fluoro-2-(methylsulfonyl)phenyl]acetyl}-4-(1-methyl-1-{[3-(trifluoromethyl)-phenyl]sulfonyl}ethyl)piperidine;

3-(cyclopropylsulfonyl)-2-{[4-(1-{[3-fluoro-5-(trifluoromethyl)phenyl]sulfonyl}-1-methylethyl)piperidin-1-yl]carbonyl}-5-(trifluoromethyl)pyridine;

3-chloro-2-{[4-(1-{[3-fluoro-5-(trifluoromethyl)phenyl]sulfonyl}-1-methylethyl)piperidin-1-yl]carbonyl}-5-(trifluoromethyl)pyridine;

1-[4-(methylsulfonyl)-2-(trifluoromethoxy)benzoyl]-4-(1-methyl-1-{[3-(trifluoromethoxy)-phenyl]sulfonyl}ethyl)piperidine;

1-[2-(methylsulfonyl)-4-(trifluoromethyl)benzoyl]-4-(1-methyl-1-{[3-(trifluoromethoxy)-phenyl]sulfonyl}ethyl)piperidine;

1-[5-fluoro-2-(methylsulfonyl)benzoyl]-4-(1-methyl-1-{[3-(trifluoromethoxy)-phenyl]-sulfonyl}ethyl)piperidine;

1-[4-chloro-2-(methylsulfonyl)benzoyl]-4-(1-methyl-1-{[3-(trifluoromethoxy)-phenyl]-sulfonyl}ethyl)piperidine;

1-[4-methoxy-2-(methylsulfonyl)benzoyl]-4-(1-methyl-1-{[3-(trifluoromethoxy)-phenyl]sulfonyl}ethyl)piperidine;

1-[4-(difluoromethoxy)-2-(methylsulfonyl)benzoyl]-4-(1-methyl-1-{[3-(trifluoromethoxy)-phenyl]sulfonyl}ethyl)piperidine;

3-(cyclopropylsulfonyl)-2-{[4-(1-methyl-1-{[3-(trifluoromethoxy)phenyl]sulfonyl}ethyl)-piperidin-1-yl]carbonyl}-5-(trifluoromethyl)pyridine;

3-(cyclopropylsulfonyl)-2-{[4-(1-{[3-(difluoromethoxy)phenyl]sulfonyl}-1-methylethyl)-piperidin-1-yl]carbonyl}-5-(trifluoromethyl)pyridine;

or pharmaceutically acceptable salts thereof and individual enantiomers and diastereomers thereof.

8. A compound according to claim 7 which is:

2-{[4-(1-{[3-fluoro-5-(trifluoromethyl)phenyl]sulfonyl}-1-methylethyl)piperidin-1-yl]carbonyl}-3-(methylsulfonyl)-5-(trifluoromethyl)pyridine;

3-(methylsulfonyl)-2-{[4-(1-methyl-1-{[3-(trifluoromethoxy)phenyl]sulfonyl}-ethyl)piperidin-1-yl]carbonyl}-5-(trifluoromethyl)pyridine;

3-(ethylsulfonyl)-2-{[4-(1-methyl-1-{[3-(trifluoromethyl)phenyl]sulfonyl}-ethyl)piperidin-1-yl]carbonyl}-5-(trifluoromethyl)pyridine;

2-{[4-(1-{[3-(difluoromethoxy)phenyl]sulfonyl}-1-methylethyl)piperidin-1-yl]carbonyl}-3-(ethylsulfonyl)-5-(trifluoromethyl)pyridine;

or pharmaceutically acceptable salts thereof and individual enantiomers and diastereomers thereof.

9. A pharmaceutical composition comprising an inert carrier and an effective amount of a compound according to claim 1.

* * * * *